United States Patent
Cai et al.

(10) Patent No.: US 10,510,435 B2
(45) Date of Patent: Dec. 17, 2019

(54) ERROR CORRECTION OF MULTIPLEX IMAGING ANALYSIS BY SEQUENTIAL HYBRIDIZATION

(71) Applicant: CALIFORNIA INSTITUTE OF TECHNOLOGY, Pasadena, CA (US)

(72) Inventors: Long Cai, Pasadena, CA (US); Sheel Shah, Pasadena, CA (US); Eric Lubeck, San Francisco, CA (US); Wen Zhou, Pasadena, CA (US)

( * ) Notice: Subject to any disclaimer, the term of this patent is extended or adjusted under 35 U.S.C. 154(b) by 152 days.

(21) Appl. No.: 15/298,219

(22) Filed: Oct. 19, 2016

(65) Prior Publication Data
US 2017/0212983 A1   Jul. 27, 2017

Related U.S. Application Data

(63) Continuation-in-part of application No. 14/435,735, filed as application No. PCT/US2014/036258 on Apr. 30, 2014.

(60) Provisional application No. 61/971,974, filed on Mar. 28, 2014, provisional application No. 61/817,651, filed on Apr. 30, 2013.

(51) Int. Cl.
| | |
|---|---|
| C12Q 1/68 | (2018.01) |
| C07H 21/00 | (2006.01) |
| G16B 25/00 | (2019.01) |
| G01N 21/78 | (2006.01) |
| G16B 40/00 | (2019.01) |
| C12Q 1/6841 | (2018.01) |
| G01N 21/64 | (2006.01) |
| C12Q 1/6881 | (2018.01) |

(52) U.S. Cl.
CPC ........... *G16B 25/00* (2019.02); *C12Q 1/6841* (2013.01); *G01N 21/6458* (2013.01); *G01N 21/78* (2013.01); *G16B 40/00* (2019.02); *C12Q 1/6881* (2013.01); *C12Q 2600/158* (2013.01)

(58) Field of Classification Search
CPC .................................. C12Q 1/68; C07H 21/00
See application file for complete search history.

(56) References Cited

U.S. PATENT DOCUMENTS

| | | | |
|---|---|---|---|
| 5,364,763 A | 11/1994 | Kacian | |
| 5,367,066 A | 11/1994 | Urdea et al. | |
| 5,424,413 A | 6/1995 | Hogan et al. | |
| 5,629,147 A | 5/1997 | Asgari et al. | |
| 5,866,331 A | 2/1999 | Singer et al. | |
| 5,955,272 A | 9/1999 | Lawrence et al. | |
| 6,194,146 B1 | 2/2001 | Utermohlen et al. | |
| 6,534,266 B1 | 3/2003 | Singer | |
| 6,537,755 B1 | 3/2003 | Drmanac | |
| 7,727,720 B2 | 6/2010 | Dhallan | |
| 8,309,306 B2 | 11/2012 | Nolan et al. | |
| 2001/0019835 A1 | 9/2001 | Usui | |
| 2001/0026918 A1 | 10/2001 | Collins et al. | |
| 2002/0172950 A1 | 11/2002 | Kenny et al. | |
| 2003/0087279 A1 | 5/2003 | Shao et al. | |
| 2003/0152490 A1 | 8/2003 | Trulson et al. | |
| 2003/0170613 A1 | 9/2003 | Straus | |
| 2004/0171075 A1 | 9/2004 | Flynn et al. | |
| 2004/0229253 A1 | 11/2004 | Hyldig-Nielsen et al. | |
| 2005/0069895 A1 | 3/2005 | Woudenberg et al. | |
| 2006/0275782 A1 | 12/2006 | Gunderson et al. | |
| 2010/0221708 A1 | 9/2010 | Yamada et al. | |
| 2010/0304994 A1 | 12/2010 | Wu et al. | |
| 2010/0323348 A1 | 12/2010 | Hamady et al. | |
| 2011/0104676 A1 | 5/2011 | Pierce et al. | |
| 2012/0021410 A1 | 1/2012 | Yin et al. | |
| 2012/0046178 A1 | 2/2012 | Van Den Boom et al. | |
| 2012/0142014 A1 | 6/2012 | Cai | |
| 2012/0301886 A1 | 11/2012 | Farrell et al. | |
| 2014/0031243 A1 | 1/2014 | Cai et al. | |
| 2014/0073520 A1 | 3/2014 | Cai et al. | |
| 2014/0099637 A1 | 4/2014 | Nolan et al. | |
| 2014/0171338 A1 | 6/2014 | Terbrueggen et al. | |
| 2015/0225801 A1* | 8/2015 | Cai ...................... | C12Q 1/6888 506/9 |
| 2015/0267251 A1* | 9/2015 | Cai .................... | C12N 15/1065 506/9 |
| 2016/0019334 A1* | 1/2016 | Cai ........................ | G06F 19/26 506/8 |
| 2016/0369329 A1 | 12/2016 | Cai et al. | |
| 2018/0142307 A1* | 5/2018 | Cai ........................ | G01N 33/50 |

FOREIGN PATENT DOCUMENTS

| | | |
|---|---|---|
| JP | H09168399 A | 6/1997 |
| JP | 2002542793 A | 12/2002 |
| JP | 2003527075 A | 9/2003 |
| WO | WO/00/65094 A | 11/2000 |
| WO | WO2010/148039 A3 | 12/2010 |
| WO | WO2012/0158967 A1 | 11/2012 |
| WO | WO2014/182528 A2 | 11/2014 |
| WO | WO2016/018960 A1 | 2/2016 |

OTHER PUBLICATIONS

Velculescu, et al., "Analysis of human transcriptomes", Nature Dec. 1999, vol. 23, pp. 387-388.
Blanco, Ana, et al., "A FRET-based assay for characterization of alternative splicing events using peptide nucleic acid fluorescence in titu hybridization", Nucleic Acids Research, vol. 37, No. 17, e116 (Jun. 26, 2009).
Choi, Harry M.T., et al., "Programmable in situ amplification for multiplexed imaging of mRNA expression", Nat Biotechnol, vol. 28, No. 11, pp. 1208-1212 (Nov. 2010).

(Continued)

*Primary Examiner* — Ethan C Whisenant
(74) *Attorney, Agent, or Firm* — Squire Patton Boggs (US) LLP

(57) ABSTRACT

Disclosed herein are methods and systems for detecting and/or quantifying cellular targets such as nucleic acids in cells, tissues, organs or organisms. Through sequential barcoding, it is possible to perform high-throughput profiling of a large number of targets, such as transcripts and/or DNA loci. In some embodiments, error correction is implemented through use of barcodes that can tolerate mistakes and missing data during sequential hybridization of probes to selected targets.

20 Claims, 61 Drawing Sheets

(56) References Cited

OTHER PUBLICATIONS

Epstein, Lucy, et al., "Reutilization fo previously hybridized slides for fluorescence in situ hybridization", Cytometry vol. 21, pp. 378-381 (Year: 1995).

Femino, Andrea, et al., "Visualization of signle RNA transcript", Science 280: 585 (Year: 1998).

Fernandez-Suarez, Marta, et al., "Fluorescent probes for super-resolution imaging in living cells", Molecular Cell Biology, vol. 9, pp. 929-943 (Dec. 2008).

Ioannou, D., et al., "Multicolour interphase cytogenetics: 24 chromosome probes, 6 colours, 4 layers", Molecular and Cellular Probes, vol. 25, pp. 199-205 (Aug. 2011).

Kitayama, Yasuhiko, et al., "Repeated fluorescence in situ hybridization by microwave-enhanced protocol", Pathology International 2006, vol. 56, pp. 490-493.

Levesque, Marshall J., et al., "Single-chromosome transcriptional profiling reveals chromosomal gene expression regulation", Nature Methods, vol. 10, No. 3, pp. 246-248 (Mar. 2013).

Levesque, Marshall J., et al., "Visualizing SNVs to quantify allele-specific expression in single cells", Nature Methods, vol. 10, No. 9, pp. 865-867 (Sep. 2013).

Levsky, Jeffrey M., et al., "Single-cell gene expression profiling", Science 297 : 836 (Year: 2002).

Liehr, T., et al., "Multicolor FISH probe sets and their applications", Histology and Histopathology, vol. 19, pp. 229-237 (Year: 2004).

Lu, Jing, et al., "Quantification of mIRNA Abundance in single cells using locked nucleic acid-FISH and enzyme-labeled fluorescence", Methods in Molecular Biology 680:77 (Year: 2011).

Lubeck, Eric, et al., "Single-cell in situ RNA profiling by sequential hybridization", Nature Methods, vol. 1, No. 4, pp. 360-361 (Apr. 2014).

Lubeck, Eric, et al., "Single-cell systems biology by super-resolution imaging and combinatorial labeling", Nature Methods, vol. 9, No. 7, pp. 743-748 (Jul. 2012).

Mali, Prashant, et al., "Barcoding cells using cell-surface programmable DNA-binding domains", Nature Methods vol. 10, No. 5, pp. 403-406 (May 2013).

Moffitt, Jeffrey R., et al., "High-throughput single-cell gene-expression profiling with multiplexed error-robust fluorescence in situ hybridization", PNAS Sep. 27, 2016, vol. 113, No. 39, pp. 11046-11051.

Muller, Stefan, et al., "Towards unlimited colors for fluorescence in situ hybridization (FISH)", Chromosome Research, vol. 10, pp. 223-232 (Year: 2002).

Muller, Stefan, et al., "A nonredundant multicolor bar code as a screening tool for rearrangements in neoplasia", Genes Chromosomes & Cancer, vol. 39, No. 1, pp. 59-70 (Jan. 2004).

Theodosiou, Zenonas, et al., "Automated analysis of FISH and immunohistochemistry images: a review", Cytometry Part A, vol. 71A, pp. 439-450 (Year: 2007).

Zhen, D.K., et al., "Poly-FISH: A technique of repeated hybridizations that improves cytogenetic analysis of fetal cells in maternal blood", Prenatal Diagnosis, vol. 18, pp. 1181-1185 (Year: 1998).

Eng, et al., Profiling the transcriptome with RNA SPOTs *Nature Methods* Published Oniine Nov. 13, 2017; doi:10.1038/NMETH. 4500, 6 pages.

Shah, et al., Dynamics and Spatial Genomics of the Nascent Transcriptome by Intron seqFISH Cell (2018) doi.org/10.1016/j. cell.2018.05.035, 15 pages.

Collins, et al., A branched DNA signal amplification assay for quantification of nucleic acid targets below 100 molecules/ml, *Nucleic Acids Research 1997*, vol. 25, No. 15, pp. 2979-2984.

Flagella, et al., A multiplex branched DNA assay for parallel quantitative gene expression profiling, *Analytical Biochemistry*, Mar. 2006, vol. 352, pp. 50-60.

Linton, et al., Microarray Gene Expression Analysis of Fixed Archival Tissue Permits Molecular Classification and Identification of Potential Therapeutic Targets in Diffuse Large B-Cell Lymphoma, *Journal Of Molecular Diagnostics*, May 2012, vol. 14, No. 3, pp. 223-232.

Pon, et al., Tandem oligonucleotide synthesis using linker phosphoramidites, *Nucleic Acids Research*, Apr. 6, 2005, vol. 33, No. 6, pp. 1940-1948.

Sinclair, et al., Improved Sensitivity of BCR-A BL Detection: A Triple Probe Three-Color Fluorescence In Situ Hybridization System, *Blood*, Aug. 15, 1997, vol. 90, No. 4, pp. 1395-1402.

Urdea, et al., A comparison of non-radioisotopic hybridization assay methods using fluorescent, chemilluminescent and enzyme labeled synthetic oligodeoxyribonucleotide probes, *Nucleic Acids Research 1988*, vol. 16, No. 11, pp. 4937-4956.

\* cited by examiner

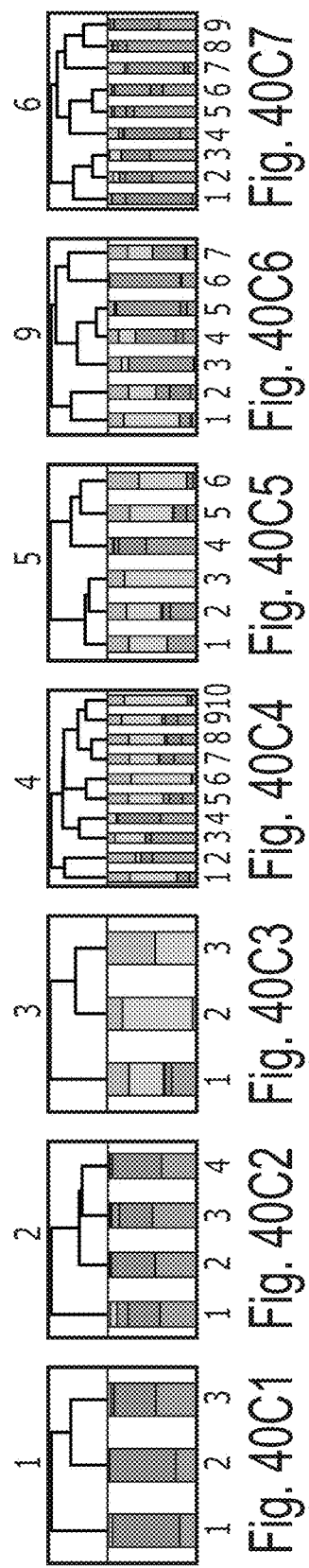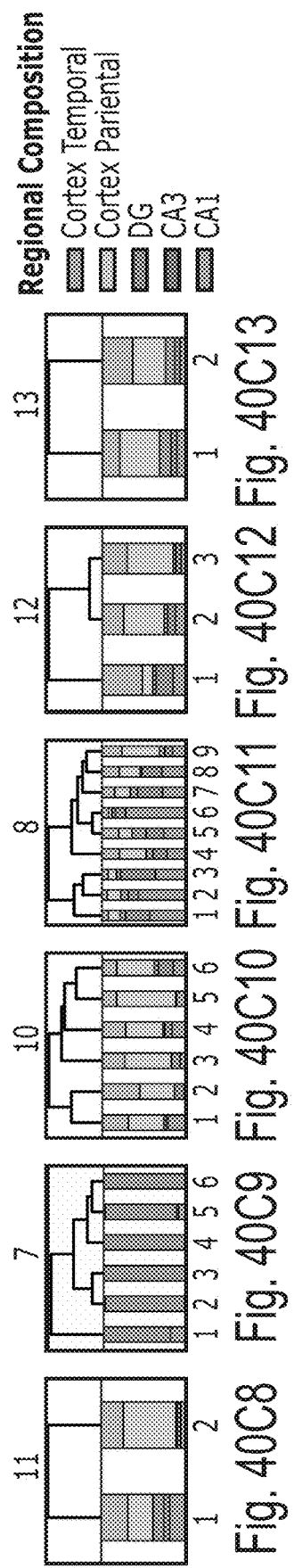

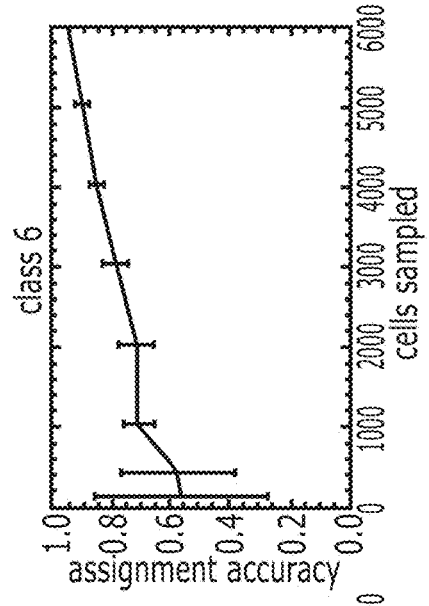
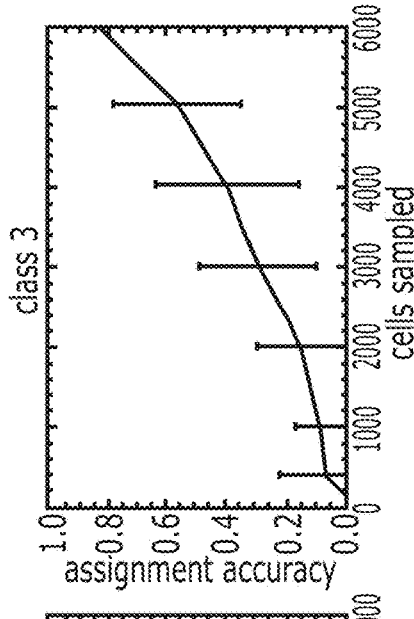
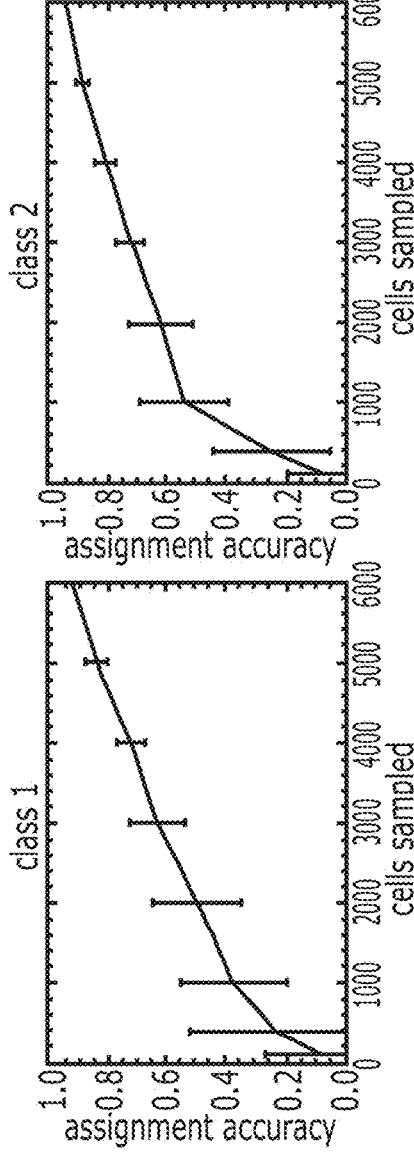
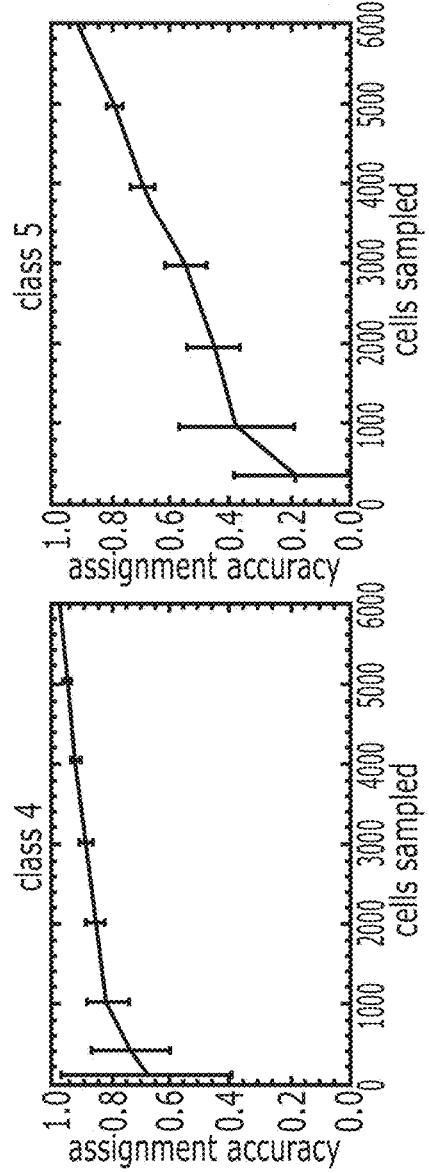
Fig. 41A, Fig. 41B, Fig. 41C, Fig. 41D, Fig. 41E, Fig. 41F

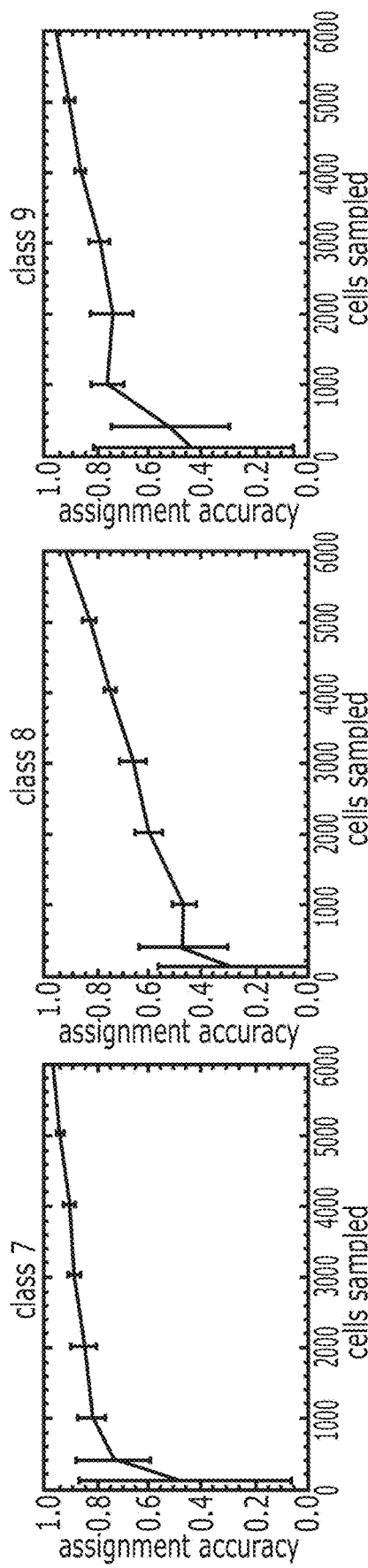
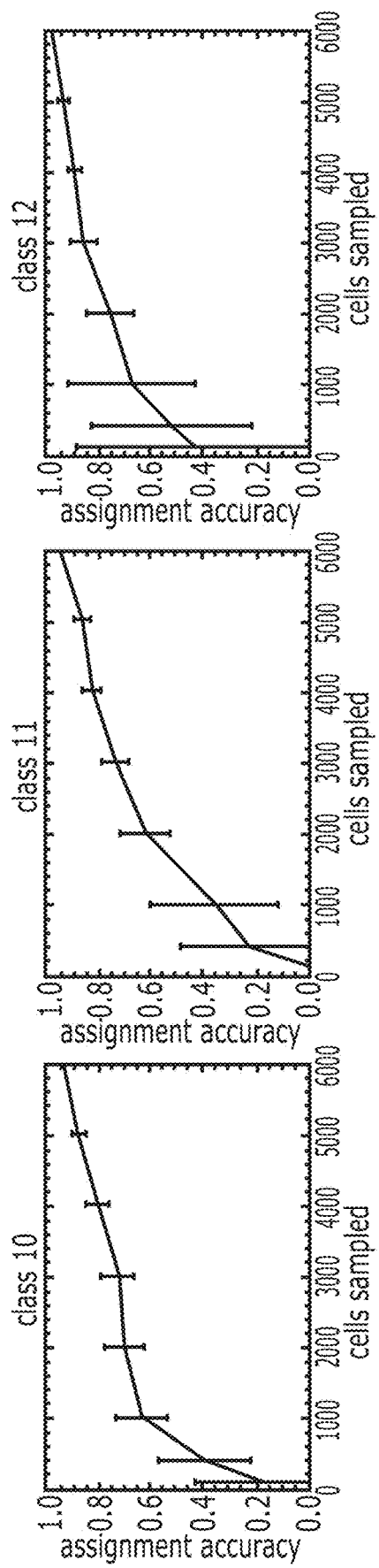
Fig. 41G
Fig. 41H
Fig. 41I
Fig. 41J
Fig. 41K
Fig. 41L

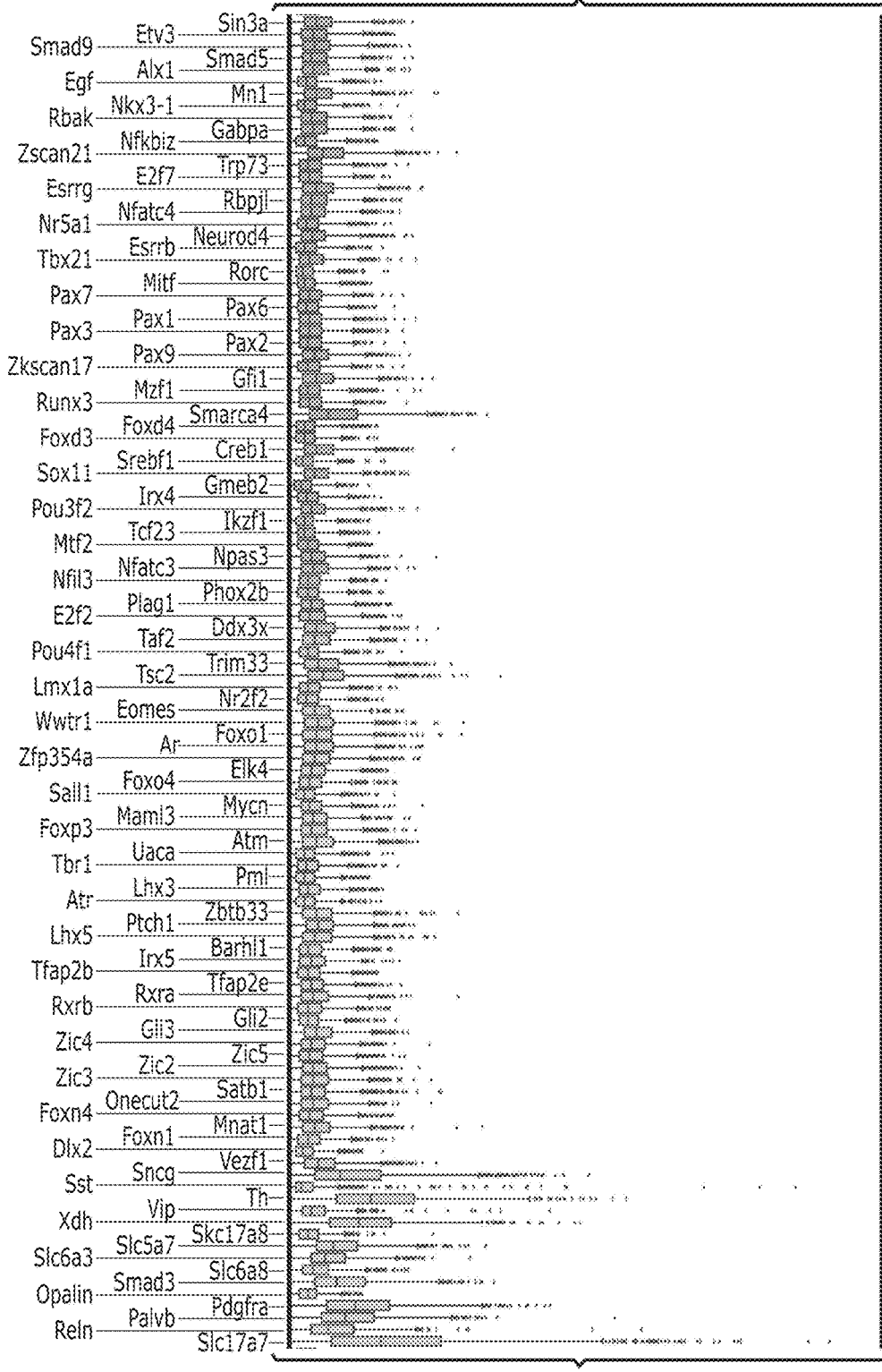

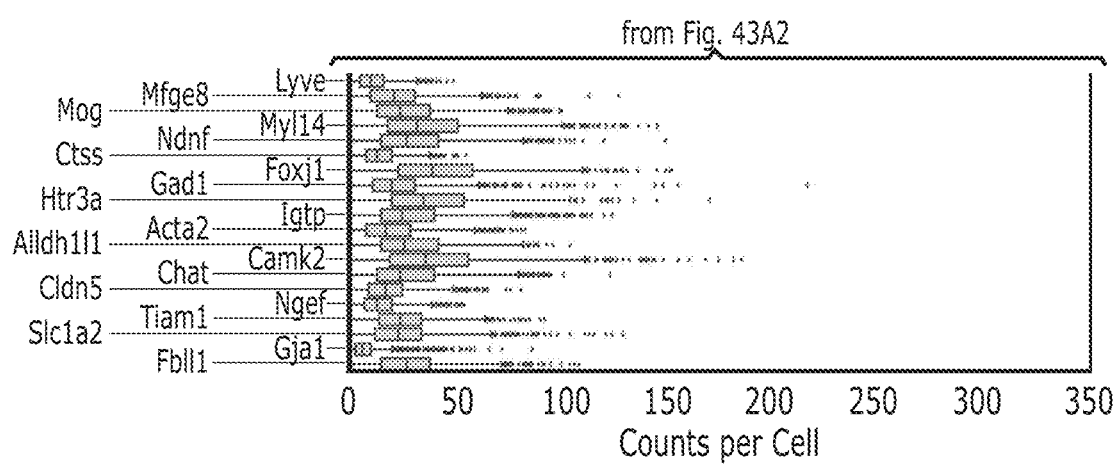
Fig. 43A3

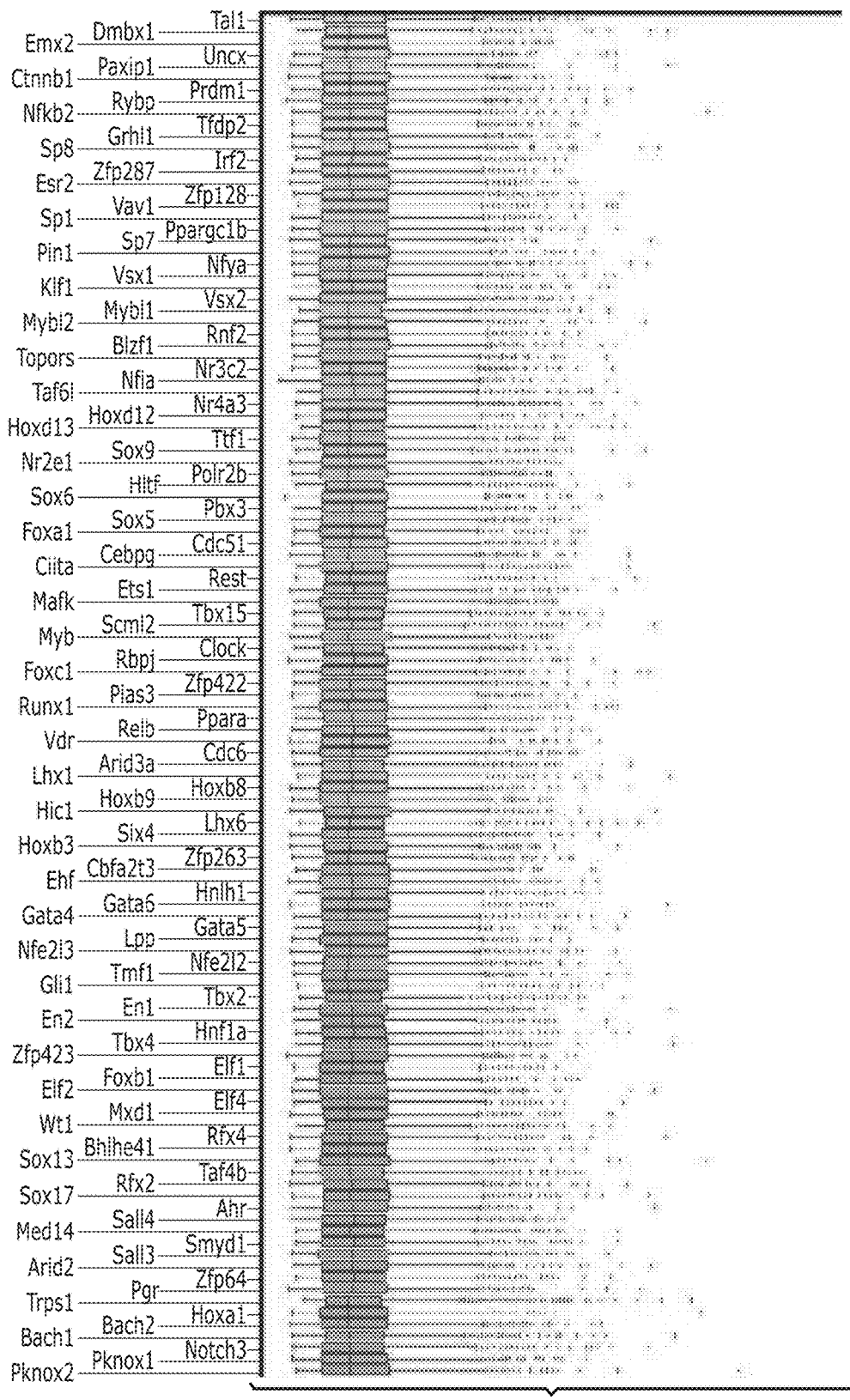
Fig. 43B1

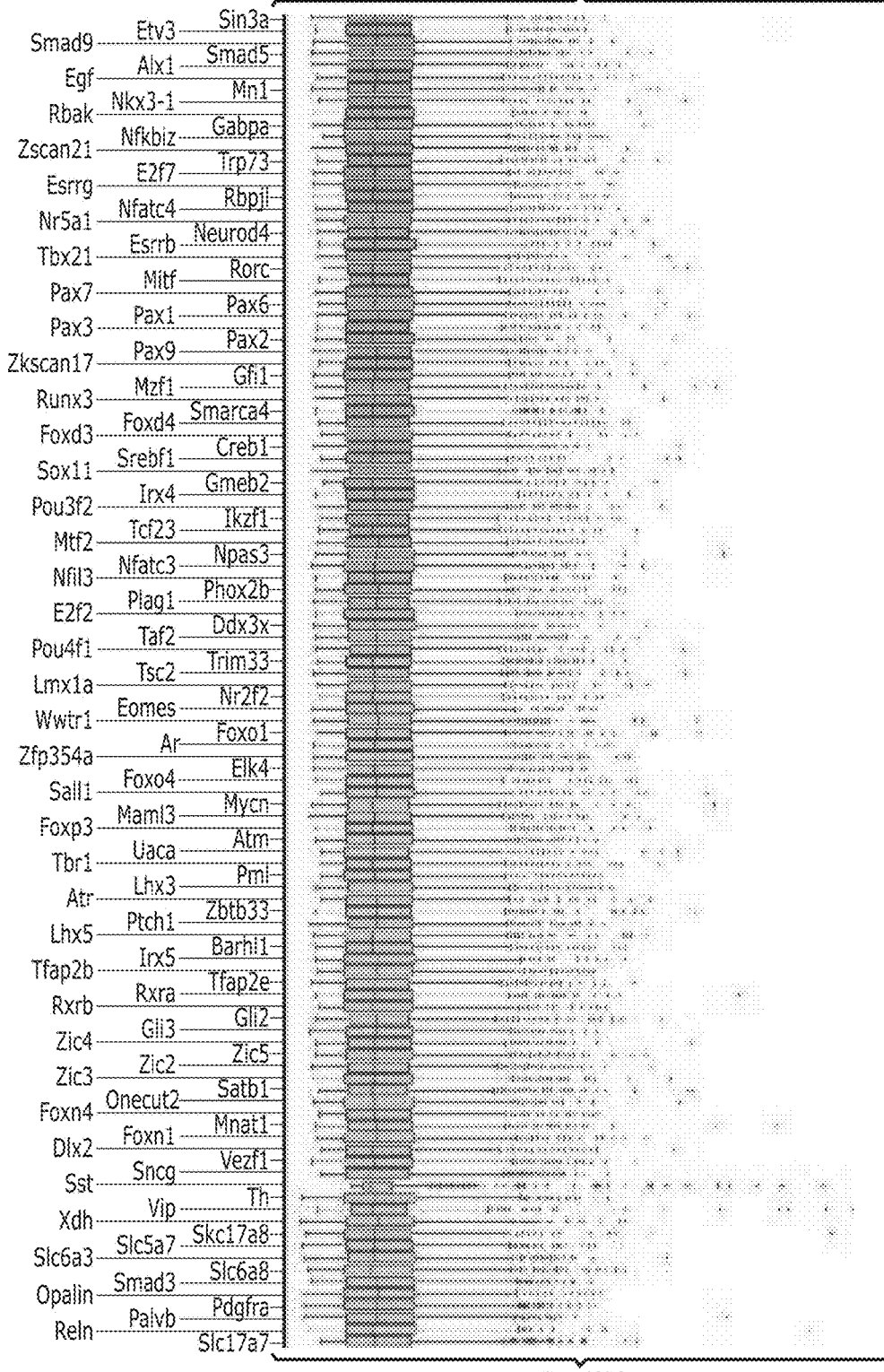
Fig. 43B2

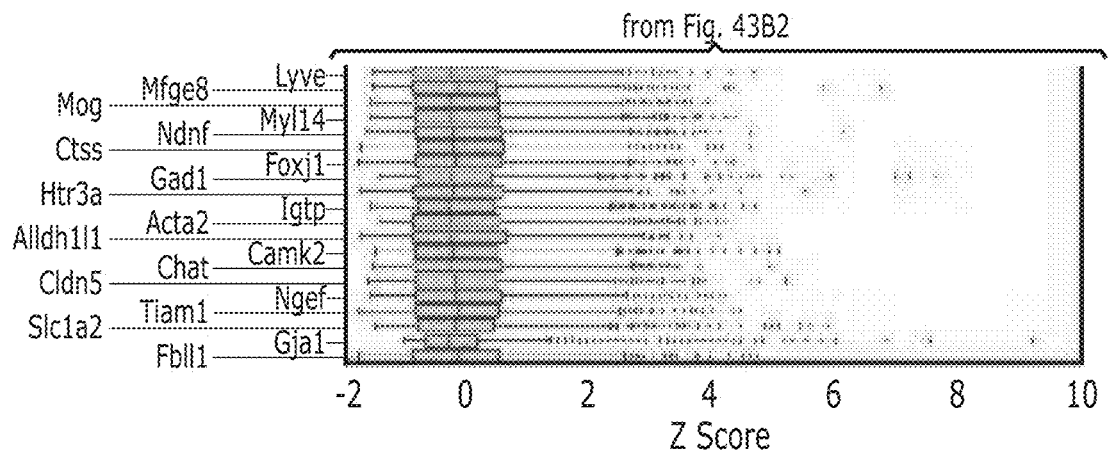
Fig. 43B3
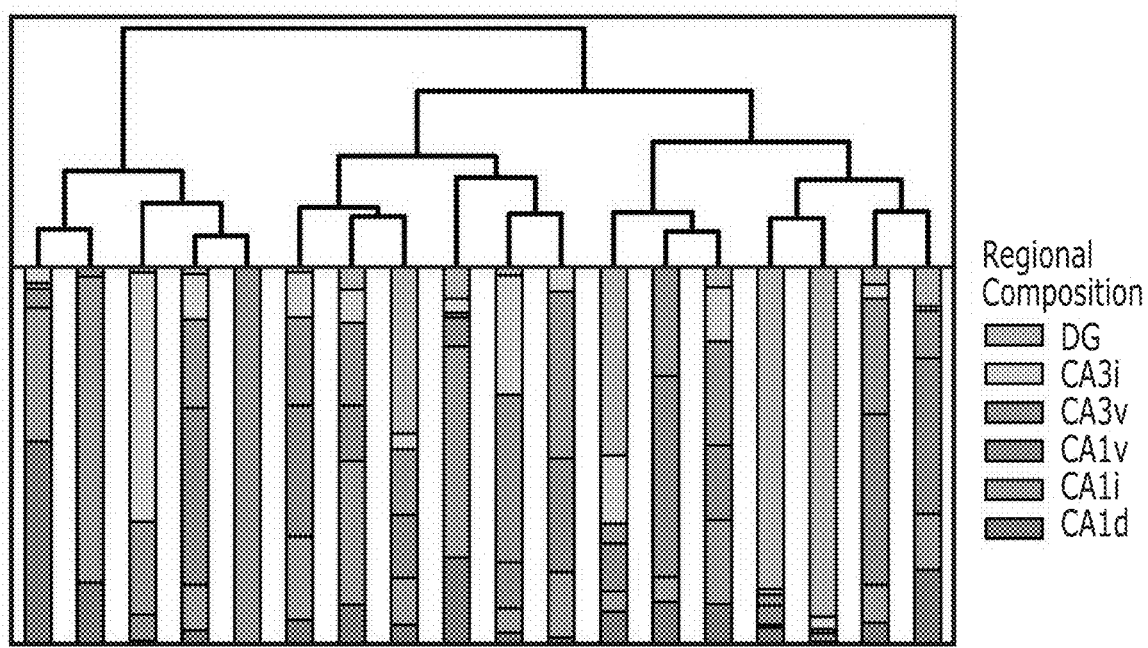
Fig. 43C

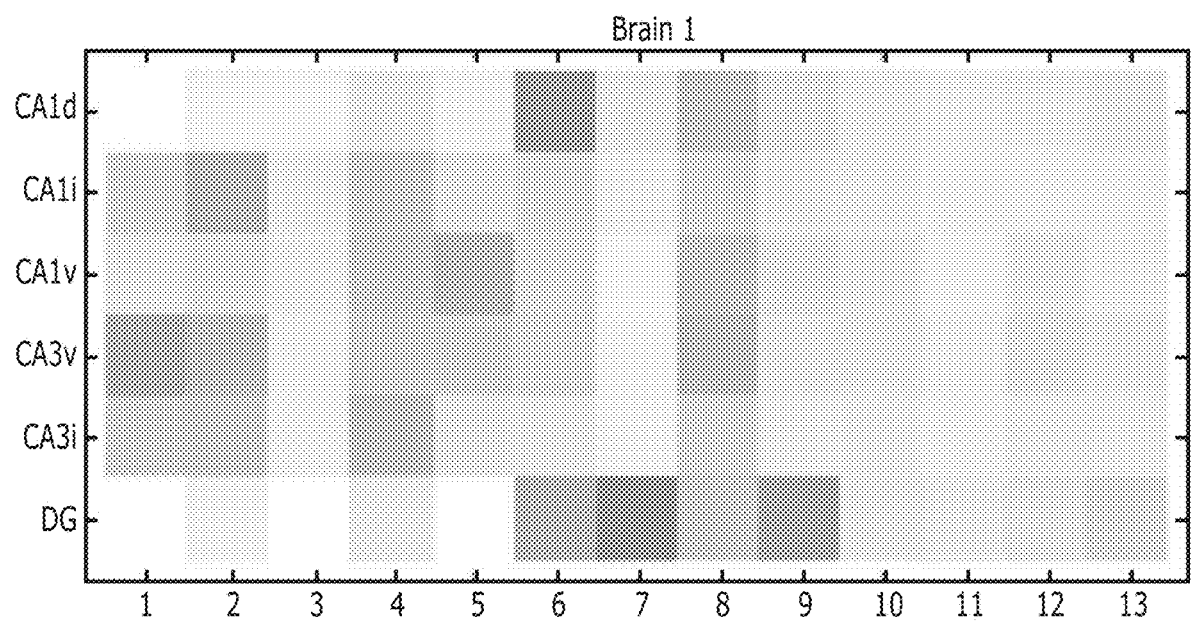
Fig. 43F1
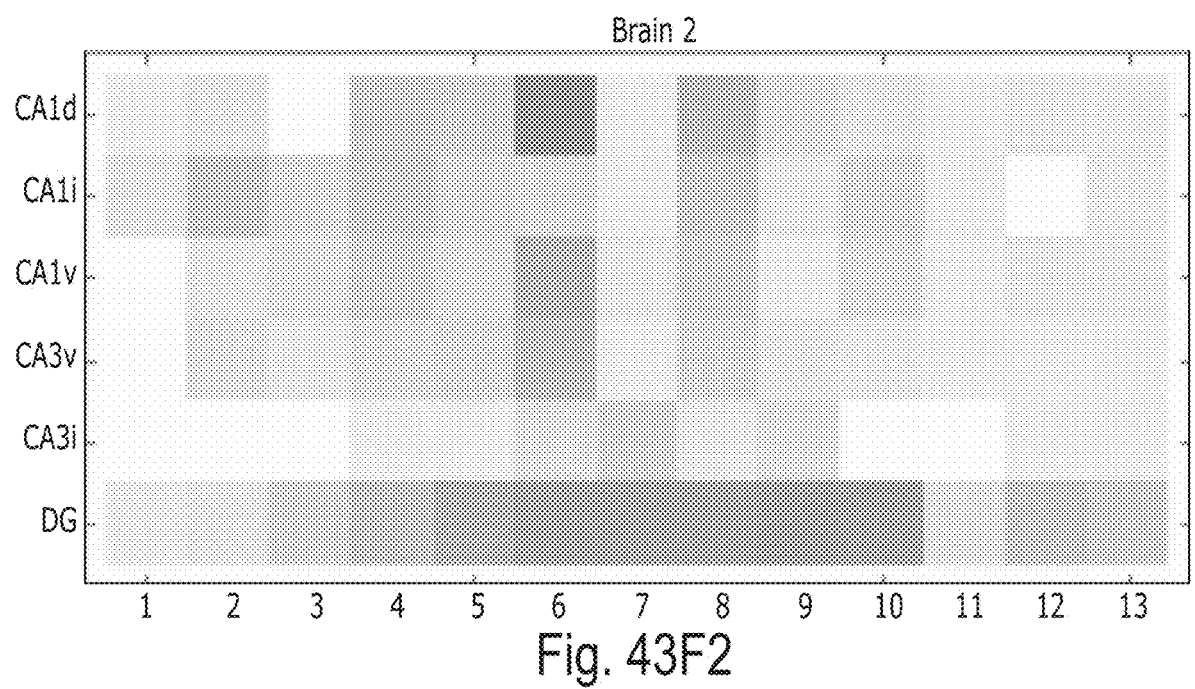
Fig. 43F2

A.
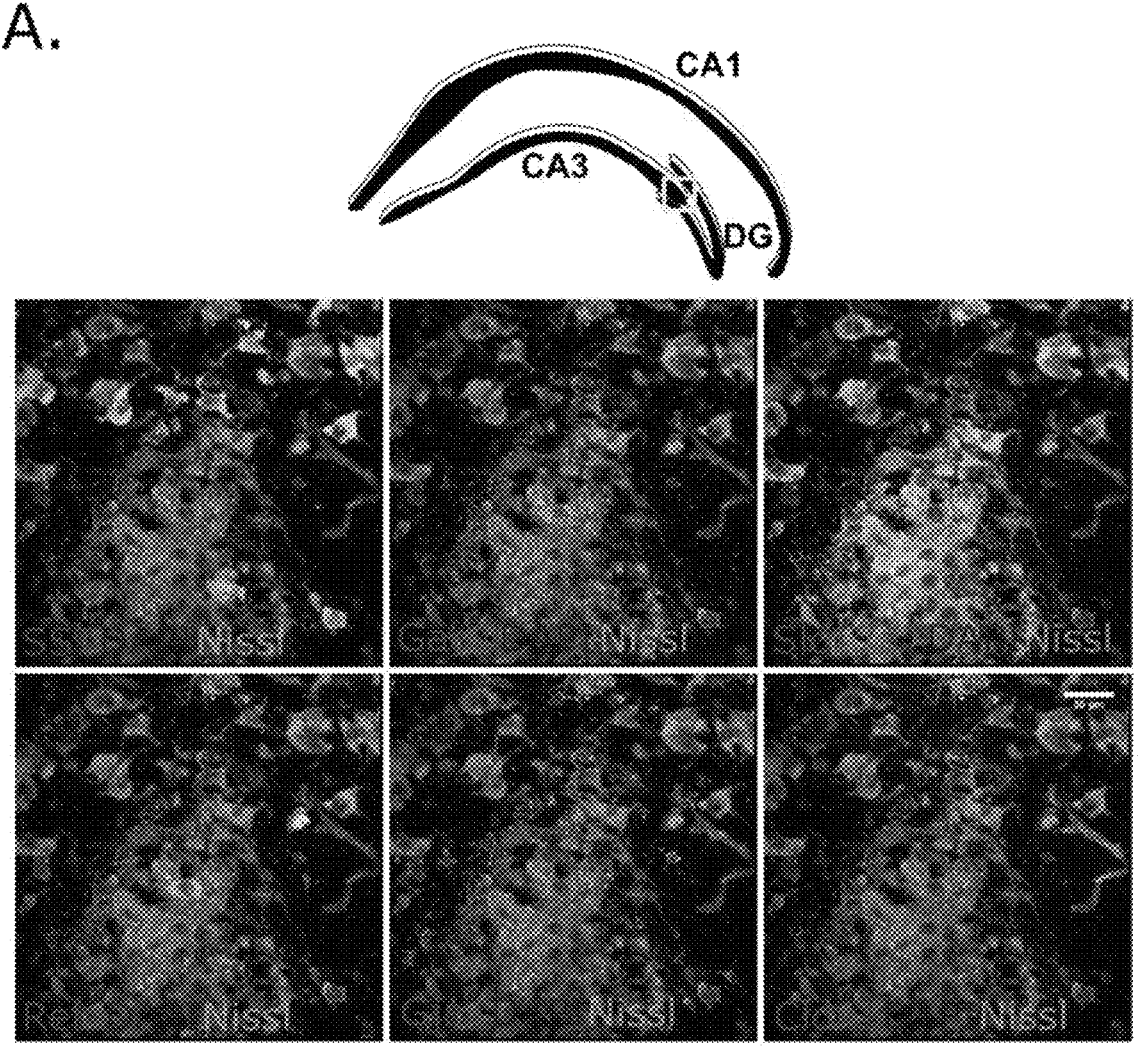
B.
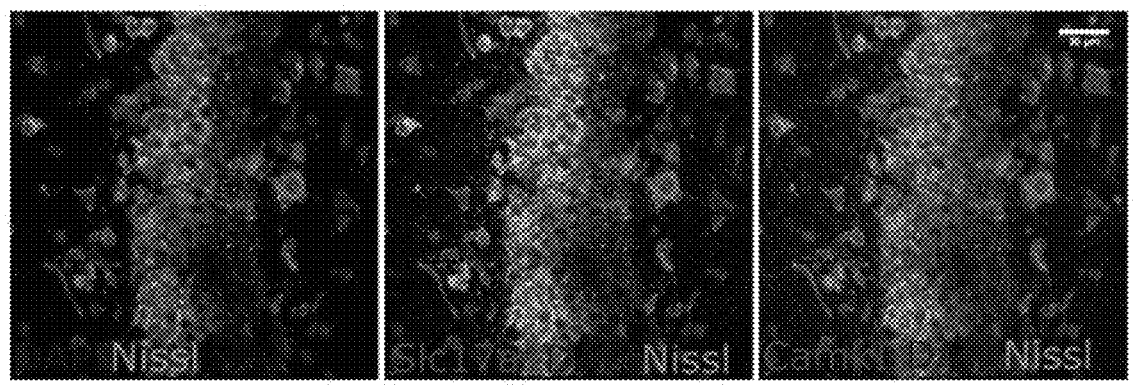
Fig. 44

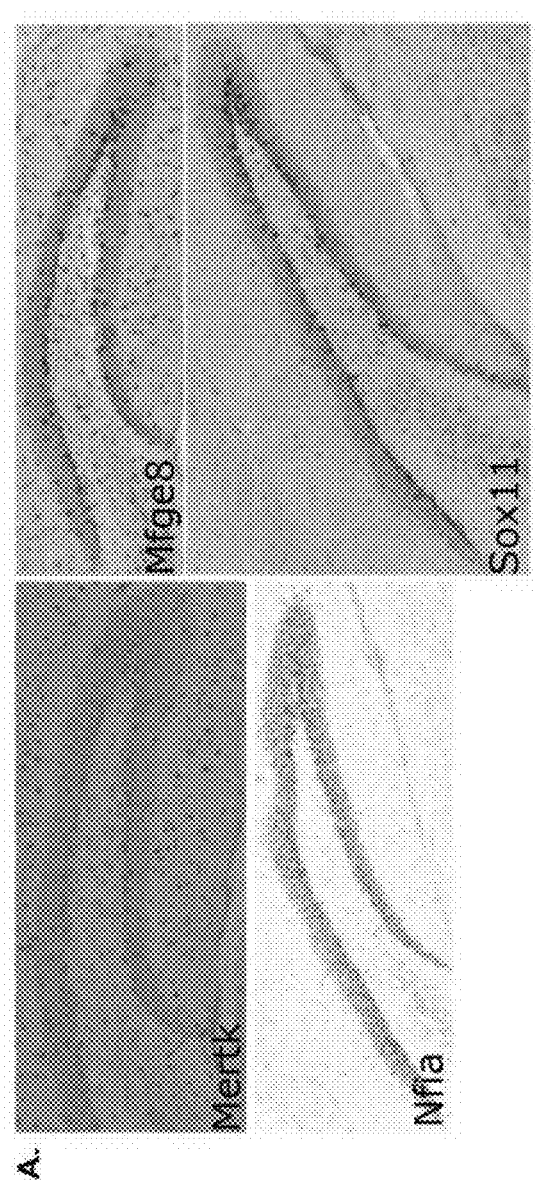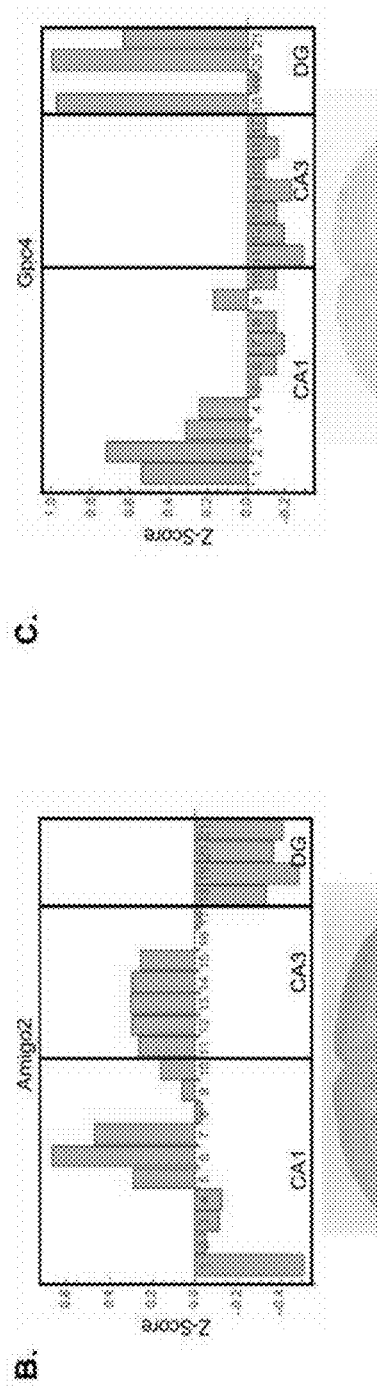
Fig. 45

ERROR CORRECTION OF MULTIPLEX IMAGING ANALYSIS BY SEQUENTIAL HYBRIDIZATION

CROSS-REFERENCE TO RELATED APPLICATIONS

This application is a continuation-in-part of U.S. patent application Ser. No. 14/435,735, filed on Apr. 14, 2015 and entitled "MULTIPLEX LABELING OF MOLECULES BY SEQUENTIAL HYBRIDIZATION BARCODING," which is a National Stage Entry of International Application No. PCT/US2014/36258 filed Apr. 30, 2014, which in turn claims priority to U.S. Provisional Application Ser. No. 61/817,651, filed Apr. 30, 2013, and 61/971,974, filed Mar. 28, 2014, each of which is hereby incorporated by reference herein in its entirety.

STATEMENT REGARDING FEDERALLY SPONSORED RESEARCH

This invention was made with government support under Grant No. HD075605 and under Grant No. OD008530 awarded by the National Institutes of Health. The government has certain rights in the invention.

FIELD OF THE INVENTION

The invention disclosed herein generally relates to sequential hybridization methods for identifying/quantitating cellular species such as nucleic acids. More specifically, disclosed herein are methods for efficient error reduction.

BACKGROUND OF THE INVENTION

Transcription profiling of cells are essential for many purposes. Microscopy imaging which can resolve multiple mRNAs in single cells can provide valuable information regarding transcript abundance and localization, which are important for understanding the molecular basis of cell identify and developing treatment for diseases. Therefore, there is a need for new and improved methods for profile transcripts in cells by, for example, microscopy imaging.

SUMMARY OF THE INVENTION

In one aspect, disclosed herein is a sequential hybridization method that comprises the steps of: identifying a plurality of target genes; and associating, via sequential hybridization of binding probes to the plurality of target genes, a first plurality of unique codes with the plurality of target genes, where each target gene in the plurality of target genes is represented by a unique code in the first plurality of unique codes, where the sequential hybridization comprises n rounds of hybridization (where n≥2). Here, each round of hybridization in n rounds of hybridization in turn comprises the steps of contacting the plurality of target genes with a plurality of binding probes, where each probe in the plurality of binding probes comprises: a binding sequence that specifically binds a target sequence in a gene in the plurality of target genes, where target genes from the plurality of target genes are spatially transfixed from each other, and where each probe is capable of emitting a detectable visual signal upon binding of the probe to a target sequence; detecting visual signals that reflect the binding between the plurality of binding probes and the plurality of target genes; and removing the visual signals, when applicable, prior to the next round of hybridization. In some embodiments, probes used in the n rounds of hybridization are capable of emitting at least F types of detectable visual signals (where F≥2 and $F^n$ is greater than the number of target genes in the plurality of target genes). In some embodiments, a unique code in the first plurality of unique codes for a target gene consists of n components. In some embodiments, each component is determined by visual signals that reflect the binding between binding probes and the target gene during one of the n rounds of hybridization. In some embodiments, the n rounds of hybridization include m error correction round (m≥1). In some embodiments, a second plurality of unique codes for the plurality of target genes is generated after the m error correction round is removed from the n rounds of hybridization. In some embodiments, each unique code in the second plurality of unique codes consists of (n−m) components and uniquely represents a target gene in the plurality of target genes.

In some embodiments, the plurality of target genes are located on immobilized nucleic acids selected from the group consisting of mRNAs, chromosomal DNAs and combinations thereof. In some embodiments, n is 4 or greater, 5 or greater, or 10 or greater. In some embodiments, the m error correction round comprises one round of the n rounds of hybridization. In some embodiments, the one round of the n rounds of hybridization is a repeat of one of the remaining one or more (n−1) rounds of the n rounds of hybridization. In some embodiments, where m≤0.5n.

In some embodiments, the at least F types of detectable visual signals comprises one selected from the group consisting of a fluorescence signal, a color signal, a red signal, a green signal, a yellow signal, a combined color signal representing two or more colors, and combinations thereof.

In some embodiments, a probe in the plurality of binding probes further comprises a signal moiety that emits a detectable visual signal upon binding of the probe to a target sequence.

In some embodiments, the signal moiety is connected to the binding sequence of the probe via a cleavable linker.

In some embodiments, each component of a n-component unique code in the first plurality of unique codes is assigned a numerical value that corresponds to one of the at least F types of detectable visual signals; and where at least one component of the n-component unique code is determined based on the numerical values of all or some of the other n−1 components. In some embodiments, the n-component unique code is determined as:

$\{j_1, j_2, \ldots (a_1{}^*j_1 + a_2{}^*j_2 \ldots + a_n{}^*j_n + C) \bmod F, \ldots, j_n\}$, where $j_1$ is a numerical value that corresponds the detectable visual signals used in the first round of hybridization, $j_2$ is a numerical value that corresponds the detectable visual signals used in the second round of hybridization, and $j_n$ is a numerical value that corresponds the detectable visual signals used in the nth round of hybridization; and where $j_1, j_2, \ldots j_n, a_1, a_2, \ldots a_n$ and n are none zero integers and C is an integer.

In some embodiments, m, n, F, i, j and k are all integers.

In one aspect disclosed herein is a hybridization method that comprises the steps of: identifying a plurality of target genes; performing sequential hybridization of binding probes to the plurality of target genes, where the sequential hybridization comprises n rounds of hybridization (where n≥2). Here, each round of hybridization in n rounds of hybridization in turn comprises: contacting the plurality of target genes with a plurality of binding probes, where each probe in the plurality of binding probes comprises: a binding sequence that specifically binds a target sequence in a gene in the plurality of target genes, where target genes from the plurality of target genes are spatially transfixed from each other, and where each probe is capable of emitting a detectable visual signal upon binding of the probe to a target sequence; detecting visual signals that reflect the binding between the plurality of binding probes and the plurality of target genes, where each target gene in the plurality of target genes is represented by visual signals that are unique for the target gene, and where probes used in the n rounds of hybridization are capable of emitting at least F types of detectable visual signals (where F≥2, and $F^n$ is greater than the number of target genes in the plurality of target genes); and removing the visual signals, when applicable, prior to the next round of hybridization; and performing serial hybridizations against one or more serial target genes, where the expression level of each serial target gene is above a predetermined threshold value, and where each serial hybridization in turn comprises: contacting the one or more serial target genes with a plurality of binding probes, where each probe in the plurality of binding probes comprises: a binding sequence that specifically binds a target sequence in a serial target gene in the one or more serial target genes, where one or more serial target genes are spatially transfixed from each other, where each probe is capable of emitting a detectable visual signal upon binding of the probe to the target sequence, and where probes binding to target sequences in the same serial target gene emit the same detectable visual signals; and detecting visual signals that reflect the binding between the plurality of binding probes and the one or more serial target gene.

In some embodiments, the n rounds of hybridization generate a first plurality of unique codes, where each target gene in the plurality of target genes is represented by a unique code in the first plurality of unique codes.

In some embodiments, where a unique code in the first plurality of unique codes for a target gene consists of n components, and where each component is determined by visual signals that reflect the binding between binding probes and the target gene during one of the n rounds of hybridization.

In some embodiments, the n rounds of hybridization include m error correction round (m≥1), where a second plurality of unique codes for the plurality of target genes is generated after the m error correction round is removed from the n rounds of hybridization, and where each unique code in the second plurality of unique codes consists of (n−m) components and uniquely represents a target gene in the plurality of target genes.

In some embodiments, the method of hybridization further comprises the step of: identifying the one or more serial target genes based on expression levels of candidate target genes.

In some embodiments, the plurality of target genes are located on immobilized nucleic acids selected from the group consisting of mRNAs, chromosomal DNAs and combinations thereof.

In some embodiments, the one or more serial target genes are located on immobilized nucleic acids selected from the group consisting of mRNAs, chromosomal DNAs and combinations thereof.

In some embodiments, each unique code in the first plurality of unique codes consists of n component, where each component of a n-component unique code in the first plurality of unique codes is assigned a numerical value that corresponds to one of the at least F types of detectable visual signals; and where at least one component of the n-component unique code is determined based on the numerical values of all or some of the other n−1 components. In some embodiments, the n-component unique code is determined as:

$\{j_1, j_2, \ldots (a_1^*j_1+a_2^*j_2 \ldots +a_n^*j_n+C) \bmod F, \ldots, j_n\}$, where $j_1$ is a numerical value that corresponds the detectable visual signals used in the first round of hybridization, $j_2$ is a numerical value that corresponds the detectable visual signals used in the second round of hybridization, and $j_n$ is a numerical value that corresponds the detectable visual signals used in the nth round of hybridization; and where $j_1, j_2, \ldots j_n, a_1, a_2, \ldots a_n$ are none zero integers and C is an integer.

In one aspect, disclosed herein is a non-transitory computer-readable medium containing instructions that, when executed by a computer processor, cause the computer processor to: associate, via sequential hybridization of binding probes to a plurality of target genes, a first plurality of unique codes with the plurality of target genes, where each target gene in the plurality of target genes is represented by a unique code in the first plurality of unique codes, where the sequential hybridization comprises n rounds of hybridization (where n≥2). Here each round of hybridization in n rounds of hybridization in turn comprises: contacting the plurality of target genes with a plurality of binding probes, where each probe in the plurality of binding probes comprises: a binding sequence that specifically binds a target sequence in a gene in the plurality of target genes, where target genes from the plurality of target genes are spatially transfixed from each other, and where each probe is capable of emitting a detectable visual signal upon binding of the probe to a target sequence; detecting visual signals that reflect the binding between the plurality of binding probes and the plurality of target genes; and removing the visual signals, when applicable, prior to the next round of hybridization.

In some embodiments, probes used in the n rounds of hybridization are capable of emitting at least F types of detectable visual signals (where F≥2 and $F^n$ is greater than the number of target genes in the plurality of target genes). In some embodiments, a unique code in the first plurality of unique codes for a target gene consists of n components. In some embodiments, each component is determined by visual signals that reflect the binding between binding probes and the target gene during one of the n rounds of hybridization. In some embodiments, the n rounds of hybridization include m error correction round (m≥1). In some embodiments, a second plurality of unique codes for the plurality of target genes is generated after the m error correction round is removed from the n rounds of hybridization. In some embodiments, each unique code in the second plurality of unique codes consists of (n−m) components and uniquely represents a target gene in the plurality of target genes.

In one aspect, disclosed herein is a non-transitory computer-readable medium containing instructions that, when executed by a computer processor, cause the computer processor to: perform sequential hybridization of binding probes to a plurality of target genes, where the sequential hybridization comprises n rounds of hybridization (where n≥2).

Here, each round of hybridization in n rounds of hybridization comprises: contacting the plurality of target genes with a plurality of binding probes, where each probe in the plurality of binding probes comprises: a binding sequence that specifically binds a target sequence in a gene in the plurality of target genes, where target genes from the plurality of target genes are spatially transfixed from each other, and where each probe is capable of emitting a detectable visual signal upon binding of the probe to a target sequence; detecting visual signals that reflect the binding between the plurality of binding probes and the plurality of target genes, where each target gene in the plurality of target genes is represented by visual signals that are unique for the target gene, and where probes used in the n rounds of hybridization are capable of emitting at least F types of detectable visual signals (where $F \geq 2$, and $F^n$ is greater than the number of target genes in the plurality of target genes); and removing the visual signals, when applicable, prior to the next round of hybridization; and perform serial hybridizations against one or more serial target genes, where the expression level of each serial target gene is above a predetermined threshold value, where each serial hybridization comprises: contacting the one or more serial target genes with a plurality of binding probes, where each probe in the plurality of binding probes comprises: a binding sequence that specifically binds a target sequence in a serial target gene in the one or more serial target genes, where one or more serial target genes are spatially transfixed from each other, where each probe is capable of emitting a detectable visual signal upon binding of the probe to the target sequence, and where probes binding to target sequences in the same serial target gene emit the same detectable visual signals; and detecting visual signals that reflect the binding between the plurality of binding probes and the one or more serial target gene.

In any of the embodiments disclosed herein, m, n, F, i, j and k are all integers. Embodiments disclosed herein can be applied individually or in combination in any aspect disclosed herein.

Definitions

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, a genetically-engineered animal, and/or a clone.

Approximately: As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). In some embodiments, use of the term "about" in reference to dosages means±5 mg/kg/day.

Homology: "Homology" or "identity" or "similarity" refers to sequence similarity between two nucleic acid molecules. Homology and identity can each be determined by comparing a position in each sequence which can be aligned for purposes of comparison. When an equivalent position in the compared sequences is occupied by the same base, then the molecules are identical at that position; when the equivalent site occupied by the same or a similar nucleic acid residue (e.g., similar in steric and/or electronic nature), then the molecules can be referred to as homologous (similar) at that position. Expression as a percentage of homology/similarity or identity refers to a function of the number of identical or similar nucleic acids at positions shared by the compared sequences. A sequence which is "unrelated" or "non-homologous" shares less than 40% identity, less than 35% identity, less than 30% identity, or less than 25% identity with a sequence described herein. In comparing two sequences, the absence of residues (amino acids or nucleic acids) or presence of extra residues also decreases the identity and homology/similarity.

In some embodiments, the term "homology" describes a mathematically based comparison of sequence similarities which is used to identify genes with similar functions or motifs. The nucleic acid sequences described herein can be used as a "query sequence" to perform a search against public databases, for example, to identify other family members, related sequences or homologs. In some embodiments, such searches can be performed using the NBLAST and XBLAST programs (version 2.0) of Altschul, et al. (1990) J. Mol. Biol. 215:403-10. In some embodiments, BLAST nucleotide searches can be performed with the NBLAST program, score=100, word length=12 to obtain nucleotide sequences homologous to nucleic acid molecules of the invention. In some embodiments, to obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and BLAST) can be used (See www.ncbi.nlm.nih.gov).

Identity: As used herein, "identity" means the percentage of identical nucleotide residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990) and Altschul et al. Nuc. Acids Res. 25: 3389-3402 (1997)). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990). The well-known Smith Waterman algorithm can also be used to determine identity.

In vitro: As used herein, the term "in vitro" refers to events that occur in an artificial environment, e.g., in a test tube or reaction vessel, in cell culture, etc., rather than within an organism (e.g., animal, plant, and/or microbe).

In vivo: As used herein, the term "in vivo" refers to events that occur within an organism (e.g., animal, plant, and/or microbe).

Oligonucleotide: the term "oligonucleotide" refers to a polymer or oligomer of nucleotide monomers, containing any combination of nucleobases, modified nucleobases, sugars, modified sugars, phosphate bridges, or modified bridges.

Oligonucleotides of the present invention can be of various lengths. In particular embodiments, oligonucleotides can range from about 2 to about 200 nucleotides in length. In various related embodiments, oligonucleotides, single-stranded, double-stranded, and triple-stranded, can range in length from about 4 to about 10 nucleotides, from about 10 to about 50 nucleotides, from about 20 to about 50 nucleotides, from about 15 to about 30 nucleotides, from about 20 to about 30 nucleotides in length. In some embodiments, the oligonucleotide is from about 9 to about 39 nucleotides in length. In some embodiments, the oligonucleotide is at least 4 nucleotides in length. In some embodiments, the oligonucleotide is at least 5 nucleotides in length. In some embodiments, the oligonucleotide is at least 6 nucleotides in length. In some embodiments, the oligonucleotide is at least 7 nucleotides in length. In some embodiments, the oligonucleotide is at least 8 nucleotides in length. In some embodiments, the oligonucleotide is at least 9 nucleotides in length. In some embodiments, the oligonucleotide is at least 10 nucleotides in length. In some embodiments, the oligonucleotide is at least 11 nucleotides in length. In some embodiments, the oligonucleotide is at least 12 nucleotides in length. In some embodiments, the oligonucleotide is at least 15 nucleotides in length. In some embodiments, the oligonucleotide is at least 20 nucleotides in length. In some embodiments, the oligonucleotide is at least 25 nucleotides in length. In some embodiments, the oligonucleotide is at least 30 nucleotides in length. In some embodiments, the oligonucleotide is a duplex of complementary strands of at least 18 nucleotides in length. In some embodiments, the oligonucleotide is a duplex of complementary strands of at least 21 nucleotides in length.

Predetermined: By predetermined is meant deliberately selected, for example as opposed to randomly occurring or achieved. A composition that may contain certain individual oligonucleotides because they happen to have been generated through a process that cannot be controlled to intentionally generate the particular oligonucleotides is not a "predetermined" composition. In some embodiments, a predetermined composition is one that can be intentionally reproduced (e.g., through repetition of a controlled process).

Sample: As used herein, the term "sample" refers to a biological sample obtained or derived from a source of interest, as described herein. In some embodiments, a source of interest comprises an organism, such as an animal or human. In some embodiments, a biological sample comprises biological tissue or fluid. In some embodiments, a biological sample is or comprises bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Subject: As used herein, the term "subject" or "test subject" refers to any organism to which a provided compound or composition is administered in accordance with the present invention e.g., for experimental, diagnostic, prophylactic, and/or therapeutic purposes. Typical subjects include animals (e.g., mammals such as mice, rats, rabbits, non-human primates, and humans; insects; worms; etc.) and plants. In some embodiments, a subject may be suffering from, and/or susceptible to a disease, disorder, and/or condition.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and/or chemical phenomena.

Suffering from: An individual who is "suffering from" a disease, disorder, and/or condition has been diagnosed with and/or displays one or more symptoms of a disease, disorder, and/or condition.

Susceptible to: An individual who is "susceptible to" a disease, disorder, and/or condition is one who has a higher risk of developing the disease, disorder, and/or condition than does a member of the general public. In some embodiments, an individual who is susceptible to a disease, disorder and/or condition may not have been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Treat: As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example for the purpose of decreasing the risk of developing pathology associated with the disease, disorder, and/or condition.

Wild-type: As used herein, the term "wild-type" has its art-understood meaning that refers to an entity having a structure and/or activity as found in nature in a "normal" (as contrasted with mutant, diseased, altered, etc.) state or context. Those of ordinary skill in the art will appreciate that wild type genes and polypeptides often exist in multiple different forms (e.g., alleles).

BRIEF DESCRIPTION OF THE DRAWINGS

FIGS. 33A through 33P depict an example embodiment, illustrating that subregions of the hippocampus are composed of distinct compositions of cell classes based on the first 125 gene experiment. Upper right panel. Cartoon of hippocampus with imaged regions labeled. Color key corresponds to the classes in FIG. 36b. FIGS. 33A-D). These images are regions from the CA1d. Astrocytes (Astro) are marked in image 33A) and a microglia cell (µGlia) is marked in image 33B). Moving along the hippocampus from CA1 dorsal to ventral, cell classes transition from a homogenous dorsal population (33C to 33D) to a mixed population in the CA1 intermediate (33E-33F) to regions of even larger cellular diversity in the CA1 ventral region (33G-I). The dotted line in 33D) marks the transition point of the CA1d to the CA1i. 33E) shows two laterally segregated cell classes (marked by a dotted line) in the CA1i along with cholinergic interneurons (Int) on the interior surface of the CA1i. The ventral (33J-33K) and intermediate CA3 (33L-33M) have similar cell classes compositions to the CA1v and CA1i. The two last regions (33O-33P) of the dorsal CA3 shows distinct cell classes compositions that are relatively homogeneous within a field but are different than other fields of CA3. The cell class composition of field 33P is similar to that of the CA1d, but these cluster 6 cells are grouped into a distinct subcluster.

FIGS. 40A through 40F depict an example embodiment, showing gene expression patterns and clustering of the 125-gene dataset (related to FIG. 31). 40A). Overview of 125 gene expression. Plots show the distribution of each transcript in all 14,908 imaged cells. Note the last 25 genes have higher expression and were imaged with serial hybridization. 40B). Violin plots of Z-score distribution for 125 genes. 40C1-40C13). Subcluster hierarchy of each of the 13 clusters identified in FIG. 31B. 40D). PCA eigenvalue analysis of the cell-to-cell correlation matrix. First 125 PC and their eigenvalues are shown. As observed in FIG. 31, the first 10 PCs explain 59.5% of the variation in the data, while the remaining 115 PCs are needed to explain remaining data. Reflecting this, the eigenvalues of the first 10 components are high, while the remaining eigenvalues are uniform. 40E). Correlation between gene expression and spatial localization. Each dot represents a pair of cell classes and their correlations in gene expression space (x) and spatial localization patterns (y) (N=153 pairwise correlations between classes, R=0.67). Classes that are similar in expression have similar localization patterns. 40F). PCA decomposition separates cells into coherent clusters corresponding to cell classes. Cells are colored according to the clusters displayed in the dendrogram.

FIGS. 41A through 41M depict an example embodiment, showing robustness of cell classes to downsampling of cells (related to FIG. 31). To measure how well cluster assignments perform with a limited number of cells, a random forest model was trained on the cell-to-cell correlation matrix of the 6872 cells in the center field of view. The robustness of the clusters was calculated by applying this model to classify the remaining cells and determining the percent accuracy of correct assignment to the clusters presented in FIG. 31b. While some classes can be assigned accurately even with a small number of cells as the initial training set, several classes require large number of cells to accurately assign (n=10 bootstrap replicates, S.E.)

FIGS. 43A1 through 43G depict an example embodiment, showing gene expression patterns and clustering of the 249-gene dataset (related to FIG. 35). FIGS. 43A1 through 43A3). Overview of 249-gene expression. Plots show the distribution of each transcript in all 2050 imaged cells in the hippocampus. Note the last 35 genes have higher expression and were imaged with serial hybridization. FIGS. 43B1 through 43B3). Violin plots of Z-score distribution for 249 genes. 43C). Dendogram with regional localization of the 18 cell clusters for the 249-gene experiment. 43D). Correlation of seqFISH counts to smHCR counts for the 249-gene experiment. The 2D density histogram shows a high density of points around the regression line that fall off towards the edges of the distribution. 43E). Cell-to-cell correlation for all 2050 cells in the 249-gene dataset. 43F). Heat map of the percentage of each cell class in each region of the hippocampus for both the 125-gene experiments. These heat maps show that in both 125-gene experiments the same cell classes are used in roughly the same proportions in each subregion. 43G). Heat map of the percentage of each cell class in each region of the hippocampus for the 249-gene experiment. The same patterns are seen as the 125 gene experiment (i.e., different regions use different cell classes in varying amounts).

FIG. 44 depicts an example embodiment, showing marker genes expression in the hippocampus (related to FIG. 35). A). The top panel outlines the region of the hippocampus being shown in a yellow box. The images show the raw gene expression patterns seen using smHCR in our data at the dorsal most tip of the CA3 for a representative set of cell identity markers used in the 249 gene experiment. The transcript expression profile is shown in red, Nissl staining is shown in green, and DAPI staining is shown in blue. Each image shown is the full field of view and a maximum intensity projection over 15 um. B). Set of images showing the distinction between the GCL and SGZ. The GCL shows a high level of Nissl staining and expression of neuronal genes such as slc17a7 and camkII. The SGZ shows an absence of Nissl staining and terminal neuron marker genes. The transcript expression profile is shown in red, Nissl staining is shown in green, and DAPI staining is shown in blue. Each image shown is the full field of view (216 um×216 um) and a maximum intensity projection over 15 um.

FIG. 45 depicts an example embodiment, showing comparison of SeqFISH expression data to Allen Brain Atlas expression data (related to FIG. 36). A). ISH data from the Allen Brain Atlas for genes seen to be enriched in the SGZ in the 125 and 249 gene seqFISH experiments. In the 125 gene experiment, mertk and mfge8 were found to be enriched in the SGZ. In the 249 gene experiment, nfia and sox11 were seen to be enriched in the SGZ. ABA ISH data shows similar patterns to those observed with seqFISH for the SGZ. B-C). Comparison of averaged z-score values per cell from seqFISH to ABA data across hippocampus. B). Amigo2 Z-score profile found across the different fields of the hippocampus using seqFISH is shown on top and the ABA ISH image for Amigo2 is shown on the bottom. C). Gpc4 Z-score profile found across the different fields of the hippocampus using seqFISH is shown on top and ABA ISH image for Gpc4 is shown on the bottom.

DETAILED DESCRIPTION

Among other things, the present invention provides new methods, compositions and/or kits for profiling nucleic acids (e.g., transcripts and/or DNA loci) in cells.

In some embodiments, the present invention provides methods for profiling nucleic acids (e.g., transcripts and/or DNA loci) in cells. In some embodiments, provide methods profile multiple targets in single cells. Provided methods can, among other things, profile a large number of targets (transcripts, DNA loci or combinations thereof), with a limited number of detectable labels through sequential barcoding.

Figure 1:
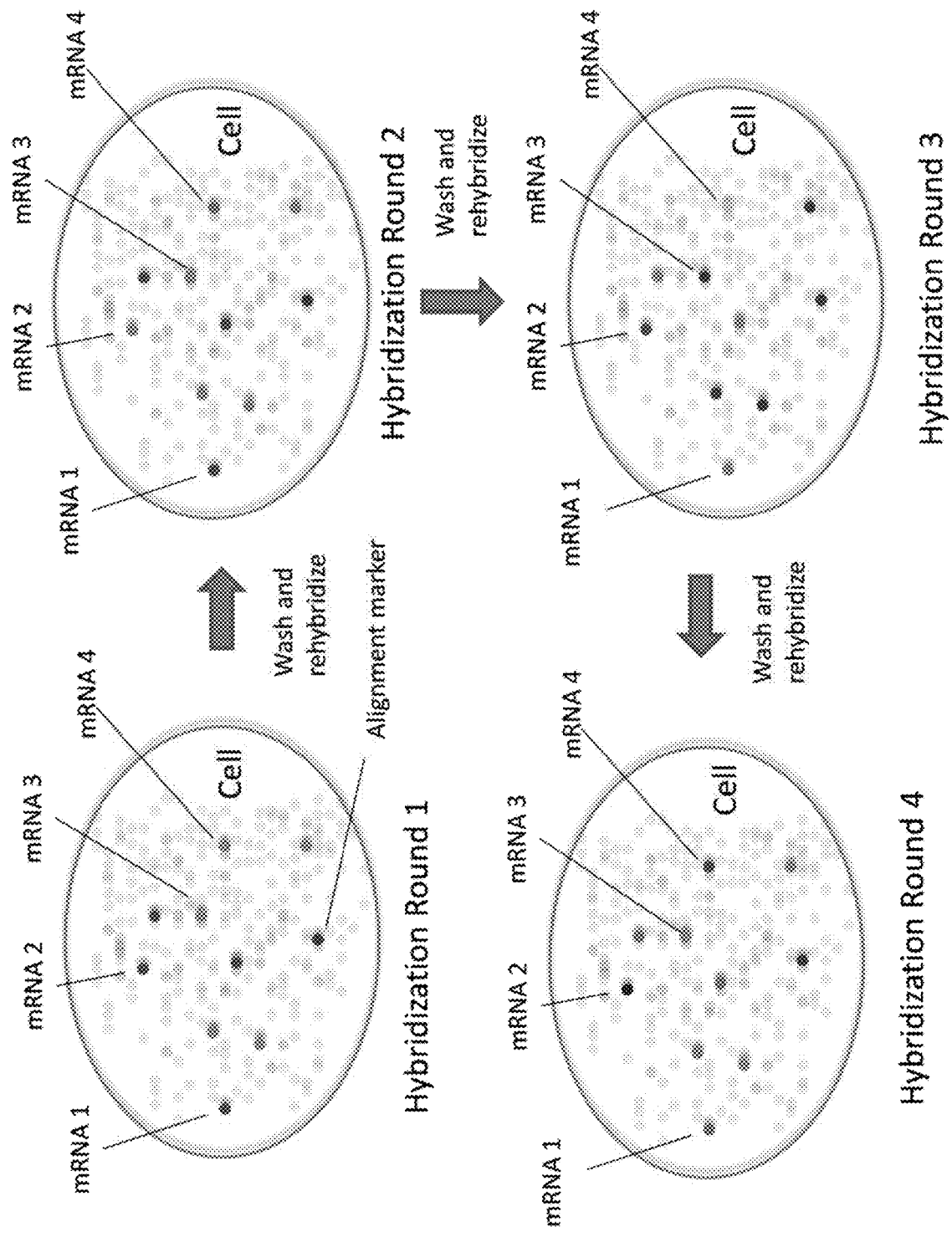
FIG. 1. Methodologies provided by the present disclosure are represented in FIG. 1.

FIG. 1 depicts methodologies in accordance with the present invention. As depicted, the present invention provides methodologies in which multiple rounds of hybridization (contacting steps) with labeled probes profiles nucleic acids (e.g., mRNAs) present in cells. Specifically, as depicted in FIG. 1, sets of probes that hybridize with nucleic acid targets in cells are provided, wherein probes (i.e., detectably labeled oligonucleotides that hybridize with different targets) are labeled within a single set and, furthermore, at least one probe is differently labeled in different sets.

In some embodiments, the present invention (e.g., as represented in FIG. 1), provides methods comprising steps of:

(a) performing a first contacting step that involves contacting a cell comprising a plurality of transcripts and DNA loci with a first plurality of detectably labeled oligonucleotides, each of which targets a transcript or DNA locus and is labeled with a detectable moiety, so that the composition comprises at least:

(i) a first oligonucleotide targeting a first transcript or DNA locus and labeled with a first detectable moiety; and (ii) a second oligonucleotide targeting a second transcript or DNA locus and labeled with a second detectable moiety;

(b) imaging the cell after the first contacting step so that hybridization by oligonucleotides of the first plurality with their targets is detected;

(c) performing a second contacting step that involves contacting the cell with a second plurality of detectably labeled oligonucleotides, which second plurality includes oligonucleotides targeting overlapping transcripts and/or DNA loci that are targeted by the first plurality, so that the second plurality comprises at least:

(i) a third oligonucleotide, optionally identical in sequence to the first oligonucleotide, targeting the first transcript or DNA locus; and (ii) a fourth oligonucleotide, optionally identical in sequence to the second oligonucleotide, targeting the second transcript or DNA locus, wherein the second plurality differs from the first plurality in that at least one of the oligonucleotides present in the second plurality is labeled with a different detectable moiety than the corresponding oligonucleotide targeting the same transcript or DNA locus in the first plurality, so that, in the second plurality:

(iii) the third oligonucleotide is labeled with the first detectable moiety, the second detectable moiety or a third detectable moiety; and (iv) the fourth oligonucleotide is labeled with the first detectable moiety, the second detectable moiety, the third detectable moiety, or a fourth detectable moiety, wherein either the third oligonucleotide is labeled with a different detectable moiety than was the first oligonucleotide, or the fourth oligonucleotide is labeled with a different detectable moiety than was the second oligonucleotide, or both;

(d) imaging the cell after the second contacting step so that hybridization by oligonucleotides of the second plurality with their targets is detected; and (e) optionally repeating the contacting and imaging steps, each time with a new plurality of detectably labeled oligonucleotides comprising oligonucleotides that target overlapping transcripts or DNA loci targeted by the first and second pluralities, wherein each utilized plurality differs from each other utilized plurality, due to at least one difference in detectable moiety labeling of oligonucleotides targeting the same transcript or DNA locus.

As used herein, a detectably labeled oligonucleotide is labeled with a detectable moiety. In some embodiments, a detectably labeled oligonucleotide comprises one detectable moiety. In some embodiments, a detectably labeled oligonucleotide comprises two or more detectable moieties. In some embodiments, a detectably labeled oligonucleotide has one detectable moiety. In some embodiments, a detectably labeled oligonucleotide has two or more detectable moiety.

In some embodiments, a detectable moiety is or comprises a fluorophore. Exemplary detectably labeled oligonucleotides labeled with fluorophores includes but are not limited to probes for fluorescence in situ hybridization (FISH). Widely known and practiced by persons having ordinary skill in the art, FISH is used to, among other things, to detect and localize the presence or absence of specific DNA sequences or RNA targets. Methods for designing and preparing detectably labeled oligonucleotides labeled are widely known in the art, including but not limited to those described in US patent application publication US 20120142014. Due to limitations such as fluorophore availability, FISH, however, can only be used to profile a limited number of targets in a given experiment. Through sequential barcoding to multiplex different targets, provided methods of the present invention can profile a large number of targets, up to $F^N$, wherein F is the number of types of detectable moieties (in the case of FISH, fluorophores) and N is the number of contacting steps (in the case of FISH, hybridization). For example, when F is four and N is 8, almost the entire transcriptome ($4^8$=65,536) can be profiled. In some embodiments, F is at least 2. In some embodiments, F is 3. In some embodiments, F is 4. In some embodiments, F is 5. In some embodiments, F is 6. In some embodiments, F is 7. In some embodiments, F is 8. In some embodiments, F is 9. In some embodiments, F is 10. In some embodiments, F is 11. In some embodiments, F is 12. In some embodiments, F is 13. In some embodiments, F is 14. In some embodiments, F is 15. In some embodiments, F is greater than 15. In some embodiments, N is 2. In some embodiments, N is greater than 2. In some embodiments, N is 3. In some embodiments, N is greater than 3. In some embodiments, N is 4. In some embodiments, N is greater than 4. In some embodiments, N is 5. In some embodiments, N is greater than 5. In some embodiments, N is 6. In some embodiments, N is greater than 6. In some embodiments, N is 7. In some embodiments, N is greater than 7. In some embodiments, N is 8. In some embodiments, N is greater than 8. In some embodiments, N is 9. In some embodiments, N is greater than 9. In some embodiments, N is 10. In some embodiments, N is greater than 10. In some embodiments, a plurality of detectably labeled oligonucleotides target at least 100 targets.

In a contacting step, a detectably labeled oligonucleotide can be labeled prior to, concurrent with or subsequent to its binding to its target. In some embodiments, a detectably labeled oligonucleotide, such as a fluorophore-labeled oligonucleotide, is labeled prior to its binding to its target. In some embodiments, a detectably labeled oligonucleotide is labeled concurrent with its binding to its target. In some embodiments, a detectably labeled oligonucleotide is labeled subsequent to its binding to its target. In some embodiments, a detectably labeled oligonucleotide is labeled subsequent to hybridization through orthogonal amplification with hybridization chain reactions (HCR) (Choi, H M., *Nat Biotechnol.* 2010 November; 28(11):1208-12). In some embodiments, a detectably labeled oligonucleotide comprises a moiety, e.g., a nucleic acid sequence, that one or more moieties that can provide signals in an imaging step can be directly or indirectly linked to the oligonucleotide.

In some embodiments, the same type of labels can be attached to different probes for different targets. In some embodiments, probes for the same target have the same label in a plurality of detectably labeled oligonucleotides used in a contacting step (a set of detectably labeled oligonucleotides). Each target, after rounds of contacting and imaging, has its own unique combination of labels (sequential barcoding), so that information, e.g., quantitative and/or spatial information, can be obtained for a target. For example, when fluorophores are used to label detectably labeled oligonucleotides, after N steps, a target would have a sequential barcode of $F_1F_2 \ldots F_N$, wherein $F_n$ is the color of fluorophore used for the target in the n-th imaging. One target can be differentiated from another by a difference in their barcodes (e.g., RedRedBlueRed compared to RedRedRedBlue).

In some embodiments, labels of the present invention is or comprise one or more fluorescent dyes, including but not limited to fluorescein, rhodamine, Alexa Fluors, DyLight fluors, ATTO Dyes, or any analogs or derivatives thereof.

In some embodiments, labels of the present invention include but are not limited to fluorescein and chemical derivatives of fluorescein; Eosin; Carboxyfluorescein; Fluorescein isothiocyanate (FITC); Fluorescein amidite (FAM); Erythrosine; Rose Bengal; fluorescein secreted from the bacterium *Pseudomonas aeruginosa*; Methylene blue; Laser dyes; Rhodamine dyes (e.g., Rhodamine, Rhodamine 6G, Rhodamine B, Rhodamine 123, Auramine O, Sulforhodamine 101, Sulforhodamine B, and Texas Red).

In some embodiments, labels of the present invention include but are not limited to ATTO dyes; Acridine dyes (e.g., Acridine orange, Acridine yellow); Alexa Fluor; 7-Amino actinomycin D; 8-Anilinonaphthalene-1-sulfonate; Auramine-rhodamine stain; Benzanthrone; 5,12-Bis(phenylethynyl)naphthacene; 9,10-Bis(phenylethynyl)anthracene; Blacklight paint; Brainbow; Calcein; Carboxyfluorescein; Carboxyfluorescein diacetate succinimidyl ester; Carboxyfluorescein succinimidyl ester; 1-Chloro-9,10-bis(phenylethynyl)anthracene; 2-Chloro-9,10-bis(phenylethynyl)anthracene; 2-Chloro-9,10-diphenylanthracene; Coumarin; Cyanine dyes (e.g., Cyanine such as Cy3 and Cy5, DiOC6, SYBR Green I); DAPI, Dark quencher, DyLight Fluor, Fluo-4, FluoProbes; Fluorone dyes (e.g., Calcein, Carboxyfluorescein, Carboxyfluorescein diacetate succinimidyl ester, Carboxyfluorescein succinimidyl ester, Eosin, Eosin B, Eosin Y, Erythrosine, Fluorescein, Fluorescein isothiocyanate, Fluorescein amidite, Indian yellow, Merbromin); Fluoro-Jade stain; Fura-2; Fura-2-acetoxymethyl ester; Green fluorescent protein, Hoechst stain, Indian yellow, Indo-1, Lucifer yellow, Luciferin, Merocyanine, Optical brightener, Oxazin dyes (e.g., Cresyl violet, Nile blue, Nile red); Perylene; Phenanthridine dyes (Ethidium bromide and Propidium iodide); Phloxine, Phycobilin, Phycoerythrin, Phycoerythrobilin, Pyranine, Rhodamine, Rhodamine 123, Rhodamine 6G, RiboGreen, RoGFP, Rubrene, SYBR Green I, (E)-Stilbene, (Z)-Stilbene, Sulforhodamine 101, Sulforhodamine B, Synapto-pHluorin, Tetraphenyl butadiene, Tetrasodium tris(bathophenanthroline disulfonate)ruthenium(II), Texas Red, TSQ, Umbelliferone, or Yellow fluorescent protein.

In some embodiments, labels of the present invention include but are not limited to Alexa Fluor family of fluorescent dyes (Molecular Probes, Oregon). Alexa Fluor dyes are widely used as cell and tissue labels in fluorescence microscopy and cell biology. The excitation and emission spectra of the Alexa Fluor series cover the visible spectrum and extend into the infrared. The individual members of the family are numbered according roughly to their excitation maxima (in nm). Certain Alexa Fluor dyes are synthesized through sulfonation of coumarin, rhodamine, xanthene (such as fluorescein), and cyanine dyes. In some embodiments, sulfonation makes Alexa Fluor dyes negatively charged and hydrophilic. In some embodiments, Alexa Fluor dyes are more stable, brighter, and less pH-sensitive than common dyes (e.g. fluorescein, rhodamine) of comparable excitation and emission, and to some extent the newer cyanine series. Exemplary Alexa Fluor dyes include but are not limited to Alexa-350, Alexa-405, Alexa-430, Alexa-488, Alexa-500, Alexa-514, Alexa-532, Alexa-546, Alexa-555, Alexa-568, Alexa-594, Alexa-610, Alexa-633, Alexa-647, Alexa-660, Alexa-680, Alexa-700, or Alexa-750.

In some embodiments, labels of the present invention comprise one or more of the DyLight Fluor family of fluorescent dyes (Dyomics and Thermo Fisher Scientific). Exemplary DyLight Fluor family dyes include but are not limited to DyLight-350, DyLight-405, DyLight-488, DyLight-549, DyLight-594, DyLight-633, DyLight-649, DyLight-680, DyLight-750, or DyLight-800.

In some embodiments, a detectable moiety is or comprises a nanomaterial. In some embodiments, a detectable moiety is or compresses a nanoparticle. In some embodiments, a detectable moiety is or comprises a quantum dot. In some embodiments, a detectable moiety is a quantum dot. In some embodiments, a detectable moiety comprises a quantum dot. In some embodiments, a detectable moiety is or comprises a gold nanoparticle. In some embodiments, a detectable moiety is a gold nanoparticle. In some embodiments, a detectable moiety comprises a gold nanoparticle.

One of skill in the art understands that, in some embodiments, selection of label for a particular probe in a particular cycle may be determined based on a variety of factors, including, for example, size, types of signals generated, manners attached to or incorporated into a probe, properties of the cellular constituents including their locations within the cell, properties of the cells, types of interactions being analyzed, and etc.

For example, in some embodiments, probes are labeled with either Cy3 or Cy5 that has been synthesized to carry an N-hydroxysuccinimidyl ester (NHS-ester) reactive group. Since NHS-esters react readily with aliphatic amine groups, nucleotides can be modified with aminoalkyl groups. This can be done through incorporating aminoalkyl-modified nucleotides during synthesis reactions. In some embodiments, a label is used in every 60 bases to avoid quenching effects.

A detectably labeled oligonucleotide can hybridize with a target, e.g., a transcript or DNA locus. In some embodiments, a target is or comprises a transcript. In some embodiments, a target is a transcript. In some embodiments, a transcript is an RNA. In some embodiments, a transcript is an mRNA. In some embodiments, a transcript is tRNA. In some embodiments, a transcript is rRNA. In some embodiments, a transcript is snRNA. In some embodiments, an RNA is a non-coding RNA. Exemplary non-coding RNA types are widely known in the art, including but not limited to long non-coding RNA (lncRNA), microRNA (miRNA), short interfering RNA (siRNA), piwi-interacting RNA (piRNA), small nucleolar RNA (snoRNA) and other short RNAs. In some embodiments, an RNA is lncRNA. In some embodiments, an RNA is miRNA. In some embodiments, an RNA is piRNA. In some embodiments, an RNA is snoRNA.

In some embodiments, a target is or comprises a DNA locus. In some embodiments, when a target is a DNA locus, a detectably labeled oligonucleotide optionally comprises one or more RNA nucleotide or RNA segments. A detectably labeled oligonucleotide comprises RNA sequences can be selectively removed, for example, through RNA-specific enzymatic digestion, after imaging without degrading the DNA target. Exemplary enzymes that specifically degrade RNA but not DNA include but are not limited to various RNase, such as RNase A and RNase H.

In some embodiments, a detectably labeled oligonucleotide directly hybridizes to its target, e.g., a transcript or DNA locus. In some embodiments, a detectably labeled oligonucleotide specifically interacts with (recognizes) its target through binding or hybridization to one or more intermediate, e.g., an oligonucleotide, that is bound, hybridized, or otherwise specifically linked to the target. In some embodiments, an intermediate oligonucleotide is hybridized against its target with an overhang such that a second oligonucleotide with complementary sequence ("bridge oligonucleotide" or "bridge probe") can bind to it. In some embodiments, an intermediate targets a nucleic acid and is optionally labeled with a detectable moiety, and comprises an overhang sequence after hybridization with the target. In some embodiments, an intermediate comprises a sequence that hybridizes to a target, an overhang sequence, and optionally a detectable moiety. In some embodiments, an intermediate comprises a sequence that hybridizes to a target and an overhang sequence. In some embodiments, an intermediate does not have a detectable moiety. In some embodiments, a second oligonucleotide is a detectably labeled oligonucleotide. In some embodiments, a second detectably labeled oligonucleotide is labeled with a dye. In some embodiments, a detectably labeled oligonucleotide is labeled with an HCR polymer. In some embodiments, intermediate oligonucleotides bound to targets are preserved through multiple contacting, removing and/or imaging steps; sequential barcodes are provided through combinations of detectable labels that are linked to intermediate oligonucleotides through bridge probes in the contacting and imaging steps. For example, when detectably labeled oligonucleotides are used as bridge probes, barcodes are provided by detectably labeled oligonucleotides that hybridize with intermediate oligonucleotides through their overhang sequences. After an imaging step, bridge oligonucleotides are optionally removed as described herein. In some embodiments, one intermediate oligonucleotide is employed for a target. In some embodiments, two or more intermediate oligonucleotides are employed for a target. In some embodiments, three or more intermediate oligonucleotides are employed for a target. In some embodiments, four or more intermediate oligonucleotides are employed for a target. In some embodiments, five or more intermediate oligonucleotides are employed for a target. In some embodiments, six or more intermediate oligonucleotides are employed for a target. In some embodiments, seven or more intermediate oligonucleotides are employed for a target. In some embodiments, eight or more intermediate oligonucleotides are employed for a target. In some embodiments, nine or more intermediate oligonucleotides are employed for a target. In some embodiments, 10 or more intermediate oligonucleotides are employed for a target. In some embodiments, 11 or more intermediate oligonucleotides are employed for a target. In some embodiments, 12 or more intermediate oligonucleotides are employed for a target. In some embodiments, 13 or more intermediate oligonucleotides are employed for a target. In some embodiments, 13 or more intermediate oligonucleotides are employed for a target. In some embodiments, 15 or more intermediate oligonucleotides are employed for a target. In some embodiments, 16 or more intermediate oligonucleotides are employed for a target. In some embodiments, 17 or more intermediate oligonucleotides are employed for a target. In some embodiments, 18 or more intermediate oligonucleotides are employed for a target. In some embodiments, 19 or more intermediate oligonucleotides are employed for a target. In some embodiments, 20 or more intermediate oligonucleotides are employed for a target. In some embodiments, 21 or more intermediate oligonucleotides are employed for a target. In some embodiments, 22 or more intermediate oligonucleotides are employed for a target. In some embodiments, 23 or more intermediate oligonucleotides are employed for a target. In some embodiments, 24 or more intermediate oligonucleotides are employed for a target. In some embodiments, 25 or more intermediate oligonucleotides are employed for a target. In some embodiments, 30 or more intermediate oligonucleotides are employed for a target. In some embodiments, 40 or more intermediate oligonucleotides are employed for a target. In some embodiments, 50 or more intermediate oligonucleotides are employed for a target.

In some embodiments, each intermediate oligonucleotide hybridizes with a different sequence of a target. In some embodiments, each intermediate oligonucleotide of a target comprises the same overhang sequence. In some embodiments, each detectably labeled oligonucleotide for a target comprises the same sequence complimentary to the same overhang sequence shared by all intermediate oligonucleotides of the target. In some embodiments, an intermediate oligonucleotide comprises a sequence complimentary to a target, and a sequence complimentary to a detectably labeled oligonucleotide.

In some embodiments, provided methods further comprises steps of: (f) performing a contacting step that involves contacting a cell comprising a plurality of nucleic acids with a plurality of intermediate oligonucleotides, each of which:
(i) targets a nucleic acid and is optionally labeled with a detectable moiety; and
(ii) comprises an overhang sequence after hybridization with the target; and (g) optionally imaging the cell so that interaction between the intermediate oligonucleotides with their targets is detected.

In some embodiments, step (f) and optionally step (g) are performed before step (a). In some embodiments, step (f) is performed step (a). In some embodiments, a removing step preserves intermediate oligonucleotides.

In some embodiments, provided technologies are used to profile different transcripts formed as a result of splicing variation, RNA editing, oligonucleotide modification, or a combination thereof. In some embodiments, a target is an RNA splicing variant. In some embodiments, provided technologies profile one or more splicing variants of a gene, e.g., locations and quantities of one or more splicing variant of a gene. In some embodiments, provided methods or compositions profile different splicing variants. In some embodiments, an exon that contains one or more variants is targeted and barcoded by sequential hybridization and barcoding. In some embodiments, a splicing variant contains one or more distinguishable sequences resulted from splicing, and such sequences are targeted. In some embodiments, by targeting exons and/or distinguishable sequences, provided technologies can profile one or more specific splicing variants, or an entire splicing repertoire of an mRNA. As widely known in the art, mRNA splicing are important to numerous biological processes and diseases, for example, neurological diseases like autism or Down syndrome. Molecules responsible for cell-to-cell adhesion and synpatogenesis are spliced and their defects are known to generate miswiring in the brain and cause diseases.

In some embodiments, detectably labeled oligonucleotides target sequence modifications caused by sequence editing, chemical modifications and/or combinations thereof. In some embodiments, a modified nucleic acid target, optionally after a conversion process, hybridizes with one or more different complementary sequences compared to an un-modified target, and is profiled using one or more oligonucleotides that selectively hybridizes with the modified nucleic acid. In some embodiments, a target is an RNA through by RNA editing (Brennicke, A., A. Marchfelder, et al. (1999). "RNA editing". *FEMS Microbiol Rev* 23 (3): 297-316). In some embodiments, provided technologies profiles different RNA variants formed by RNA editing. In some embodiments, provided technologies profile modified oligonucleotide. In some embodiments, provided technologies profiles methylated RNA (Song C X, Yi C, He C. Mapping recently identified nucleotide variants in the genome and transcriptome. Nat Biotechnol. 2012 November; 30(11):1107-16). In some embodiments, provided technologies profile methylated DNA. In some embodiments, a target is single-nucleotide polymorphism (SNP).

In some embodiments, by profiling a target, provided technologies provide, among other things, quantitative and/or positioning information of a target, in some cases, in single cells, a tissue, an organ, or an organism. In some embodiments, profiling of transcripts can be used to qualitatively and/or quantitatively define the spatial-temporal patterns of gene expression within cells, tissues, organs or organisms.

In some embodiments, each detectably labeled oligonucleotide in a set has a different target, e.g., a transcript or DNA locus. In some embodiments, two or more detectably labeled oligonucleotides in a set have the same target. In some embodiments, two or more detectably labeled oligonucleotides target the same transcript. In some embodiments, two or more detectably labeled oligonucleotides target the same DNA locus. In some embodiments, about 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90 or 100 detectably labeled oligonucleotides the same target. In some embodiments, two or more detectably labeled oligonucleotides target the same target. In some embodiments, five or more detectably labeled oligonucleotides target the same target. In some embodiments, 10 or more detectably labeled oligonucleotides target the same target. In some embodiments, 15 or more detectably labeled oligonucleotides target the same target. In some embodiments, 20 or more detectably labeled oligonucleotides target the same target. In some embodiments, 25 or more detectably labeled oligonucleotides target the same target. In some embodiments, 30 or more detectably labeled oligonucleotides target the same target. In some embodiments, 35 or more detectably labeled oligonucleotides target the same target. In some embodiments, 40 or more detectably labeled oligonucleotides target the same target. In some embodiments, 45 or more detectably labeled oligonucleotides target the same target. In some embodiments, 50 or more detectably labeled oligonucleotides target the same target. In some embodiments, 60 or more detectably labeled oligonucleotides target the same target. In some embodiments, 70 or more detectably labeled oligonucleotides target the same target. In some embodiments, 80 or more detectably labeled oligonucleotides target the same target. In some embodiments, 90 or more detectably labeled oligonucleotides target the same target. In some embodiments, 100 or more detectably labeled oligonucleotides target the same target. In some embodiments, about 1-10 detectably labeled oligonucleotides target the same target. In some embodiments, about 5-15 detectably labeled oligonucleotides target the same target. In some embodiments, about 10-20 detectably labeled oligonucleotides target the same target. In some embodiments, about 15-25 detectably labeled oligonucleotides target the same target. In some embodiments, about 20-30 detectably labeled oligonucleotides target the same target. In some embodiments, about 25-35 detectably labeled oligonucleotides target the same target. In some embodiments, about 30-40 detectably labeled oligonucleotides target the same target. In some embodiments, about 35-45 detectably labeled oligonucleotides target the same target. In some embodiments, about 40-50 detectably labeled oligonucleotides target the same target. In some embodiments, about 45-55 detectably labeled oligonucleotides target the same target. In some embodiments, about 50-70 detectably labeled oligonucleotides target the same target. In some embodiments, about 60-80 detectably labeled oligonucleotides target the same target. In some embodiments, about 70-90 detectably labeled oligonucleotides target the same target. In some embodiments, about 80-100 detectably labeled oligonucleotides target the same target.

In some embodiments, among other things, using multiple detectably labeled oligonucleotides for the same target increases signal intensity. In some embodiments, each detectably labeled oligonucleotide in a set targeting the same target interacts with a different portion of a target.

In some embodiments, all detectably labeled oligonucleotides for a target in a set have the same detectable moieties. In some embodiments, all detectably labeled oligonucleotides are labeled in the same way. In some embodiments, all the detectably labeled oligonucleotides for a target have the same fluorophore.

In some embodiments, detectably labeled oligonucleotides for a target are positioned within a targeted region of a target. A targeted region can have various lengths. In some embodiments, a targeted region is about 20 bp in length. In some embodiments, a targeted region is about 30 bp in length. In some embodiments, a targeted region is about 40 bp in length. In some embodiments, a targeted region is about 50 bp in length. In some embodiments, a targeted region is about 60 bp in length. In some embodiments, a targeted region is about 80 bp in length. In some embodiments, a targeted region is about 100 bp in length. In some embodiments, a targeted region is about 150 bp in length. In some embodiments, a targeted region is about 200 bp in length. In some embodiments, a targeted region is about 250 bp in length. In some embodiments, a targeted region is about 300 bp in length. In some embodiments, a targeted region is about 350 bp in length. In some embodiments, a targeted region is about 400 bp in length. In some embodiments, a targeted region is about 450 bp in length. In some embodiments, a targeted region is about 500 bp in length. In some embodiments, a targeted region is about 600 bp in length. In some embodiments, a targeted region is about 700 bp in length. In some embodiments, a targeted region is about 800 bp in length. In some embodiments, a targeted region is about 900 bp in length. In some embodiments, a targeted region is about 1,000 bp in length. In some embodiments, detectably labeled oligonucleotides for a target are positioned in proximity to each other on the target.

As understood by a person having ordinary skill in the art, different technologies can be used for the imaging steps. Exemplary methods include but are not limited to epifluorescence microscopy, confocal microscopy, the different types of super-resolution microscopy (PALM/STORM, SSIM/GSD/STED), and light sheet microscopy (SPIM and etc).

Exemplary super resolution technologies include but are not limited to $I^5M$ and 4Pi-microscopy, Stimulated Emission Depletion microscopy (STEDM), Ground State Depletion microscopy (GSDM), Spatially Structured Illumination microscopy (SSIM), Photo-Activated Localization Microscopy (PALM), Reversible Saturable Optically Linear Fluorescent Transition (RESOLFT), Total Internal Reflection Fluorescence Microscope (TIRFM), Fluorescence-PALM (FPALM), Stochastical Optical Reconstruction Microscopy (STORM), Fluorescence Imaging with One-Nanometer Accuracy (FIONA), and combinations thereof. For examples: Chi, 2009 "Super-resolution microscopy: breaking the limits, Nature Methods 6(1):15-18; Blow 2008, "New ways to see a smaller world," *Nature* 456:825-828; Hell, et al., 2007, "Far-Field Optical Nanoscopy," *Science* 316: 1153; R. Heintzmann and G. Ficz, 2006, "Breaking the resolution limit in light microscopy," *Briefings in Functional Genomics and Proteomics* 5(4):289-301; Garini et al., 2005, "From micro to nano: recent advances in high-resolution microscopy," *Current Opinion in Biotechnology* 16:3-12; and Bewersdorf et al., 2006, "Comparison of $I^5M$ and 4Pi-microscopy," 222(2):105-117; and Wells, 2004, "Man the Nanoscopes," *JCB* 164(3):337-340.

In some embodiments, electron microscopes (EM) are used.

In some embodiments, an imaging step detects a target. In some embodiments, an imaging step localizes a target. In some embodiments, an imaging step provides three-dimensional spatial information of a target. In some embodiments, an imaging step quantifies a target. By using multiple contacting and imaging steps, provided methods are capable of providing spatial and/or quantitative information for a large number of targets in surprisingly high throughput. For example, when using F detectably different types of labels, spatial and/or quantitative information of up to $F^N$ targets can be obtained after N contacting and imaging steps.

In some embodiments, provided methods comprise additional steps before or after a contacting and/or an imaging step. In some embodiments, provided methods comprise a step of removing a plurality of detectably labeled oligonucleotides after each imaging step. In some embodiments, a step of removing comprises degrading the detectably labeled oligonucleotides. In some embodiments, a step of removing does not significantly degrade a target, so that a target can be used for the next contacting and/or imaging step(s) if desired. In some embodiments, a step of removing comprises contacting the plurality of detectably labeled oligonucleotides with an enzyme that digests a detectably labeled oligonucleotide. In some embodiments, a step of removing comprises contacting the plurality of detectably labeled oligonucleotides with a DNase or RNase. For example, in some embodiments, a detectably labeled oligonucleotide comprises a DNA sequence, and a DNase is used for its degradation; in some other embodiments, a detectably labeled oligonucleotide comprises an RNA sequence, and an RNase is used for its degradation. In some embodiments, a step of removing comprises degrading a detectable moiety. In some embodiments, a step of removing comprises photobleaching.

In some embodiments, targets of one set of detectably labeled oligonucleotides are also targets of another set. In some embodiments, targets of one set of detectably labeled oligonucleotides overlap with those of another set. In some embodiments, the overlap is more than 10%. In some embodiments, the overlap is more than 20%. In some embodiments, the overlap is more than 30%. In some embodiments, the overlap is more than 40%. In some embodiments, the overlap is more than 50%. In some embodiments, the overlap is more than 60%. In some embodiments, the overlap is more than 70%. In some embodiments, the overlap is more than 80%. In some embodiments, the overlap is more than 90%. In some embodiments, the overlap is more than 91%. In some embodiments, the overlap is more than 92%. In some embodiments, the overlap is more than 93%. In some embodiments, the overlap is more than 94%. In some embodiments, the overlap is more than 90%. In some embodiments, the overlap is more than 95%. In some embodiments, the overlap is more than 96%. In some embodiments, the overlap is more than 97%. In some embodiments, the overlap is more than 98%. In some embodiments, the overlap is more than 99%. In some embodiments, the overlap is more than 99.5%. In some embodiments, the overlap is more than 99.6%. In some embodiments, the overlap is more than 99.7%. In some embodiments, the overlap is more than 99.8%. In some embodiments, the overlap is more than 99.9%. In some embodiments, the overlap is 100%. In some embodiments, targets of one set of detectably labeled oligonucleotides are the same as targets of another set. In some embodiments, each set of detectably labeled oligonucleotides targets the same targets.

In some embodiments, a third detectably labeled oligonucleotide in a second contacting step targeting the first transcript or DNA locus (the first target) optionally has an identical sequence to the first detectably labeled oligonucleotide targeting the first transcript or DNA locus. In some embodiments, the sequences are identical. In some embodiments, the sequences are different. Similarly, in some embodiments, a fourth detectably labeled oligonucleotide in a second contacting step targeting the second transcript or DNA locus (the first target) optionally has an identical sequence to the second detectably labeled oligonucleotide targeting the first transcript or DNA locus. In some embodiments, the sequences are identical. In some embodiments, the sequences are different.

In some embodiments, the second plurality differs from the first plurality in that at least one of the oligonucleotides present in the second plurality is labeled with a different detectable moiety than the corresponding oligonucleotide targeting the same transcript or DNA locus in the first plurality. In some embodiments, each plurality of detectably labeled oligonucleotides is different from another, in that at least one of the oligonucleotides present in a plurality is labeled with a different detectable moiety than the corresponding oligonucleotide targeting the same transcript or DNA locus in another plurality.

In some embodiments, a detectably labeled oligonucleotide has the structure of [S]-[L], wherein [S] is an oligonucleotide sequence, [L] is a detectable moiety or a combination of detectable moieties. In some embodiments, [L] comprises multiple units of detectable labels, e.g., fluorophores, each of which independently associates with one or more nucleotidic moieties of an oligonucleotide sequence, e.g., [S]. In some embodiments, each detectable label attached to the same detectably labeled oligonucleotide provides the same detectable signal. In some embodiments, all detectable labels attached to the same oligonucleotide sequence are the same.

In some embodiments, oligonucleotides targeting the same target have the same set of sequences among two or more sets of detectably labeled oligonucleotides, i.e., the differences, if any, among the detectably labeled oligonucleotides are within the detectable moieties, not the sequences. For example, in one set of detectably labeled oligonucleotides, the detectably labeled oligonucleotides targeting a first target all have the same detectable moiety, or combination of detect moieties $[L]_1$:

$[S]_1\text{-}[L]_1, [S]_2\text{-}[L]_1, \ldots, [S]_n\text{-}[L]_1$, wherein n is the number of detectably labeled oligonucleotides for a target, e.g., an integer of 3-50;

In another set of detectably labeled oligonucleotides, wherein oligonucleotides targeting the same target are differently labeled, the oligonucleotides targeting the same target are having the same set of oligonucleotide sequences $([S]_1, [S]_2, \ldots, [S]_n)$ yet a different $[L]_2$:

$[S]_1\text{-}[L]_2, [S]_2\text{-}[L]_2, \ldots, [S]_n\text{-}[L]_2$, wherein $[L]_1$ is detectably different than $[L]_2$.

To exemplify certain embodiments of the present invention, a two-step, two-label, 4-target ($F^N=2^2=4$) process, wherein all detectably labeled oligonucleotides targeting the same target in each set independently have the same detectable moiety, is provided below:

Step 1. Contacting the targets with the first plurality (P1) of detectably labeled oligonucleotides:

Target T1: $[S]_{P1\text{-}T1\text{-}1}[L]_1$, $[S]_{P1\text{-}T1\text{-}2}[L]_1$, $[S]_{P1\text{-}T1\text{-}3}[L]_1, \ldots, [S]_{P1\text{-}T1\text{-}P1T1}[L]_1$, wherein P1T1 is the number of detectably labeled oligonucleotides targeting T1 in the first plurality, and $[L]_1$ is the first detectable label;

Target T2: $[S]_{P1\text{-}T2\text{-}1}[L]_1$, $[S]_{P1\text{-}T2\text{-}2}[L]_1$, $[S]_{P1\text{-}T2\text{-}3}[L]_1, \ldots, [S]_{P1\text{-}T2\text{-}P1T2}[L]_1$, wherein P1T2 is the number of detectably labeled oligonucleotides targeting T2 in the first plurality;

Target T3: $[S]_{P1\text{-}T3\text{-}1}[L]_2$, $[S]_{P1\text{-}T3\text{-}2}[L]_2$, $[S]_{P1\text{-}T3\text{-}3}[L]_2, \ldots, [S]_{P1\text{-}T3\text{-}P1T3}[L]_2$, wherein P1T3 is the number of detectably labeled oligonucleotides targeting T3 in the first plurality, and $[L]_2$ is a detectably different label than $[L]_1$;

Target T4: $[S]_{P1\text{-}T4\text{-}1}[L]_2$, $[S]_{P1\text{-}T4\text{-}2}[L]_2$, $[S]_{P1\text{-}T4\text{-}3}[L]_2, \ldots, [S]_{P1\text{-}T4\text{-}P1T4}[L]_2$, wherein P1T4 is the number of detectably labeled oligonucleotides targeting T4 in the first plurality.

Step 2: Imaging;

Step 3: Removing P1 from the targets;

Step 4: Contacting the targets with the second plurality (P2) of detectably labeled oligonucleotides:

Target T1: $[S]_{P2\text{-}T1\text{-}1}[L]_1$, $[S]_{P2\text{-}T1\text{-}2}[L]_1$, $[S]_{P2\text{-}T1\text{-}3}[L]_1$, ..., $[S]_{P2\text{-}T1\text{-}P2T1}[L]_1$, wherein P2T1 is the number of detectably labeled oligonucleotides targeting T1 in the second plurality;

Target T2: $[S]_{P2\text{-}T2\text{-}1}[L]_2$, $[S]_{P2\text{-}T2\text{-}2}[L]_2$, $[S]_{P2\text{-}T2\text{-}3}[L]_2$, ..., $[S]_{P2\text{-}T2\text{-}P2T2}[L]_2$, wherein P2T2 is the number of detectably labeled oligonucleotides targeting T2 in the second plurality;

Target T3: $[S]_{P2\text{-}T3\text{-}1}[L]_1$, $[S]_{P2\text{-}T3\text{-}2}[L]_1$, $[S]_{P2\text{-}T3\text{-}3}[L]_1$, ..., $[S]_{P2\text{-}T3\text{-}P2T3}[L]_1$, wherein P2T3 is the number of detectably labeled oligonucleotides targeting T3 in the second plurality;

Target T4: $[S]_{P2\text{-}T4\text{-}1}[L]_2$, $[S]_{P2\text{-}T4\text{-}2}[L]_2$, $[S]_{P2\text{-}T4\text{-}3}[L]_2$, ..., $[S]_{P2\text{-}T4\text{-}P2T4}[L]_2$, wherein P2T4 is the number of detectably labeled oligonucleotides targeting T4 in the second plurality.

Step 5: Imaging.

After the two imaging steps, each target has its own unique sequential barcode:

T1: $[L]_1[L]_1$;
T2: $[L]_1[L]_2$;
T3: $[L]_2[L]_1$; and
T4: $[L]_2[L]_2$.

In some embodiments, additional barcodes, T1--, T2--, --T1, --T2 can also be used, wherein -- indicates no signal for that step.

In the exemplified process above, each of P1T1, P1T2, P1T3, P1T4, P2T1, P2T2, P2T3 and P2T4 is independently a natural number (an integer greater than 0). In some embodiments, P1T1=P2T1. In some embodiments, P1T2=P2T2. In some embodiments, P1T3=P2T3. In some embodiments, P1T4=P2T4. In some embodiments, one detectably labeled oligonucleotide is used for a target. In some embodiments, two or more detectably labeled oligonucleotides are used for a target.

In some embodiments, detectably labeled oligonucleotides targeting the same target have the same set of sequences in each plurality. For example, for target T1 in the example above, each of $[S]_{P1\text{-}T1\text{-}1}$ to $[S]_{P1\text{-}T1\text{-}P1T1}$ independently has the same sequence as one of $[S]_{P2\text{-}T1\text{-}1}$ to $[S]_{P2\text{-}T1\text{-}P2T1}$, and each of $[S]_{P2\text{-}T1\text{-}1}$ to $[S]_{P2\text{-}T1\text{-}P2T1}$ independently has the same sequence as one of $[S]_{P1\text{-}T1\text{-}1}$ to $[S]_{P1\text{-}T1\text{-}P1T1}$. In some embodiments, detectably labeled oligonucleotides targeting the same target have different sets of sequences in each plurality.

In some embodiments, provided methods optionally comprise a step of removing a plurality of detectably labeled oligonucleotides after an imaging step. In some embodiments, provided methods comprise a removing step after an imaging step. In some embodiments, provided methods comprise a removing step after each imaging step but the last imaging step. In some embodiments, provided methods comprise a removing step after each imaging step.

A removing step in provided methods can serve one or more of a variety of purposes. In some embodiments, a removing step removes a plurality of detectably labeled oligonucleotides from targets so that targets are available for interacting with another plurality of detectably labeled oligonucleotides. In some embodiments, a removing step removes a plurality of detectably labeled oligonucleotides so that detectable moieties of one plurality of detectably labeled oligonucleotides do not interfere with detection of another plurality of detectably labeled oligonucleotides bound to targets. In some embodiments, a removing step removes at least 80% detectably labeled oligonucleotides. In some embodiments, a removing step removes at least 85% detectably labeled oligonucleotides. In some embodiments, a removing step removes at least 90% detectably labeled oligonucleotides. In some embodiments, a removing step removes at least 91% detectably labeled oligonucleotides. In some embodiments, a removing step removes at least 92% detectably labeled oligonucleotides. In some embodiments, a removing step removes at least 93% detectably labeled oligonucleotides. In some embodiments, a removing step removes at least 94% detectably labeled oligonucleotides. In some embodiments, a removing step removes at least 95% detectably labeled oligonucleotides. In some embodiments, a removing step removes at least 96% detectably labeled oligonucleotides. In some embodiments, a removing step removes at least 97% detectably labeled oligonucleotides. In some embodiments, a removing step removes at least 98% detectably labeled oligonucleotides. In some embodiments, a removing step removes at least 99% detectably labeled oligonucleotides. In some embodiments, a removing step removes at least 99.1% detectably labeled oligonucleotides. In some embodiments, a removing step removes at least 99.2% detectably labeled oligonucleotides. In some embodiments, a removing step removes at least 99.3% detectably labeled oligonucleotides. In some embodiments, a removing step removes at least 99.4% detectably labeled oligonucleotides. In some embodiments, a removing step removes at least 99.5% detectably labeled oligonucleotides. In some embodiments, a removing step removes at least 80% of the detectable signal. In some embodiments, a removing step removes at least 85% of the detectable signal. In some embodiments, a removing step removes at least 90% of the detectable signal. In some embodiments, a removing step removes at least 91% of the detectable signal. In some embodiments, a removing step removes at least 92% of the detectable signal. In some embodiments, a removing step removes at least 93% of the detectable signal. In some embodiments, a removing step removes at least 94% of the detectable signal. In some embodiments, a removing step removes at least 95% of the detectable signal. In some embodiments, a removing step removes at least 96% of the detectable signal. In some embodiments, a removing step removes at least 97% of the detectable signal. In some embodiments, a removing step removes at least 98% of the detectable signal. In some embodiments, a removing step removes at least 99% of the detectable signal. In some embodiments, a removing step removes at least 99.5% of the detectable signal. In some embodiments, a removing step removes 100% of the detectable signal. In some embodiments, after a removing step no signal can be detected by an imaging step.

A removing step optionally preserves targets (e.g., transcripts or DNA loci) for further use, for example, further detection or quantification by additional contacting and/or imaging steps. In some embodiments, a removing step preserves at least 80% targets. Percentage of preserved targets can be measured, for example, by comparing data collected before and after a removing step, optionally using the same contacting and imaging protocols. In some embodiments, a removing step preserves at least 85% targets. In some embodiments, a removing step preserves at least 90% targets. In some embodiments, a removing step preserves at least 91% targets. In some embodiments, a removing step preserves at least 92% targets. In some embodiments, a removing step preserves at least 93% targets. In some embodiments, a removing step preserves at least 94% targets. In some embodiments, a removing step preserves at least 95% targets. In some embodiments, a removing step preserves at least 96% targets. In some embodiments, a removing step preserves at least 97% targets. In some embodiments, a removing step preserves at least 98% targets. In some embodiments, a removing step preserves at least 99% targets.

Methods for removing detectably labeled oligonucleotides are widely known in the art. In some embodiments, a removing step comprising degrading a detectably labeled oligonucleotide. In some embodiments, a detectably labeled oligonucleotide is removed by enzymatic digestion. In some embodiments, a removing step comprising contacting a plurality of detectably labeled oligonucleotides with an enzyme that digests a detectably labeled oligonucleotide.

Suitable enzymes are widely used in the art. For example, depending on the type(s) of detectably labeled oligonucleotides and/or targets, either DNase or RNase can be used. In some embodiments, a detectably labeled oligonucleotide comprising a DNA sequence for detecting/quantifying a RNA target is digested by a DNase, e.g., DNase I. In some embodiments, a detectably labeled oligonucleotide comprising an RNA sequence for detecting/quantifying a DNA target is digested by a RNase. In some embodiments, a detectably labeled RNA oligonucleotide is used to target a DNA loci.

In some embodiments, a detectably labeled oligonucleotide interacts with its target through binding or hybridization to one or more intermediate, such as an oligonucleotide, that is bound, hybridized, or otherwise linked to the target. In some embodiments, a detectably labeled oligonucleotide interacts with a target through hybridization with an intermediate oligonucleotide hybridized to a target, wherein the intermediate oligonucleotide comprises a sequence complimentary to the target, and a sequence complementary to the detectably labeled oligonucleotide (overhang). In some embodiments, a removing step removes detectably labeled oligonucleotides, optionally keeping intermediate oligonucleotides intact. In some embodiments, a removing step removes detectably labeled oligonucleotides and keeps intermediate oligonucleotides intact. In some embodiments, detectably labeled oligonucleotides differ from intermediates in a chemical or enzymatic perspective, so that detectably labeled oligonucleotides can be selectively removed.

In some embodiments, intermediate DNA oligonucleotides are used to hybridize against DNA loci, with an overhang (e.g., 20 nt) such that a bridge oligonucleotide comprising an RNA sequence and with complementary sequence (e.g., RNA bridge probe) can bind. An RNA bridge probe can be labeled directly with a dye or a HCR polymer (which can also be DNA). After imaging, RNase can be used to digest away the RNA bridge probes, while leaving the DNA probe intact hybridized on the DNA loci. Such a method provides multiple advantages. For example, subsequent contacting steps only involve RNA bridge probes hybridizing against DNA oligonucleotides with overhangs, and avoid getting double stranded DNA to melt and hybridize with DNA oligonucleotides, which can be a difficult process. Further, the overhang can be made to be the same for all DNA oligonucleotides (e.g., 20-40) targeting the same gene, so that only one type of RNA bridge probe is needed per gene per round of hybridization. To switch colors on different hybridization (contacting steps), one can change RNA bridge probes with a different label or different HCR polymer. DNA bridge probes that can be specifically removed, e.g., with a specific enzyme restriction site like EcoRI on the bridge or the HCR hairpins, can also be used. Incubating the cells with the appropriate nuclease can digest away all detectable moieties without affecting the DNA loci and/or the probe hybridized on them.

In some embodiments, detectably labeled oligonucleotides comprises 5' phosphorylation and can be degraded by Lambda exonuclease, while intermediate oligonucleotides are not 5'-phosphoralated and cannot be degraded by Lambda exonuclease.

In some embodiments, a detectably labeled oligonucleotide comprises uracil. In some embodiments, detectably labeled oligonucleotides contain uracil, and can be degraded by USER™ enzyme (New England BioLabs, Ipswich, Mass., MA, US), while intermediate oligonucleotides contain no uracil and cannot be degraded by USER™ enzyme.

In some embodiments, an oligonucleotide hybridized against an overhang of an intermediate oligonucleotide has a recessed 3'-end when hybridized against the overhang. Detectably labeled oligonucleotides with recessed 3'-end when hybridized against intermediate oligonucleotides can be selectively digested by Exonuclease III. Intermediate oligonucleotides which do not have recessed 3'-ends, or whose 3'-ends are in RNA-DNA duplexes, can be kept intact due to the much weaker activities of exonuclease III toward them.

In some embodiments, when an enzyme is involved, a removing step is performed at a temperature that produces optimal results. In some embodiments, a removing step is performed at about 37° C. In some embodiments, a removing step is performed at room temperature. In some embodiments, digestion with Lambda exonuclease is conducted at about 37° C. In some embodiments, digestion with USER™ enzyme is conducted at about 37° C. In some embodiments, digestion with USER™ enzyme is conducted at room temperature. In some embodiments, digestion with Exonuclease III is conducted at about 37° C. In some embodiments, digestion with Exonuclease III is conducted at room temperature.

In some embodiments, use of an intermediate oligonucleotide and an overhang sequence for detectably labeled oligonucleotide binding provides a variety of advantages. In some embodiments, kinetics of hybridization between an overhang sequence and a detectably labeled oligonucleotide is faster than that between an intermediate oligonucleotide and a target. In some embodiments, all intermediate oligonucleotides for a target comprise the same overhang sequence, and all detectably labeled oligonucleotides for a target comprises the same complimentary sequence for binding to the same overhang sequence. In some embodiments, hybridization between a set of detectably labeled oligonucleotides and a set of intermediate oligonucleotides is up to about 20-40 times faster than that between a set of an intermediate oligonucleotides and a set of targets. In some embodiments, hybridization between detectably labeled oligonucleotides and intermediate oligonucleotides can be done in 30 minutes, compared to, in some cases, up to about 12 hours for hybridization between intermediate oligonucleotides and targets.

In some embodiments, strand displacement is used in a removing step to remove a detectably labeled oligonucleotide. In some embodiments, heat is used to dissociate a detectably labeled oligonucleotide in a removing step.

In some embodiments, a removing step comprises photobleaching. In some embodiments, photobleaching destroys a dye, such as a fluorophore, of a detectably labeled oligonucleotide.

In some embodiments, a first and a second sets of detectably labeled oligonucleotides target different sequences of each target, and a removing step after a first imaging step is optional. For example, one strategy is to target the same RNA with different DNA probes (detectably labeled DNA oligonucleotides), such that the first plurality of probes can target one set of sequences on the RNA, and the second plurality of probes target a different set of sequences on the same RNA. On the first hybridization (contacting), the first plurality of probes is used. They can then be imaged and optionally photobleached or digested by DNase, or other methods of destroying either the oligos or the dyes. The second set of probes can be hybridized and imaged without interferences from the first set of probes.

In some embodiments, provide methods optionally comprise HCR, light sheet microscopy, CLARITY, or combinations thereof. In some embodiments, provided methods allow direct profiling of targets in a tissue, an organ or an organism. In some embodiments, an organ is a brain. In some embodiments, provided methods allow direct imaging of transcripts in intact brains or tissues. In some embodiments, provided methods further comprise HCR. In some embodiments, provided methods further comprise light sheet microscopy. In some embodiments, provided methods further comprise CLARITY.

Provided methods offer many advantages over methods prior to the present invention. For example, in some embodiments, provided methods provide high-throughput at reasonable cost. In some embodiments, provided methods provide direct probing of target without transformation or amplification of a target. In some embodiments, provided methods enable quick scale up without the requirement of a large number of detectable labels. In some embodiments, provided methods can apply multiple labels to the same target and therefore increase signal intensity. In some embodiments, provided methods provide a combination of the advantages.

In some embodiments, the present invention provides compositions comprising a plurality of detectably labeled oligonucleotides, for, e.g., use in provided methods. Exemplary compositions include but are not limited to those described in exemplary method embodiments herein.

In some embodiments, the present invention provides compositions comprising a plurality of detectably labeled oligonucleotides, each of which targets a nucleic acid and is labeled with a detectable moiety, so that the composition comprises at least:
(i) a first oligonucleotide targeting a first nucleic acid and labeled with a first detectable moiety; and
(ii) a second oligonucleotide targeting a second nucleic acid and labeled with a second detectable moiety.

In some embodiments, the present invention provides compositions comprising a plurality of detectably labeled oligonucleotides, each of which targets a transcript or DNA locus and is labeled with a detectable moiety, so that the composition comprises at least:
(i) a first oligonucleotide targeting a first transcript or DNA locus and labeled with a first detectable moiety; and
(ii) a second oligonucleotide targeting a second transcript or DNA locus and labeled with a second detectable moiety.

In some embodiments, the present invention provides kits comprising a plurality of detectably labeled oligonucleotides, each of which targets a transcript or DNA locus and is labeled with a detectable moiety, so that the kit comprises at least:
(i) a first oligonucleotide targeting a first transcript or DNA locus and labeled with a first detectable moiety;
(ii) a second oligonucleotide targeting a second transcript or DNA locus and labeled with a second detectable moiety.
(iii) a third oligonucleotide, optionally identical in sequence to the first oligonucleotide, targeting the first transcript or DNA locus and labeled with the first, the second or a third detectable moiety; and
(iv) a fourth oligonucleotide, optionally identical in sequence to the second oligonucleotide, targeting the second transcript or DNA locus, and labeled with the first, the second, the third or a fourth detectable moiety,
wherein either the third oligonucleotide is labeled with a different detectable moiety than the first oligonucleotide, or the fourth oligonucleotide is labeled with a different detectable moiety than the second oligonucleotide, or both.

In some embodiments, detectably labeled oligonucleotides targeting the same target (transcript or DNA locus) in a composition are labeled with moieties providing the same detectable signal, or detectable signals that cannot be differentiated in an imaging step. In some embodiments, detectably labeled oligonucleotides targeting the same target in a composition are labeled with the same detectable moiety.

In some embodiments, a detectable moiety is or comprises a fluorophore. In some embodiments, a detectable moiety is a fluorophore. Exemplary fluorophores are widely known and used in the art, for example but not limited to fluorescein, rhodamine, Alexa Fluors, DyLight fluors, ATTO Dyes, or any analogs or derivatives thereof.

In some embodiments, a first and a second detectably labeled oligonucleotides target different target. In some embodiments, a first and a second detectably labeled oligonucleotides target the same target. In some embodiments, detectably labeled oligonucleotides in a composition or a kit targets two or more targets, e.g., transcripts and/or DNA loci. In some embodiments, detectably labeled oligonucleotides in a composition or a kit targets two or more transcripts. In some embodiments, detectably labeled oligonucleotides in a composition or a kit targets two or more DNA loci. In some embodiments, detectably labeled oligonucleotides in a composition or kit targets at least 4 targets. In some embodiments, detectably labeled oligonucleotides in a composition or kit targets at least 9 targets. In some embodiments, detectably labeled oligonucleotides in a composition or kit targets at least 16 targets. In some embodiments, detectably labeled oligonucleotides in a composition or kit targets at least 25 targets. In some embodiments, detectably labeled oligonucleotides in a composition or kit targets at least 36 targets. In some embodiments, detectably labeled oligonucleotides in a composition or kit targets at least 50 targets. In some embodiments, detectably labeled oligonucleotides in a composition or kit targets at least 100 targets. In some embodiments, detectably labeled oligonucleotides in a composition or kit targets at least 200 targets. In some embodiments, detectably labeled oligonucleotides in a composition or kit targets at least 500 targets. In some embodiments, detectably labeled oligonucleotides in a composition or kit targets at least 1,000 targets. In some embodiments, detectably labeled oligonucleotides in a composition or kit targets at least 5,000 targets. In some embodiments, detectably labeled oligonucleotides in a composition or kit targets at least 10,000 targets. In some embodiments, detectably labeled oligonucleotides in a composition or kit targets at least 50,000 targets. In some embodiments, detectably labeled oligonucleotides in a composition or kit targets at least 100,000 targets. In some embodiments, detectably labeled oligonucleotides in a composition or kit targets at least 1,000,000 targets.

In some embodiments, a first and a second oligonucleotides have different oligonucleotide sequences. In some embodiments, a first and a second detectable moieties are different. In some embodiments, a first and a second detectable moieties are the same.

In some embodiments, a first and a second oligonucleotides share less than 5% sequence identity. In some embodiments, a first and a second oligonucleotides share less than 10% sequence identity. In some embodiments, a first and a second oligonucleotides share less than 20% sequence identity. In some embodiments, a first and a second oligonucleotides share less than 30% sequence identity. In some embodiments, a first and a second oligonucleotides share less than 40% sequence identity. In some embodiments, a first and a second oligonucleotides share less than 50% sequence identity. In some embodiments, a first and a second oligonucleotides share less than 60% sequence identity. In some embodiments, a first and a second oligonucleotides share less than 65% sequence identity. In some embodiments, a first and a second oligonucleotides share less than 68% sequence identity. In some embodiments, a first and a second oligonucleotides share less than 70% sequence identity. In some embodiments, a first and a second oligonucleotides share less than 80% sequence identity. In some embodiments, a first and a second oligonucleotides share less than 90% sequence identity.

In some embodiments, each oligonucleotide shares less than 5% sequence identity with any other oligonucleotide. In some embodiments, each oligonucleotide shares less than 10% sequence identity with any other oligonucleotide. In some embodiments, each oligonucleotide shares less than 20% sequence identity with any other oligonucleotide. In some embodiments, each oligonucleotide shares less than 30% sequence identity with any other oligonucleotide. In some embodiments, each oligonucleotide shares less than 40% sequence identity with any other oligonucleotide. In some embodiments, each oligonucleotide shares less than 50% sequence identity with any other oligonucleotide. In some embodiments, each oligonucleotide shares less than 55% sequence identity with any other oligonucleotide. In some embodiments, each oligonucleotide shares less than 60% sequence identity with any other oligonucleotide. In some embodiments, each oligonucleotide shares less than 65% sequence identity with any other oligonucleotide. In some embodiments, each oligonucleotide shares less than 68% sequence identity with any other oligonucleotide. In some embodiments, each oligonucleotide shares less than 70% sequence identity with any other oligonucleotide. In some embodiments, each oligonucleotide shares less than 80% sequence identity with any other oligonucleotide. In some embodiments, each oligonucleotide shares less than 90% sequence identity with any other oligonucleotide.

In some embodiments, a composition or kit comprises two or more detectably labeled oligonucleotides targeting the same target. In some embodiments, 5, 10, 20, 30, 40, 50 or more detectably labeled oligonucleotides target the same target.

Detectably labeled oligonucleotides can be of various suitable lengths. In some embodiments, a detectably labeled oligonucleotide is 15 base pairs in length. In some embodiments, a detectably labeled oligonucleotide is 16 base pairs in length. In some embodiments, a detectably labeled oligonucleotide is 17 base pairs in length. In some embodiments, a detectably labeled oligonucleotide is 18 base pairs in length. In some embodiments, a detectably labeled oligonucleotide is 19 base pairs in length. In some embodiments, a detectably labeled oligonucleotide is 20 base pairs in length. In some embodiments, a detectably labeled oligonucleotide is 21 base pairs in length. In some embodiments, a detectably labeled oligonucleotide is 22 base pairs in length. In some embodiments, a detectably labeled oligonucleotide is 23 base pairs in length. In some embodiments, a detectably labeled oligonucleotide is 24 base pairs in length. In some embodiments, a detectably labeled oligonucleotide is 25 base pairs in length. In some embodiments, a detectably labeled oligonucleotide is 26 base pairs in length. In some embodiments, a detectably labeled oligonucleotide is 27 base pairs in length. In some embodiments, a detectably labeled oligonucleotide is 28 base pairs in length. In some embodiments, a detectably labeled oligonucleotide is 29 base pairs in length. In some embodiments, a detectably labeled oligonucleotide is 30 base pairs in length. In some embodiments, a detectably labeled oligonucleotide is at least 15 base pairs in length. In some embodiments, a detectably labeled oligonucleotide is at least 16 base pairs in length. In some embodiments, a detectably labeled oligonucleotide is at least 17 base pairs in length. In some embodiments, a detectably labeled oligonucleotide is at least 18 base pairs in length. In some embodiments, a detectably labeled oligonucleotide is at least 19 base pairs in length. In some embodiments, a detectably labeled oligonucleotide is at least 20 base pairs in length. In some embodiments, a detectably labeled oligonucleotide is at least 21 base pairs in length. In some embodiments, a detectably labeled oligonucleotide is at least 22 base pairs in length. In some embodiments, a detectably labeled oligonucleotide is at least 23 base pairs in length. In some embodiments, a detectably labeled oligonucleotide is at least 24 base pairs in length. In some embodiments, a detectably labeled oligonucleotide is at least 25 base pairs in length. In some embodiments, a detectably labeled oligonucleotide is at least 26 base pairs in length. In some embodiments, a detectably labeled oligonucleotide is at least 27 base pairs in length. In some embodiments, a detectably labeled oligonucleotide is at least 28 base pairs in length. In some embodiments, a detectably labeled oligonucleotide is at least 29 base pairs in length. In some embodiments, a detectably labeled oligonucleotide is at least 30 base pairs in length. In some embodiments, a detectably labeled oligonucleotide is at least 35 base pairs in length. In some embodiments, a detectably labeled oligonucleotide is at least 40 base pairs in length. In some embodiments, a detectably labeled oligonucleotide is at least 50 base pairs in length. In some embodiments, a detectably labeled oligonucleotide is about 15-25 base pairs in length. In some embodiments, a detectably labeled oligonucleotide is about 20-30 base pairs in length. In some embodiments, a detectably labeled oligonucleotide is about 25-35 base pairs in length. In some embodiments, a detectably labeled oligonucleotide is about 30-40 base pairs in length. In some embodiments, a detectably labeled oligonucleotide is about 35-45 base pairs in length. In some embodiments, a detectably labeled oligonucleotide is about 40-50 base pairs in length. In some embodiments, a detectably labeled oligonucleotide is about 15-30 base pairs in length. In some embodiments, a detectably labeled oligonucleotide is about 20-30 base pairs in length. In some embodiments, a detectably labeled oligonucleotide is about 15-35 base pairs in length. In some embodiments, a detectably labeled oligonucleotide is about 20-35 base pairs in length.

In some embodiments, a plurality of detectably labeled oligonucleotides contains two detectable moieties. In some embodiments, a plurality of detectably labeled oligonucleotides contains three detectable moieties. In some embodiments, a plurality of detectably labeled oligonucleotides contains four detectable moieties. In some embodiments, a plurality of detectably labeled oligonucleotides contains five detectable moieties. In some embodiments, a plurality of detectably labeled oligonucleotides contains six detectable moieties. In some embodiments, a plurality of detectably labeled oligonucleotides contains seven detectable moieties. In some embodiments, a plurality of detectably labeled oligonucleotides contains eight detectable moieties. In some embodiments, a plurality of detectably labeled oligonucleotides contains nine detectable moieties. In some embodiments, a plurality of detectably labeled oligonucleotides contains ten detectable moieties.

In some embodiments, a plurality of detectably labeled oligonucleotides comprises at least two detectable moieties. In some embodiments, a plurality of detectably labeled oligonucleotides comprises at least three detectable moieties. In some embodiments, a plurality of detectably labeled oligonucleotides comprises at least four detectable moieties. In some embodiments, a plurality of detectably labeled oligonucleotides comprises at least five detectable moieties. In some embodiments, a plurality of detectably labeled oligonucleotides comprises at least six detectable moieties. In some embodiments, a plurality of detectably labeled oligonucleotides comprises at least seven detectable moieties. In some embodiments, a plurality of detectably labeled oligonucleotides comprises at least eight detectable moieties. In some embodiments, a plurality of detectably labeled oligonucleotides comprises at least nine detectable moieties. In some embodiments, a plurality of detectably labeled oligonucleotides comprises at least ten detectable moieties.

In some embodiments, a composition further comprises:

(iii) a third oligonucleotide, optionally identical in sequence to the first oligonucleotide, targeting the first transcript or DNA locus; and (iv) a fourth oligonucleotide, optionally identical in sequence to the second oligonucleotide, targeting the second transcript or DNA locus wherein either the third oligonucleotide is labeled with a different detectable moiety than the first oligonucleotide, or the fourth oligonucleotide is labeled with a different detectable moiety than the second oligonucleotide, or both.

In some embodiments, a third oligonucleotide is identical in sequence to a first oligonucleotide. In some embodiments, a third oligonucleotide comprises a sequence overlapping with a first oligonucleotide. In some embodiments, a third oligonucleotide has less than 50% sequence identity with a first oligonucleotide. In some embodiments, a third oligonucleotide has less than 40% sequence identity with a first oligonucleotide. In some embodiments, a third oligonucleotide has less than 30% sequence identity with a first oligonucleotide. In some embodiments, a third oligonucleotide has less than 20% sequence identity with a first oligonucleotide. In some embodiments, a third oligonucleotide has less than 10% sequence identity with a first oligonucleotide. In some embodiments, a third oligonucleotide has less than 5% sequence identity with a first oligonucleotide.

In some embodiments, a fourth oligonucleotide is identical in sequence to a second oligonucleotide. In some embodiments, a fourth oligonucleotide comprises a sequence overlapping with a second oligonucleotide. In some embodiments, a fourth oligonucleotide has less than 50% sequence identity with a second oligonucleotide. In some embodiments, a fourth oligonucleotide has less than 40% sequence identity with a second oligonucleotide. In some embodiments, a fourth oligonucleotide has less than 30% sequence identity with a second oligonucleotide. In some embodiments, a fourth oligonucleotide has less than 20% sequence identity with a second oligonucleotide. In some embodiments, a fourth oligonucleotide has less than 10% sequence identity with a second oligonucleotide. In some embodiments, a fourth oligonucleotide has less than 5% sequence identity with a second oligonucleotide.

In some embodiments, a third oligonucleotide is labeled with a different detectable moiety than the first oligonucleotide. In some embodiments, a fourth oligonucleotide is labeled with a different detectable moiety than the second oligonucleotide.

In some embodiments, amount of a detectably labeled oligonucleotide in a plurality, composition, kit or method is pre-determined. In some embodiments, amounts of 5% detectably labeled oligonucleotides in a plurality, composition, kit or method are pre-determined. In some embodiments, amounts of 10% detectably labeled oligonucleotides in a plurality, composition, kit or method are pre-determined. In some embodiments, amounts of 20% detectably labeled oligonucleotides in a plurality, composition, kit or method are pre-determined. In some embodiments, amounts of 30% detectably labeled oligonucleotides in a plurality, composition, kit or method are pre-determined. In some embodiments, amounts of 40% detectably labeled oligonucleotides in a plurality, composition, kit or method are pre-determined. In some embodiments, amounts of 50% detectably labeled oligonucleotides in a plurality, composition, kit or method are pre-determined. In some embodiments, amounts of 60% detectably labeled oligonucleotides in a plurality, composition, kit or method are pre-determined. In some embodiments, amounts of 70% detectably labeled oligonucleotides in a plurality, composition, kit or method are pre-determined. In some embodiments, amounts of 80% detectably labeled oligonucleotides in a plurality, composition, kit or method are pre-determined. In some embodiments, amounts of 90% detectably labeled oligonucleotides in a plurality, composition, kit or method are pre-determined.

In some embodiments, amounts of at least 5 detectably labeled oligonucleotides in a plurality, composition, kit or method are pre-determined. In some embodiments, amounts of at least 10 detectably labeled oligonucleotides in a plurality, composition, kit or method are pre-determined. In some embodiments, amounts of at least 20 detectably labeled oligonucleotides in a plurality, composition, kit or method are pre-determined. In some embodiments, amounts of at least 30 detectably labeled oligonucleotides in a plurality, composition, kit or method are pre-determined. In some embodiments, amounts of at least 40 detectably labeled oligonucleotides in a plurality, composition, kit or method are pre-determined. In some embodiments, amounts of at least 50 detectably labeled oligonucleotides in a plurality, composition, kit or method are pre-determined. In some embodiments, amounts of at least 60 detectably labeled oligonucleotides in a plurality, composition, kit or method are pre-determined. In some embodiments, amounts of at least 70 detectably labeled oligonucleotides in a plurality, composition, kit or method are pre-determined. In some embodiments, amounts of at least 80 detectably labeled oligonucleotides in a plurality, composition, kit or method are pre-determined. In some embodiments, amounts of at least 90 detectably labeled oligonucleotides in a plurality, composition, kit or method are pre-determined. In some embodiments, amounts of at least each detectably labeled oligonucleotides in a plurality, composition, kit or method is pre-determined.

In some embodiments, two or more detectably labeled oligonucleotides are provided for one target. In some embodiments, total amount of all detectably labeled oligonucleotides for a target is pre-determined. In some embodiments, total amount of all detectably labeled oligonucleotides for a target is pre-determined, wherein the amount of each of the detectably labeled oligonucleotide for the target is independently and optionally pre-determined. In some embodiments, total amount of all detectably labeled oligonucleotides for each of a plurality of targets is independently pre-determined. In some embodiments, a plurality of targets has at least two targets. In some embodiments, a plurality of targets has at least five targets. In some embodiments, a plurality of targets has at least 10 targets. In some embodiments, a plurality of targets has at least 50 targets. In some embodiments, a plurality of targets has at least 100 targets. In some embodiments, a plurality of targets has at least 500 targets. In some embodiments, a plurality of targets has at least 1,000 targets.

In some embodiments, a target of a plurality, composition, kit or method is pre-determined. In some embodiments, at least 10 targets of a plurality, composition, kit or method are pre-determined. In some embodiments, at least 50 targets of a plurality, composition, kit or method are pre-determined. In some embodiments, at least 100 targets of a plurality, composition, kit or method are pre-determined. In some embodiments, at least 1,000 targets of a plurality, composition, kit or method are pre-determined. In some embodiments, up to $F^N$ targets of a plurality, composition, kit or method are pre-determined, wherein F is the number of detectable moieties in a pluralities, and N is the number of imaging steps.

Methods for synthesizing detectably labeled oligonucleotides are widely known and practiced in the art, for example, see Lubeck, E. & Cai, L. *Nat. Methods* 9, 743-48 (2012). Oligonucleotides are also commercially available from various vendors. In some embodiments, the present invention provides methods for preparing detectably labeled oligonucleotides. In some embodiments, the present invention provides methods for preparing intermediate oligonucleotides. In some embodiments, the present invention provides methods for preparing bridge oligonucleotides.

In some embodiments, the present invention provides methods for preparing a target nucleic acid having a first sequence, comprising steps of:
1) providing a first nucleic acid comprising the first sequence, wherein the first sequence is flanked by nicking endonuclease sites at both ends;
2) amplifying the first nucleic acid or part of the first nucleic acid to provide a second nucleic acid comprising the first sequence and the flanking nicking endonuclease sites; and
3) contacting the second nucleic acid with one or more nicking endonuclease corresponding to the flanking nicking endonuclease sites.

In some embodiments, a target nucleic acid having a first sequence is single-stranded. In some embodiments, an amplifying step comprises polymerase chain reaction (PCR). In some embodiments, provided methods further comprise a step of denaturing, wherein double-stranded second nucleic acid is denatured and the two strands become single-stranded. In some embodiments, provided methods further comprise isolating the nucleic acid having a first sequence. In some embodiments, a second nucleic acid is optionally modified before contacting with nicking endonucleases. In some embodiments, provided methods further comprise labeling a nucleic acid having a first sequence.

In some embodiments, the two flanking endonuclease sites are the same. In some embodiments, one nicking endonuclease corresponding to the same nicking endonuclease sites is used. In some embodiments, the two flanking endonuclease sites are different. In some embodiments, two nicking endonucleases, each of which independently corresponds to a nicking endonuclease site, are used.

Figure 25:
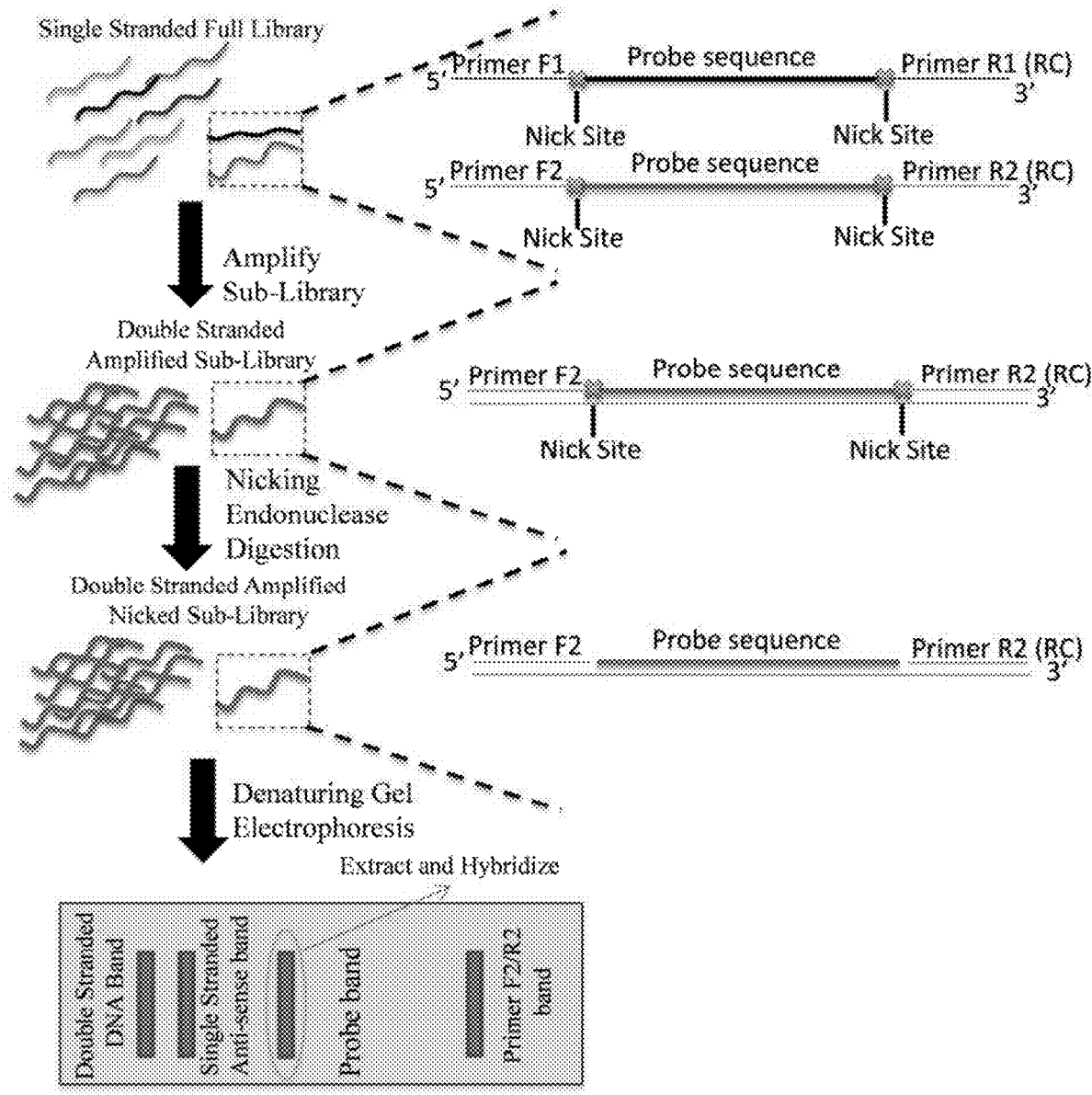
FIG. 25. Exemplary oligonucleotide preparation. The original oligonucleotide (as exemplified in this Figure, probe) library contains several probe sub-libraries. Each sub-library has a specific set of primers that can be used to amplify the sub-library using PCR. Once the desired sub-library is amplified, the product is incubated with a nicking enzyme. The enzyme cleaves the phosphodiester bond on the probe strand at its recognition site. Denaturing the resulting product and running it on a denaturing gel allows the desired probe sequence to be released. The probe band can then be cut out of the gel and extracted. The extracted product can be used for hybridization.

In some embodiments, oligonucleotides of provided technologies are generated from oligonucleotide pools. In some embodiments, such pools are available commercially. An initial DNA oligonucleotide pool in some embodiments consists of up to 12,000 or more different single stranded sequences organized into subsets. Each sequence is designed such that nicking endonuclease sites and a forward and reverse primer sequence flank a desired sequence (e.g., a probe sequence). The forward and reverse primer sequences specify to which subset with the desired sequence belongs. The primer pair can be used to amplify the subset using polymerase chain reaction (PCR). The product of the PCR reaction is isolated and digested by the nicking endonucleases. The incubation time with the nicking enzyme varies based on the amount of enzyme used and the amount of DNA recovered. In some embodiments, about 10 units of enzyme digest about 1 µg of DNA in about 1 hour. The sample is then purified and reconstituted in a buffer, e.g., 2× loading buffer (96% formamide/20 mM EDTA) and water to make a final loading buffer (48% formamide/10 mM EDTA), and denatured, e.g., by heating to 95° C. to completely denature the DNA. The denatured DNA is purified and the desired product isolated. In some embodiments, purification and/or isolation comprise electrophoresis. An exemplary process is illustrated in FIG. 25.

In some embodiments, the present invention provides a method for preparing a target nucleic acid having a first sequence, comprising steps of:
1) providing a first nucleic acid comprising the first sequence or its complimentary sequence, wherein the first sequence or its complementary sequence is flanked by at least one restriction site;
2) amplifying the first nucleic acid or part of the first nucleic acid to provide a second nucleic acid comprising the first sequence and the at least one flanking restriction site; and
3) contacting the second nucleic acid with a restriction enzyme corresponding to the at least one flanking restriction site to provide a third nucleic acid comprising a recessed end;
4) contacting the third nucleic acid with a nuclease to selectively digest the strand comprising the complementary sequence, if any, while keeping the strand comprising the first sequence.

In some embodiments, the first sequence or its complementary sequence is independently flanked by a restriction site at each end.

In some embodiments, the present invention provides a method for preparing a target nucleic acid having a first sequence, comprising steps of:
1) providing a first nucleic acid comprising the first sequence or its complimentary sequence, wherein the first sequence or its complementary sequence is flanked by restriction sites at both ends;
2) amplifying the first nucleic acid or part of the first nucleic acid to provide a second nucleic acid comprising the first sequence and the flanking restriction sites; and
3) contacting the second nucleic acid with restriction enzymes corresponding to the flanking restriction sites to provide a third nucleic acid comprising a recessed end;
4) contacting the third nucleic acid with a nuclease to selectively digest the strand comprising the complementary sequence, if any, while keeping the strand comprising the first sequence.

In some embodiments, a target nucleic acid having a first sequence is single-stranded. In some embodiments, an amplifying step comprises PCR. In some embodiments, provided methods further comprise isolating the nucleic acid having a first sequence. In some embodiments, a second nucleic acid is optionally modified before contacting with restriction enzymes. In some embodiments, a third nucleic acid is optionally modified before contacting with a nuclease. In some embodiments, a nuclease is exonuclease III, which preferentially degrade a strand with 3'-recessed ends, and can preserve a strand with a 5' recessed ends. In some embodiments, a restriction enzyme creates a 5'-recessed end. In some embodiments, a restriction enzyme creates a 3'-recessed end. In some embodiments, the complementary sequence has a 3' recessed end after restriction digestion. In some embodiments, the strand comprising the complementary sequence has a 3' recessed end after restriction digestion, and the strand comprising a first sequence has a 5' recessed end after restriction digestion. In some embodiments, provided methods further comprise labeling a nucleic acid having a first sequence.

In some embodiments, single stranded oligonucleotides, e.g., probes for seqFISH or intermediate oligonucleotides, can be generated using nuclease digestion, such as exoIII nuclease digestion. Instead of two nick sites on the amplification (e.g., PCR) products, two restriction sites can be used flanking the probe and/or adaptor sequence. In some embodiments, one restriction site leaves a 3' recessed end while the other leaves a 5' recessed ends. For example, EcoRI and BamHI leave 5' recessed ends, while BmtI and PacI leave 3' recessed ends. Such restriction enzymes are widely known and used in the art. Exonuclease III degrades the 3' recessed ends preferentially, and preserve the strand with the 5' recessed ends. This provides another mechanism to generate single stranded probes from oligonucleotide pools using PCR and restriction nucleases.

In some embodiments, a provided target nucleic acid is DNA. In some embodiments, a target nucleic acid has the same sequence a first sequence. In some embodiments, a target nucleic acid is an intermediate oligonucleotide, comprising a first sequence that hybridizes to a target, e.g., a transcript or a DNA locus, and a second sequence that hybridizes to a second oligonucleotide, e.g., a detectably labeled oligonucleotide. In some embodiments, a target nucleic acid is an intermediate oligonucleotide, comprising a first sequence that hybridizes to a target, and a second sequence that hybridizes with a detectably labeled oligonucleotide labeled by HCR. In some embodiments, a target nucleic acid is a bridge probe.

In some embodiments, provided methods are used for diagnosis of a disease, wherein the disease is related to an abnormal number of a transcript or a DNA locus. In some embodiments, provided methods are used for selecting subjects for a treatment. In some embodiments, provided methods are used for monitoring a treatment regimen. In some embodiments, a cell in provide methods is from a subject. In some embodiments, a cell in provide methods is a mammalian cell. In some embodiments, a cell in provide methods is a human cell. In some embodiments, a cell in provide methods is from a subject. In some embodiments, a cell in provide methods is from an animal. In some embodiments, a cell in provide methods is from a human subject. In some embodiments, a cell in provide methods is isolated from a human subject. In some embodiments, a cell in provide methods is from a diseased tissue, or a tissue that is susceptible to a disease. Being capable of detecting and quantifying a number of targets at the same time, provided methods provides significant advantages for diagnosis, treatment monitoring and patient stratification.

In some embodiments, provided technologies optionally comprises profiling proteins, neural activities, and/or structural arrangements. In some embodiments, provided methods comprise profiling proteins in the same sample. In some embodiments, provided methods comprise profiling neural activities in the same sample. In some embodiments, provided method comprise profiling structural arrangement.

As exemplified herein, provided technologies work for a wide variety of samples. For example, HCR-seqFISH worked in brain slices and that SPIMs can robustly detect single mRNAs in CLARITY brain slices. In some embodiments, provided technologies are useful for profiling targets in mouse models of neurodegenerative diseases, or human brains. No other technology prior to the present invention can deliver the same quality and quantity of data.

Overall Process

Figure 27A:
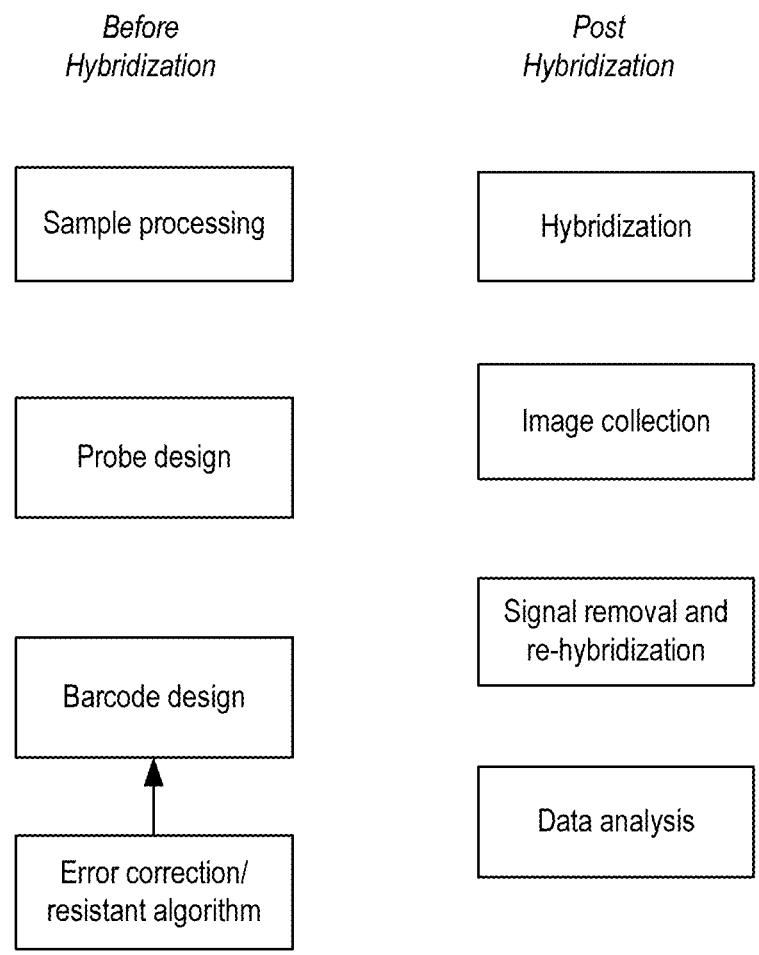
FIG. 27A illustrates exemplary aspects that may contribute to error correction during a sequential hybridization process.

FIG. 27A illustrates general aspects of a sequential hybridization analysis that may contribute to quality of the analysis. Sequential hybridization includes multiple rounds of hybridization, where each round of hybridization is a multiple step process. Errors can be introduced at any step during any round of hybridization. Such errors can lead to misidentification of target genes in a sample.

Prior to hybridization, samples that will be subject to analysis are processed. The main purpose of such processing is to immobilize target molecules; for example, mRNAs, chromosomal DNAs, and proteins. It is essential that the target molecules remain spatially fixed through different rounds of hybridization.

Figure 28:
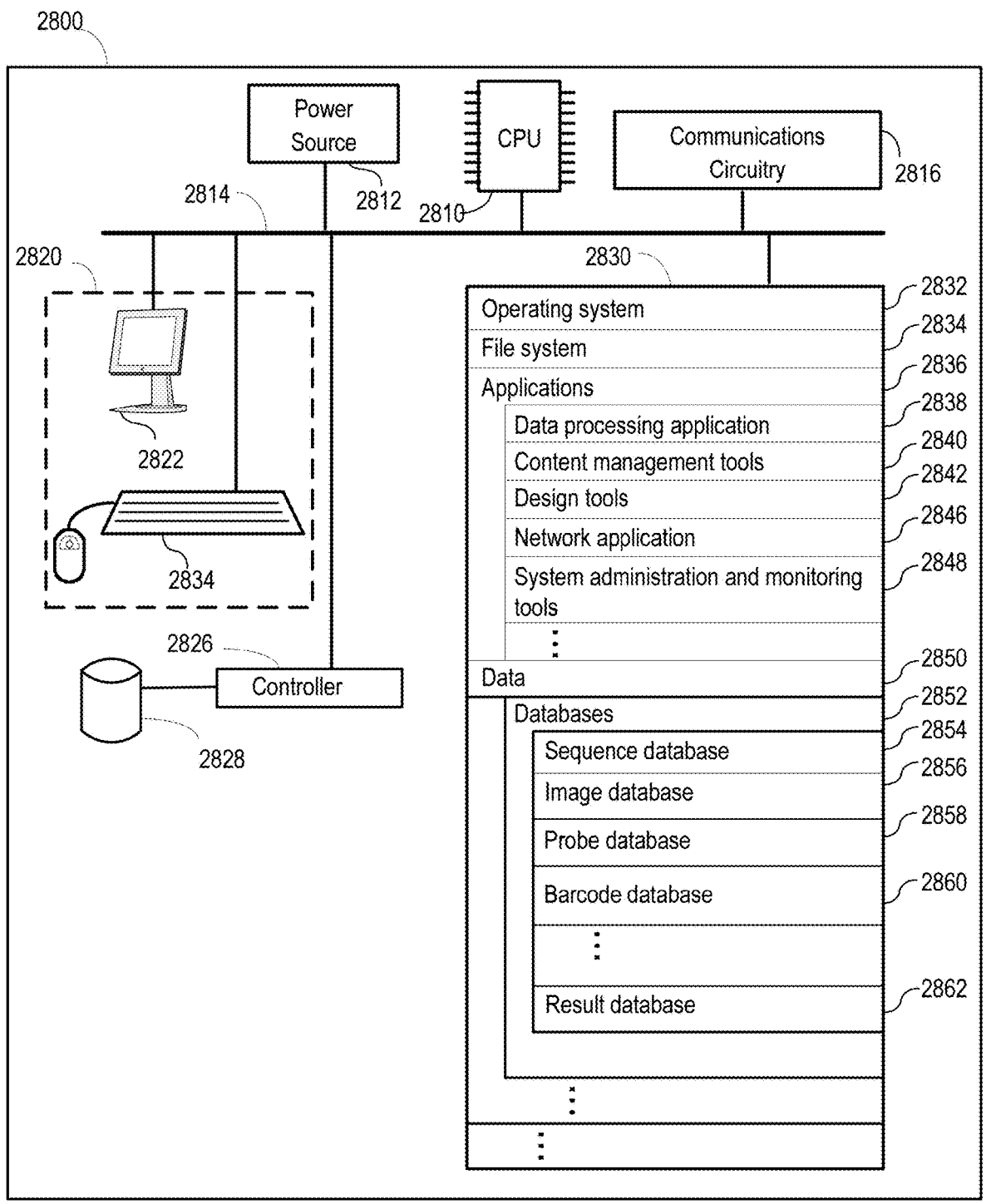
FIG. 28 illustrate an exemplary computer system for implementing the error correction methods disclosed herein.
Figure 29:
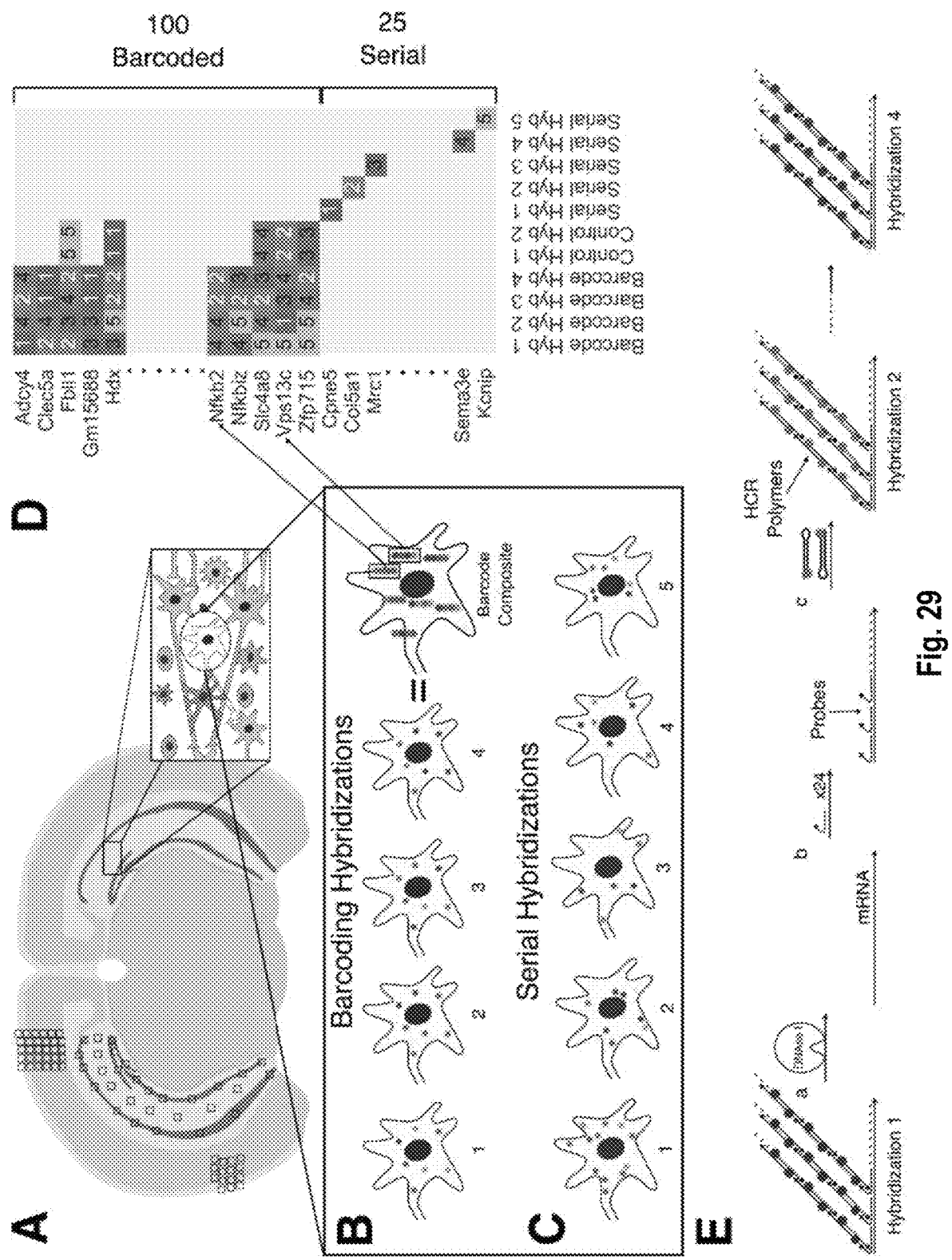
FIG. 29 depicts an overview of the Sequential barcode FISH (seqFISH) in brain slices. A). A coronal section from a mouse brain was mounted on a slide and imaged in all boxed areas. Each image was taken at 60× magnification. B). Example of barcoding hybridizations from one cell in field from A. The same points are re-probed through a sequence of 4 hybridizations (numbered). The sequence of colors at a given location provides a barcode readout for that mRNA ("barcode composite"). These barcodes are identified through referencing a lookup table abbreviated in D and quantified to obtain single cell expression. In principle, the maximum number of transcripts that can be identified with this approach scales to FN, where F is the number of fluorophores and N is the number of hybridizations. Error correction adds another round of hybridization. C). Serial smHCR is an alternative detection method where 5 genes are quantified in each hybridization and repeated N times. Serial hybridization scales as F*N. D). Schematic for multiplexing 125 genes in single cells. 100 genes are multiplexed in 4 hybridizations by seqFISH barcoding. This barcode scheme is tolerant to loss of any round of hybridization in the experiment. 25 genes are serially hybridized 5 genes at a time by 5 rounds of hybridization. Each number represents a color channel in single molecule HCR. As a control, 5 genes are measured both by double rounds of smHCR as well as barcoding in the same cell. E. SmHCR amplifies signal from individual mRNAs. After imaging, DNAse strips the smHCR probes from the mRNA, enabling rehybridization on the same mRNA (step a). The "color" of an mRNA can be modulated by hybridizing probes that trigger HCR polymers labeled with different dyes (step b). mRNA are amplified following hybridization by adding the complementary hairpin pair (step c). The DNAse smHCR cycle is repeated on the same mRNAs to construct a predefined barcode over time.
Figure 30:
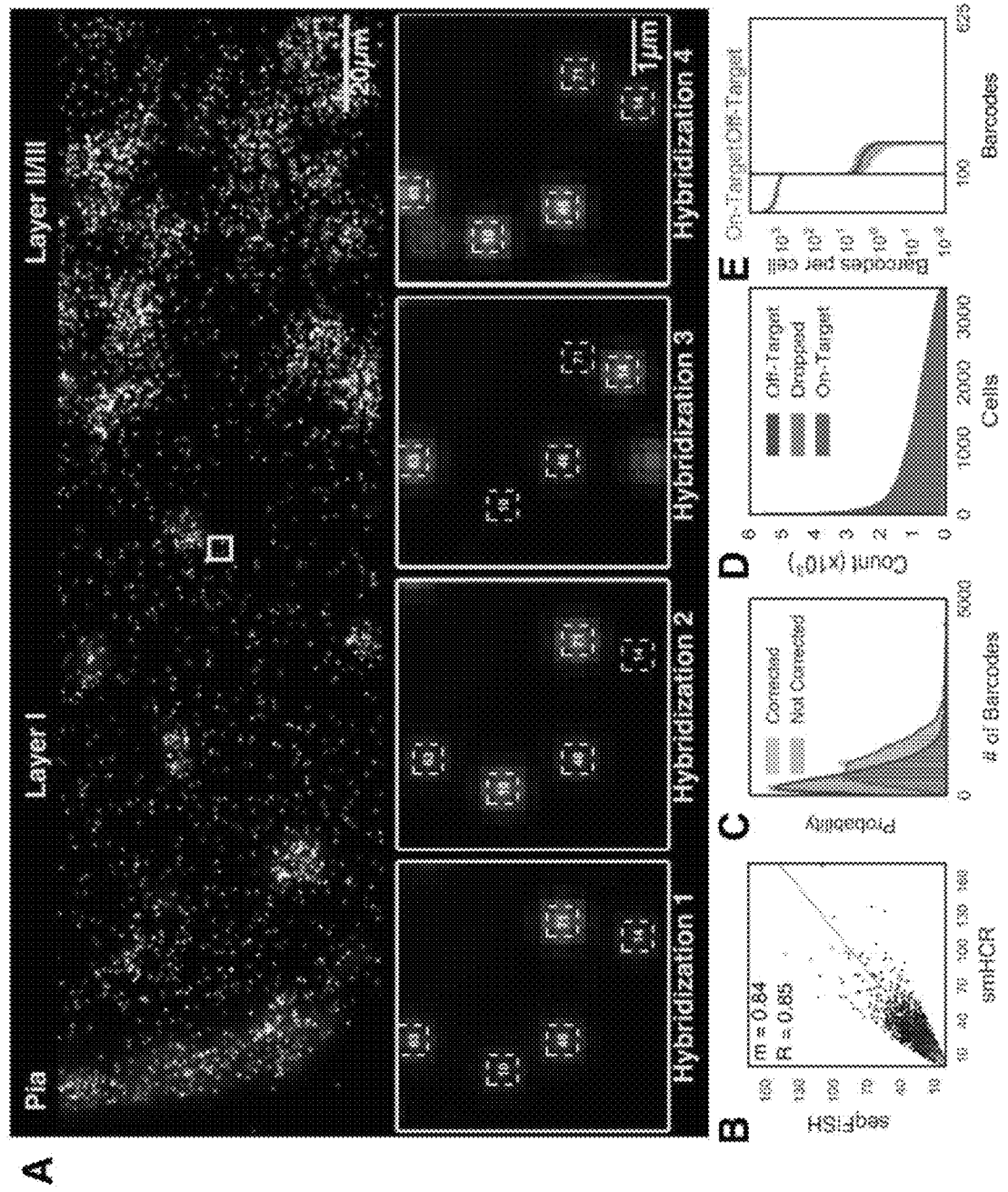
FIG. 30 illustrates an example accurate in situ quantification of mRNA levels generated by seqFISH. A). Image of seqFISH barcoding 100 genes in the outer layer of the mouse cortex. RNA dots in the image are z projected over 15 µm. Individual mRNA points are shown across 4 hybridizations in the inset images. White squares correspond to identified barcodes, yellow squares correspond to missing transcripts in a particular hybridization, red squares correspond to spurious false positives and are not counted in any barcode measurements. Numbers in the squares correspond to barcode indices. B). seqFISH correlates with smHCR counts. After barcoding, 5 target mRNAs were measured twice by smHCR in the same cells, providing absolute counts of the transcripts. The two techniques correlate with an R=0.85 and a slope (m) of 0.84 (n=3851 measurements). The 2D histogram intensity shows the distribution of points around the regression line. A high density of points is seen along the regression line. The density falls off steeply around the regression line. C). Error correction results in a median gain of 373 (25%) counts per cell (n=3497). Red and blue curves correspond to the total barcode counts per cell before and after error correction. D). Dropped and off-target barcodes represent a small source of error in seqFISH. 100 on-target barcodes and 525 off-target barcodes are measured per cell. Dropped barcodes are due to at least two overlapping dots appearing within the same region. E. Off-target barcodes are rarely observed and contribute minimally to the expression profile in single cells. Each of the 100 on-target barcodes (blue) and 525 off-target barcodes (red) are quantified per cell. The mean is shown with shaded regions corresponding to 1 SD (N=41 imaged regions).

Probe design contributes to specificity of binding between the probes and target sequences. It is possible to apply hybridization chain reaction to allow multiple probes to bind at the same target sequence to amplify detectable signals. Additionally, as illustrated in FIGS. 28 and 29, it is possible to insert a cleavable linker between the binding sequence (that binds a target sequence) and signal moiety (that emits visible signals) of a probe. Here, error can be reduced because no removal of probes is needed for the next round of hybridization. Instead, only visible signals are switched.

Barcodes implemented during the analysis are unique. Nonspecific binding or other mistakes can render the results from one or more rounds of hybridization unreliable. A simple solution is to remove data that are unreliable. However, if data from one or more rounds of hybridization are eliminated from analysis, some of the barcodes would become indistinguishable from each other.

During and after hybridization of probes to target sequences, there are also aspects that are important for improving the quality of the sequential analysis, including hybridization, image collection, signal removal and re-hybridization and data analysis.

Barcodes and Error Correction

In one aspect, disclosed herein are methods for designing barcodes with built-in error correction mechanisms such that the multi-component barcodes can withstand the loss of the data from one or more rounds of hybridization (i.e., drop-safe). As disclosed herein the terms "barcode" and "code" are used interchangeably.

As disclosed herein, by using probes that are associated with F detectable visual signals ($F \geq 2$), a sequential hybridization of N rounds ($N \geq 2$) can generate a total of $F^N$ combinations of visual signals. In some embodiments, these combinations of visual signals can be used as barcodes to uniquely identify cellular targets such as mRNA, DNA, or even protein.

Figure 27B:
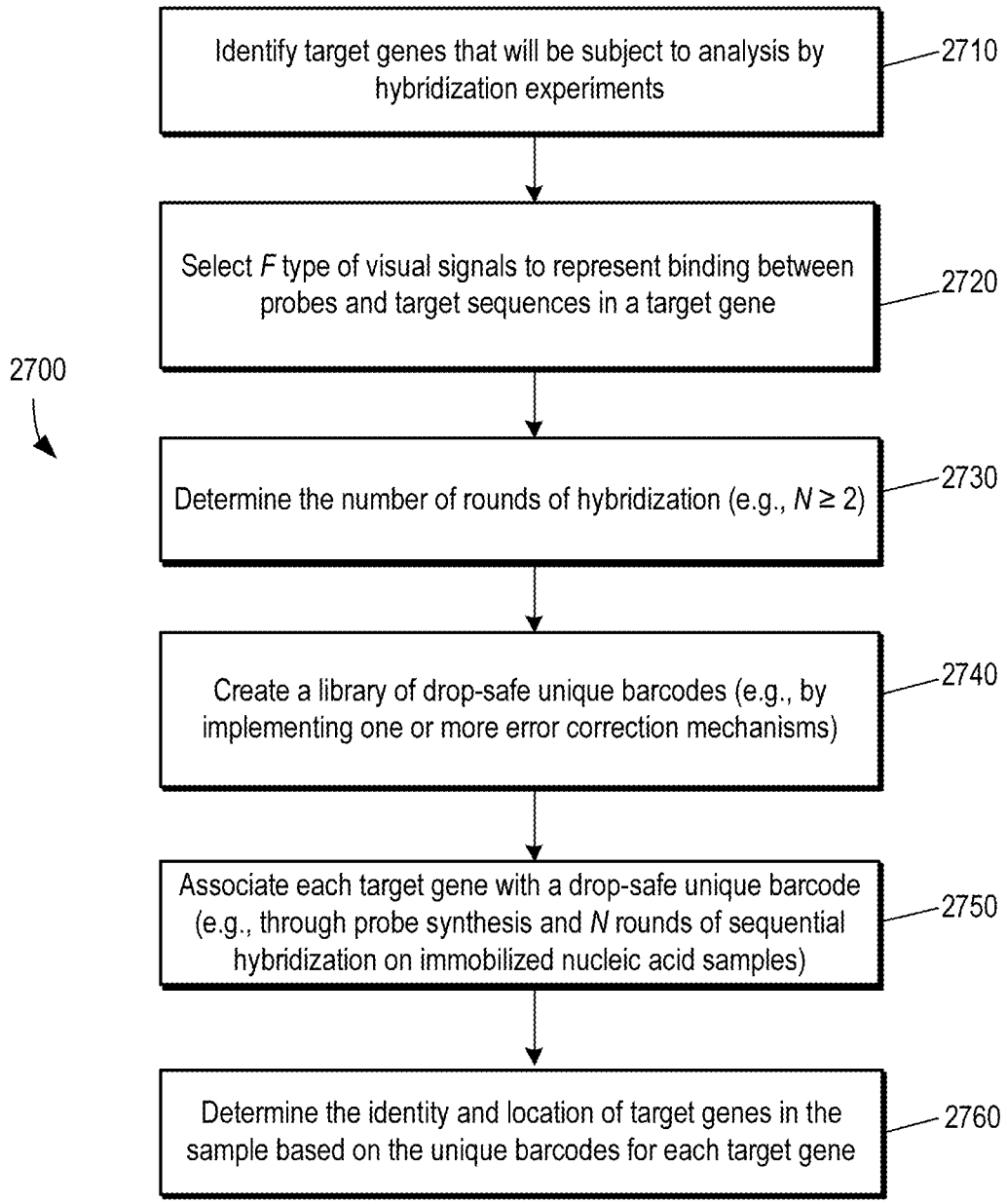
FIG. 27B illustrates an exemplary process for error correction.

FIG. 27B illustrates an exemplary process 2700 for generating drop safe barcodes.

At step 2710, the total number of genes that will be analyzed during the hybridization experiments is determined. This number sets the threshold values for the number of detectable visual signals (F) and the total number of rounds in the sequential hybridization (N).

Once the total number of genes is determined, steps 2720 and 2730 are performed simultaneously. The number of genes being analyzed must be smaller than the total number of possible combinations of visual signals ($F^N$). Practical aspects of the hybridization analysis need to be considered when selecting values for F and N. One would tend to reduce the number of rounds of hybridization to as few as possible. Theoretically, this can be achieved by using a high number of detectable visual signals (F). In practice, however, too many different types of visual signals may interfere with each other. For example, overlapping of visual signals can lead to barcode misidentification.

At step 2740, a library of drop-safe unique barcodes are generated by implementing one or more error correction mechanisms.

In some embodiments, a repeat round can be performed for any round during a sequential hybridization of N rounds, rendering a new sequential hybridization of (N+1) rounds. The extra repeat round can be an error correction round. The repeat round can be a duplicate of any round of the n rounds sequential hybridization. The repeat round can take place as any round during the sequential hybridization (N+1) rounds.

After the repeat, there are two rounds of hybridization that should be identical to each other. Consequently, the complete loss of one of the repeat rounds does not affect the outcome of the sequential hybridization. As such, either of the repeat rounds is a drop-safe round.

Figure 2:
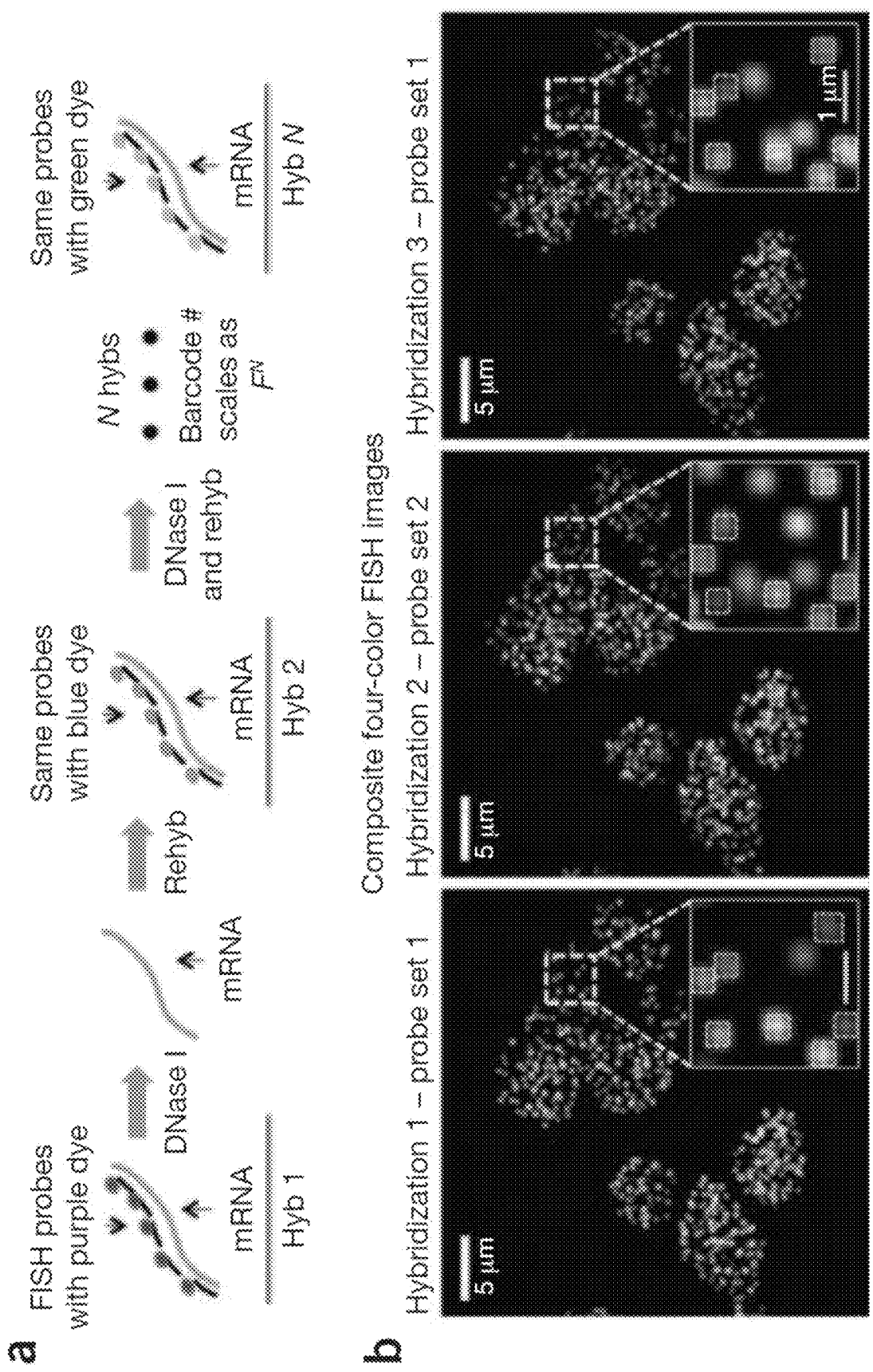
FIG. 2. Exemplary sequential barcoding of provided methods. (a) Schematic of sequential barcoding. In each round of hybridization, multiple probes (e.g., 24) were hybridized on each transcript, imaged and then stripped by DNase I treatment. The same probe sequences could be used in different rounds of hybridization, but probes were coupled to different fluorophores. (b) Composite four-color FISH Data from 3 rounds of hybridizations on multiple yeast cells. Twelve genes were encoded by 2 rounds of hybridization, with the third hybridization using the same probes as hybridization 1. The boxed regions were magnified in the bottom right corner of each image. The matching spots were shown and barcodes were extracted. Spots without co-localization, without the intention to be limited by theory, could be due to nonspecific binding of probes in the cell as well as mis-hybridization. The number of each barcode were quantified to provide the abundances of the corresponding transcripts in single cells. (c) Exemplary barcodes. mRNA 1: Yellow-Blue-Yellow; mRNA 2: Green-Purple-Green; mRNA 3: Purple-Blue-Purple; and mRNA 4: Blue-Purple-Blue.
Figure 2:
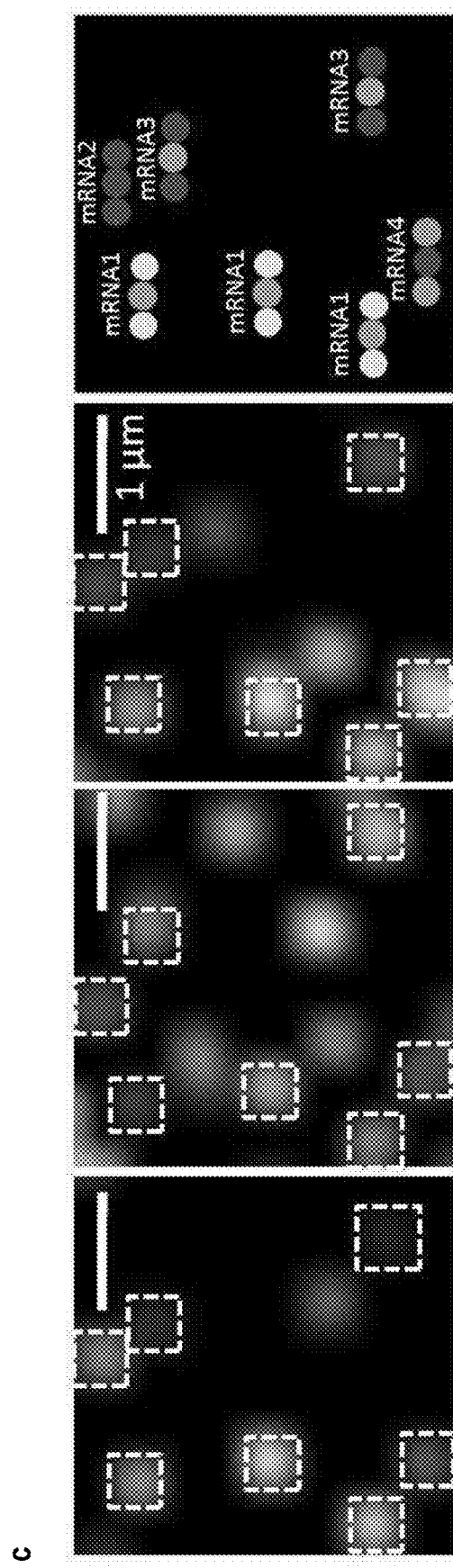

FIG. 2 illustrates an experiment where 3 rounds of hybridization using probes with 4 types of detectable visual signals (red: R, yellow: Y, green: G, and cyan: C) are used to create barcodes for 4 different mRNA molecules. Hybridization round 3 is a repeat of hybridization round 1, as summarized in Table 1 below.

TABLE 1

Illustration of the effect of repeat hybridization rounds.

| mRNA molecules | Color barcodes (3 rounds) | Color barcodes (dropping round 1) | Color barcodes (dropping round 3) |
|---|---|---|---|
| mRNA1 | Y-C-Y | C-Y | Y-C |
| mRNA2 | G-R-G | R-G | G-R |
| mRNA3 | R-C-R | C-R | R-C |
| mRNA4 | C-R-C | R-C | C-R |

As shown in the table above, data from one of the repeat rounds can be dropped completely in case of major experiment error, barcodes derived from the remaining rounds of hybridization still uniquely represent the mRNA molecules.

In some embodiments, even in a questionable hybridization round, most of the information is still reliable. Only some of the bindings between probes and target sequences include inaccurate information. In some embodiments, partial data from a questionable round of hybridization are used. For example, in the illustration above, binding signals can be missing or ambiguous for a particular location during hybridization round 1, which can produce an incomplete three letter barcode *-C-Y for the particular location, where * remains undetermined. In the scheme illustrated, the identity of * is not needed to decipher that the code is for mRNA1. Similarly, binding signals can be missing or ambiguous for a particular location during hybridization round 2, which can produce an incomplete three letter barcode R-*-R for the particular location, where * remains undetermined. Once again, the identity of * is not needed to decipher that the code is for mRNA3.

Additionally, data from repeat rounds can validate each other. For example, in FIG. 2C, a circle highlights a cyan data point in the image corresponding to hybridization round 2. In the same location, the image corresponding to hybridization round 3 reveals a yellow data point. Based on only information from hybridization rounds 2 and 3, this location would be identified as part of mRNA1. However, no signals are identified at the location during hybridization round 1, which suggests that the highlighted data points may be due to non-specific binding.

In some embodiments, a sophisticated barcode generating algorithm is used such that the resulting barcodes can withstand the loss of any round or even multiple rounds of hybridization data. In some embodiments, a barcode generator is used to generate the drop-safe barcodes. For example, FIG. 29 illustrates an example, where probes with 5 different visual signals (blue, green, red, purple and yellow) are used in 4 rounds of hybridization. One of the hybridization round is an error correction round where barcodes are generated based on barcodes from the previous 3 rounds. The following is an example that illustrates how barcodes are generated.

Designing an error correction code to correct for m number of errors in a message of n length is analogous to packing as many spheres of radius m in a n dimensional cube. There are examples of "perfect codes" such as Golay and Hamming codes that can be as efficient as possible in this packing design. These perfect codes are important in digital communication because the word lengths are long, up to billions of letters for gigabytes of data, and many forms of errors can occur, including deletion and insertions. However, in the seqFISH experiments, as the code lengths are short, a perfect code correction system is not necessary, especially as the "correct" codes are already defined. One of the major source of error is deletions due to loss of a hybridization. Thus, it is possible to design simple correction schemes that are not completely efficient (i.e. obtain the tightest packing density for the n-spheres) but can achieve good error correction with just a few extra rounds of hybridization.

To design a barcode scheme that can tolerate loss of a single round of hybridization is akin to a problem where any n-dimensional hypercube is collapsed by 1 dimension to a n−1 dimensional hypercube without having any two points on the n-dimensional hypercube mapping to the same point. In order for this to be true, no two barcodes can be connected by a 1D line running parallel to any of the axes. There are many solutions to generate this 1 round loss tolerant code.

In this example, 4 rounds of hybridization is used. Here, 5 different visual signals (blue, green, red, purple and yellow) are assigned numerical values. In some embodiments, the numerical values are integers. For example, blue=1; green=2; red=3; purple=4; and yellow=5. It would be understood that these are mere sample values. Any non-redundant numerical values can be assigned to represent the different types of visual signals. In some embodiments, a barcode generator is used to generate the barcodes used in the experiment. In the exemplary embodiment, a drop-safe barcode for a particular target gene can be defined as a four-component linear array: $\{i, (i+j+k) \bmod 5, j, k\}$. Here, mod (modulo operation or modulus) finds the remainder after division of one number by another. For example, 8 mod 5 is 3. 5 mod 5 is 0, which is equivalent to 5.

In this example, i represents the numerical values corresponding to the visual signals observed for the particular target gene during the first round of hybridization. (i+j+k) mod 5 represents the numerical values corresponding to the visual signals observed for the particular target gene during the second round of hybridization. j represents the numerical values corresponding to the visual signals observed for the particular target gene during the third round of hybridization. k represents the numerical values corresponding to the visual signals observed for the particular target gene during the found round of hybridization. In this example, i, j, and k each can be 1, 2, 3, 4 or 5, or any one of the numerical values that have been assigned to the five types of visual signals used in the experiment.

In this example, (i+j+k)mod 5 is determined as the error correction round. However, once complete barcodes are generated, any of round 1 through round 4 can be dropped to yield unique 3-component barcodes. As such, the barcodes determined by this method can be used to correct errors in any round.

The following table illustrates how the 1 drop tolerant barcodes can be generated using the equation (i+j+k)mod 5.

TABLE 2

Illustration of the effect of repeat hybridization rounds.

| Genes | $1^{st}$ round of hyb* | $2^{nd}$ round of hyb | $3^{rd}$ round of hyb | $4^{th}$ round of hyb (i + j + k) mod 5 |
|---|---|---|---|---|
| mRNA1 | 1 | 2 | 4 | 2 |
| mRNA2 | 3 | 3 | 1 | 2 |
| mRNA3 | 5 | 1 | 2 | 3 |
| mRNA4 | 2 | 3 | 5 | 5 |
| ... | ... | | | |
| mRNA125 | 5 | 2 | 1 | 3 |

*The term "hyb." stands for hybridization. Numerical values are assigned to color signals as follows: blue = 1; green = 2; red = 3; purple = 4; and yellow = 5.

As illustrated above, although the $4^{th}$ round of hybridization is generated using an error correction algorithm, any one round of four rounds of hybridization in Table 2 can be dropped and still yield a unique set of barcodes for 125 genes.

Figure 37:
FIG. 37 depicts an example embodiment, showing barcode assignments for all genes in the combined hybridization experiment (FIG. 29). Barcode assignments in the 125-gene seqFISH and serial experiment (FIG. 29). 125 genes are profiled, 100 of which are barcoded and 25 are identified by serial smHCR hybridizations. Five control genes (Hdx, Vps13c, Zfp715, Fbll1, Slc4a8) were quantified by both techniques. The smHCR round of hybridization of control genes were performed twice to co-localize signal to obtain an absolute count.
Figure 38:
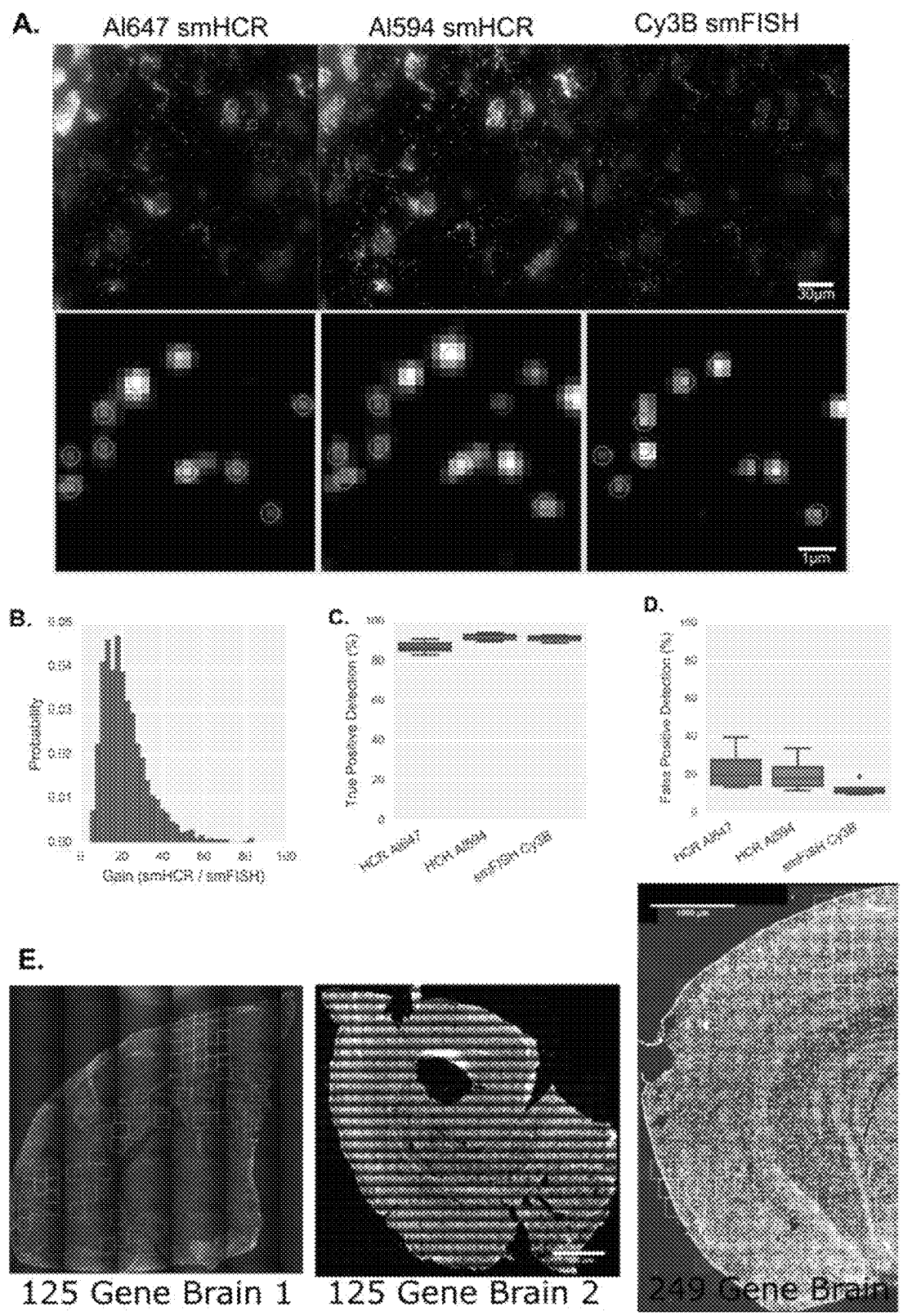
FIG. 38 depicts an example embodiment, showing smHCR performance metrics as compared to smFISH, (related to FIG. 29). A). Raw data of Pgk1 transcripts imaged in a brain slice. The transcript was targeted with 2 her probes sets and 1 smFISH probe set, each consisted of 24 oligonucleotide probes. The probe sets were hybridized together and were imaged in 3 different channels. Green circles are transcripts detected in all channels, yellow circles signify transcripts detected in 2 out of 3 channels, and red circles represent signal found in only 1 channel (false positives due to nonspecific binding). These images show that smHCR and smFISH have similar sensitivity, specificity, and spot size. B). Gain of smHCR vs smFISH. The mean gain of smHCR is 22.1±11.55 vs smFISH (n=1338). C). True positive detection rate of smHCR and smFISH per channel. The percent of true positives (transcripts detected with at least 2 out of 3 probe sets) detected with each probe set (n=1338). D). False positive rate of smHCR and smFISH. Percent of total dots in a channel not detected in any other channel for 3 color Pgk1 (n=1338). E). All the regions imaged in the coronal section are boxed. Each box represents a field of 216 um×216 um. The brain section used for FIGS. 32 and 33 is shown on the left. The middle section is used for FIG. 34 and the right section is used for FIG. 35.

More generally, a barcode that can resist the elimination of one round of hybridization can be defined as:

$$\{j_1, j_2 \ldots (a_1{}^*j_1 + a_2{}^*j_2 + \ldots + a_n{}^*j_n + C) \mod F, \ldots j_n\} \quad (1)$$

where $j_1$ is a numerical value that corresponds the detectable visual signals used in the first round of hybridization, $j_2$ is a numerical value that corresponds the detectable visual signals used in the second round of hybridization, and $j_n$ is a numerical value that corresponds the detectable visual signals used in the nth round of hybridization. In some embodiments, $j_1, j_2, \ldots j_n$ are non-redundant integers. In some embodiments, $a_1, a_2, \ldots a_n$ can be any integers that are not none zero. In some embodiments, C is a constant integer. In some embodiments, C is zero. The remainder of F divided by F is 0 (F mod F=0), so F and 0 are equivalent. There is no limitation on the number of hybridization. One of such examples is shown in FIG. 37.

Array (1) is a general representation of a barcode that is safe against the drop or loss of one round of hybridization. Although $(a_1{}^*j_1 + a_2{}^*j_2 + \ldots + a_n{}^*j_n + C)$ mod F is the designated error correction round, in some embodiments, the barcode is safe against the loss or drop of any round of hybridization.

As disclosed herein, array (1) consists of n-component, each corresponding to the visual signals from a particular round of hybridization. In some embodiments, probes binding to a particular gene are all associated with the same detectable visual signal, for example, red, green or blue. In some embodiments, probes binding to a particular gene are all associated with multiple types of detectable visual signal, for example, green+yellow or blue+red. Through combinations of visual signals, the total number of different types of detectable visual signals can be further expanded.

In some embodiments, barcodes can be designed such that drop or loss of data from two rounds of hybridization can be tolerated. Using 2 additional rounds of hybridization does not correct for all possible 2 drops, but it does correct for a large fraction of the 2 drops. For example, for detecting 100 genes with F=5 dyes, 3 rounds of hybridization are needed for basic barcoding of these genes. When adding two rounds of hybridization, the error correction code:

$$\{i,j,k,(i+j+k)\mod F,(i-j)\mod F\} \quad (2)$$

Such codes can correct for 2 drops all except dropping hybridization round 3 and round 4 together. Here, each component in the 5-member array represents one round of hybridization.

Similarly, an error correction code such as $$\{i,j,k,(i+j+k)\mod F,(i-k)\mod F\} \quad (3)$$

can correct for dropping hybridization round 2 and hybridization round 4 together. Again, each component in the 5-member array represents one round of hybridization.

For example, to code for most of the transcriptome, only 6 rounds of hybridization are needed when F=5 ($6^5$=15,625). When adding two rounds of hybridization, the following error correction code is generated:

$$\{i,j,k,l,m,n,(i+k+1+m+n)\mod F,(i-j-k-l+n)\mod F\} \quad (4)$$

There are a total of 28 combinations of how 2 rounds of hybridization can be lost or dropped. This type of code can correct for 24 out of the total 28 combinations. Here, each component in the 8-member array represents one round of hybridization. Similarly, the $1^{st}$ error correction round can be any liner combination of 5 out of 6 rounds of hybridization (e.g., without j) and $2^{nd}$ error correction can be a subset of the linear combination of 5 out of 6 rounds of hybridization (e.g., without m). In these embodiments, in the $2^{nd}$ error correction round, indices include different coefficients as long as the it is not exactly the same 5 indices used in the $1^{st}$ error correction round.

To correct for all combinations of drop or loss of 2 rounds of hybridization (2 drops) fully, 3 additional hybridizations are needed. Again for 6 rounds of hybridization with 5 types of detectable signals (F=5), three extra rounds of hybridizations are added to create the full 9-member error correction code:

$$\{i,j,k,l,m,n,(i+j+k+1+m+n)\text{Mod } F,(i-j-k-l)\text{Mod } F,(m-n-j+k)\mod F\} \quad (5)$$

In some embodiments, there are many equivalent codes that can correct for 2 drops with 3 additional rounds of hybridization. They can be all empirically determined. The number of hybridization for any reasonable number can be simulated to determine the complete correcting barcode.

In some embodiments, three additional hybridization can correct for majority of the errors due to drop or loss of three rounds of hybridization. For example, for 6 rounds of hybridization with 5 types of detectable signals (F=5), three extra rounds of hybridizations are added to create the full 9-member error correction code:

$$\{i,j,k,l,m,n,(k+i-l+m-n)\mod F,(i-l+j-k+m)\mod F,(l-n-j-k+i)\mod F\} \quad (6)$$

Similar to the previous example, 3 additional rounds of hybridizations can correct for a majority of the loss or drop of 3 rounds of hybridization. There are a total of 84 combinations how 3 rounds of hybridization can be lost or dropped. A 9-component code as illustrated in (6) can correct for 72 out of the 84 combinations.

In some embodiments, 4 additional rounds of hybridizations can correct for the drop or loss of all and any three rounds of hybridization. An example 10-component code is as follows:

$$\{i,j,k,l,m,n,(k+i+l+m+n) \bmod F, (i-l+j-k+m) \bmod F, (l-n-j-k+i) \bmod F, (n-k-i-j+m) \bmod F\} \quad (7)$$

It will be understood that there are many other solutions that can be determined empirically. For higher number of drops, similar correction schemes can be determined empirically.

For 16,000 species, this scheme allows 10 hybs with the ability to correct 3 drops. In comparison, in MERFISH, 16 hybs are needed to target 140 species, with only 2 round correction ability. Because the more round of hybridization one implements, the more mistakes can be made, keeping the number of hybs low is crucial. Thus, this error correction scheme is very powerful compared to the Hamming Distance scheme used in MERFISH. This is because hamming distance correction is used in telecommunications with binary numbers, which uses much longer strings of 0,1.

As described above, the design disclosed above can correct for loss of 1 hybridization for an arbitrarily long barcode sequence with minimal extra effort. In this example, only one round of error correction is needed in a total of 4 rounds of hybridization that analyzes 100 genes, which below the capacity of 54 (625).

For example, 7 rounds of hybridization with 5 colors can cover $5^7=78,125$ transcripts, more than the transcriptome, with 8 hybridizations the entire transcriptome can be coded with error correction using the barcoding system disclosed herein.

Another consideration in designing error-tolerant barcodes is that the mechanism of re-hybridization should guide the robustness of error correction. In the merFISH implementation of seqFISH (Chen 2015), null signal, or "0", along with "1" which is cy5 fluorescence, is used to form a binary barcode. However, it is difficult to determine whether no signal is due to mis-hybridization or actual null signal. In the seqFISH implementation using positive signals as readouts during each round of hybridization reduces the need for error correction because false positive signal is unlikely to re-occur in the same position during another hybridization due to DNAse stripping between hybridizations. Thus, implementation of seqFISH with 5 colors and 1 extra round of hybridization to error correct is both efficient and accurate, and allows imaging of a large tissue sections since imaging time is ultimately limiting in multiplexing experiments.

At step 2750, sequential hybridization is carried out to associate or assign barcodes from step 2740 to target genes in a sample. As disclosed herein, the sample can be immobilized mRNAs, DNAs, chromosomal DNAs, and combinations thereof. For example, in the 100-gene sequential hybridization example (see FIG. 29 and FIG. 37), 4 rounds of hybridization are carried out using probes associated with 5 different types of visual signals. Barcodes are assigned through selection of probes during the 4 rounds of hybridization experiment on immobilized nucleic acid samples.

At step 2760, after hybridization, visual signals are collected and used in further analysis. For example, images are collected from different hybridization are used to readout the barcodes for specific locations on the immobilized nucleic acid samples. Such barcodes can then be used to decipher the identity of the nucleic acid targets (see, for example, FIGS. 2, 29, 30, 37 and 38).

In one aspect, sequential hybridization and serial hybridization are combined for gene identification. In serial hybridization, only one round of hybridization is used to identify target genes. The method is particularly helpful when analyzing genes whose expression level is too high. In some embodiments, genes that are highly expressed, if included in hybridization analysis with genes that are not so highly expressed, would overpower the signals for the genes that are not so highly expression. In some embodiment, the method can also applied to genes whose expression level is too low.

In some embodiments, expression levels of genes are pre-determined. For example, gene expression levels (e.g., measured by mRNA transcription level) can be already available for certain species. It is possible to identify highly expressed genes by mining publically available data, thus obviating the need to conduct additional experiments to measure expression level.

In some embodiments, initial experiments are performed to determine relative expression level of candidate genes. In some embodiments, genes are grouped according to their expression levels. For example, genes with moderate or low expression levels can be grouped together and subject to sequential hybridization analysis. Genes that are highly expressed can be subject to serial hybridization analysis. In some embodiments, expression levels of different genes are compared to the same control gene to derive a relative expression level. For example, the expression level of actin can be used as a control. It will be understood that gene expression level may vary by organisms and can change with respect to different internal and environmental controls. In some embodiments, data from existing expression analysis can be used in identifying highly expressed gene. In some embodiments, preliminary expression analysis is carried out before sequential and/or serial hybridization analysis.

In some embodiments, a threshold value is set for high expression. Any genes having expression level above the threshold will be excluded from sequential hybridization.

Depending on types of detectable visual signals that are available, a serial hybridization experiment can detect as many target genes as the number of types of detectable visual signals. For example, in the experiment illustrated in FIGS. 29 and 37, 5 genes are analyzed at the same time during one serial hybridization experiment.

In some embodiments, when multiple target genes are present in one serial hybridization round, the number of probes that recognize each target gene is selected such that overlapping of signals is minimize or avoided. In some embodiments, the concentration of probes are selected to avoid or minimize overlapping of detectable signals.

Computer System

In some embodiments, a computer system 2800, local or accessible via remote access, may comprise a central processing unit 2810, a power source 2812, a user interface 2820, communications circuitry 2816, a bus 2814, a controller 2826, an optional non-volatile storage 2828, and at least one memory 2830. In some embodiments, computer 2800 is a local computer device. In some embodiments, computer 2800 is a remote server.

Memory 2830 may comprise volatile and non-volatile storage units, for example random-access memory (RAM), read-only memory (ROM), flash memory and the like. In preferred embodiments, memory 2830 comprises high-speed RAM for storing system control programs, data, and application programs, e.g., programs and data loaded from non-volatile storage 2828. It will be appreciated that at any given time, all or a portion of any of the modules or data structures in memory 2830 can, in fact, be stored in memory 2828.

User interface 2820 may comprise one or more input devices 2824, e.g., keyboard, key pad, mouse, scroll wheel, touch screen, and the like, and a display 2822 or other output device. A network interface card or other communication circuitry 2816 may provide for connection to any wired or wireless communications network, which may include the Internet and/or any other wide area network, and in particular embodiments comprises a telephone network such as a mobile telephone network. Internal bus 2814 provides for interconnection of the aforementioned elements of centralized data server 2800.

In some embodiments, operation of computer 2800 is controlled primarily by operating system 2832, which is executed by central processing unit 2810. Operating system 2832 can be stored in system memory 2830. In addition to operating system 2832, a typical implementation system memory 2830 may include a file system 2834 for controlling access to the various files and data structures used by the present invention, one or more application modules 2836, and one or more databases or data modules 2850.

In some embodiments in accordance with the present invention, applications modules 2836 may comprise one or more of the following modules described below and illustrated in FIG. 28.

Data Processing Application 2838. In some embodiments, a data processing application 2838 receives and processes data collected during hybridization experiments (for either sequential or serial hybridization). For example, detectable signals are collected as images and stored computer 2800. Standard image processing algorithms can be applied to enhance signal detection. In some embodiments, coordinates are assigned to data locations where signals are detected to precisely define the binding between probes and target sequences. The positions of such target sequences do not change between different rounds of hybridization because the target sequences are part of the immobilized nucleic acid samples. Thus, by comparing coordinates of data locations between different images, it is possible to identify the same target sequence in each image and characterize the detectable signals associated with the same target sequence between different images.

In some embodiments, the detectable signals for the same location (target sequence) change from one color to another between different images. In some embodiments, the detectable signals for the same location (target sequence) remain the same color between different images. The characteristics of these detectable signals are compiled between images from all hybridization rounds to derive a barcode that uniquely represents the binding interaction at the particular location.

In some embodiments, data processing application 2838 detects and corrects minor shifts between different images. In some embodiments, data processing application 2838 detects major changes between different images that cannot be corrected.

For image data collection during serial hybridization, data processing application 2838 identifies and characterizes detectable signals by their type. In this case, the same detectable signal represents binding sequences in the same target gene. Data processing application 2838 identifies and characterizes each type of detectable signal.

The methods and systems are provided by way of illustration only. They should in no way limit the scope of the present invention.

Content Management Tools 2840.

In some embodiments, content management tools 2840 are used to organize different forms of data 2850 into multiple databases 2852, e.g., a sequence database 2854, an image database 2856, a probe library database 2858, a barcode library database 2860, and result database 2862. In some embodiments in accordance with the present invention, content management tools 2840 are used to search and compare any of the databases hosted on the computer system 2800. Contents in accordance with the invention may be an image, a simple text file (e.g., ASCII), a formatted text file, a sequence file, a two-dimension map, or a video file.

The databases stored on computer system 2800 comprise any form of data storage system including, but not limited to, a flat file, a relational database (SQL), and an on-line analytical processing (OLAP) database (MDX and/or variants thereof). In some specific embodiments, the databases are hierarchical OLAP cubes. In some embodiments, the databases each have a star schema that is not stored as a cube but has dimension tables that define hierarchy. Still further, in some embodiments, the databases have hierarchy that is not explicitly broken out in the underlying database or database schema (e.g., dimension tables are not hierarchically arranged). In some embodiments, the databases in fact are not hosted on computer system 2800 but are in fact accessed by centralized data server through a secure network interface. In such embodiments, security measures such as encryption is taken to secure the sensitive information stored in such databases.

Design Tools 2842.

In some embodiments, design tools 2842 are used to design probes for specific binding of target sequences. For example, for nucleic acid probe design, design tools 2842 can utilize sequence information from sequence database 2854 to create probes that will likely bind to a specific target sequence. In some embodiments, design tools 2842 can utilize secondary and tertiary structure information from sequence database 2854 to design probes that will avoid regions containing hairpins or other structures that may interfere with binding between the probes and their respective target sequences.

In some embodiments, design tools 2842 are used to create barcodes. For example, design tools 2842 can utilize a barcode generator with built-in error correction mechanisms. In some embodiments, error correction mechanisms are saved as additional data 2862. In some embodiments, a user can define the number hybridization rounds that the final barcode can tolerate to loss. For example, depending on the total number of rounds of hybridization, a user can set the barcode to be one drop safe, two-drop safe or three-drop safe.

Network Application 2846.

In some embodiments, network applications 2846 connect computer system 2800 with multiple network services. Computer system 2800 can be connected to multiple types of client devices, which requires that remote data server be adapted to communications based on different types of network interfaces, for example, router based computer network interface, switch based phone like network interface, and cell tower based cell phone wireless network interface, for example, an 802.11 network or a Bluetooth network. In some embodiments in accordance with the present invention, upon recognition, a network application 2846 receives data from intermediary gateway servers before it transfers the data to other application modules such as data processing application 288, content management tools 2840, and system administration and monitoring tools 2842.

System Administration and Monitoring Tools 2848.

In some embodiments, system administration and monitoring tools 2842 administer and monitor all applications and data files of computer system 2800. Because some of the information stored on remote data server 2800 can relate to a person's privacy (e.g., personal data associated with certain biological samples and analytical results of these samples), it is important that access those files that are strictly controlled and monitored. System administration and monitoring tools 2842 determine which users or devices have access, locally or remotely, to computer system 2800. In some embodiments, security administration and monitoring is achieved by restricting data download access from computer system 2800 such that the data are protected against malicious Internet traffic. In some embodiments, system administration and monitoring tools 2842 use more than one security measure to protect the data stored on computer system 3800. In some embodiments, a random rotational security system may be applied to safeguard the data stored on computer system 2800.

Sequence Database 2854.

Sequence database store information relating to potential targets for hybridization analysis, such as sequence, secondary and tertiary structure information. For example, secondary and tertiary structure in nucleic acids may prevent probes from binding to such regions. In some embodiments, sequence database 2854 includes a subset database including regions that would likely be good probe binding targets. In some embodiments, sequence database 2854 includes a subset database including regions that would likely be poor probe binding targets. Such information is provided to design tools 2842 to facilitate probe design.

In some embodiments, sequence database 2854 further includes gene expression information. For example, sequence database 2854 can include a subset of genes whose expression levels may be too high for sequential hybridization analysis. In some embodiments, a user may receive a warning message if one of the gens in the subset is identified as a target gene.

Image Database 2856.

In some embodiments, computer system 2800 hosts an Image database 2856. Raw data collected off the detectable signals are organized and stored in image database 2856.

Probe Database 2858.

In some embodiments, probes that have been designed are stored in designated probe database on computer system 2800. In some embodiments, information concerning previously designed probes includes binding sequence, a signal moiety that can emit detectable signals. In some embodiments, a linker for connecting the signal moiety to the binding sequence is also included in probe database 2858.

In some embodiments, certain probe designs are ranked based on existing data showing the efficacy of binding of these probes. The existing data can be publically available information or information generated by the user. In some embodiments, a user is given the option to edit entries in probe database 2858.

Barcode Database 2860.

In some embodiments, barcodes that have been designed are stored in designated barcode database 2860 on computer system 2800. In some embodiments, information concerning previously designed barcodes includes types of detectable signals forming the barcodes. In some embodiments, barcode database 2860 further includes information on whether any ambiguities or errors are associated with certain barcodes.

In some embodiments, barcodes used in the past are ranked based on their efficiency and accuracy in identifies cellular targets.

Additional Data 2862.

In some embodiments, additional data 2862, including for example, results and conclusions from sequential hybridization and serial hybridization analysis are also stored on computer system 2800. In some embodiments, error correction mechanisms are saved as additional data 2862. In some embodiments, data needed for image processing are also saved as additional data 2862.

The methods and systems are provided by way of illustration only. They should in no way limit the scope of the present invention.

Computer System and Program Product

The present invention can be implemented as a computer system and/or a computer program product that comprises a computer program mechanism embedded in a computer readable storage medium. Further, any of the methods of the present invention can be implemented in one or more computers or computer systems. Further still, any of the methods of the present invention can be implemented in one or more computer program products. Some embodiments of the present invention provide a computer system or a computer program product that encodes or has instructions for performing any or all of the methods disclosed herein. Such methods/instructions can be stored on a CD-ROM, DVD, magnetic disk storage product, or any other computer readable data or program storage product. Such methods can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. Such methods encoded in the computer program product can also be distributed electronically, via the Internet or otherwise, by transmission of a computer data signal (in which the software modules are embedded) either digitally or on a carrier wave.

Some embodiments of the present invention provide a computer system or a computer program product that contains any or all of the program modules as disclosed herein. These program modules can be stored on a CD-ROM, DVD, magnetic disk storage product, or any other computer readable data or program storage product. The program modules can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. The software modules in the computer program product can also be distributed electronically, via the Internet or otherwise, by transmission of a computer data signal (in which the software modules are embedded) either digitally or on a carrier wave.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Further, the foregoing has been a description of certain non-limiting embodiments of the invention. Accordingly, it is to be understood that the embodiments of the invention herein described are merely illustrative of the application of the principles of the invention. Reference herein to details of the illustrated embodiments is not intended to limit the scope of the claims.

Example 1

Sequential Hybridization and Barcoding

In Situ Profiling of Nucleic Acids by Sequential Hybridization and Barcoding

As described in the non-limiting examples herein, nucleic acids in cells, for example, mRNAs, were profiled by provided methods through sequential rounds of contacting, imaging and removing steps (FIGS. 2 (a) and 3). As the transcripts are fixed in cells, the corresponding fluorescent spots remain in place during multiple rounds of hybridization, and can be aligned to read out a fluorophore sequence. This sequential barcode is designed to uniquely identify an mRNA.

During each round of hybridization, each transcript was targeted by a set of detectably labeled oligonucleotides, in this case, FISH probes labeled with a single type of fluorophore. The sample was imaged and then treated it with DNase I to remove the FISH probes. In a subsequent round the mRNA was hybridized with FISH probes with the same set of oligonucleotide sequences, but now labeled with a different dye. The number of barcodes available scales as $F^N$, where F is the number of fluorophores and N is the number of hybridization rounds. For example, with 4 dyes, 8 rounds of hybridization can cover almost the entire transcriptome ($4^8=65,536$).

Figure 4:
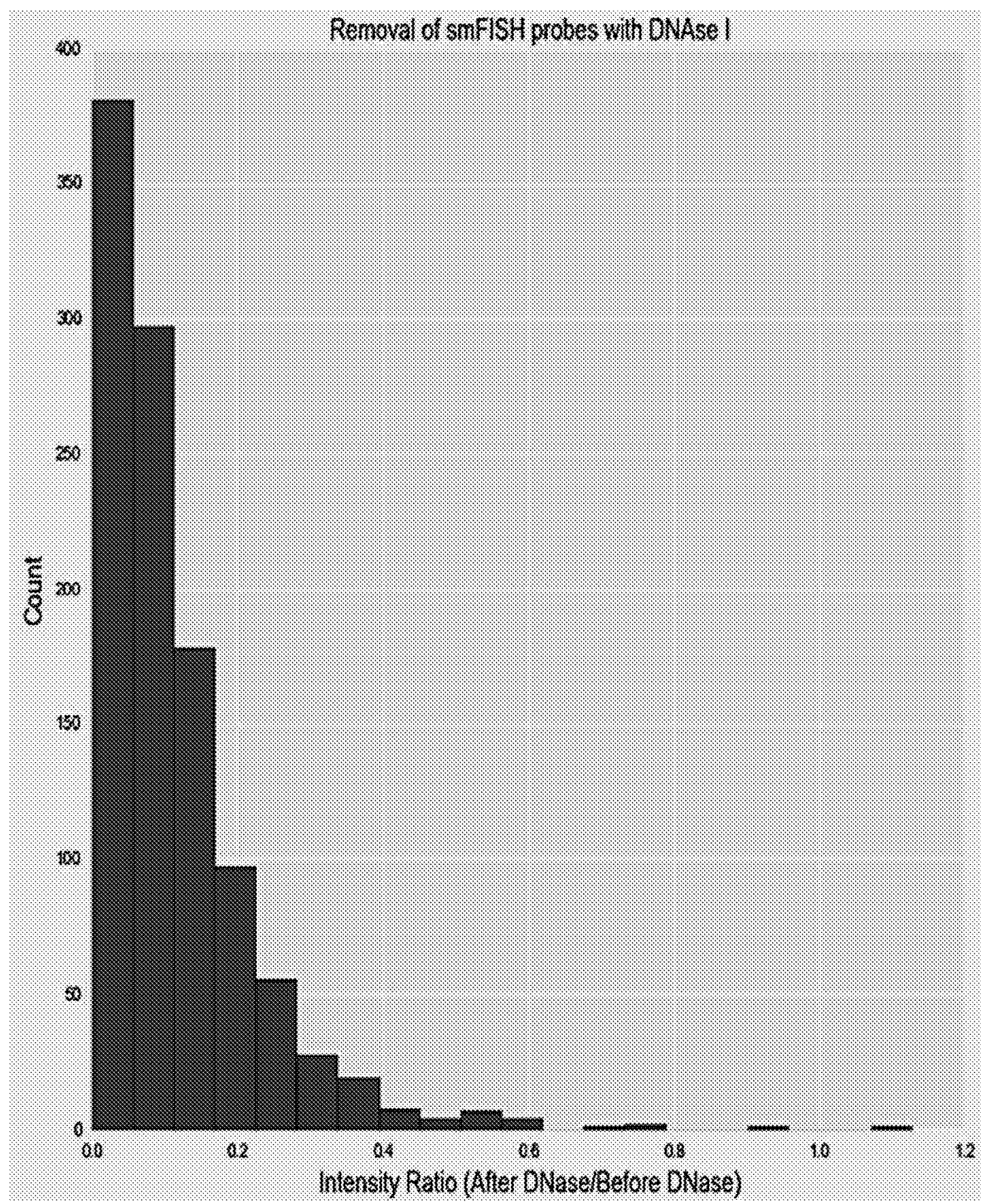
FIG. 4. DNase I efficiently removes smFISH probes bound to mRNA. DNase I efficiently removes smFISH probes bound to mRNA. Spots were imaged before and after a 4 hour DNase I treatment in anti-bleaching buffer. The mean, median and STD of the intensity ratio after treatment were 11.5%, 8.3% and 11%. The ratio of the spot intensities after and before DNase I treatment was plotted for each spot. n=1084 spots.
Figure 5:
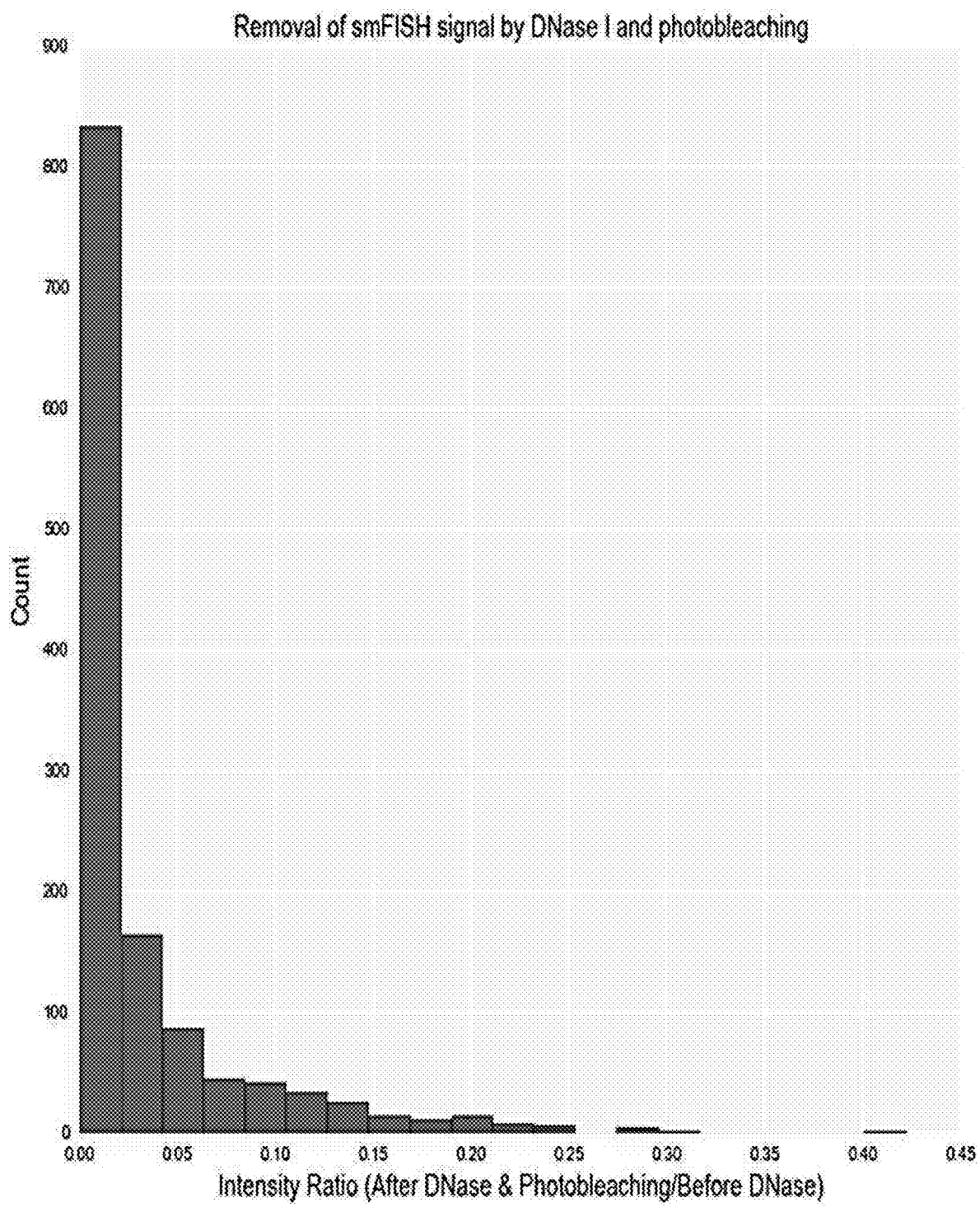
FIG. 5. Photobleaching removes residual intensity following DNase I treatment. Photobleaching removed residual intensity following DNase I treatment. Spots were bleached by 10 seconds of excitation following a 4 hour DNase I treatment. The mean, median and STD of the intensity ratio after bleaching were 0.03%, 0.01% and 0.049%. The ratio of the spot intensities after and before DNase I treatment was plotted for each spot. n=1286 spots.
Figure 6:
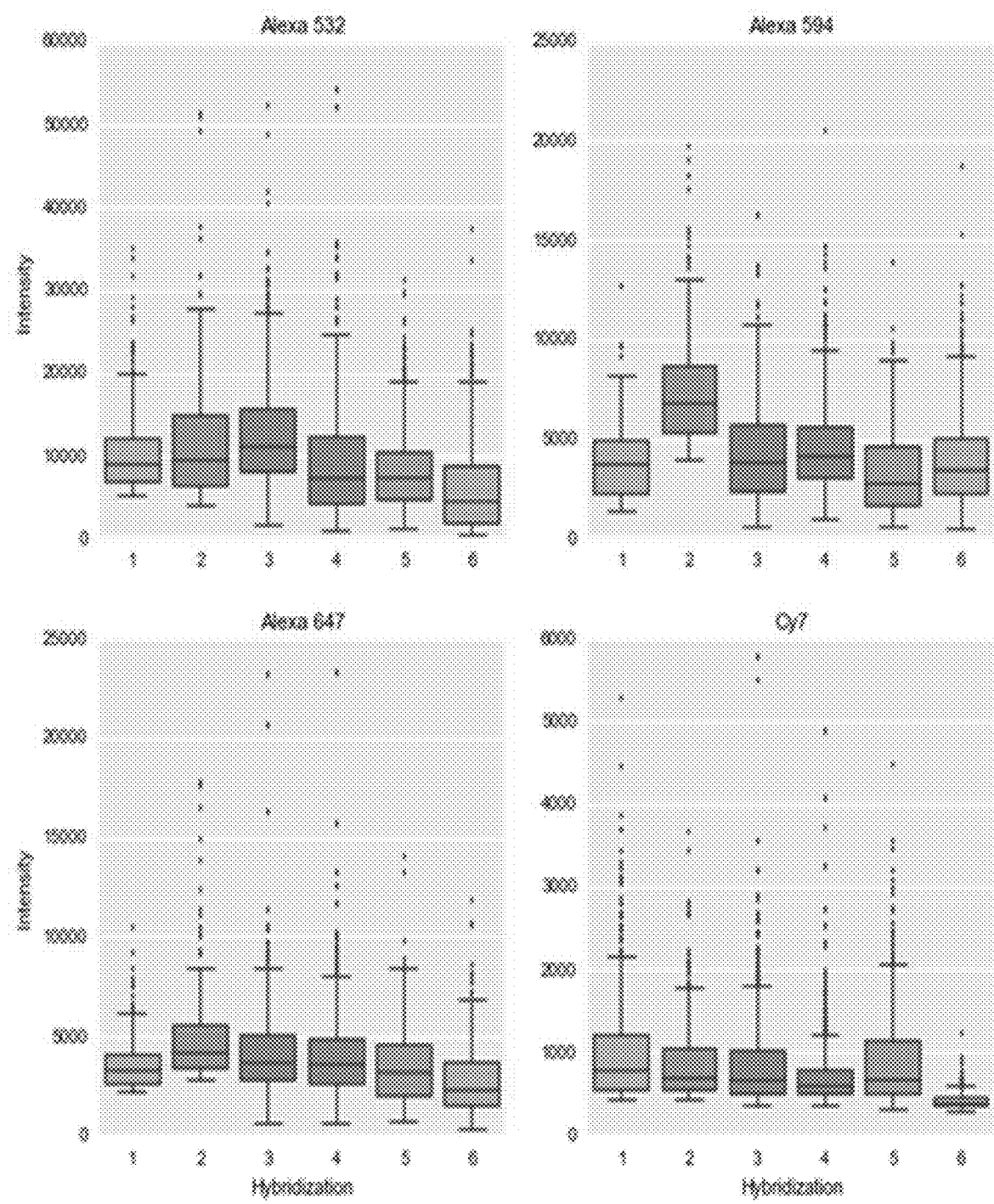
FIG. 6. mRNAs are stable over multiple rounds of re-hybridization. mRNAs were stable over multiple rounds of re-hybridization. The intensity distributions of smFISH spots were plotted over 6 hybridizations. Two hybridizations were repeated 3 times to make 6 total hybridizations. Spots were identified by their co-localization with spots in the next identical hybridization. For each boxplot the number of spots counted was between 191 and 1337.
Figure 7:
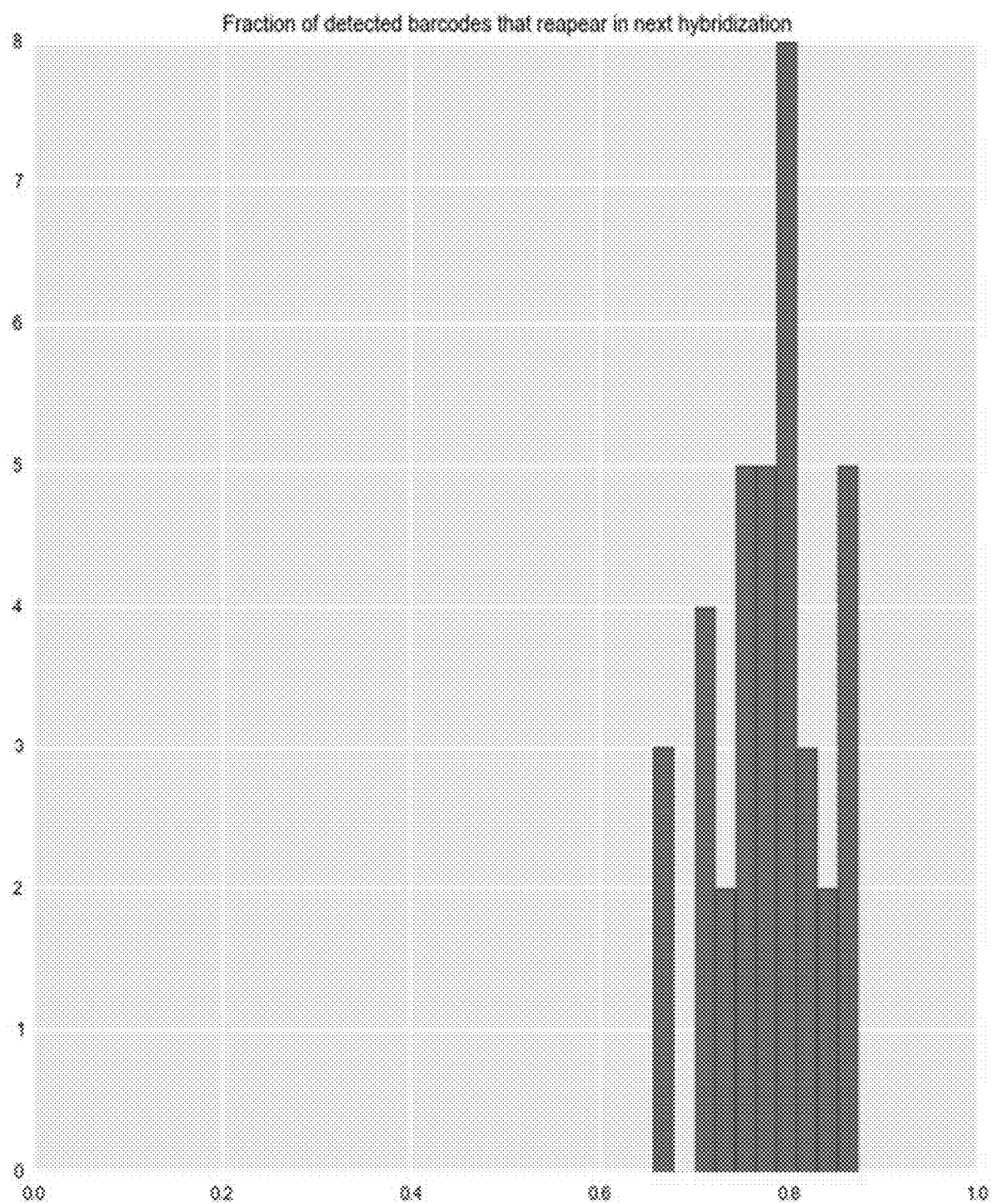
FIG. 7. Fraction of barcodes identified from first two rounds of hybridization that reoccur in following round of hybridization per cell. Fraction of barcodes identified from first two rounds of hybridization that reoccur in following round of hybridization per cell. Barcodes were identified by co-localization through all three hybridizations. 77.9±5.6% of barcodes reoccur. n=37 cells.
Figure 8:
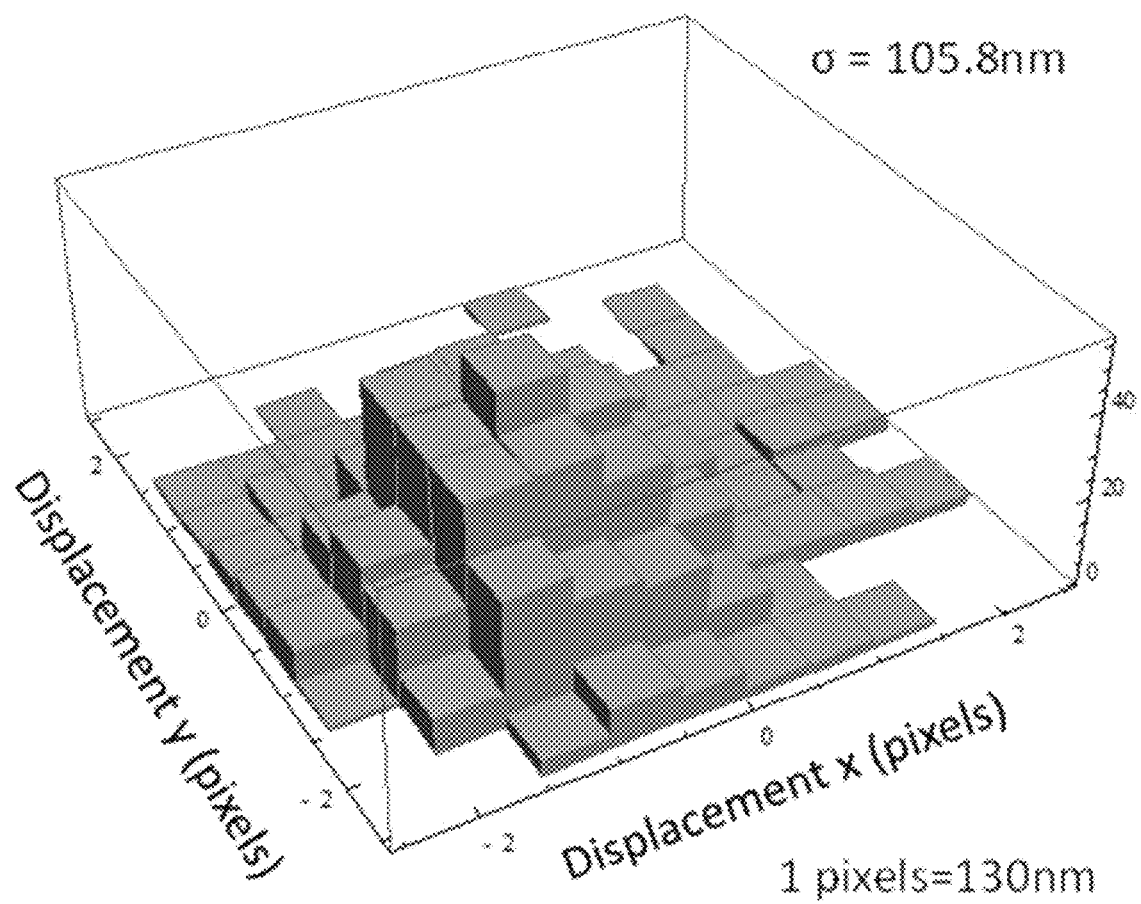
FIG. 8. Point-wise displacement between FISH points in Hybridizations 1 and 3. Point-wise displacement between FISH points in Hybridizations 1 and 3. FISH dots in the Cy5 images in Hybridization 1 and 3 were extracted, fitted with 2D Gaussians. The point-wise displacements were shown in the 3D histogram. The standard deviation was 105.8 nm, indicating that mRNAs can be localized to 100 nm between 2 rounds of hybridizations. n=1199 spots.
Figure 9:
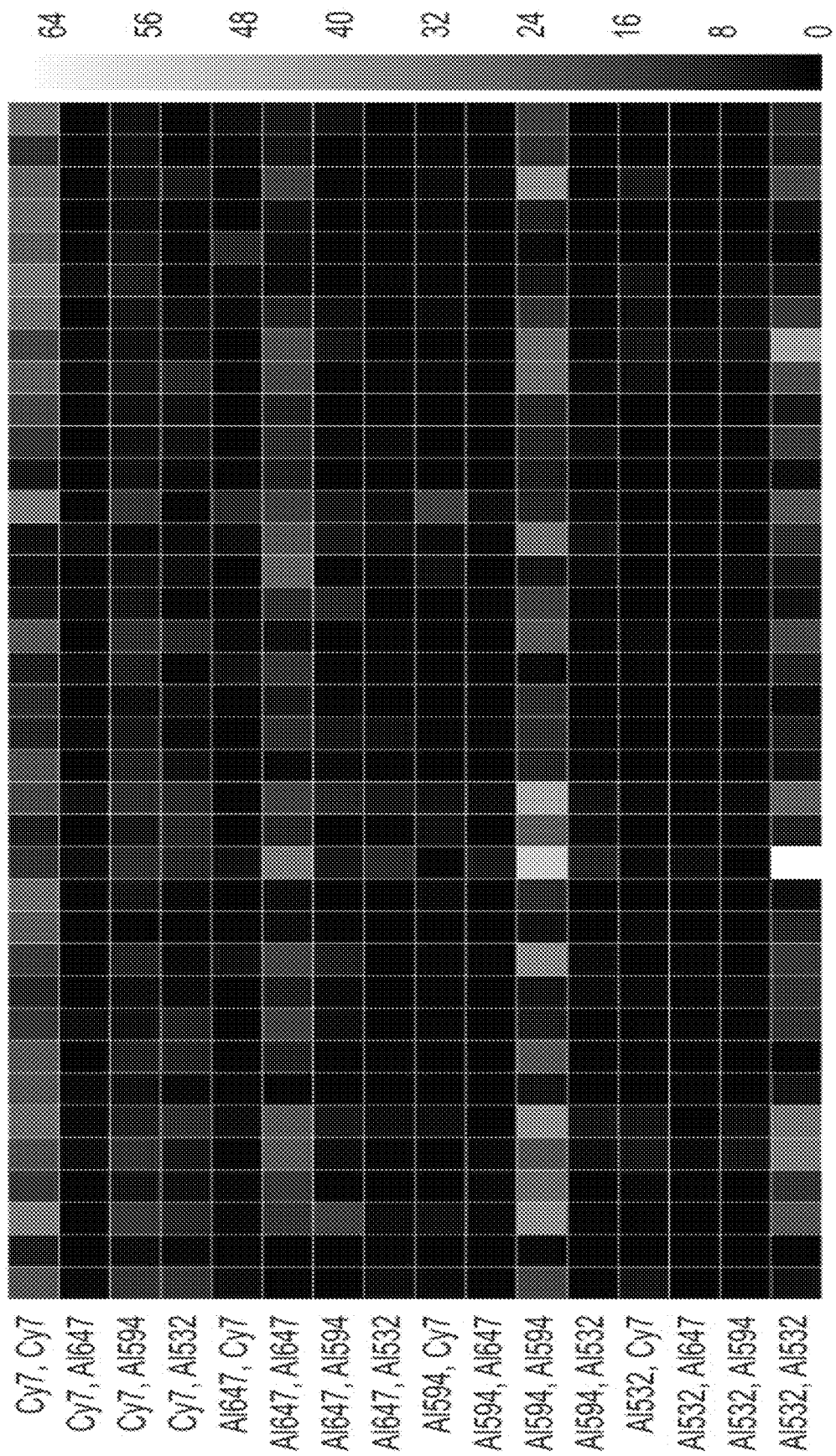
FIG. 9. Barcodes identified between repeat hybridizations of the same probe set (hybridization 1 and 3). Barcodes identified between repeat hybridizations of the same probe set (hybridization 1 and 3). Barcodes were identified by co-localization between the hybridizations. Each column corresponds to an individual cell. Each row corresponds to a specific barcode identified between hybridization 1 and 3. Bolded row names correspond to repeated color barcodes that should co-localize between hybridization 1 and 3. Non-bolded row names correspond to false positive barcodes. For example, a large number of barcodes were detected for (Alexa 532, Alexa 532), indicating co-localization of spots in the Alexa 532 channels. n=37 cells. A1532=Alexa 532. A1594=Alexa 594. A1647=Alexa 647.
Figure 10:
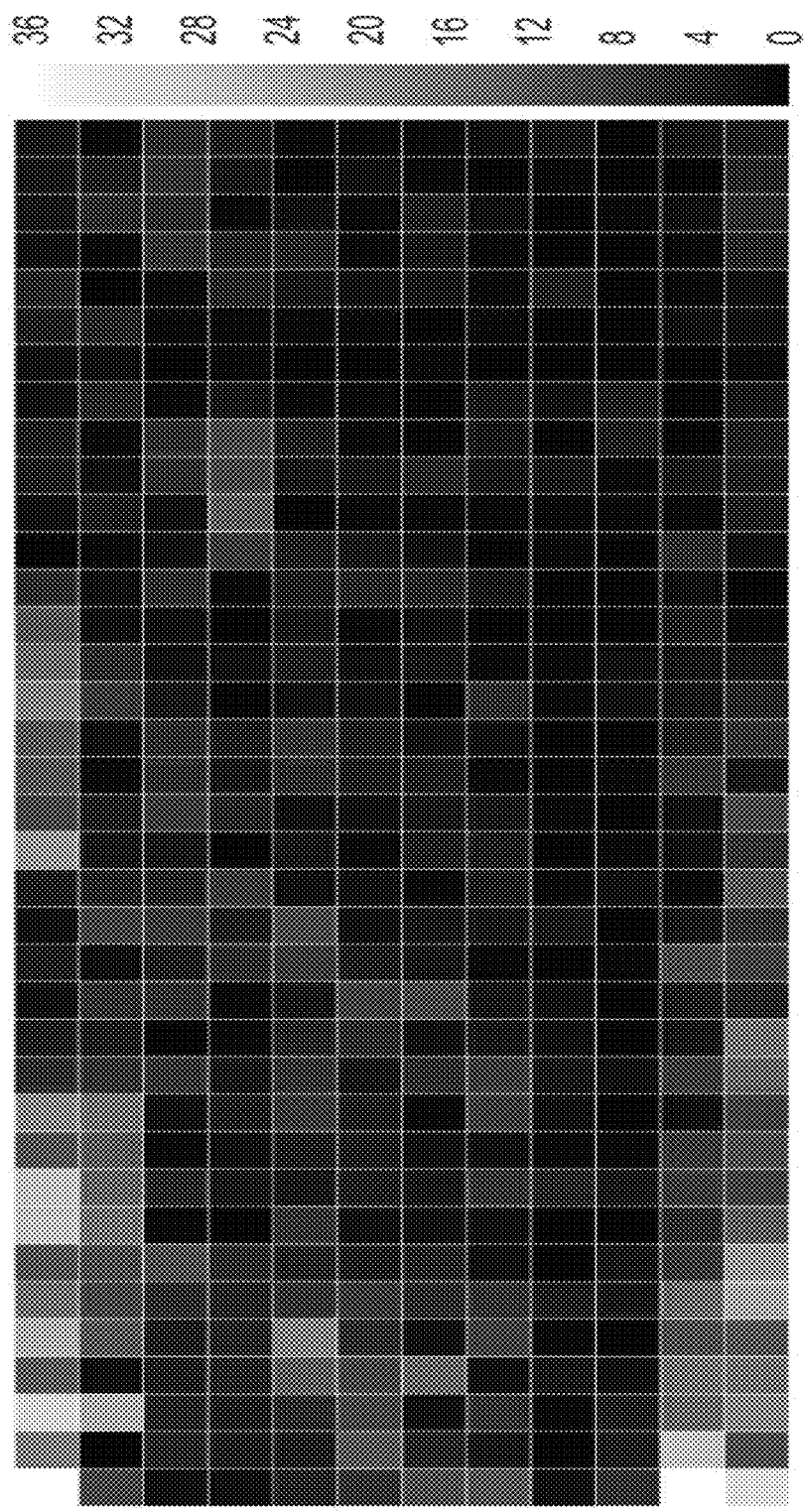
FIG. 10. Single cell mRNA levels from barcode extraction. Single cell mRNA levels from barcode extraction. Barcodes were identified by co-localization between hybridizations 1 and 2. Each column corresponds to an individual cell. n=37 cells. A1532=Alexa 532. A1594=Alexa 594. A1647=Alexa 647. From top to bottom: YLR194c, CMK2, GYP7, PMC1, NPT1, SOK2, UIP3, RCN2, DOA1, HSP30, PUN1 and YPS1.
Figure 11:
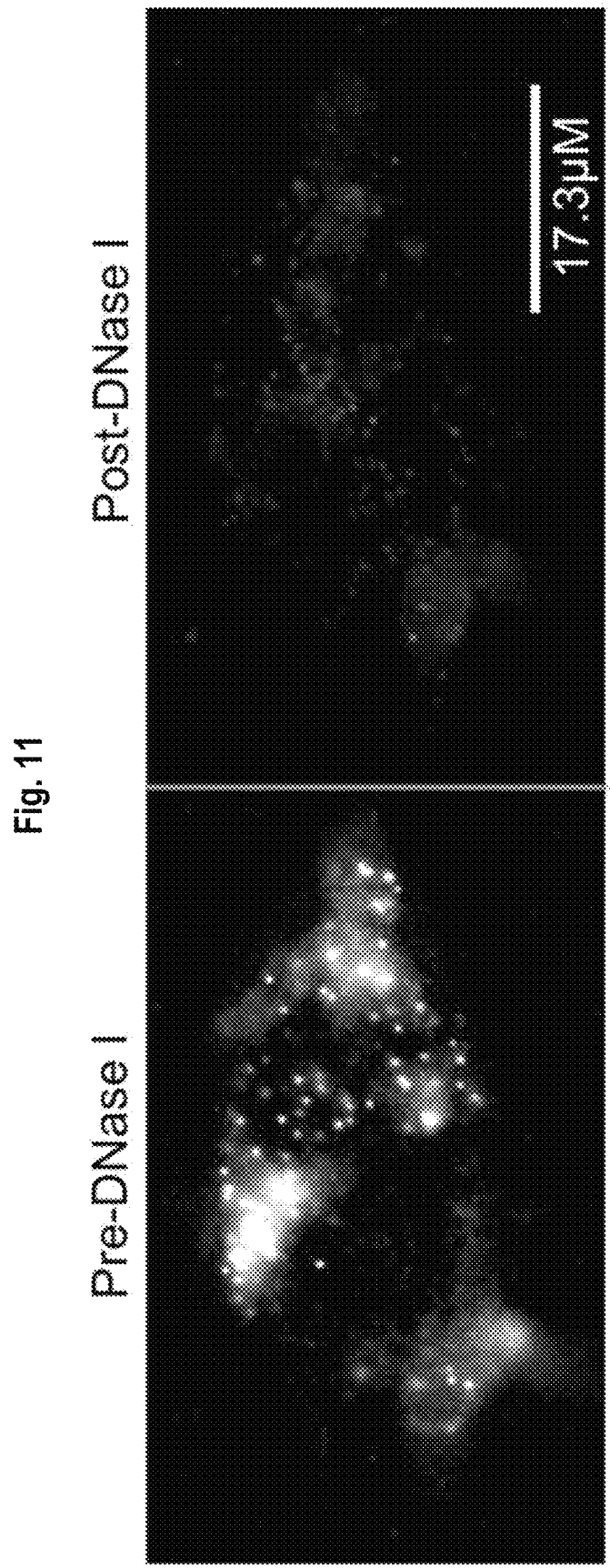
FIG. 11. DNase I stripping of Nanog Alexa 647 probes in mouse embryonic stem cells (mESCs). DNase I stripping of Nanog Alexa 647 probes in mouse embryonic stem cells (mESCs). Forty-eight probes targeting Nanog were hybridized in mESCs. Probes were stripped off by 30 minutes of DNase I incubation at a concentration of 3 Units/μL.
Figure 12:
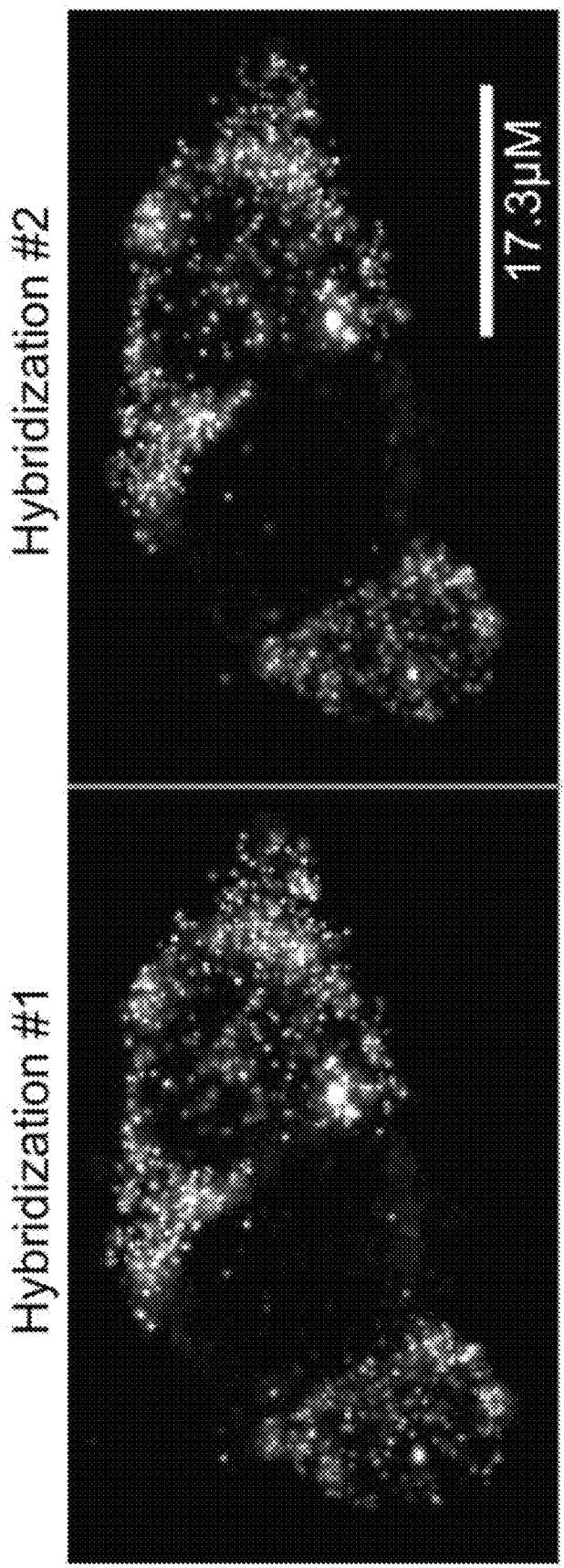
FIG. 12. Re-Hybridization of Nanog mRNA in Mouse Embryonic Stem Cells (mESCs). Re-Hybridization of Nanog mRNA in Mouse Embryonic Stem Cells (mESCs). Probes were stripped off by 30 minutes of DNase I incubation at a concentration of 3 Units/μL. Nanog Alexa 647 probes were re-hybridized for 12 hours and imaged. Images were 2D maximum projections created from z stacks of 11 images taken every 1.5 μm.

As a demonstration, 12 genes were barcoded in single yeast cells with 4 dyes and 2 rounds of hybridization ($4^2=16$, with 4 barcodes left out; each hybridization was conducted for 3 cycles). Cells were immobilized on glass surfaces. The DNA probes were hybridized, imaged, and then removed by DNase I treatment (88.5±11.0% (SE) efficiency, FIG. 4). The remaining signal was photobleached (FIG. 5). Even after 6 hybridizations, mRNAs were observed at 70.9±21.8% (SE) of the original intensity (FIG. 6). It was observed that 77.9±5.6% (SE) of the spots that co-localized in the first two hybridizations also co-localize with the third hybridization (FIGS. 7 and 8). The mRNA abundances were quantified by counting the occurrence of corresponding barcodes in the cell (FIGS. 9 and 10, n=37 cells). It was shown that mRNAs can be stripped and re-hybridized efficiently in mammalian cells (FIGS. 11 and 12). As demonstrated here, provided methods have many advantages over methods known prior to the present invention. For example, provided methods scale up quickly; with even two dyes the coding capacity is in principle unlimited ($2^N$). During each contacting step, all available detectably labeled oligonucleotides, in this example, FISH probes, against a target can be used, increasing the brightness of the signals. Readouts of provided methods are also robust and enable full Z-stacks on native samples. Provided methods can take advantage of the high hybridization efficiency of detectably labeled oligonucleotides, such as FISH probes (>95% of the mRNAs are detected; Lubeck, E. & Cai, L. *Nat. Methods* 9, 743-48 (2012)). Applicant notes that detectably labeled oligonucleotides, for example FISH probes, can also be designed to resolve a large number of splice-isoforms, SNPs, as well as chromosome loci (Levesque, M. J. & Raj, A. *Nat Meth* 10, 246-248 (2013)) in single cells. In combination with super-resolution methods (Lubeck, E. & Cai, L. *Nat. Methods* 9, 743-48 (2012)), provided methods enable a large number of targets, for example the transcriptome, to be directly imaged at single cell resolution in complex samples, such as the brain.

Methods and Procedures

Sample Preparation:

MDN1-GFP yeast cells were grown in YPD supplemented with 50 mM $CaCL_2$ to OD 0.3. Cells were fixed in 1% Formaldehyde 5% Acetic Acid for 5 minutes, rinsed 3× in Buffer B and spheroplasted for 1 hour at 30° C. Cells were stored in 70% EtOH at −20° C. for up to two weeks.

Coverslips were prepared by sonicating 3× with alternating solutions of 1M NaOH and 100% EtOH followed by a final round of sonication in acetone. A 2% solution of (3-Aminopropyl) triethoxysilane (Sigma 440140) was prepared in acetone and the cleaned coverslips were immediately submerged in it for two minutes. Amine-modified coverslips were rinsed and stored in ultra-pure water at room temperature.

Fixed yeast cells were pre-treated with a 0.5 U/μL solution of DNase I (Roche 04716728001) for 30 minutes at 23° C. Following treatment, yeast cells were adhered to coated coverslips by physically compressing a dilute solution of yeast between two amine-modified coverslips. The coverslips were then carefully pealed apart and immediately submerged in a 1% formaldehyde solution for 2.5 minutes. Following fixation coverslips were dried and a flow cell was constructed by adhering an adhesive coated flow cell to the coverslip (GraceBio Labs SA84-0.5-SecureSeal). Fluo-Sphere 365 nm fluorescent beads were added to the coverslip to measure drift over multiple hybridizations (Life F8805). Flow cells were stored at 4° C. covered with parafilm.

Preparation of Detectably Labeled Oligonucleotides:

Probes were prepared according to the method in Lubeck, E. & Cai, L. *Nat. Methods* 9, 743-48 (2012). For each target, 24 probes were used. All 24 probes for each set of genes were coupled to one of the four dyes used, Alexa 532, 594, Cy5 and Cy7.

Hybridization:

Flow cells were hybridized at a concentration of 2 nM/probe overnight in a hybridization buffer of 10% Dextran Sulfate (Sigma D8906), 10% formamide, and 2×SSC. Following hybridization, samples were washed in a 30% formamide, 0.1% Triton-X 100 buffer pre-heated to 37° C.

before adding to room temperature samples for 10 minutes. Samples were washed several times with 2×SSC to remove diffusing probes.

Imaging:

Samples were immersed in an anti-bleaching buffer (Swoboda, M. *ACS Nano* 6, 6364-69 (2012)): 20 mM Tris-HCL, 50 mM NaCl, 0.8% glucose, saturated Trolox (Sigma: 53188-07-1), pyranose oxidase(Sigma P4234) at an $OD_{405nm}$ of 0.05, and catalase at a dilution of 1/1000 (Sigma: 9001-05-2).

Probe Displacement:

Following imaging, cells were washed in DNase I buffer (Roche) and allowed to sit in 0.5 U/µL DNase I (Roche) for 4 hours. To inhibit DNase cells were washed 2× with 30% formamide, 0.1% Trition-X 100, 2×SSC. Following DNase treatment cells were imaged once more in anti-bleaching buffer to determine DNase I probe stripping rates. To remove remaining probe signal, samples were bleached with 10 seconds of excitation in all imaging channels and imaged once more with standard excitation times to record residual signal.

Re-Hybridization:

Samples were re-hybridized on the microscope according to the previously outlined conditions. Samples were covered with parafilm during hybridization on the scope to prevent evaporation.

At least six rounds of hybridizations were carried out on the same sample. Each round of hybridization took place overnight on the microscope, with DNase treatment and imaging occurring during the day. In the iterative hybridization scheme applied in this correspondence, two rounds of hybridization were used to barcode the mRNAs. The barcode scheme was then repeated, such that hyb1 and hyb3 were performed using the same probes, while hyb2 and hyb4 were done with another set of probes. The co-localization between hyb1 and hyb3 gave a calibration for transcripts that were detected, while hyb1 and hyb2 yielded the barcoding data.

Data Analysis:

Data analysis was carried out with ImageJ, Python and Matlab. Since the sample drifted during the experiments, the raw images were aligned using cross-correlation based registration method that was determined from the DAPI channel of each imaging position. The drift-correction was then propagated to the other 4 color channels corresponding to the same position. The images were then deconvolved to decrease the overlap between adjacent FISH spots. Spots overlaps in individual channels were rarely observed, but spots in different channels could overlap in their point spread functions (PSFs) when the images were overlaid. The raw data were processed based on an iterative Lucy-Richardson algorithm (Lucy, L. B. *The Astronomical Journal.* 79, 745 (1974) and Richardson, W. H. *J. Opt. Soc. Am.* 62, 55-59 (1972)). The PSF of the microscope was estimated by averaging the measured bead images (~200 nm diameter) in the DAPI channel of the microscope. Using this measured point spread function with the Lucy-Richardson algorithm, we performed maximum-likelihood estimation of fluorescent emitter distribution in the FISH images after computing this process over ~20 iterations. The output of this deconvolution method provides resolved FISH data and increases the barcode assignment fidelity.

Dots corresponding to FISH signals in the images were identified using a local maximum function. Dots below a threshold were discarded for further analysis. The value of the threshold was determined by optimizing the co-localization between hyb1 and hyb3 images, which were hybridized with the same probe sets. The maximum intensity pixel for each PSF was used as a proxy for the location of that mRNA molecule.

The barcodes were extracted automatically from the dots corresponding to mRNAs in hyb1 and hyb2. The algorithm calculated the pairwise distances between each point identified in hyb1 with all the points identified in hyb2. For each point in hyb1, the closest neighbor in hyb2 was identified. If that distance were 0 or 1 pixel and the closest neighbor of the point in hyb2 were also the original point in hyb1, then the barcode pair was confirmed. The symmetrical nearest neighbor requirements decreased the false assignment of barcodes. To reduce false positives in cy7, points detected in hyb1 cy7 were required to reappear in hyb3 in cy7.

In this non-limiting example, Applicant removed probes with DNase I due to its low cost and rapid activity. Applicant notes that any method that removes probes from mRNA and leaves it intact could be used in provided barcoding approaches, for example but not limited to, strand-displacement (Duose, D. Y. *Nucleic Acids Research,* 40, 3289-3298 (2012)) and high temperature or formamide washes. Applicant notes that DNase I does not require probe redesigns from standard smFISH probes, and does not perturb the sample with harsh washes.

In some embodiments, a rapid loss of DAPI signal from dsDNA within seconds was observed, while smFISH probes took a substantially longer period of time (10 s of minutes) to be degraded. Without the intention to be limited by theory, the efficiency of DNase I probe removal could be low relative to the dsDNA cleavage rate. The removal process was still observed in a short amount of time.

In certain experiments, 11.5% of the fluorescent signal remained on mRNA after DNase I treatment. The remaining signal was reduced almost to zero by bleaching. Applicant notes that more complete removal of signal and/or probes can be achieved prior to photobleaching, so that more mRNAs are available for the following rounds of hybridization. Applicant notes that photobleaching is not necessary for barcoding, but in some embodiments, it does simplify the process by removing residual signal that might give false positives in further rounds of barcoding. Some of the 11.5% of residual probes bound to mRNA may inhibit further rounds of hybridization. Applicant notes that residual probes were not significantly inhibiting progressive rounds of hybridization as presented data showed a minor drop in hybridization efficiency for 5 hybridizations.

Profiling of Nucleic Acids in Brain Tissues

Transcription profiling of cells in intact brain slices are essential for understanding the molecular basis of cell identity. However, prior to the present invention it was technically difficult to quantitatively profile transcript abundance and localization in single cells in the anatomical context of native neural networks. The cortical somatic sensory subnetworks are used as an example to demonstrate the feasibility and utility of exemplary provided technologies, for example, using in situ sequencing by FISH (seqFISH) and connectomics to profile multiple genes in distinct neuronal populations within different functional domains, such as those in the primary somatic sensory (SSp), primary somatomotor (MOp), secondary somatomotor (MOs), and supplementary somatosensory (SSs) cortical areas.

As described extensively herein, in some embodiments, the present invention provides technologies to profile gene expression in single cells via in situ "sequencing" by FISH, e.g., as illustrated by FIGS. 1 and 2. To detect individual mRNAs, single molecule fluorescence in situ hybridization (smFISH) was used with 20mer oligonucleotide probes complementary to the mRNA sequence (Fan, Y., Braut, S A, Lin, Q., Singer, R H, Skoultchi, A I. Determination of transgenic loci by expression FISH. Genomics. 2001 Oct. 2; 71(1): 66-9; Raj A, Peskin C S, Tranchina D, Vargas D Y, Tyagi S. Stochastic mRNA synthesis in mammalian cells. PLoS Biol. 2006 October; 4(10):e309). By putting 24 such fluorophore labeled probes on an mRNA, single transcripts in cells become readily detectable in situ. It was shown that almost all mRNAs that can be detected are observed by smFISH (Lubeck, E. L. Cai. Single cell systems biology by super-resolution imaging and combinatorial labeling. Nature Methods 9, 743-48 (2012)). Provided methods are highly quantitative and preserve the spatial information within a tissue sample without physically isolating single cells or using homogenates.

Figure 3:
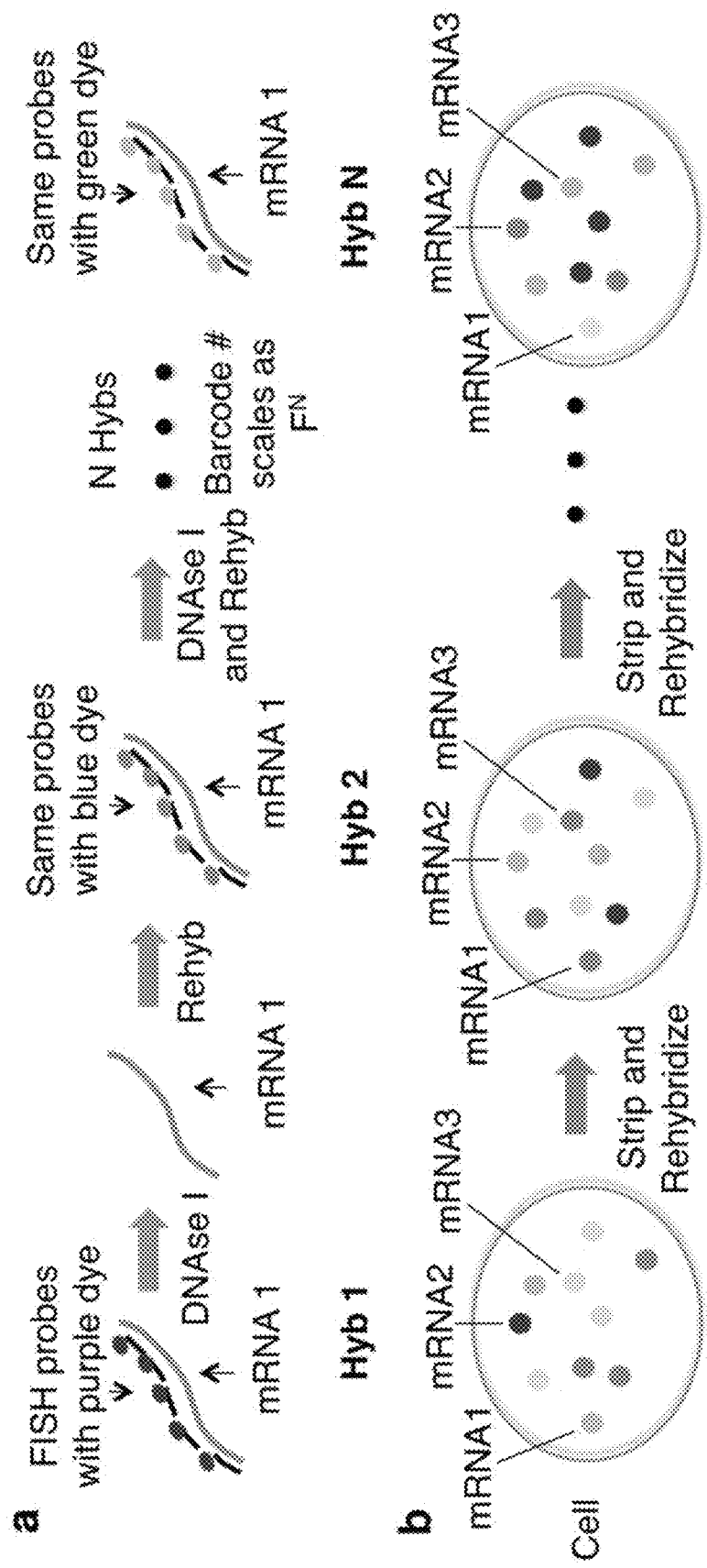
FIG. 3. Schematic of sequential hybridization and barcoding. (a) Schematic of sequential hybridization and barcoding. (b) Schematic of the FISH images of the cell. In each round of hybridization, the same spots were detected, but the dye associated with the transcript changes. The identity of an mRNA was encoded in the temporal sequence of dyes hybridized.

In some embodiments, to distinguish different mRNA species, mRNAs are barcoded with detectably labeled oligonucleotides, such as FISH probes using sequential rounds of hybridization. During a round of hybridization, each transcript is targeted by a set of multiple, for example, 24 FISH probes, labeled with a single type of fluorophore. The sample is imaged and the FISH probes are removed by enzymatic digestion. Then the mRNA is hybridized in a subsequent round with the same FISH probes, but now labeled with, in some cases, a different dye. As the transcripts are fixed in cells, the fluorescent spots corresponding to single mRNAs remain in place during multiple rounds of hybridization, and can be aligned to read out a color sequence. Each mRNA species is therefore assigned a unique barcode. The number of each transcript in a given cell can be determined by counting the number of the corresponding barcode. An exemplary process is illustrated in FIG. 1, 2, or 3.

Provided technologies can take advantage of the high hybridization efficiency of FISH (>95% of the mRNAs are detected). In some embodiments, base pair resolution is not needed to identify a transcript, although can be achieved if desired. The number of barcodes available with provided methods scales as $F^N$, where F is the number of distinct fluorophores and N is the number of hybridization rounds. With 5 distinct dyes and 3 rounds of hybridization, 125 unique nucleic acids can be profiled. Almost the entire transcriptome can be covered by 6 rounds of hybridization ($5^6$=15,625), for example, using super-resolution microscopy which resolves all of the transcripts in a cell. In some embodiments, conventional microscopy, such as conventional epi-fluorescence microscopy which is simple and robust to implement, is used to detect fewer but still large number of targets, for example, at 100 genes multiplex.

Probes can be stripped and rehybridized to the same mRNA in multiple cycles of hybridization (FIG. 2). Many commercially available fluorophores work robustly, such as Alexafluor 488, 532, 594, 647, 700, 750, and 790, giving at least 7 colors for barcoding. Even at the end of 6 rounds of hybridizations, probes can be re-hybridized to the stripped mRNA with 70.9+21.8% (FIG. 6) of the original intensity. As a demonstration, barcoded 12 genes were barcoded in single yeast cells with 4 dyes and 2 rounds of hybridization ($4^2$=16, FIG. 3, *c*).

There is sufficient optical space in cells to perform multiple, e.g., 100 gene multiplex, as 12 genes multiplex images only occupied 5% of the optical space in each fluorescent channel. Although the composite image of all 4 fluorescent channels in FIG. 3 appears dense, spots in each fluorescent channel are sparsely distributed. Each spot can be fitted with a 2 dimensional Gaussian profile to extract its centroid positions and further reduce the overlaps with spots in other fluorescent channels. It was shown that the same spots realign to 100 nm between different rounds of hybridization (FIG. 8).

In some embodiments, a 100 genes multiplex can be performed quickly with 3 rounds of hybridization. In some embodiments, each hybridization cycle involves about 4 hours of hybridization, about 1 hour of imaging and about 1 hour of DNase treatment and washing, the time length of each can be optionally and independently varied. In some embodiments, 3 rounds of hybridization take approximately 18 hours. In some embodiments, imaging time is the rate limiting step, rather than the hybridization time, because one brain slice can be imaged while another slice on the same microscope is hybridizing. In some embodiments, a single microscope can multiplex up to 8 slices simultaneously and obtain 100 gene data on all 8 slices at the end of the 3 cycles of hybridization in 18 hours.

In some embodiments, a 10 mm×5 mm×10 µm brain slice containing $10^6$ cells can be imaged and analyzed in 35 minutes on microscopes. In some embodiments, a single field of view (FOV) on a microscope is 0.5 mm×0.5 mm×2 µm with a 20× air objective and 13 mm×13 mm camera chip. In some embodiments, each FOV is exposed and read out in 100 msec. In some embodiments, scanning the sample in xyz and in the different color channels introduces a time delay of 200 msec between snapshots. In some embodiments, an entire brain slice can be imaged in 2000 sec or 35 minutes. With 3 rounds of hybridization needed for the 100 gene multiple, the total imaging time is 105 minutes. In some embodiments, an entire mouse brain can be imaged in 30 days on one microscope. When multiple microscope is used, the time frame can be further shortened. In some embodiments, provided methods can image an entire mouse brain with 500 slices with a cost less than $25,000.

Compared with other methods known prior to the present invention, provided technologies provide a variety of advantages. Among other things, provided technologies is quantitative, preserve spatial information and inexpensively scales up to a whole tissue, organ and/or organism.

Comparison with Single Cell RNA-Seq Prior to the Present Invention.

Unlike single cell RNA-seq or qPCR, which require single cells to be isolated and put into a 96 well format, provided methods, such as seqFISH, can scan a large number of cells in their native anatomical context with automated microscopy at little additional cost. To achieve the same level of throughput with a microfluidics device would be economically impossible and labor intensive. In some embodiments, major cost of provided technologies is the initial cost of probe synthesis, which is offset by the fact that once probes are synthesized, they can be used in many, e.g., 1000 to 10,000 or even more reactions.

Provided methods such as seqFISH are based on single molecule FISH and can measure low copy number transcripts with absolute quantitation. The data obtained with this method is highly quantitative and enables high quality statistical analysis. In comparison, current single cell qPCR and RNA-seq experiments are limited in quantitative powers with biases from reverse transcription (RT) and PCR amplification errors.

Comparison with Other In Situ Sequencing Method Prior to the Present Invention.

One major advantage of the smFISH approach is that almost all mRNAs that are targeted can be observed. It was determined that the efficiency of each FISH probes binding on a mRNA is 50-60% (Lubeck, E. & Cai, L. *Nat. Methods* 9, 743-48 (2012); Levesque, M. J. & Raj, A. *Nat Meth* 10, 246-248 (2013)). Targeting multiple, e.g., 24-48 probes per mRNAs ensures that at least 10 probes are hybridized on almost every mRNA, providing good signals over the non-specific background. Directly probing the mRNA with FISH probes is highly specific and ensures that all transcripts are detected.

In contrast, many other in situ sequencing methods, instead of targeting the mRNA directly, use enzymatic reactions to convert the mRNA into a DNA template first, before detecting the DNA template by sequencing reactions. However, the mRNA to DNA conversion process is highly inefficient, and only a small fraction of the RNAs are converted and detected. One exemplary major downside of low efficiency, which is estimated at 1% for reverse transcription (RT) and 10% for padlock ligation (PLA), is that it can introduce significant noise and bias in the gene expression measurements.

Given the typical cell size of (10-20 $\mu m^3$), there are approximately 25,000 diffraction limited spots in the cell. In some embodiments, this is the available real estate for transcript detection in single cells. In seqFISH, a chosen set of genes, such as transcription factors (TFs) and cell adhesion molecules (CAMs), can be imaged and quantitated with high accuracy. If target genes with average copy numbers of 100 transcripts per gene are chosen, a highly quantitative 100-200 gene profiling experiment can be performed. In contrast, with many other in situ sequencing methods, most of that real estate is used to sequence ribosomal RNAs as well as house-keeping genes; genes of interest, such as those specific for neuronal cell identity, are severely under-represented and poorly detected.

In some embodiments, provided methods use hybridization chain reaction (HCR) (Choi, et al., Programmable in situ amplification for multiplexed imaging of mRNA expression *Nature Biotechnol,* 28, 1208-1212, (2010)) to amplify FISH signal that allows large FOV imaging with 20× air objectives, but at the same time preserves the high detection efficiency of smFISH.

Comparison with Super-Resolution Barcoding Method of Multiplexing RNA Prior to the Present Invention.

In some embodiments, provided methods have many advantages compared to spectral barcoding of mRNAs by smFISH prior to the present invention (Femino et al., Visualization of single RNA transcripts in situ. Science. 1998 Apr. 24; 280(5363):585-90; Kosman et al., Multiplex detection of RNA expression in *Drosophila* embryos. Science. 2004 Aug. 6; 305(5685):846; Levsky et al., Single-cell gene expression profiling. Science. 2002 Aug. 2; 297(5582): 836-40; Lubeck et al., Single cell systems biology by super-resolution imaging and combinatorial labeling. Nature Methods 9, 743-48 (2012); and Levesque et al., *Nat Meth* 10, 246-248 (2013)), in which the probes against a particular mRNA are split up into subsets which are labeled with different dyes. Among other things, provided technologies do not require many distinct fluorophores to scale up; with even two dyes, the coding capacity is huge, and repeated barcodes can be used (e.g., Red-Red-Red). In comparison, spectral barcoding of RNA prior to the present invention is limited in the number of barcodes that can be generated (~30). In provided methods, during each round of hybridization, all the detectably labeled oligonucleotides such as FISH probes against a transcript can be used at once instead of splitting probes into subsets. Among other things, provided technologies provide improved robustness of barcode readout, as the signal on each mRNA is stronger. Compared to methods prior to the present invention, density of objects in the image is lower as each mRNA can have fewer colors, in some embodiments, a single color, during each round of hybridization instead of at least 3 colors in the spectral barcoding schemes prior to the present invention. If desirable, the lower image density can greatly simplifies data analysis and allows more genes to be multiplexed before super-resolution microscopy is necessary. Applicant notes that certain spectral barcoding methods, probes, and/or super-resolution microscopy, can be used, and can be useful embodiments, in provided embodiments. To profile the transcriptome with provided technologies such as seqFISH, in some embodiments, super-resolution microscopy is used to resolve the millions of transcripts in the cells.

Besides transcriptional profiling, provided technologies can resolve multiple alternative splicing choices and RNA editing on the same mRNA molecule. Alternative spliced isoforms are difficult to probe by sequencing methods as the sequencing reads are usually too short to correlate the exon choices within the same transcript. Provided methods such as seqFISH allow direct visualization of the entire repertoire of splice isoforms within individual cells in brain slices. Similarly, smFISH methods of detecting single nucleotide polymorphisms (SNPs) can be adapted to seqFISH to image edited transcripts in neurons or other cell types.

In some embodiments, provided technologies provide efficient and cost effective pipelines for gene profiling in situ by sequential FISH (seqFISH), and integrate seqFISH and connectomics to profile somatic motor neurons in the cortex to identify combinatorial molecular markers that correspond to cell identity.

Quantitative In Situ Gene Expression Mapping in Brain

Light sheet microscopy is applied to directly image CLARITY cleared brains slices. In some embodiments, a mouse brain is mapped in 1 month per machine. In some embodiments, a mouse brain is mapped in one week with 4-5 machines.

Amplification: Amplification of FISH signals allows large FOV imaging of brain slices with 20× low NA objectives. In some embodiments, provided methods use detectably labeled oligonucleotides labeled with hybridization chain reaction (HCR) (Choi et al., 2010) to increase the signal-to-background and/or preserve the specificity and multiplexing capabilities of FISH methods. With this approach, nucleic acid probes complementary to mRNA targets trigger chain reactions in which metastable fluorophore-labeled nucleic acid hairpins self-assemble into tethered fluorescent amplification polymers. Using orthogonal HCR amplifiers carrying spectrally distinct fluorophores, in situ amplification can be performed simultaneously for all channels.

In some embodiments, detectably labeled oligonucleotides with HCR (HCR probes) contain a 20-nt domain complementary to the target mRNA plus a 40-nt HCR initiator. The hybridization of probes is performed under stringency of 10% formamide followed by the amplification step at a permissive condition. Conditions like concentration of hairpins can be optimized to achieve optimal results; Applicant notes that, in certain cases, higher concentrations of hairpins increase reaction rate. Every HCR probe can be amplified to a diffraction-limited spot. In some embodiments, FISH signal is amplified by approximately 10-20 times within a diffraction-limited spot size. Spot brightness can be further enhanced while maintaining a diffraction-limited spot size by, for example, incorporating multiple HCR initiators within each probe and/or labeling each HCR amplification hairpin with multiple fluorophores.

Figure 13:
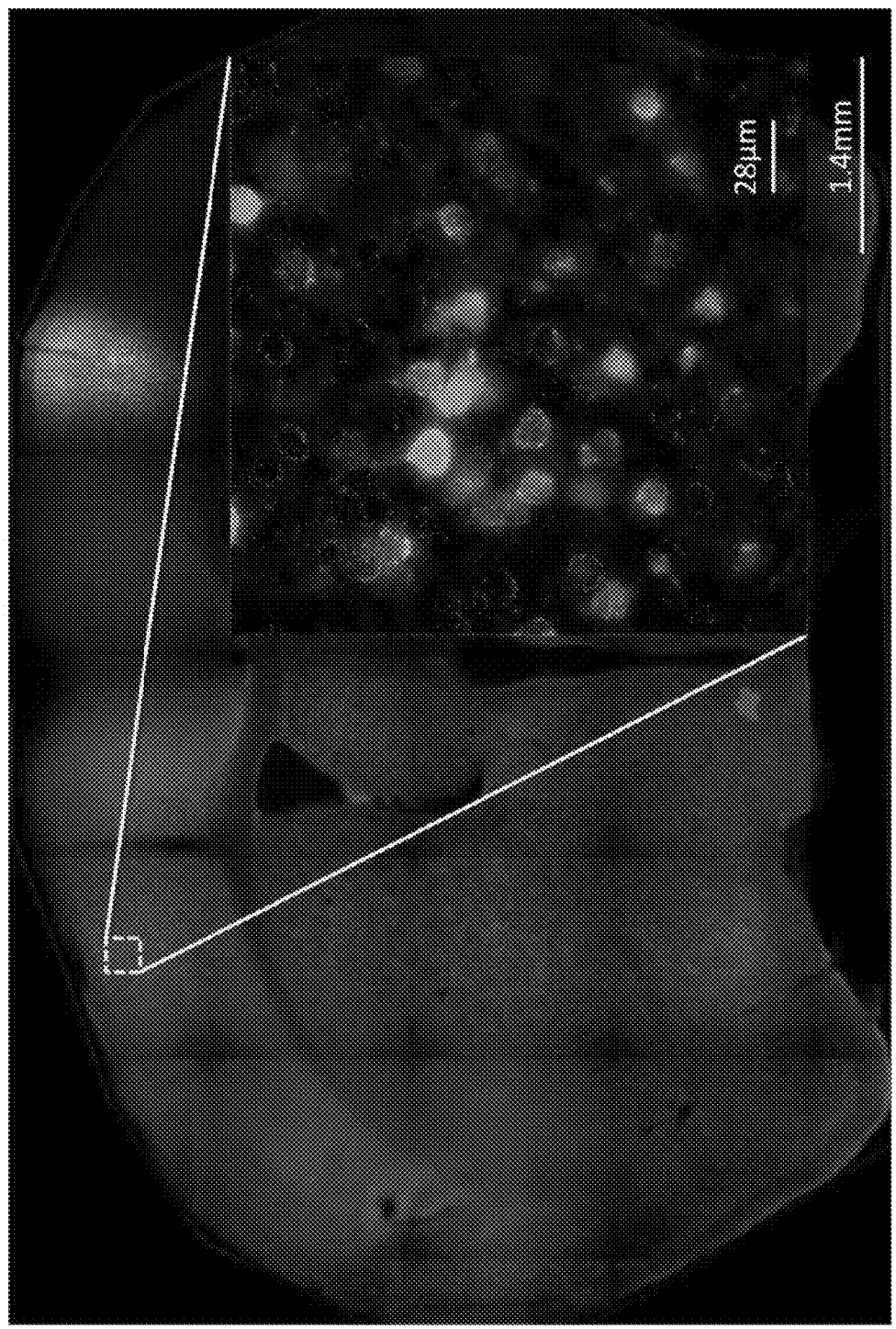
FIG. 13. HCR detection of β-actin (red) in the cortex and visualized with retrograde tracers (fluorogold, green) in a 100 μm coronal section. An entire coronal section was imaged at both 10× and 60× (magnified inset). In the 60× image, individual red dots correspond to single β-actin mRNA molecules. β-actin expression can be quantified by counting fluorescent foci while simultaneously detecting a distal sub-population of neurons tagged with the retrograde tracer (green).
Figure 14:
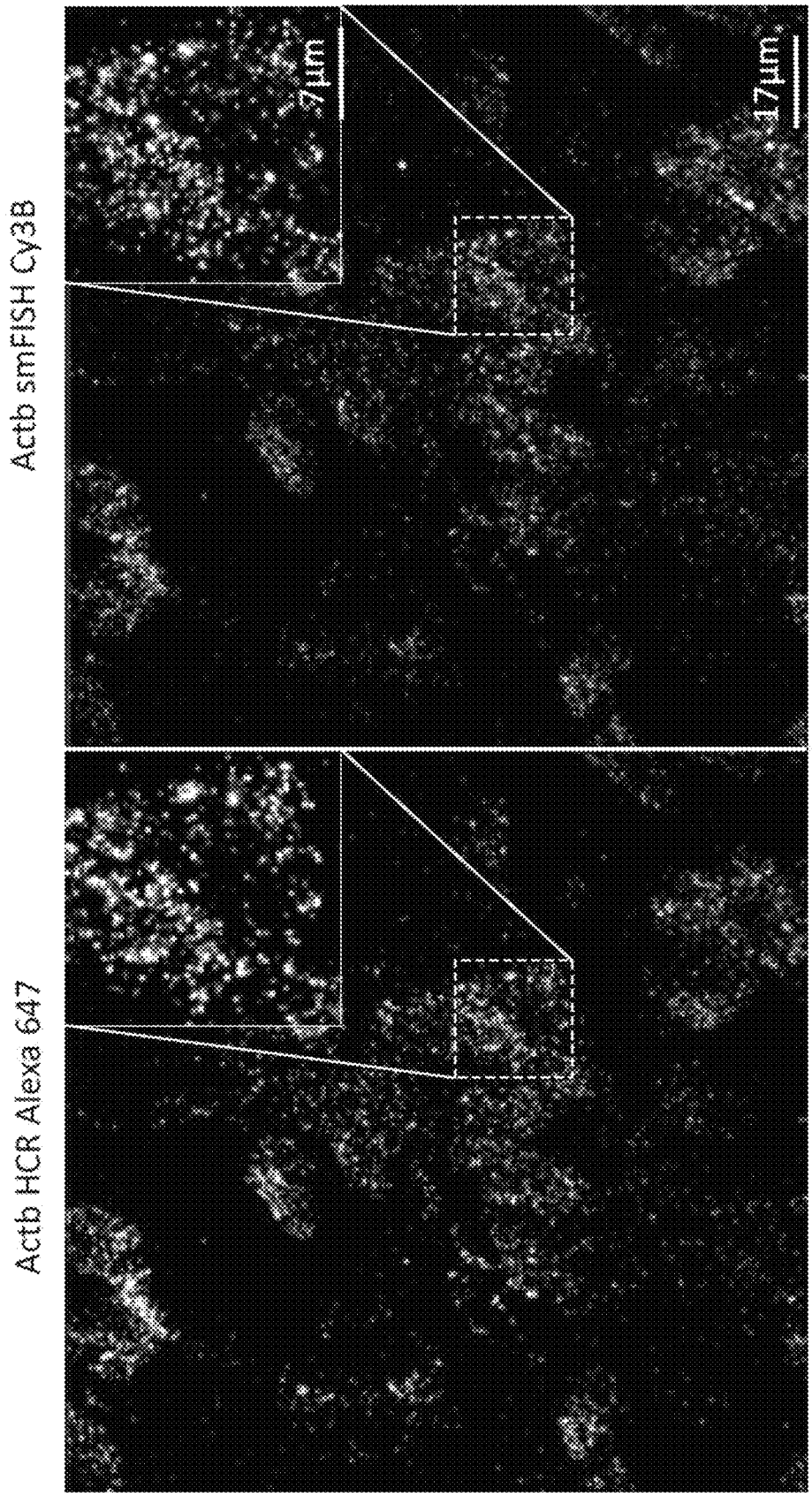
FIG. 14. Detectably labeled oligonucleotides labeled with HCR were as specific as smFISH probes directly labeled with fluorophores in detecting single molecules of RNA in 20 μm brain slices. HCR probes (left) and smFISH probes (right) targeted β-actin simultaneously and co-localized. Note the improved S/N of the HCR.

HCR amplified signals were observed from mRNAs directly in brain slices. When targeted to the same mRNA, HCR probes colocalize with smFISH dots with 90% rate, but are 10-20 times brighter (FIG. 14). This allows HCR probes to be readily detected above the autofluorescence of the brain (FIG. 13). The high colocalization rate proves that HCR is as specific as smFISH and most transcripts are detected.

Figure 15:
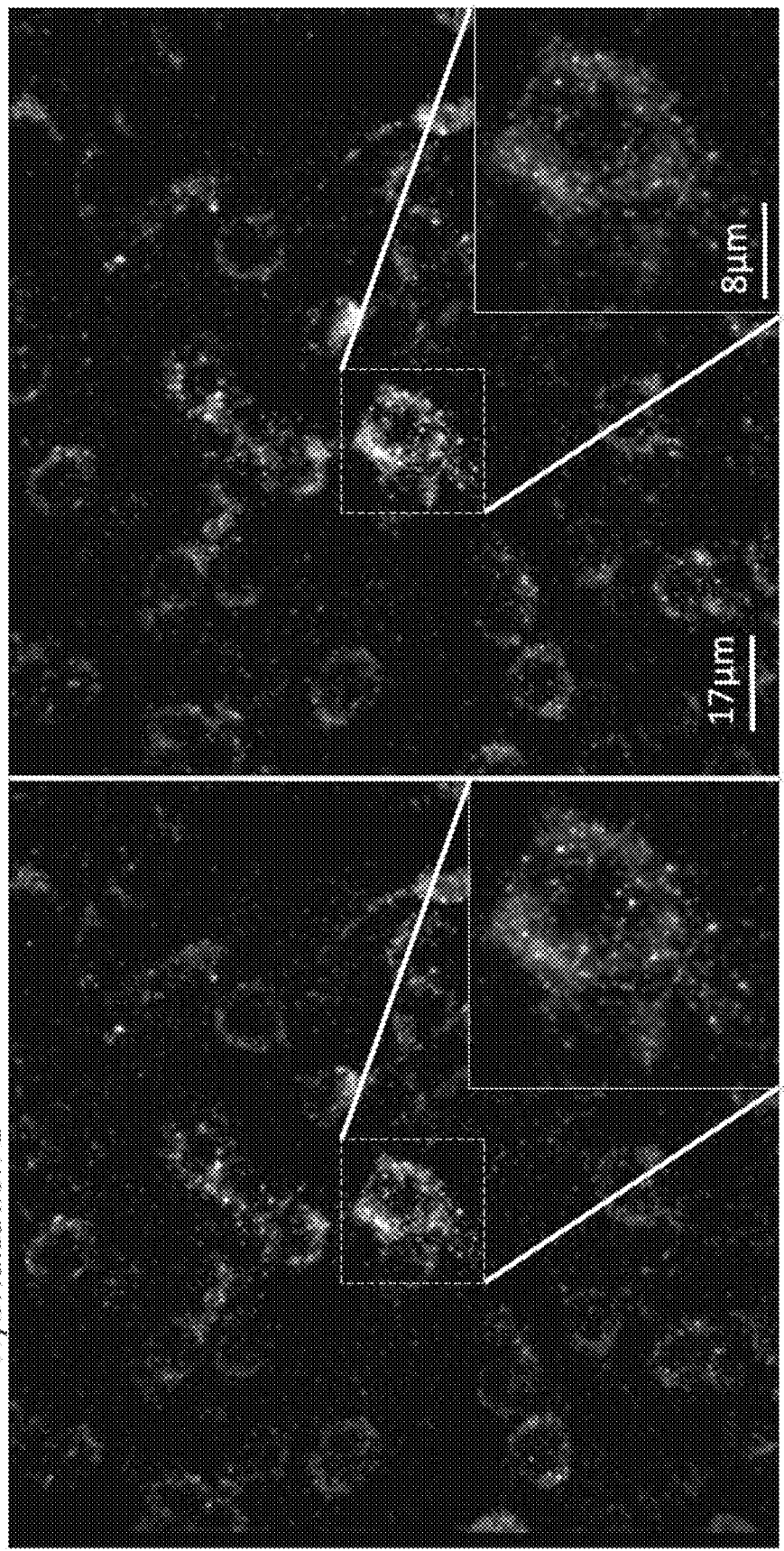
FIG. 15. Detectably labeled oligonucleotides labeled with HCR rehybridized well in 20 μm brain slices. HCR spots in hyb1 and hyb2 colocalized, with DNase treatment in between two hybridizations. This showed that HCR can be fully integrated with the seqFISH protocol.

HCR probes are readily stripped and rehybridized, and can be fully integrated with the seqFISH protocol described herein. FIG. 15 showed the same genes targeted by HCR in brain slices in two different rounds of hybridization. The good colocalization between the two hybridizations shows that HCR-seqFISH works robustly to barcode mRNAs in brain.

HCR protocols work on the same time scale as smFISH hybridization and do not increase the cycle time of the assay. The initial hybridization step in HCR is similar to smFISH in time, while the second amplification step occurs in 30 minutes to 1 hour. Alternative methods of hybridizing RNA probes to the transcripts, and optionally using alternative types of hairpins to amplify the signal can further reduce cycle time. In some embodiments, HCR removes the need to purchase amine labeled oligo probes. Among other things, HCR can potentially decrease the cost of the reagents by approximately one half, to e.g., $10,000 per brain.

Automation.

Automation of both hardware and software can be applied to efficiently scale up, for example, to map 100 genes and/or reduce human labor and/or errors. In some embodiments, key pieces of technology are integrated to generate a pipeline and/or optimize workflow for tissue and/or organ imaging, such as imaging of brain slices. Among other things, automated fluidics, image acquisition and/or integrated analysis can be independently and optionally combined with fast hybridization cycle time and imaging time.

Hardware.

In some embodiments, an automated system requires minimum intervention from users and can perform the image acquisition automatically once the user has set up the experiments. In some embodiments, each sequencer consists of or comprises an automated epi-fluorescence microscope to perform the imaging and an automated fluidics system to perform the sequential hybridizations. In some embodiments, compressed air is used to push reagents into a 1 cm×1 cm well with cells and tissues fixed on the bottom coverslip. Without the intention to be limited by theory, Applicant notes that, in some embodiments, because of the high viscosity of the hybridization buffer, a compressed air driven system eliminates dead volume and also can be precisely controlled to deliver defined volumes of reagents. In some embodiments, a separate vacuum line is used to purge the chamber. In some embodiments, work flow of a provided protocol is similar to existing DNA sequencers at the time of the present invention, which is well known in the art.

In some embodiments, during each cycle of hybridization, a machine automatically hybridizes samples with probes, washes with buffer to remove excess probes, and/or scans the brain slices for imaging. In some embodiments, wherein DNase is used in a removing step, after imaging DNase is flown in to remove the probes. After extensive wash, another round of hybridization can proceed afterwards. During hybridization time, a microscope moves to a different location on the stage to image another brain slice that has been hybridized and washed already. In such a way, a camera is acquiring images most of the time, while other samples on the stage are being hybridized.

Software.

In some embodiments, software is used, for example, to automate the control process and analysis of data. In some embodiments, codes are written in Micromanager, a free software supported by the National Institute of Health, to control a microscope as well as fluidics elements. In some embodiments, valves, stages, light sources, cameras and/or microscopes are controlled through Micromanager.

In some embodiments, compressed sensing is used for dense images (Zhu et al., Faster STORM using compressed sensing. Nat. Methods. 2012, 9(7):721-3) and deconvolution methods are used to separate out the spots in dense clusters. In some embodiments, improvement in image analysis increases multiplex capacity of provided methods, e.g., seqFISH (for example, by about 4-5 folds beyond the 100 gene multiplex). In some embodiments, efficiency is improved in a similar fashion to improvement from the Illumina GAII sequencer to the HiSeq machines, wherein using image processing methods to analyze densely packed clusters on the sequencing chip increased the throughput. In some embodiments, data acquisition and analysis are integrated in a user-friendly package.

In some embodiments, provided technology provides software packages for data analysis. In some embodiments, provided technologies provide software packages for data analysis in Python and Matlab. Images of provided technologies can be a variety of sizes, and can the optionally optimized if desirable. In some embodiments, each FOV is 6 Megapixels at 14 bits depth, corresponding to 1.5 MB of data per image. In some embodiments, about 100 GB of data are generated per run. In some embodiments, provided technologies provide methods for data processing and/or mitigating data log jam. In some embodiments, data log jam is mitigated by segmenting out the spots from each image, fitting them with 2 dimensional Gaussian distributions and recording the center position of the fits. In some embodiments, provided technologies save computer space by discarding raw images and saving processed data.

Light Sheet Microscopy with CLARITY Cleared Brain Slices.

In some embodiments, provided technologies provide methods for imaging a tissue, an organ and/or an organism. In some embodiments, provided technologies provide methods for measuring thick tissues or organs. In some embodiments, a thick tissue or organ has a thickness of about or more than 100 μm. In some embodiments, provided technologies preserves long range projections and morphology beyond within single cells. In some embodiments, light sheet microscopy is used for measuring thick tissues or organs. In some embodiments, a tissue, an organ, and/or an organism is cleared by CLARITY (Chung et al., Structural and molecular interrogation of intact biological systems, *Nature,* 2013, doi:10.1038/nature12107).

Figure 16:
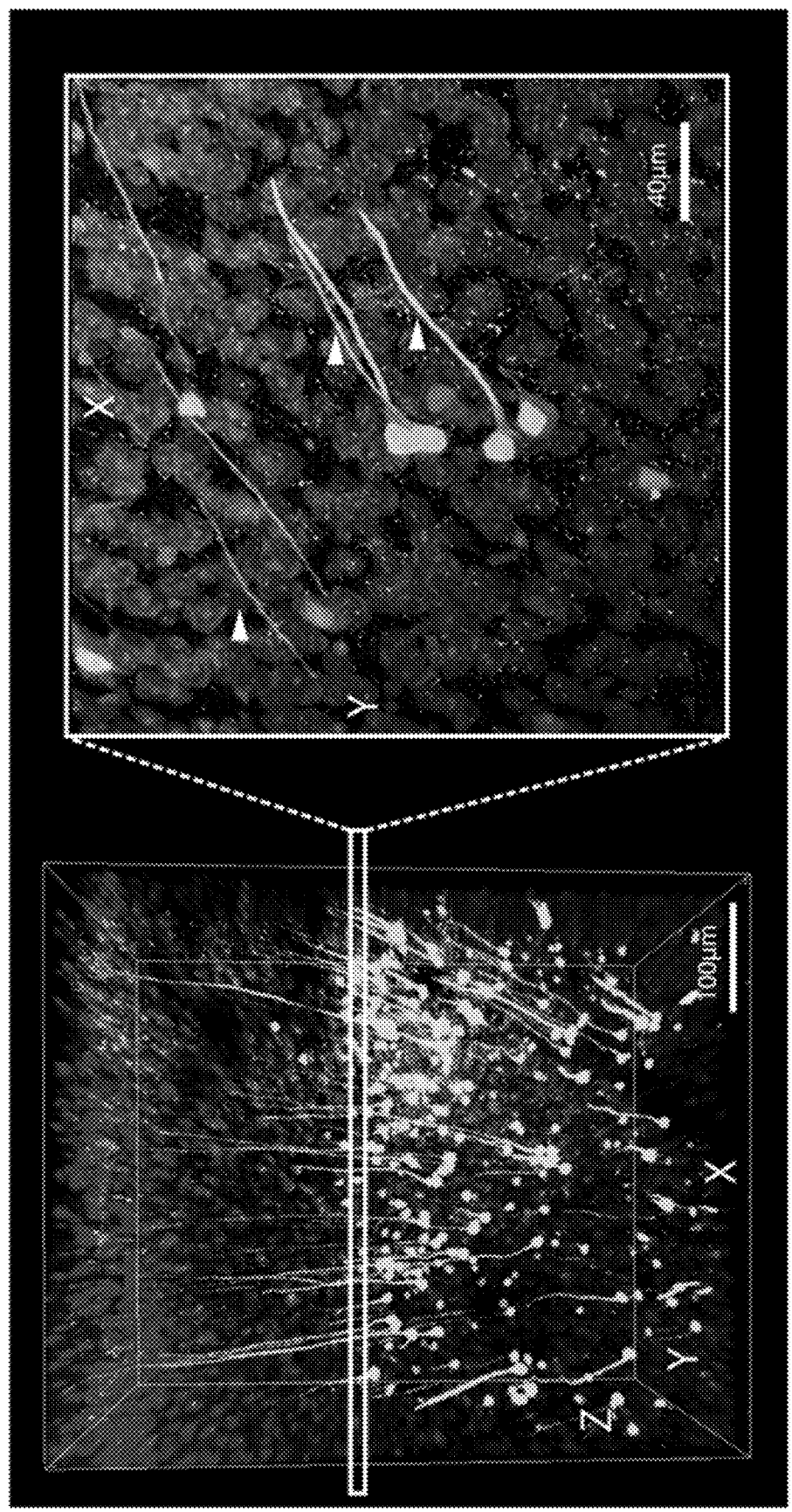
FIG. 16. CLARITY with Nissl: 1 mm-thick coronal section (Bregma A P, 2.3-1.3 mm) of a Thy-1-eYFP mouse brain was cleared and stained with NeuroTrace fluorescent Nissl stain (1:100 dilution, 48 hours, RT). Left, 3d coronal rendering of the motor cortex. Right, 100 µm-thick section of layer V motor cortex. Arrows indicate apical dendrites of the pyramidal neurons (Red-Fluorescent Nissl, Green-eYFP).

In some embodiments, to image thicker brain slices (>100 μm) which better preserves long range projections and morphology, light sheet microscopy, a.k.a. selective plane illumination microscopy (SPIM), are applied on CLARITY cleared brains tissues. In some embodiments, the CLARITY methodology renders the brain transparent for visualization and identification of neuronal components and their molecular identities. In some embodiments, CLARITY turns brain tissue optically transparent and macromolecule-permeable by removing light scattering lipids, which are replaced by a porous hydrogel to preserve the morphology of brain tissue, so that studies can be conducted without thinly sectioning the brain, which enables visualization of neurons of interest as well as their long-range synaptic connectivity. Without the intention to be limited by theory, Applicant notes that compared to FISH that was previously performed in culture or thin slices prior to the present invention, provided technologies can use thicker tissues and allow for more accurate reconstructions of individual neurons or 3D neuronal networks transcriptome. FIG. 16 illustrates a successful, validated Clarity-based protocol to prepare optically clear thick slices compatible with FISH staining: (1) 100 micron coronal brain slices in 2 mL Eppendorf tubes were incubated in 1.5 mL of 4% Acrylamide, 2% formaldehyde, 0.25% thermo-initiator, 1× PBS at 4 degrees overnight; (2) nitrogen gas was bubbled through the hydrogel solution for 10 seconds; (3) degassed samples were incubated for 2 hours at 42 degrees to polymerize; (4) samples were washed 3 times in PBS and incubated in 10% SDS, 1×PBS at 37 degrees for 4 hours to clear; and (5) samples were washed 3 times in PBS and ready to be used for seqFISH.

In some embodiments, provided technologies provide methods for minimizing or preventing out-of-focused background. In some embodiments, provided technologies utilize imaging technologies that minimize or prevent out-of-focused background. In some embodiments, SPIM is used for thicker slices that have higher out-of-focused background. In some embodiments, while confocal microscope can reject this background, it scans slowly and photobleaches the upper layers of sample while imaging the lower layers. In some embodiments, in SPIM only the layer that is being imaged is illuminated by excitation light. In some embodiments, in a SPIM setup useful for provided technologies, two objectives placed perpendicular to each other are suspended over the sample at approximately 55Ο. In some embodiments, a light sheet is generated using a cylindrical lens to focus one axis of the beam into an about 10 μm height and an effective width or FOV of about 200 μm.

Figure 17:
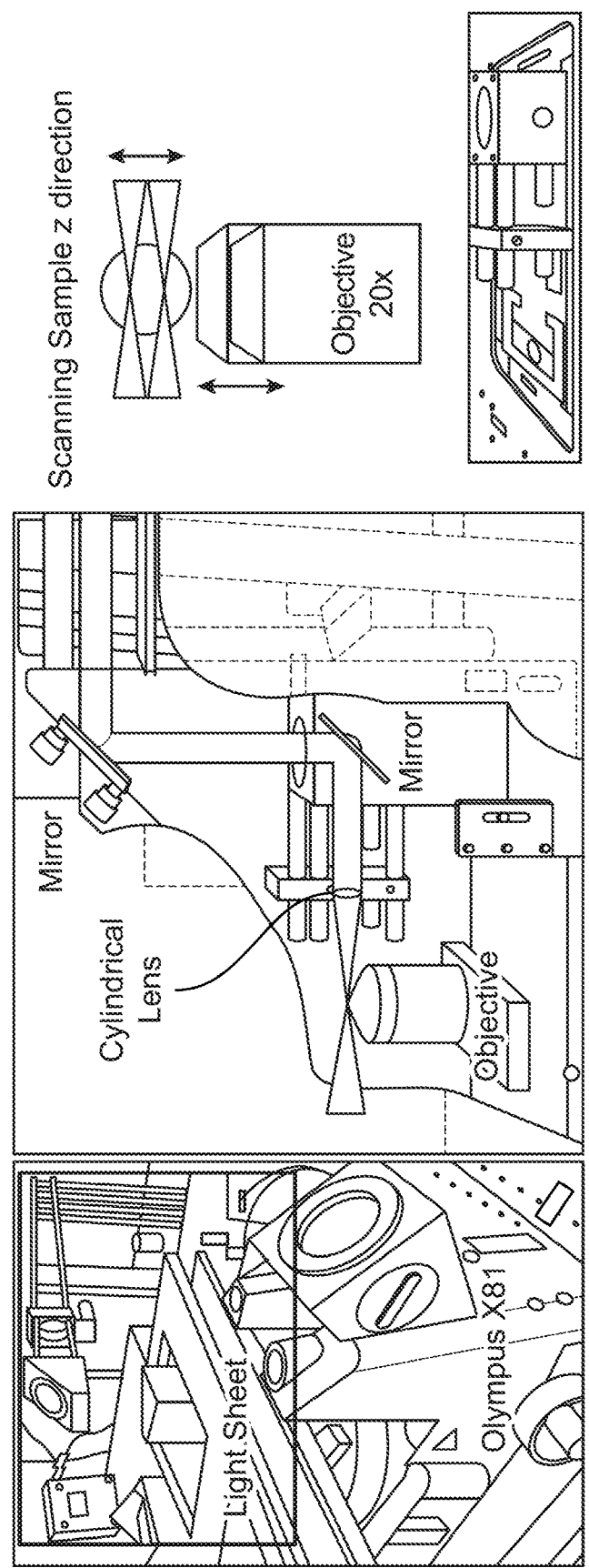
FIG. 17. A schematic display of an exemplary light sheet microscope.

In some embodiments, the present invention provides microscope setups for provided methods. In some embodiments, the present invention provides a light sheet microscope, wherein the sample is illuminated from the side. In some embodiments, a light sheet is parallel to a sample stage. In some embodiments, a light sheet is perpendicular to the detection objective. An exemplary setup of light sheet microscope is illustrated in FIG. 17. By adapting two mirrors and a cylindrical lens, a plane of light sheet is created and illuminates the sample from the side, and is perpendicular to the detection objective (middle). The bottom mirror is connected to the cylindrical lens and mounted directly onto the same base of objective. With this configuration, the objective is moving synchronically with the illumination sheet, allowing scanning the sample along z-axis (right, top). The right (bottom) figure also shows that, the sample is mounted inside the hybridization chamber, and imaged by an air objective below.

Figure 18:
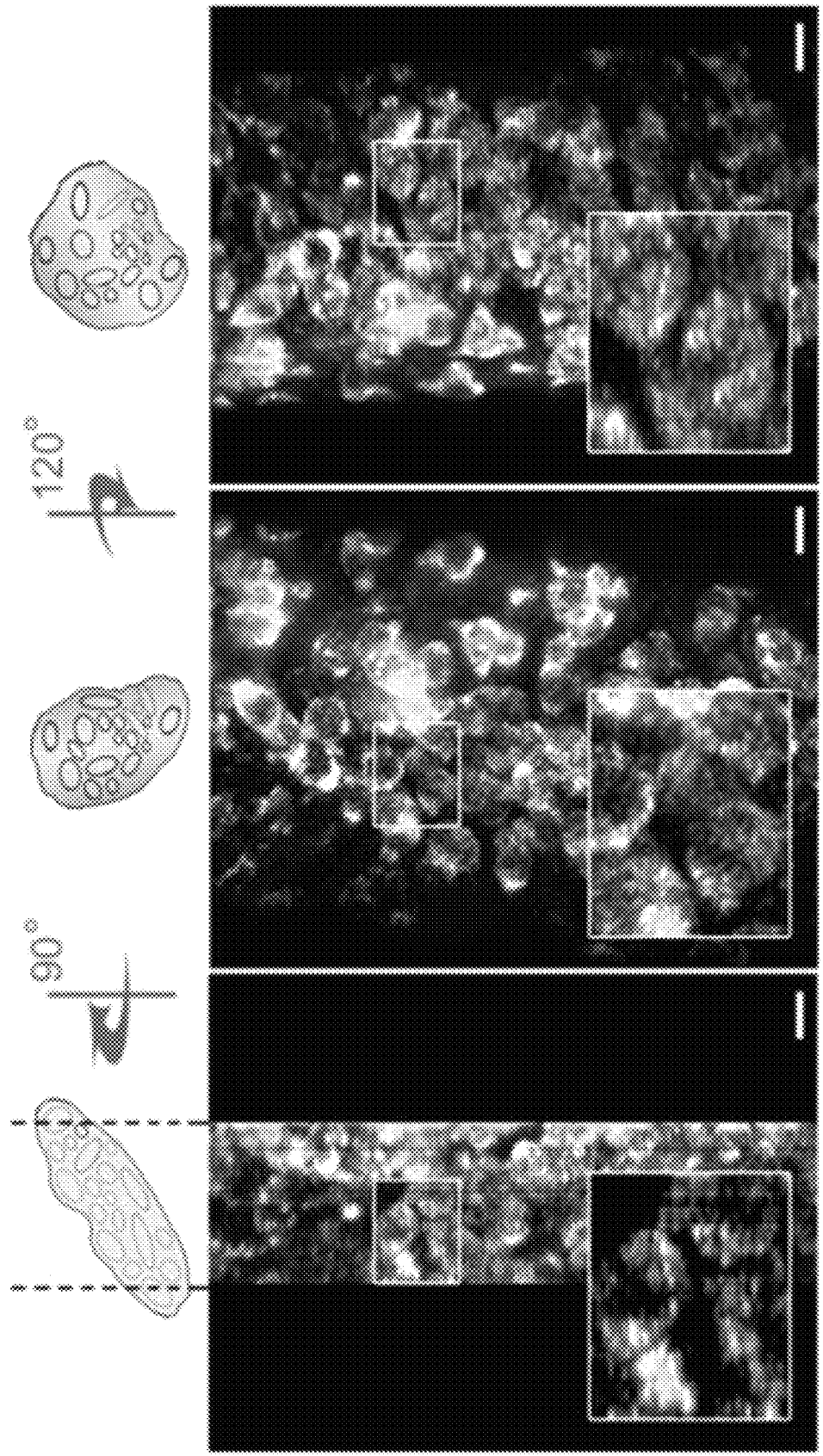
FIG. 18. SPIM detects single mRNAs in 100 µm CLARITY brain slices. The slice was scanned over 100 µm. The images were then registered and stitched to a 3D reconstruction. Diffraction limited dots in the image corresponded to single β-Actin mRNAs detected by HCR. Scale bar is 15 µm.

As illustrated in FIG. 18, SPIM images were acquired with a 100 μm brain slice that was CLARITY cleared and hybridized with HCR probes against β-actin. 200 optical sections with 0.5 μm spacing were taken to generate the reconstruction. Clear HCR signals were observed with a 20× water immersion objective. The β-actin mRNA is highly expressed, accounting for the large number of dots in the cell bodies. However, clear diffraction limited spots were also observed in axons.

In some embodiments, HCR-seqFISH protocol to CLARITY cleared brains and SPIM microscopy can be adapted. 100 μm slices were efficiently hybridized in 4-5 hours, indicating that detectably labeled oligonucleotide probes can diffuse readily in 100 μm thick but cleared slices. In addition, DNase enzyme diffused readily as well to strip HCR signal from the slice (FIG. 15). In some embodiments, provided technologies provide detectably labeled oligonucleotides, such as FISH and HCR probes, that are smaller than antibodies that persons having ordinary skill in the art routinely diffuse into 1 mm thick coronal slices, and provide profiling of targets for whole tissues or organs, e.g., performance of seqFISH on CLARITY cleared whole brains.

In some embodiments, provided technologies provide geometries of microscopy. In some embodiments, provided technologies provide alternative geometry of SPIM such that thick brain slices (>100 μm) and potentially entire CLARITY cleared brain can be mounted on an epifluorescence microscope with a long working distance objective. In some embodiments, a light sheet is generated perpendicular to the imaging axis, and sections the sample, mounted at an angle on the microscope, with 10 μm width over 200-300 μm. In some embodiments, a provided geometry allows direct carry-over of a developed flow chamber and automation design. In some embodiments, fiducial markers in brain slices are used to register successive slices. In some embodiments, nanoscopic rods are injected into the brain prior to sectioning, allowing good registration between different sections.

Speed.

In some embodiments, imaging speed limits the ultimate throughput. In some embodiments, provided HCR amplification provides more than sufficient number of photons for imaging, and less expensive cameras can be used to image the sample. In some embodiments, light from the collection objective can be split into multiple, e.g., 6 distinct paths (e.g., 5 fluorescence and 1 DAPI) with imaging flat dichroics and filters. This dramatically increases the throughput of in situ "sequencers," such that an entire brain can be completed in 1 week on a single microscope.

Target Genes Selection.

In some embodiments, the present invention provides technologies for selecting and imaging a set of targets, such as a set of transcripts and/or DNA loci (e.g, a set of 100 targets as exemplified). In some embodiments, target genes are chosen from the in situ database from the Allen brain atlas (ABA). Multiple criteria can be used to select genes of interest, e.g., those likely to represent the cellular identity in the cortex region. Computational selection of an optimal set of genes from overlapping criteria is well-known (2.

Alon, N; Moshkovitz, Dana; Safra, Shmuel (2006), "Algorithmic construction of sets for k-restrictions", ACM Trans. Algorithms (ACM) 2 (2): 153-177, ISSN 1549-6325; 8.

Cormen, T H.; Leiserson, Charles E.; Rivest, Ronald L.; Stein, Clifford (2001), Introduction to Algorithms, Cambridge, Mass.: MIT Press and McGraw-Hill, pp. 1033-1038, ISBN 0-262-03293-7; 12. Feige, U (1998), "A threshold of ln n for approximating set cover", Journal of the ACM (ACM) 45 (4): 634-652, ISSN 0004-5411). In some embodiments, set-cover-heuristics (Pe'er, 2002) are used to select genes that: 1. are known to define sub cell types; 2. exhibit "salt and pepper" expression patterns in the ABA; 3. belong to a family of genes such as transcription factors, ion channels, GPCRs, and neurotropins; and 4. culled from RNA-seq experiments from cortex samples. For instance, SLC1A3 marks glia cells while SLC6A1 marks inhibitory neurons, and SLC17A7 marks excitatory neurons. In some embodiments, genes with heterogeneous expression pattern such as PVALB, SST and CALB2 mark out subsets of inhibitory neurons. An exemplary set of 100 genes is shown below:

| Gene Name | Expression Profile |
|---|---|
| SLC6A1 | all inhibitory (I) |
| SLC17A7 | all excitatory (E) |
| SLC1A3 | glia |
| PVALB | subset I |
| SST | subset I |
| CALB2 | subset I |
| LER5 | Isocortex |
| TNNC1 | Isocortex |
| MYL4 | Isocortex |
| SATB2 | Isocortex |
| CCL27a | Isocortex |
| BOC | Primary Motor L1 |
| DACT2 | Primary Motor L1 |
| LHX1 | Primary Motor L1 |
| PVRL3 | Primary Motor L1 |
| SLC44a3 | Primary Motor L2/L3 |
| KLK5 | Primary Motor L2/L3 |
| TNNC1 | Primary Motor L2/L3 |
| WNT6 | Primary Motor L2/L3 |
| ZMAT4 | Primary Motor L5 |
| STARD8 | Primary Motor L5 |
| TCF21 | Primary Motor L5 |
| MYL4 | Primary Motor L5 |
| KRT80 | Primary Motor L6a |
| OLFR19 | Primary Motor L6a |
| TBC1d30 | Primary Motor L6a |
| OLF16 | Primary Motor L6b |
| EAR6 | Primary Motor L6b |
| CHIT1 | Primary Motor L6b |
| SLN | Secondary Motor L1 |
| ADAMTS8 | Secondary Motor L1 |
| EPYC | Secondary Motor L1 |
| KCNV1 | Secondary Motor L1 |
| pcdh7 | Secondary Motor L2/L3 |
| GLT8d2 | Secondary Motor L2/L3 |
| HKDC1 | Secondary Motor L2/L3 |
| SRPX | Secondary Motor L3 |
| ZFP458 | Secondary Motor L3 |
| SLC30a8 | Secondary Motor L3 |
| GK5 | Secondary Motor L5 |
| TEX28 | Secondary Motor L5 |
| MS4a10 | Secondary Motor L5 |
| KRT16 | Secondary Motor L6a |
| KRT42 | Secondary Motor L6a |
| DOC2a | Secondary Motor L6a |
| KRT33b | Secondary Motor L6b |
| YBX | Secondary Motor L6b |
| PNPLA5 | Secondary Motor L6b |
| TMEM215 | Primary Somatosensory L1 |
| SDC1 | Primary Somatosensory L1 |
| PREX1 | Primary Somatosensory L1 |
| DIEXF | Primary Somatosensory L1 |
| DHRS7c | Primary Somatosensory L2/L3 |
| DDIT4l | Primary Somatosensory L2/L3 |
| TDG | Primary Somatosensory L2/L3 |
| EPSTI1 | Primary Somatosensory L2/L3 |
| RORb | Primary Somatosensory L4 |
| GSC2 | Primary Somatosensory L4 |
| KRT10 | Primary Somatosensory L4 |
| GCA | Primary Somatosensory L4 |
| DCBLD2 | Primary Somatosensory L5 |
| ABCD2 | Primary Somatosensory L5 |
| GTDC1 | Primary Somatosensory L5 |
| IL17RA | Primary Somatosensory L6a |
| TBR1 | Primary Somatosensory L6a |
| PPID | Primary Somatosensory L6a |
| IGHM | Primary Somatosensory L6b |
| MMGT1 | Primary Somatosensory L6b |
| CPLX3 | Primary Somatosensory L6b |
| ART2b | Secondary Somatosensory L1 |
| GNB4 | Secondary Somatosensory L1 |
| B3GAT2 | Secondary Somatosensory L1 |
| PDC | Secondary Somatosensory L2/L3 |
| ADIG | Secondary Somatosensory L2/L3 |
| FPR1 | Secondary Somatosensory L2/L3 |
| INHBC | Secondary Somatosensory L4 |
| RUFY4 | Secondary Somatosensory L4 |
| HGFAC | Secondary Somatosensory L4 |
| EFCAB4b | Secondary Somatosensory L5 |
| SSTR2 | Secondary Somatosensory L5 |
| ZFP395 | Secondary Somatosensory L5 |
| CCDC36 | Secondary Somatosensory L6a |
| ST14 | Secondary Somatosensory L6a |
| MYL12b | Secondary Somatosensory L6b |
| RSPO2 | Secondary Somatosensory L6b |
| NDNF | L1 (I) |
| RASGRF2 | L2/3 (I) |
| CUX2 | L2/3/4 |
| RORB | L4 |
| SCNN1A | L4 |
| ETV1 | L5 |
| FEZF2 | L5 |
| BCL6 | L5 |
| TRIB2 | L5a |
| FOXP2 | L6 |
| TLE4 | L6/L6b |
| CTGF | L6b |
| CYLD | L2/3 |
| CMTM3 | L2/3 |
| ANKRD6 | L2/3 |

Integration of seqFISH with Protein Detection, Organelle Markers and Activity Measurements.

In some embodiments, provided technologies, e.g., seqFISH, allow multiplex analysis of RNA, as well as proteins, neural activities, and structural arrangements in the same sample in situ with single cell resolution. Antibodies for specific targets can be hybridized in one additional round of hybridization to the sample. In some embodiments, provided methods optionally comprise a step of immunostaining. In some embodiments, multiple antibodies are used to detect many protein targets in sequential rounds of hybridization (Schubert W et al. Analyzing proteome topology and function by automated multidimensional fluorescence microscopy. Nat Biotechnol (2006) 24(10):1270-1278). Applicant notes that there are up to about 100-1000 or more fold higher abundance of proteins over mRNAs in cells. Targeted proteins can mark cellular organelles such as mitochondria, ER, transport vesicles, cytoskeleton, as well as synaptic junctions. For example, MAP2 antibodies can be used to mark out cell boundaries to help segmentation of axons and dendrites.

Live observation of brain slices can be imaged on the epi-fluorescence and light sheet microscope prior to transcription profiling by provided methods (e.g., seqFISH). Calcium (Nakai J, Ohkura M, Imoto K (February 2001). "A high signal-to-noise Ca(2+) probe composed of a single green fluorescent protein". Nat. Biotechnol. 19 (2): 137-41; Akerboom et al., "Optimization of a GCaMP calcium indicator for neural activity imaging." J Neurosci. 2012 Oct. 3; 32(40):13819-40; Stosiek et al., "In vivo two-photon calcium imaging of neuronal networks." Proceedings of the National Academy of Sciences 100 (12): 7319) and voltage sensor (Cohen, et al., "Optical Measurement of Membrane Potential" in Reviews of Physiology." Biochemistry and Pharmacalogy, vol. 83, pp. 35-88, 1978 (June); Mutoh et al., Genetically Engineered Fluorescent Voltage Reporters ACS Chem Neurosci. 2012 August 15; 3(8): 585-592; Peterka et al., Imaging voltage in neurons. Neuron. 2011 Jan. 13; 69(1):9-21) can be imaged in the brain slices. SPIM allows efficient and fast imaging of these sensors in brain slices. Brain slices are fixed on the microscope and provided protocols such as seqFISH protocols can be performed with automated fluidics. In some embodiments, in addition to the live measurements, mRNAs of activity dependent immediate early genes (IEGs) are detected as a measure of the integrated neural activities in the neurons. For example, CamKII and cFos were readily detected in neurons with heterogeneous expression levels; they can be incorporated in a set of genes, e.g., an exemplary 100 gene multiplex or FISHed separately in additional cycles depending on abundance.

Integrating Connectomics and seqFISH to Identify Molecular Identities of Distinct Neurons within Different Somatic Sensorimotor Neural Networks.

To Systematically Characterize the Molecular Identities of Distinct Neuronal Populations within the Somatic Sensorimotor Neural Networks Using Provided Technologies.

In some embodiments, neuronal populations within the same functional subnetworks can share common sets of marker genes, but also have heterogeneous expression of other genes that defines identity at a cellular level. In some embodiments, cells in different subnetworks differ more in their expression patterns. Exemplary cortico-cortical somatic subnetworks each of which controls a basic class of sensorimotor function are: (1) orofaciopharyngeal for eating and drinking, (2) upper limbs for reaching and grabbing, (3) lower limbs for locomotion, and (4) whisker for rhythmic whisker movements. In some embodiments, provided technologies provide a novel and rigorous approach for characterizing molecular identities of cortical neurons with distinct neural networks and provide invaluable information for understanding genetic circuits underlying the wiring diagram of the mammalian brain.

Figure 19:
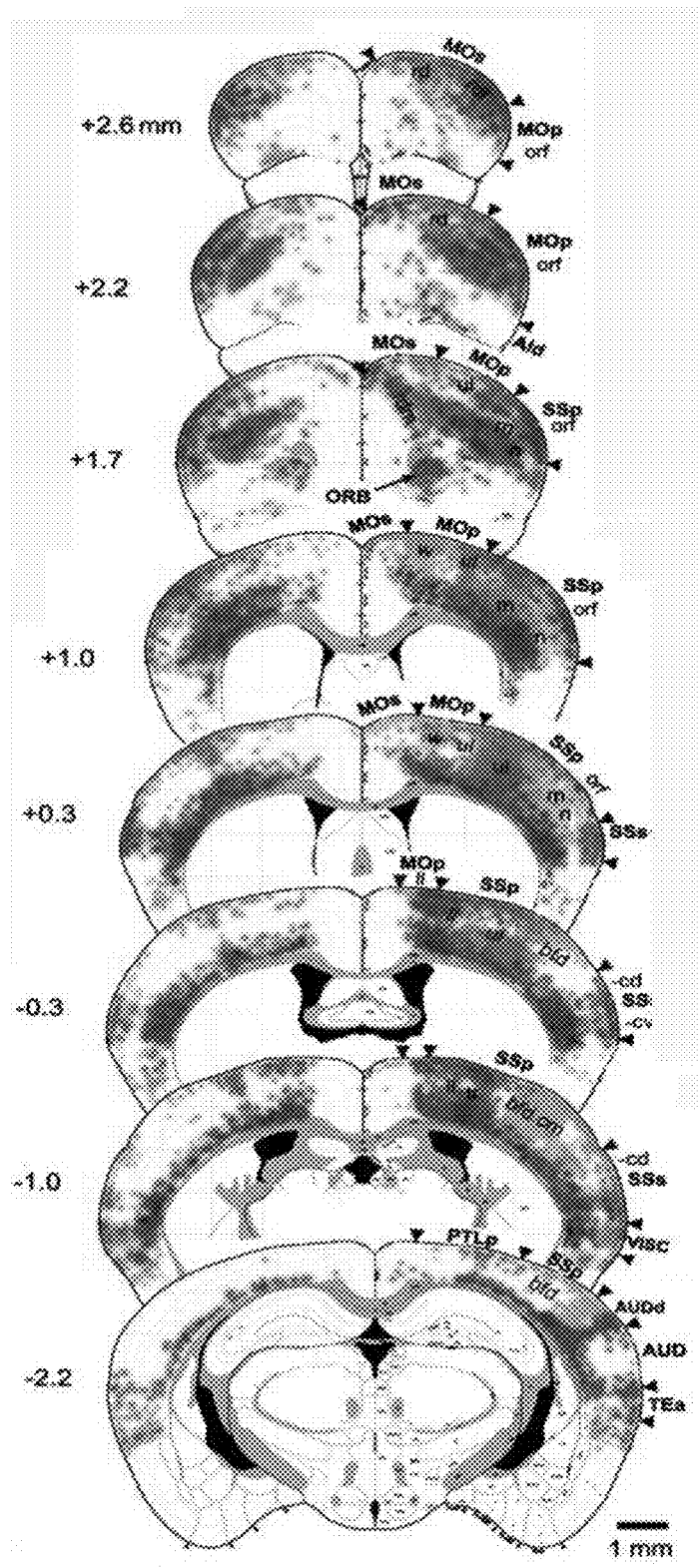
FIG. 19. A connectivity map of the cortical somatic sensorimotor subnetworks on serial coronal levels of the Allen Reference Atlas. It shows that each of the four major components of somatic sensorimotor areas, SSp, SSs, MOp, and MOs, are divided into 4 functional domains. These functionally correlated domains are extensively interconnected with all others and form four major cortical somatic sensorimotor subnetworks: orofaciopharyngeal (orf, blue), upper limb (ul, green), lower limb and trunk (ll/tr, red), and whisker (bfd.cm & w, yellow). Numbers indicate position of sections relative to bregma (mm). Provided methods can characterize connectivity and molecular identities of projection neurons in each of these distinct domains within different subnetworks.
Figure 20:
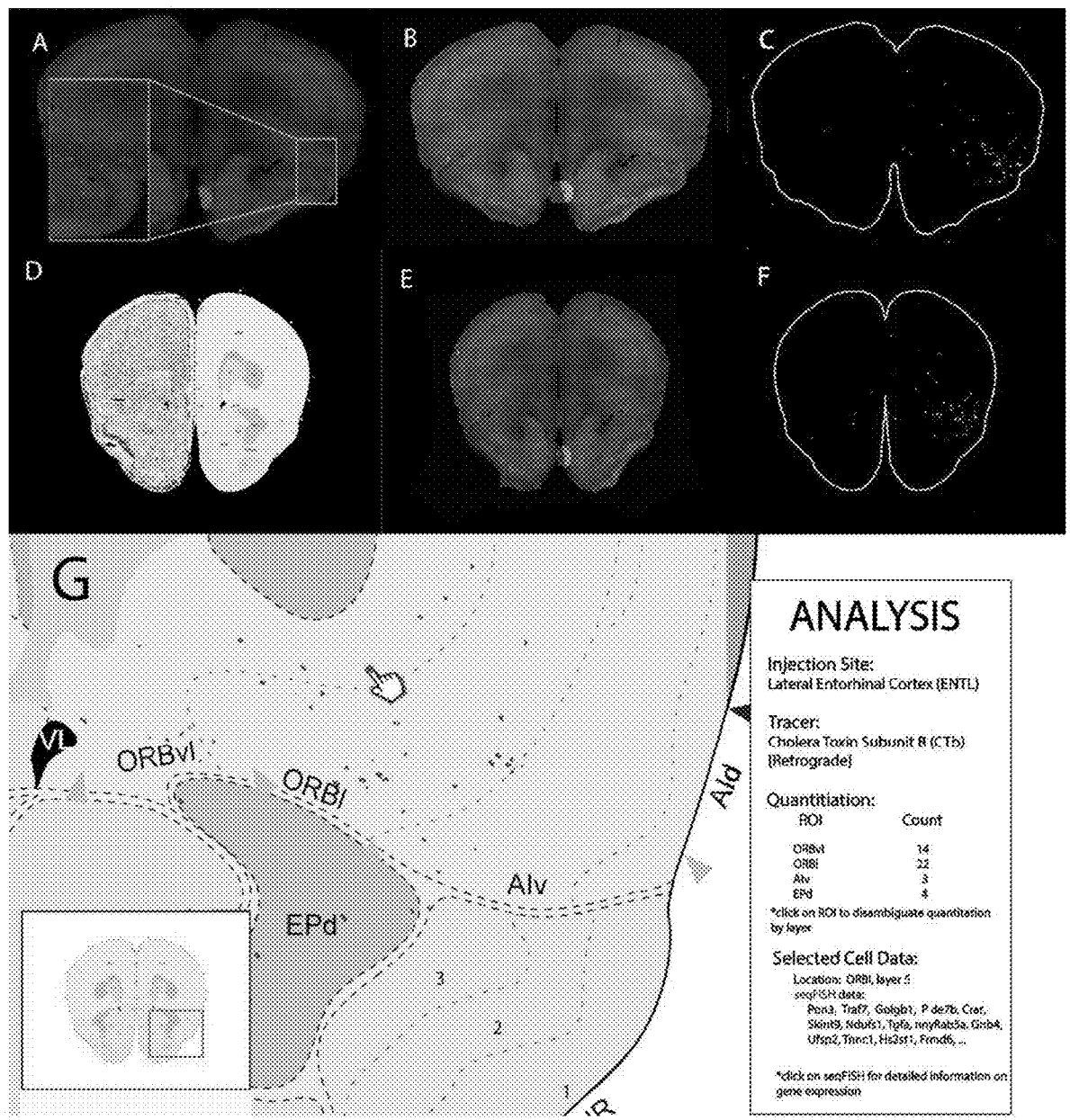
FIG. 20. Exemplary informatics workflow for automatically detecting and mapping retrogradely labeled neurons and gene barcoding information. A. Raw image with CTb labeling (pink) and Nissl staining (blue). The boxed area shows a close-up view of CTb labeled neurons. B. Multi-channel raw image are converted into grayscale for segmentation. C. Individual tracer channel images are run through a segmentation pipeline that discretely separates the tissue background from labeled cells. White dots are reconstructions of labeled somata. D. Reintegrated multi picture tiffs are associated with a coronal section in the ARA for registration. E. Using provided developed registration software, multi picture tiffs are warped to align both the tissue's silhouette and cytoarchitectural delineations to its corresponding ARA level. F. Cells extracted via the segmentation process are spatially normalized and can be associated with a layer- or sub-nucleus-specific ROI within the ARA. G. Segmented and registered labeling reconstructions are made available to the public on the iConnectome FISH viewer, along with their accompanying seqFISH data. An analysis tab provides information about the injection site, tracer type, number of labeled cells by ROI, which can be further disambiguated into layer-specific cell counts, and gene expression by cell.

Using a collection of neuronal pathways, digital cortical connectivity atlas can be generated to display raw images of tract tracing studies. Pathways can be graphically reconstructed to create cortico-cortical connectivity map to help analysis of large-scale data. Based on intracortical connectivity, four distinct cortico-cortical somatic subnetworks can be established each of which controls a basic class of sensorimotor function. Each of these subnetworks comprises 4-5 distinct functional domains in the primary somatic sensory (SSp), primary somatomotor (MOp), secondary somatomotor (MOs), and supplementary somatosensory (SSs) cortical areas, which were further subdivided according to their strength of connectivity with other somatic sensorimotor areas corresponding to a specific body subfield. In some embodiments, the orofaciopharyngeal subnetwork comprises five major nodes: (1) the SSp mouth and nose domain (SSp-m/n); (2) the MOp orofacial domain (MOp-orf); (3) the MOs rostrodorsolateral domain (MOs-rdl); (4) the SSp barrel field anterolateral domain (SSp-bfd.al); and (5) the SSs rostral and caudoventral domain (SSs-r & cv). In some embodiments, the four major nodes of the upper limb subnetwork comprise (1) the SSp upper limb (SSp-ul); (2) MOp-ul; (3) rostrodorsal MOs (MOs-rd); and (4) caudodorsal SSs (SSs-cd). In some embodiments, the lower limb/trunk subnetwork comprise the SSp lower limb/trunk region (SSp-ll/tr), the MOp-ll/tr, and the rostrodorsomedial MOs (MOs-rdm) (FIG. 10 B-D). In some embodiments, the whisker subnetwork comprises the caudomedial SSp-bfd (SSp-bfd.cm), MOp-w, which corresponds to the vibrissal primary motor cortex (vM1) and the caudodorsal SSs (SSs-cd; FIG. 19). Exemplary data are described by the Mouse Connectome Project (www.mouseconnectome.org).

To determine molecular identities of distinct neuronal populations in each of these somatic sensorimotor subnetworks, multi-fluorescent retrograde tracers are used to label neurons, and provided technologies such as seqFISH can be applied to determine the gene expression profile of retrogradely labeled population at single cell resolution. To label the neuronal populations, multiple (e.g., five) retrograde tracers are injected into five of the main targets of one of the main nodes of each sensorimotor subnetwork in the same animal (tracer information below). For example, in one animal, circuit tracers are injected into two of the major cortical nodes (SSp-bfd.al and SSs-r & cv) and three of the subcortical nodes (caudoputamen ventrolateral domain, CP-vl; ventral posteromedial thalamic nucleus, VPM; and ventral spinal trigeminal nucleus, SPV) of the orofaciopharyngeal subnetwork. This simultaneously back labels five different neuronal populations in all of the other nodes of the orofaciopharyngeal subnetwork. In this example, labeled neurons are in the SSp-m/n domain and in the MOp-oro.

On the other hand, tracer can be injected into four different SSp body subfield domains (i.e. SSp-m/n, SSp-ul, SSp-ll/tr, and SSp-bfd.cm), each of which belongs to a distinct somatic subnetwork. This simultaneously labels distinct neuronal populations in cortical areas associated with the different subnetworks. In this case for example, back labeled neurons are observed in the MOp domains associated with each subnetwork, i.e MOp-orf, MOp-ul, MOp-ll/tr, and MOp-w. This injection strategy applied to all the main nodes and subcortical targets of each of the four somatic sensorimotor subnetworks labels distinct neuronal populations of each of the subnetworks.

After injection of the tracers (e.g., one week following the injection of the tracers), animals are sacrificed, and their brains are harvested and coronally sectioned at 20 μm or 100 μm thickness for seqFISH analysis of back labeled neurons. Genes, such as the exemplified approximately 100 genes that are richly expressed in the somatic sensorimotor cortical areas (SSp, MOp, MOs, SSs) can be preselected for profiling using, for example, the online digital gene expression database of the Allen Brain Atlas project (www.Brian-Map.org) (Lein et al., 2007 Genome-wide atlas of gene expression in the adult mouse brain. Nature, 11; 445(7124):168-76).

Injection Strategy and Post Injection Processing.

Three hundred 4-week-old male C57Bl/6 mice are used. In one animal, five fluorescent retrograde tracers are injected into either different nodes within the same somatic sensorimotor subnetworks, or different nodes in different somatic subnetworks as described above (FIG. 19). The tracers are Fluorogold (FG, yellow), cholera toxin b conjugated with 488 or 647 (CTb-488 [green], CTb-647 [pink]), red retrobeads (RR, red), and wheat germ agglutinin conjugated with 655 (WGA-Qdot655, white). Since Qdot655 has an excitation wavelength that differs from CTb 647, it can be captured into a different channel and pseudocolored with a unique hue. The tracers are injected (either iontophoretically or with pressure injection) via stereotaxic surgeries. Details on surgeries and perfusions are described, e.g., in Hintiryan et al., Comprehensive connectivity of the mouse main olfactory bulb:analysis and online digital atlas. Front Neuroanat. 2012 Aug. 7; 6:30. eCollection 2012. In some embodiments, two paired mice are injected with the same tracers used in the exact same coordinates. One of the animals is used to validate locations of labeled cells and injection sites, while the other is subjected to provided, e.g., seqFISH methods. One is perfused following tracer transport, and brains are coronally sectioned into 50 μm thickness sections and collected in four series. One in four series of sections is counterstained with a fluorescent Nissl stain solution (NeuroTrace Blue [NTB]), mounted onto glass slides, and imaged using an Olympus VS120 virtual microscopy system. In some embodiments, the Nissl stain provides cytoarchitectonic background for visualizing precise anatomical location of back labeled cells. These images are processed through an informatics pipeline so that every individual image is faithfully registered onto its corresponding level of the Allen Reference Atlas (ARA). This Nissl, along with provided informatics tools, enables automatical and precise counting of the approximate number of each tracer labeled neuronal population in each ROI (in this case, the different domains of somatic sensorimotor areas). The distribution patterns are automatically plotted onto the corresponding atlas level to create their connectivity map.

The paired mice are sacrificed at the same time and their brains are sectioned at either 20 μm or 100 μm thickness for seqFISH analysis. These sections are first imaged under 20× (or 10×) objective to reveal back labeled neurons with different tracers. Brain sections through all coronal levels containing the somatic sensorimotor areas are used to perform seqFISH for an exemplified set of 100 genes. This method reveals the gene expression in every tracer labeled neuron. All images are analyzed first for gene expression profiles of each individual tracer labeled neurons. Each section is registered back to the closest matched section of its paired brain so that sections at approximately the same coronal level from the paired brains can be displayed alongside in a connectome viewer. As such, molecular profiles of different neuronal populations are displayed within its closest matched anatomic background. In some embodiments, gene expression profiles are correlated in each retrogradely labeled neuronal population.

Results.

In some embodiments, distinct retrogradely labeled neuronal populations within different somatic sensorimotor areas display different transcriptome profiles; even neuronal populations in the same domain (e.g., SSp-m) that are labeled with different tracers display distinct gene expression profile from its neighboring neurons that have different connectivity profiles. In some embodiments, different neuronal populations within different somatic sensorimotor nodes within the same subnetwork (e.g., SSp-m, MOp-orf, SSp-bfd.al, and SSs-r) share common network-specific genes, while neuronal populations within different neural networks (e.g., the orofaciopharyngeal and lower limb/trunk subnetworks) display very distinct transcriptome profiles. In some embodiments, regional (e.g., SSp or MOp) or laminar (different layers) specific genes are identified for those neurons in different cortical areas and different layers.

As exemplified, provided technologies provide a unique combination of fluorescent tract tracing with seqFISH technology to characterize molecular identities of connectivity-based neuronal populations (cell types) within distinct somatic sensorimotor networks with subneuronal resolution and faithful anatomic background. See, e.g., FIGS. 3 and 9 for exemplary results. In some embodiments, provided technologies comprise measuring other parameters in parallel (i.e. antibody and organelle stains, as well as IEG expression levels), and can be applied to the entire neocortex or brain.

High Throughput Pipelines and Informatics Tools for Analyzing and Presenting Data Online.

In some embodiments, provided technologies provide high throughput pipelines and informatics tools for analyzing and presenting data online through, e.g., a publicly accessible database, such as www.MouseConnectome.org). In some embodiments, provided technologies provide integration with Mouse Connectome Project, whose broad scope of study and use of multi-fluorescent imaging make it a valuable tool among the connectomic community and well suited for studying long-range connectivity in the mouse brain. For example, it offers online visualization tools that allow users to visualize multiple fluorescent labeled pathways on the top of their own cytoarchitectural background and corresponding ARA atlas level. In some embodiments, to faithfully associate seqFISH information with its corresponding retrogradely labeled somata, labeled cell bodies are discretely segmented from tissue background and from images of the same section, but acquired at different rounds (e.g., first for image retrograde tracers, then for different mRNA in seqFISH), and spatially indexed by their coordinates relative to a fixed reference point on either the slide and/or an anatomical landmark in the tissue. In some embodiments, to associate data with a stereotaxic coordinate defined in the ARA, the present invention provides a novel registration pipeline that dramatically increases registration accuracy (i.e. warping each scanned microscopy image to the shape of the corresponding level of the ARA), and image segmentation that automatically and accurately enumerates fluorescently labeled neurons in a given ROI (e.g., SSp-m, MOp-ll). In some embodiments, provided technologies collectively allow for labeling and seqFISH data from multiple tracers within a brain, and across multiple brains, to be collated into a single anatomical framework for the purposes of visualization and annotation.

In some embodiments, images are registered at corresponding atlas levels of the Allen Reference Atlas (Dong, H. W. (2008). The Allen Reference Atlas: A Digital Color Brain Atlas of C57BL/6J Male Mouse, John Wiley & Sons). The deformation matrix resulting from the registration process is applied on the original resolution images to get the high-resolution warped images. Following registration and registration refinement, the NeuroTrace® fluorescent Nissl stain is converted to a bright-field image. Next, each channel for every image is adjusted for brightness and contrast to maximize labeling visibility and quality in tools, e.g., iConnectome. After modifications (i.e. skewness, angles) and JPEG2000 file format conversions, images can be published to iConnectome view (www.MouseConnectome.org).

FISH Visualization Tool.

In some embodiments, all connectivity data produced in are processed through the MCP informatics pipeline and presented online through a new iConnectome FISH Viewer (www.MouseConnectome.org). Different from available iConnectome viewer, which displays two anterograde (PHAL and BDA) and two retrograde (FG and CTb) labeling, iConnectome FISH can display up to five different neuronal populations with retrograde fluorescent dyes. As mentioned above, each set of injections can be given to a pair of mice. One can be processed following a regular MCP pipeline and be presented in iConnectome FISH viewer to display multiple fluorescent labeled neuronal populations within their own Nissl-stained cytoarchitetural background and within their corresponding ARA level. These can provide precise anatomic information for each of the fluorescent labeled neuronal populations across the entire brain. Brain sections from its paired partner following seqFISH are registered onto the closest ARA level that its paired partner was registered to and can be displayed side by side in different window. A list of genes that were expressed in the neurons can be listed on the side panel. Upon clicking on the gene, the fluorescently labeled neurons that expressed this gene can light up to indicate its expression locations. This provides a practical way to display the molecular identities of neuronal populations within the global context of connectivity and anatomical background.

In some embodiments, a corresponding database is developed that allows users to analyze these data and to correlate neural connectivity with their molecular identities. This informatics tool is built on top of a database that stores information associated with each retrograde labeled neuronal population (e.g. cell numbers, anatomic location) with gene barcoding. This database can help users to identify corresponding gene barcodes for neurons within the same neural networks or distinct neural networks.

Mapping the Whole Brain.

In some embodiments, provided technologies have sufficient sensitivity, selectivity, automation, and/or spatiotemporal resolution at single neuron level for high-throughput analysis of gene expression in retrogradely labeled neurons for whole brains.

Additional Exemplary Methods for Removing Steps

Figure 21:
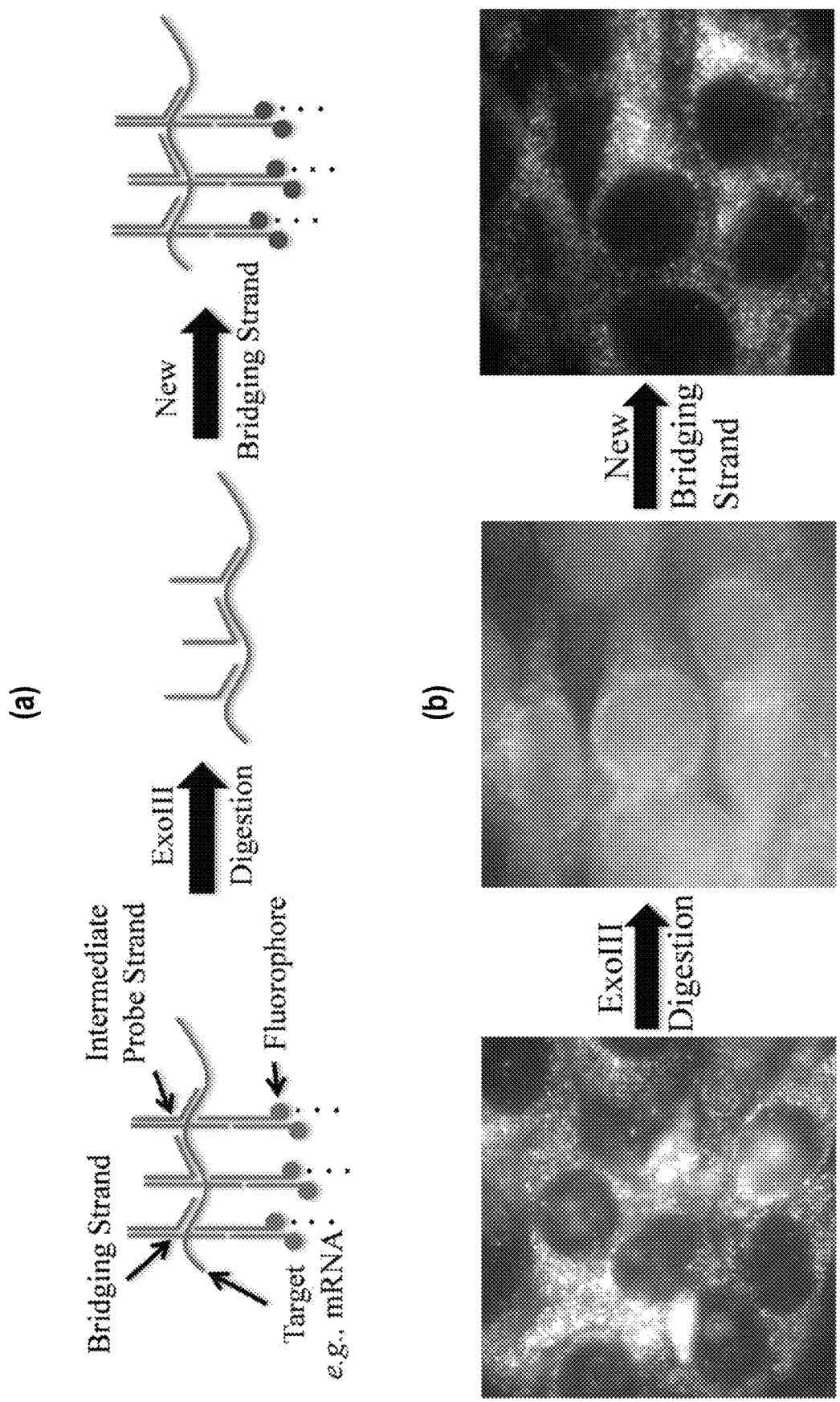
FIG. 21. Hybridization Chain Reaction (HCR) Re-hybridization Using Exonuclease III (ExoIII). (a) Schematic representation of exoIII digestion of bridging strands and HCR polymers. ExoIII digests bridging strands and HCR polymers from the 3' to 5' direction into dNMP's leaving behind intermediate probe strands bound to targets, e.g., mRNAs. A new bridging strand can then by hybridized to target bound probe with a different initiator sequence which initiates polymerization of a different hairpin set with a different fluorescent dye. (b) Raw data illustrating use of the schematic shown in (a) in T3T mouse fibroblast cell line using probes against beta-actin (Actb) transcripts.

In some embodiments, the present invention provides a varieties of methods for removing detectably labeled oligonucleotides from targets. In some embodiments, exonuclease III (ExoIII) is used to remove detectably labeled oligonucleotides. FIG. 21 illustrates an exemplary process for HCR re-hybridization using Exo III. In FIG. 21, Exo III digests bridging strands and HCR polymers, keeping intermediate oligonucleotides intact for hybridization with new bridging strands. Exemplary data were presented in FIG. 21 (b) using detectably labeled oligonucleotides targeting beta-actin (Actb) transcripts in T3T mouse fibroblast cells. The left image showed the initial hybridization and amplification of Actb transcripts using Alexa 488 dye. The middle image showed complete loss of signal in the Alexa 488 channel after a 1 hour incubation in exoIII at room temperature. The right image showed re-amplification of Actb transcripts after addition of only the new bridging strand and the corresponding hairpins tagged with Alexa 647 dye. The contrast ratio of the images was adjusted to illustrate certain features of the method.

Figure 22:
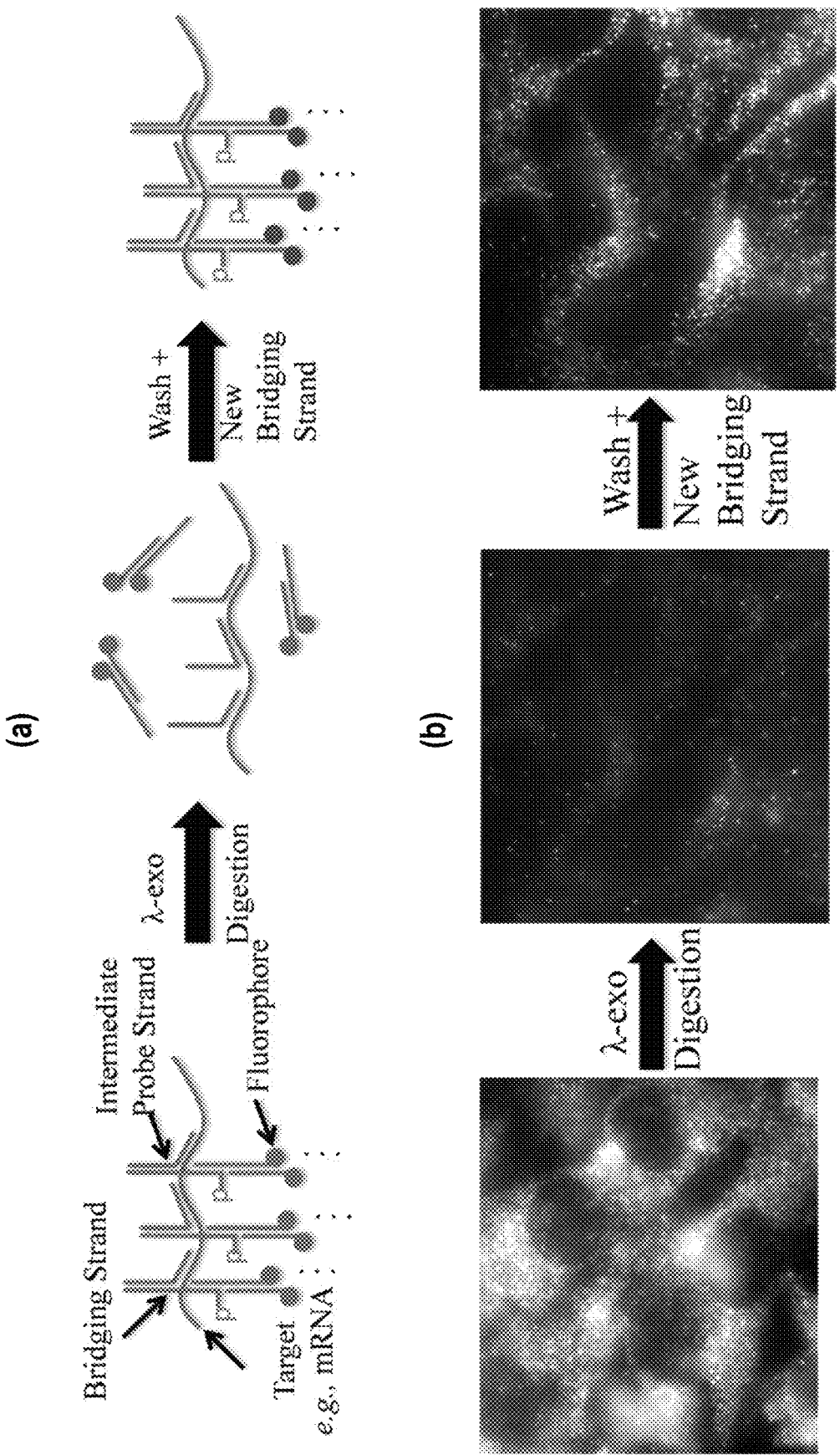
FIG. 22. Hybridization Chain Reaction (HCR) Re-hybridization Using Lambda Exonuclease (λ-exo). (a) Schematic representation of λ-exo digestion of bridging strands. λ-exo selectively digests 5' phosphorylated bridging strands in the 5' to 3' direction releasing HCR polymers from intermediate probe strands bound to targets, e.g., mRNAs. Released polymers are washed out with wash buffer. A new bridging strand can then by hybridized to target bound probe with a different initiator sequence which initiates polymerization of a different hairpin set with a different fluorescent dye. (b) Raw data illustrating use of the schematic shown in (a) in T3T mouse fibroblast cell line using probes against beta-actin (Actb) transcripts.

In some embodiments, Lambda Exonuclease (λ-exo) is used to remove detectably labeled oligonucleotides. FIG. 22 illustrates an exemplary process for HCR re-hybridization using λ-exo. In FIG. 22, λ-exo digests 5' phosphorylated bridging strands and releases HCR polymers from intermediate oligonucleotides bound to targets, e.g., mRNAs and keeps intermediate oligonucleotides intact for hybridization with new bridging strands after washing out released polymers. Exemplary data were presented in FIG. 22 (b) using detectably labeled oligonucleotides targeting beta-actin (Actb) transcripts in T3T mouse fibroblast cells. The left image showed the initial hybridization and amplification of Actb transcripts using Alexa 488 dye. The middle image showed loss of signal in the Alexa 488 channel after a 1 hour incubation in λ-exo at 37° C. The right image showed re-amplification of Actb transcripts after washing with wash buffer and addition of only the new bridging strand along with the corresponding hairpins tagged with Alexa 647 dye. The contrast ratio of the images was adjusted to illustrate certain features of the method.

Figure 23:
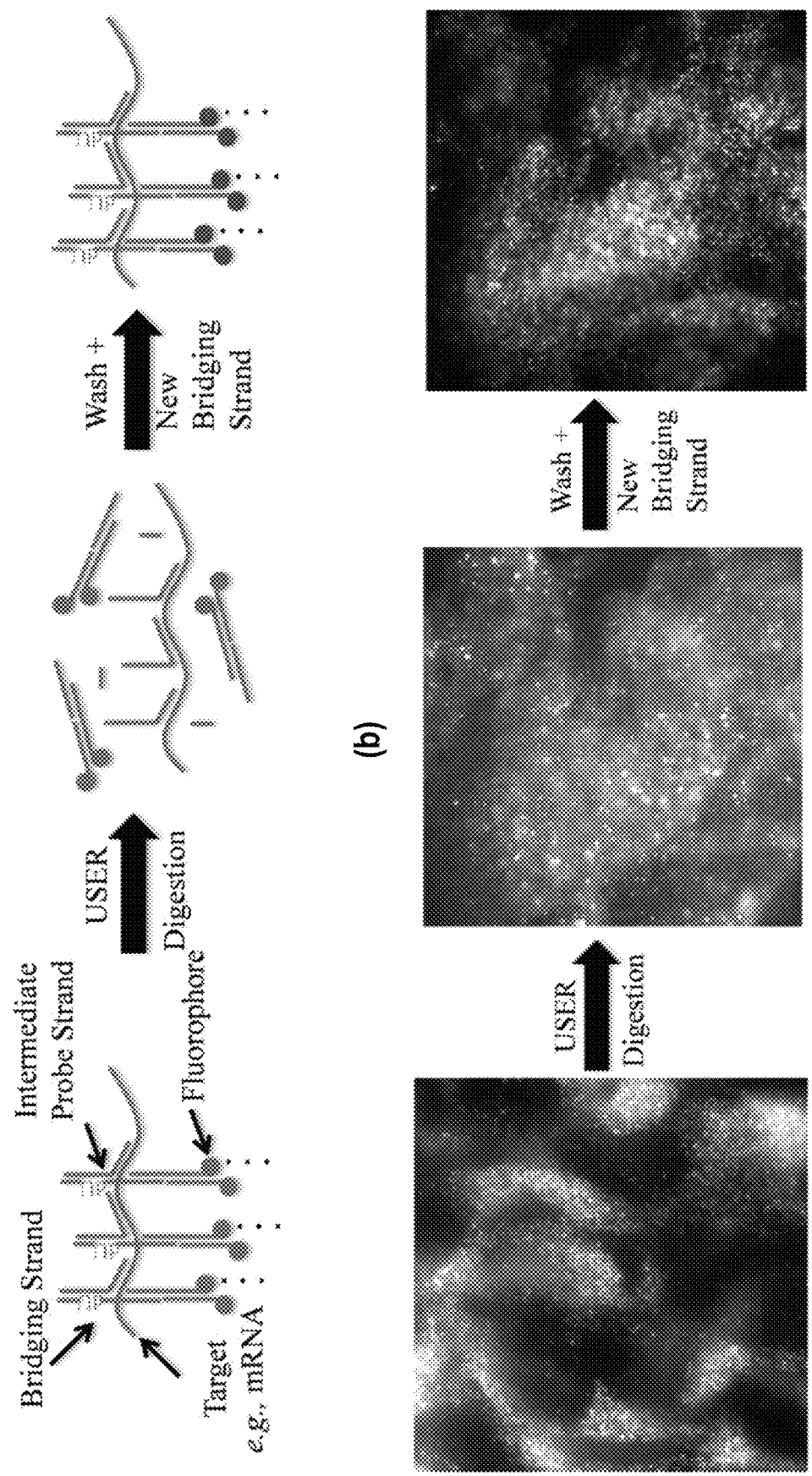
FIG. 23. Hybridization Chain Reaction (HCR) Re-hybridization Using Uracil-Specific Excision Reagent (USER). (a) Schematic representation of USER digestion of bridging strands. USER selectively digests deoxyuridine nucleotides in bridging strands causing bridging strands to become fragmented. Fragments then dissociate from intermediate probe strands releasing HCR polymers from probes bound to targets, e.g., mRNAs. Released polymers are washed out with wash buffer. A new bridging strand can then be hybridized to target bound probe with a different initiator sequence which initiates polymerization of a different hairpin set with a different fluorescent dye. (b) Raw data illustrating use of the schematic shown in (a) in T3T mouse fibroblast cell line using probes against beta-actin (Actb) transcripts.

In some embodiments, Uracil-Specific Excision Reagent (USER) is used to remove detectably labeled oligonucleotides. FIG. 23 illustrates an exemplary process for HCR re-hybridization using USER. In FIG. 23, USER digests at deoxyuridine nucleotides in bridging strands and releases HCR polymers from intermediate oligonucleotides bound to targets, e.g., mRNAs and keeps intermediate oligonucleotides intact for hybridization with new bridging strands after washing out fragments and released polymers. Exemplary data were presented in FIG. 23 (b) using detectably labeled oligonucleotides targeting beta-actin (Actb) transcripts in T3T mouse fibroblast cells. The left image showed the initial hybridization and amplification of Actb transcripts using Alexa 488 dye. The middle image showed loss of signal in the Alexa 488 channel after a 1 hour incubation in USER at 37° C. The right image showed re-amplification of Actb transcripts after washing with wash buffer and addition of only the new bridging strand along with the corresponding hairpins tagged with Alexa 647 dye. The contrast ratio of the images was adjusted to illustrate certain features of the method.

Figure 24:
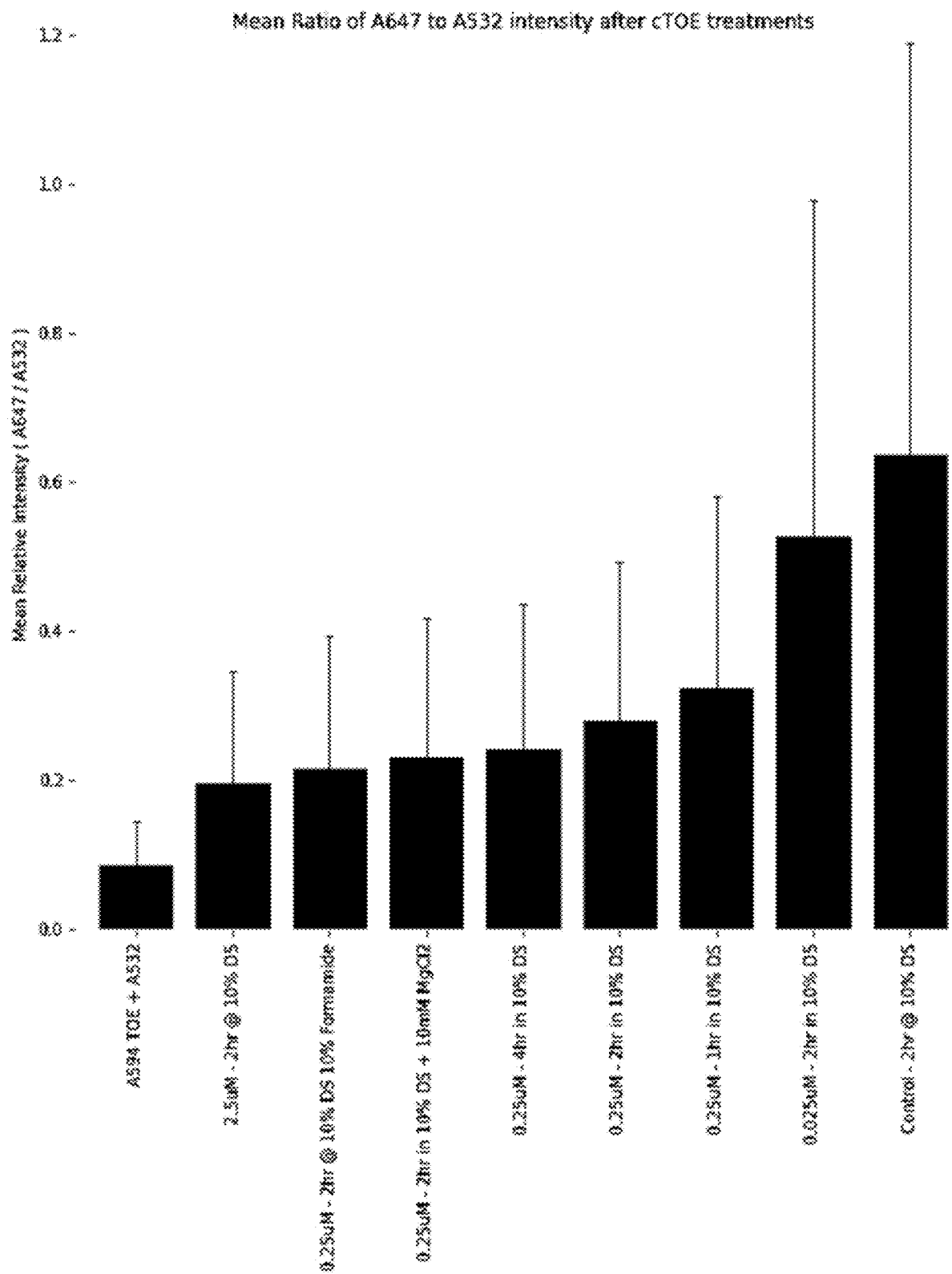
FIG. 24. Exemplary removal of detectably labeled oligonucleotides using complementary oligonucleotides (cTOE).

In some embodiments, detectably labeled oligonucleotides are removed by displacement using complementary oligonucleotides (cTOE). In some embodiments, displacement comprises use of a dextran or a derivative thereof, a salt, and/or an organic solvent. In some embodiments, displacement comprises use of a dextran or a derivative thereof. In some embodiments, displacement comprises use of dextran sulfate. In some embodiments, displacement comprises use of a salt. In some embodiments, a salt is $MgCl_2$. In some embodiments, displacement comprises use of an organic solvent. In some embodiments, an organic solvent is formamide. A variety of factors, for example but not limited to cTOE concentration, incubation time, buffer composition and type and/or concentration of organic solvent can be optimized individually or in combination. FIG. 24 showed exemplary data of displacement of smFISH probes using cTOE. The mean ratio of fluorescence intensity between the smFISH probe to be displaced (Alexa 647) and a colocalized smFISH probe (Alexa 532) is shown. Various treatments were performed in which the concentration of cTOE, hybridization buffer composition and displacement time were compared. All displacement probe conditions resulted in significantly more displacement than the control in which cells were placed in 10% DS and no cTOE was added. Without the intention to be limited by theory, Applicant notes that, among other things, increasing the concentration of cTOE, increasing the amount of time that cTOE probes hybridized, adjusting buffers to 10 mM $MgCl_2$ or 10% formamide all resulted in increased displacement. cTOE at 2.5 μM for 2 hours in 10% Dextran sulfate(DS) results in minimal residual Alexa 647 smFISH signal but a minor increase over the baseline signal determined by hybridizing Alexa 594(A594) in place of Alexa 647 and not adding cTOE.

Additional Examples for Oligonucleotide Preparation

Figure 26:
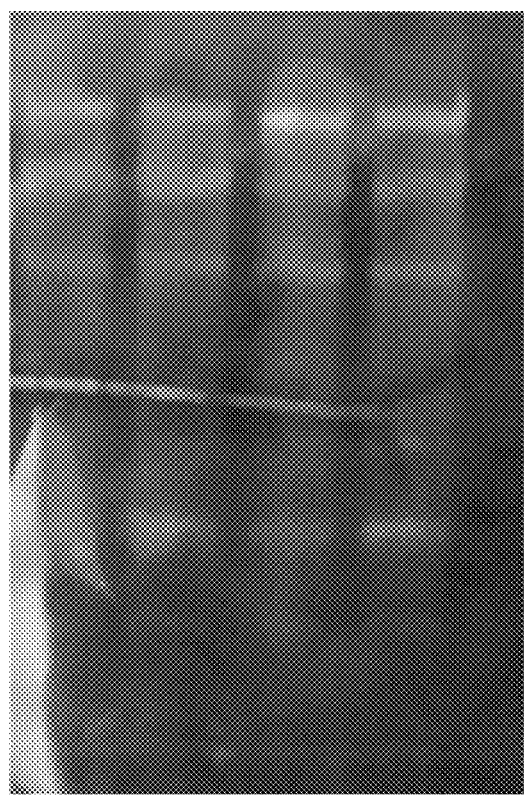
FIG. 26. Exemplary oligonucleotide preparation. Product was the third band on gel. The library has many different primers associated with it, one primer set for each subset of probes. Exemplified primers were random 20 nucleotide sequences with a GC content of 45-55% and a Tm of around 55° C. Nicking endonucleases sites were GTCTCNN; corresponding nicking endonuclease is Nt. BsmAI. Product probes were 20mer DNA sequences complementary to mRNA of interest with a GC content between 45-55%.

A set of sequences were amplified by PCR (FIG. 25). The product was isolated, e.g., precipitated using 5 volumes of precipitation buffer (30:1 EtOH: 1M NaOAc) at −20 OC for at least 10 minutes. The precipitation mixture was centrifuged for 10 minutes. The supernatant was discarded and the oligonucleotide pellet was reconstituted in nicking enzyme buffer with the appropriate units of enzyme, based on that about 10 units of enzyme digest about 1 μg of DNA in 1 hour. Once the incubation time had elapsed, the sample was again precipitated and reconstituted in 2× loading buffer (96% formamide/20 mM EDTA) and water to make a final loading buffer (48% formamide/10 mM EDTA). The sample was heated to 95° C. to completely denature the DNA. The denatured DNA was then loaded into a denaturing acrylamide gel (8M urea 10-12% acrylamide). The gel was run at 250V for 1 hour, or optimized as desired. After electrophoresis, the gel was stained using 1× sybr gold for 15 minutes and then visualized. The appropriate band was cut out, crushed, and incubated in DI water for 2 hours. After incubation, the sample was precipitated again and then purified using a vacuum column. The column was eluted with 30 L of RNase free water to yield the final product, as shown in FIG. 26.

In some embodiments, provided methods use restriction sites instead of nicking endonuclease sites. Similar to the amplification step in FIG. 25, a set of sequences are amplified by PCR, with a BamHI site flanking the 5'-end, and an AatII site flanking the 3'-end. The PCR product is precipitated with 5 volumes of precipitation buffer (30:1 EtOH: 1M NaOAc) at −20 OC for at least 10 minutes and isolated, followed by digestion with BamHI and AatII. The product is again purified, and subjected to exo III digestion. Removal of the digested nucleic acids provides the product oligonucleotides.

Example 2

Brain Slice Analysis

As an illustration, barcodes generated using the error correction mechanisms disclosed herein are used for in situ transcription profiling of single cells reveals spatial organization of cells in the mouse hippocampus.

Identifying the spatial organization of tissues at cellular resolution from single cell gene expression profiles is essential to understanding many biological systems. In particular, there exist conflicting evidence on whether the hippocampus is organized into transcriptionally distinct subregions. Here, a generalizable in situ 3D multiplexed imaging method was applied to quantify hundreds of genes with single cell resolution via Sequential barcoded Fluorescence in situ hybridization (seqFISH) (Lubeck et al., 2014). seqFISH was used to identify unique transcriptional states by quantifying and clustering up to 249 genes in 16,958 cells. By visualizing these clustered cells in situ, we identified distinct layers in the dentate gyrus corresponding to the granule cell layer, composed of predominantly a single cell class, and the subgranular zone, which contains cells involved in adult neurogenesis. Furthermore, it was discovered that distinct subregions within the CA1 and CA3 are composed of unique combinations of cells in different transcriptional states, instead of a single state in each sub-region as previously proposed. In addition, it was revealed that while the dorsal region of the CA1 is relatively homogenous at the single cell level, the ventral part of the CA1 has a high degree of cellular heterogeneity. These structures and patterns are observed in sections from different mice, as well as in seqFISH experiments with different sets of genes. Together, these results demonstrate the power of seqFISH in transcriptional profiling of complex tissues.

The mouse brain contains about $10^8$ cells arranged into distinct anatomical structures. While cells in these complex structures have been traditionally classified by morphology and electrophysiology, their characterization has been recently aided by gene expression studies. In particular, the Allen Brain Atlas (ABA) provides a systematic gene expression database using in situ hybridization (ISH) of the entire mouse brain one gene at a time (Dong et al., 2009; Fanselow and Dong, 2010; Thompson et al., 2008). This comprehensive reference provides regional gene expression information, but lacks the ability to correlate the expression of different genes in the same cell. More recently, single cell RNA sequencing (RNA-seq) has identified many cell types based on gene expression profiles (Darmanis et al., 2015; Tasic et al., 2016; Zeisel et al., 2015). However, while single cell RNA-seq provides useful information on multiple genes in individual cells, it has relatively low detection efficiencies and requires cells to be removed from their native environment resulting in the loss of spatial information. These different approaches can lead to contradictory descriptions of cellular organization in the brain and other biological systems.

In the hippocampus, recent RNA-seq data suggests that CA1 is composed of cells with a continuum of expression states (Cembrowski et al., 2016, Zeisel et al 2015), while ABA analysis indicates that sub-regions within the CA1 have distinct expression profiles (Thompson et al, 2008). To resolve the two conflicting descriptions of hippocampal organization, a method to profile transcription in situ in the hippocampus with single cell resolution is needed. Here, we demonstrate a general method that enables the mapping of cells and their transcription profiles with single molecule resolution in tissue, allowing an unprecedented resolution of cellular transcription states for molecular neuroscience (FIG. 29A).

A great deal of progress has been made recently in developing highly quantitative methods to profile the transcriptome of single cells. Building upon single molecule fluorescence in situ hybridization (smFISH) (Femino et al., 1998; Raj et al., 2006;), Lubeck et al. devised a general method to highly multiplex single molecule in situ mRNA imaging irrespective of transcript density using super-resolution microscopy (Betzig et al., 2006; Rust et al., 2006; Lubeck and Cai, 2012). However, the spectral barcoding methods used in these previous works is difficult to scale up beyond 20-30 genes because of limited number of fluorophores (Fan et al., 2001; Lubeck and Cai, 2012).

To overcome the scalability problem, a temporal barcoding scheme was developed that uses a limited set of fluorophores and scales exponentially with time (Lubeck et al., 2014). Specifically, by using sequential rounds of probe hybridizations on the mRNAs in fixed cells to impart a unique pre-defined temporal sequence of colors, different mRNAs can be uniquely identified in situ. The multiplex capacity scales as $F^N$, where F is the number of fluorophores and N is the number of rounds of hybridization. Thus, one can increase the multiplex capacity by increasing the number of rounds of hybridization with a limited pool of fluorophores. This approach is called Sequential barcoded Fluorescence in situ Hybridization (seqFISH) (Lubeck et al., 2014). In parallel, in situ sequencing methods were developed to directly sequence transcripts in tissue sections, but these methods suffer from low detection efficiency (<1%) (Ke et al., 2013; Lee et al., 2014). Recently, Chen et al. expanded the error correction method in the original seqFISH demonstration by using a Hamming distance 2 based error correcting barcode system, called merFISH. However, this implementation requires larger transcripts (>6 kb) and many more rounds of hybridization than the method described here (Chen et al., 2015b). Furthermore, seqFISH and its variants have only been applied in cell culture systems due to the difficulty of smFISH detection in tissue. Here, an improved version of seqFISH in complex tissues by including signal amplification and a time-efficient error correction scheme (FIGS. 29A-D, FIG. 37) were demonstrated to resolve the structural organization of the hippocampus with single cell resolution.

Example 3

Brain Slice Analysis with Error Correction

Signal Amplification and Error Correction Enable Robust Detection of mRNAs in Tissues.

To overcome the autofluorescence and scattering inherent to brain tissues, we used an amplified version of smFISH, called single molecule Hybridization Chain Reaction (sm-HCR) (FIG. 29E) (Shah et al., 2016). Single molecule HCR amplified signal 22.1±11.5 (mean±s.d., n=1288, FIG. 38B) fold compared to smFISH, enabling robust and rapid detection of individual mRNA molecules in tissues and facile alignment of spots between hybridizations (FIG. 30A). Single transcripts can be detected and localized in 3D with just 24 probes in tissues, enabling detection of transcripts<1 kb in size, with a fidelity comparable to the smFISH gold standard (FIGS. 38C-D) but with signals 20-fold brighter (Shah et al., 2016). Single molecule HCR DNA polymers can also be digested by DNAse and re-hybridized in brain slices, allowing HCR-seqFISH to be robustly implemented (FIG. 30A). We note the smHCR enables true 3D imaging in tissues, whereas the previous sequential FISH demonstrations (Lubeck et al., 2014, Chen et al., 2015) were performed only in flat cell cultures.

Furthermore, we improved upon our existing barcode system by implementing a time-efficient error correction scheme. The major source of error in seqFISH is the loss of signal due to mis-hybridization, which increases with the numbers of hybridization. We introduced an extra round of hybridization to correct loss of signal during any round of hybridization (FIG. 29D). By minimizing the number of hybridizations, this error correction scheme is efficient in practical implementation. For example, using 5 fluorophores and 4 rounds (instead of 3 rounds) of hybridization to code for 125 genes, we can still uniquely assign barcodes to genes even when signal from any single round of hybridization is missing. Although merFISH can tolerate 2 errors in the barcodes, it requires 16 rounds of hybridization to code 140 genes (Chen et al. 2015). As increasing the number of hybridizations can potentially lead to more experimental error and analysis complexity, our simple error correction method corrects for the most common error, dropped signal. Also, the fewer rounds of hybridizations decreases the total imaging time, which is rate-limiting for tissue experiments. HCR-seqFISH with simpler error-correction scheme allows efficient and accurate quantification of transcription profiles in tissues.

Using this HCR-seqFISH method, we surveyed the regional and sub-regional transcriptional heterogeneity within the temporal and parietal cortex and hippocampus of the mouse brain by imaging similar coronal sections collected from 3 different animals. Two similar sections from separate mice were profiled with probes for 125 genes, while one additional brain slice was imaged for 249 genes. In each of the coronal slices, between 60-80 fields of view were imaged, each 216 µm×216 µm×15 µm, in the cortex and hippocampus (FIG. 29A and FIG. 38E). For the 125 gene set, 56 of the genes (FIG. 29D, FIG. 37) were selected because they showed spatially heterogeneous expression based on the ABA (Lein et al., 2007), another 44 were selected from a list of transcription factors, and 25 marker genes were selected from single cell RNA-seq datasets (Zeisel et al., 2015). One hundred of these genes were barcoded by 4 rounds of hybridization (FIG. 29B). The remaining 25 high abundance genes were measured individually using 5-color smHCR in 5 serial rounds of hybridizations (FIG. 29C). This hybrid approach of measuring medium expression genes with barcoding seqFISH and high copy number genes serially in subsequent hybridizations allows a large dynamic range of transcripts to be profiled in the same cell.

seqFISH is an Accurate and Efficient Method to Multiplex RNA In Situ.

To determine the accuracy of the seqFISH method in quantifying mRNA levels in single cells in tissue, we compared the copy number of 5 of the 100 target genes measured by barcoding to the copy number found by colocalized smHCR detection in the same cell (FIG. 30B, FIG. 39A) in 15 µm brain sections. We found that the copy number of the RNAs per cell as measured by barcoding and smHCR agreed with an R-value of 0.85 and a slope of 0.84 (N=3851). As colocalized smHCR matches smFISH transcript quantitation (Shah et al., 2016), the barcoded seqFISH method can quantify mRNA molecules in single cells with 84% efficiency compared to the gold standard of smFISH. In comparison, single cell RNA-seq measurements are 5-20% efficient based on spike-in controls and in situ sequencing is less than 1% efficient (Darmanis et al., 2015; Klein et al., 2015; Lee et al., 2014; Macosko et al., 2015; Tasic et al., 2016; Zeisel et al., 2015; Stahl et al., 2016). This high efficiency of detection results from a low transcript drop rate and a high barcode recovery rate due to the error correction round of hybridization. In our experiment, 78.9% of barcodes (N=2,115,477 barcodes) were found in all 4 hybridization rounds and 21.1% were identified in 3 out of the 4 hybridizations (FIG. 30C), indicating that the probability of detecting a given mRNA molecule is 94% in each round of hybridization (FIG. 39B).

Figure 39:
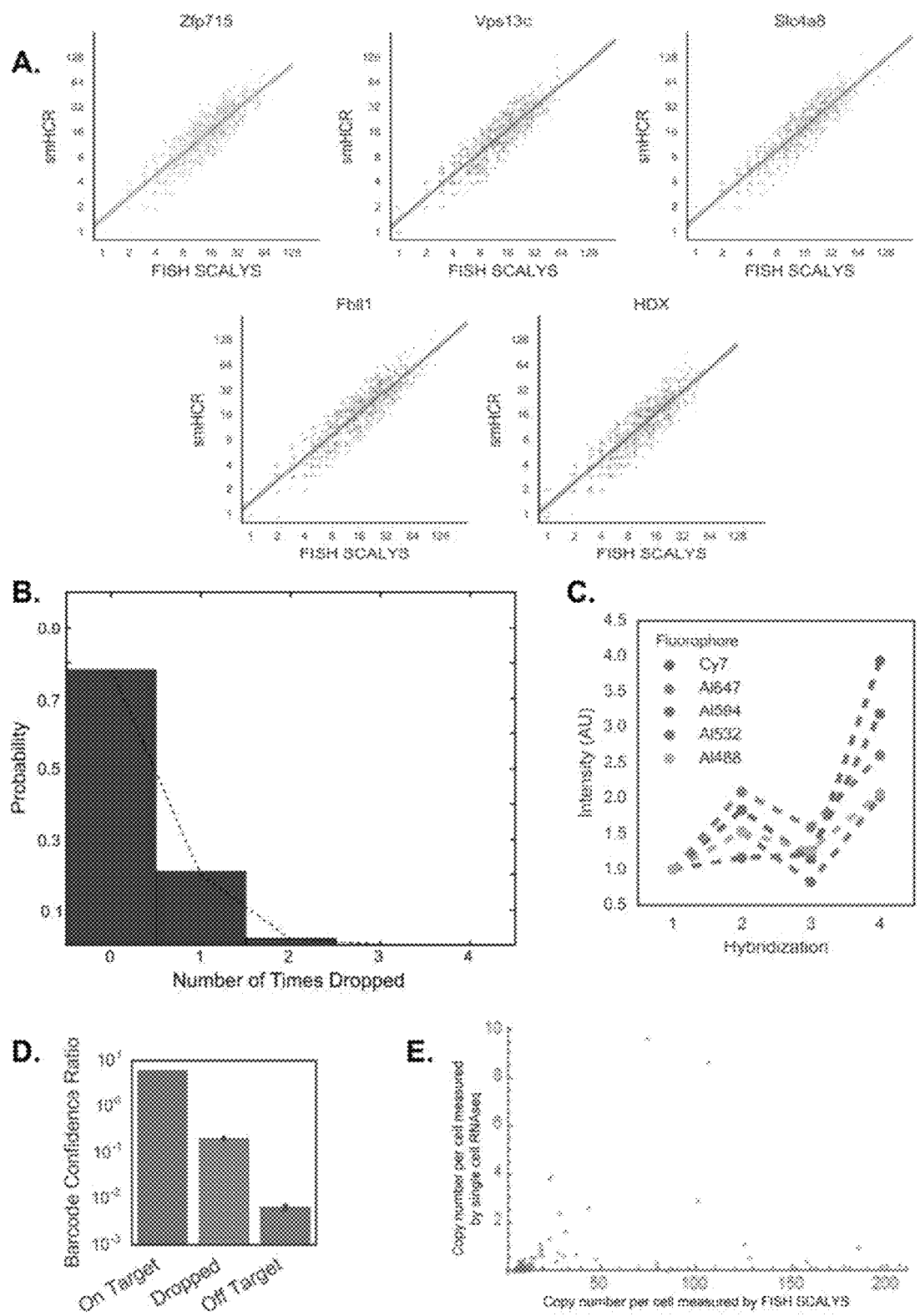
FIG. 39 depicts an example embodiment, showing quantitation of seqFISH (related to FIG. 30). A). All control genes show high correlations between seqFISH and smHCR. B). Number of dropped hybridizations from the barcode. Blue bars represent measured probability and the red bars represent inferred values from binomial distribution fitting of measured probability. The ratio of the full barcodes (4 hybridizations) vs 3 hybridization barcodes indicate that transcripts that are mis-hybridized in 2 rounds are rare. Transcripts missed in 2 or more hybridizations (red bars) could not be recovered from the error-correction algorithm and would be dropped from our quantifications (N=2,115, 477 total barcodes). C). Intensity of barcode hybridizations overtime. All dots belonging to barcodes are quantified in each hybridization and their mean intensity is plotted over time normalized to the first hybridization. 99% CI ratio of mean is plotted as a bar over points, but is not visible due to its small size (n=60143 to 111284 points per channel). D). Barcoding confidence ratio. Barcode classes in D) are compared to a null model of barcode observations where random chance observation should give a ratio of 1. Off target barcodes are observed 0.005 times less than expected, suggesting that seqFISH has high accuracy in correctly counting barcoded transcripts (n=3493 cells). Dark bars on top of bar plots correspond to 99.999% confidence interval determined by bootstrap resampling. E). Comparison of average copy numbers per gene as measured by Zeisel et al. and seqFISH. Single cell RNA-seq underestimates copy numbers compared to seqFISH.

To quantify the amount of false positive signal due to misalignment of barcodes and nonspecific binding of probes, the amount of off-target barcodes that were detected was measured. With four rounds of hybridizations and 5 fluorophores, there were $5^4$=625 unique codes. 100 of these barcodes were assigned to measure mRNAs detected at 914.8±570.5 counts per cell (mean±s.d., N=3439). In comparison, the 525 remaining off-target barcodes that were not used were detected at 4.6±4.7 (mean±s.d., N=3439) counts per cell (FIG. 30D). False positives, due to chance alignment of nonspecifically bound spots, contributed minimally to the barcode readouts because of this three order of magnitude difference in detected barcodes (on target vs. off target). The false positives we observe fall only on barcodes hamming distance one away from on-target barcodes, yet minimally contribute to undercounting on-target barcodes (FIG. 30E). Furthermore, even the most frequent off-target barcode was observed 65.57 times less frequently than the most infrequent mRNA coding barcode (FIG. 30E, FIG. 39). Even though during each round of hybridization, 24.8±0.4% (mean±s.e., N=4 rounds of hybridization) of the spots were nonspecifically bound probes, barcode miss-assignments did not occur frequently because non-specifically bound probes do not reappear in the same location after digestion with DNAse and re-hybridization (FIG. 30A). Together the quantifications of false positive and false negative barcodes demonstrate that this method is highly efficient and accurate at detecting RNAs in situ in single cells within tissues.

Cell Clusters are Based on Combinatorial Expression Profiles.

We imaged the expression of 125 genes in coronal sections from two mice for a total of 14,908 cells (FIG. 38E). Cortical and hippocampal cells were segmented based on DAPI and Nissl staining. A tessellation algorithm was developed to accurately segment densely packed cells in the hippocampus. To avoid capturing mRNA from neighboring cells, we contracted by 10% the borders of cells determined by the segmentation algorithm.

To group the single cell data into distinct transcriptional states, we Z-score normalized the copy number of each transcript in every cell (FIG. 31A) and hierarchically clustered the cells to identify cells with similar expression patterns (FIG. 40). Many of these clusters, based on overall expression patterns, contain clear transcriptional markers of known cell types previously identified by single cell RNA-seq (FIG. 31B) (Zeisel et al., 2015, Tasic et al 2016). Cell clusters 12 and 13 contained clear expression of Gja1 which marks out astrocytes (Zeisel et al., 2015, Tasic et al 2016).

Figure 31:
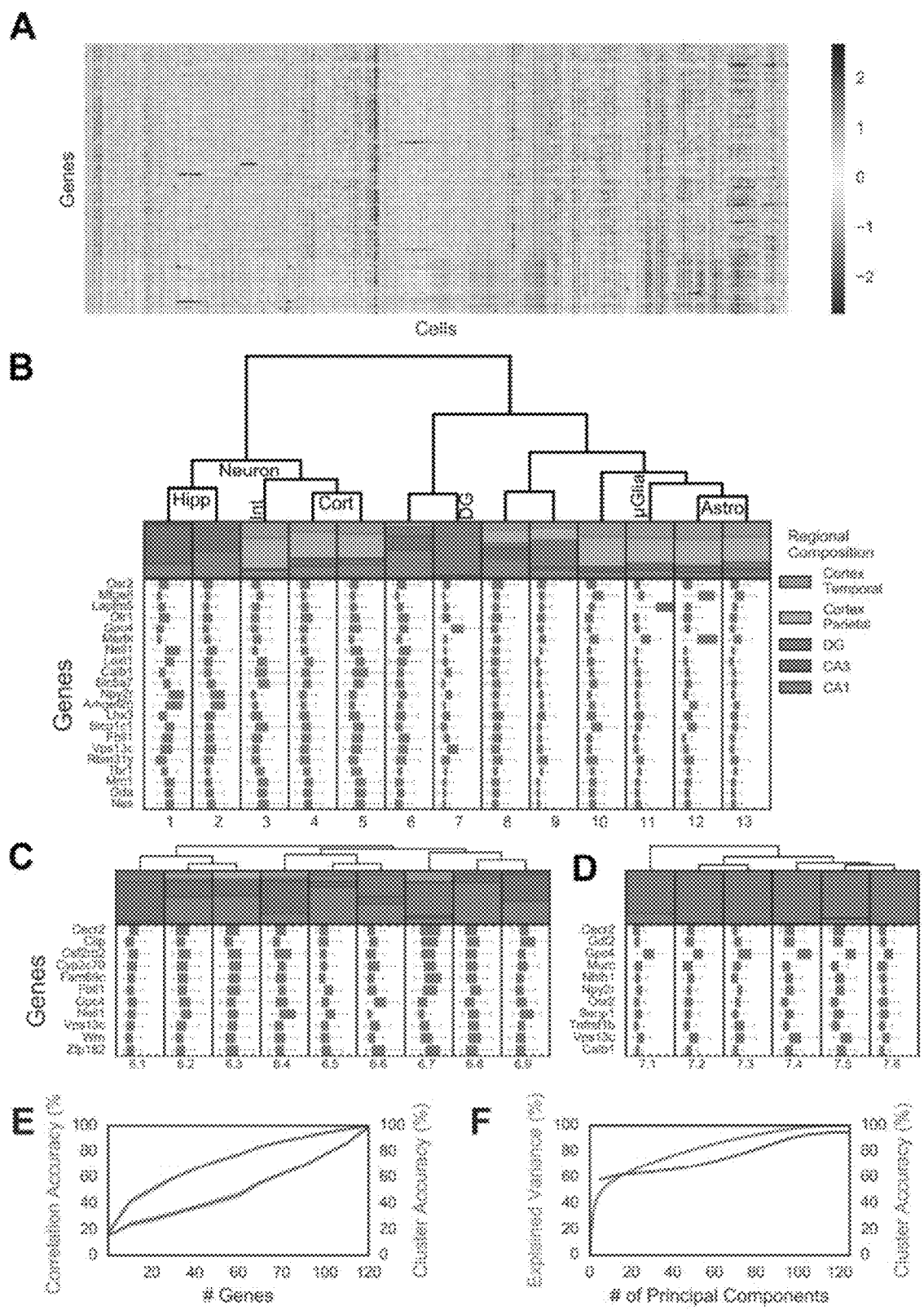
FIG. 31 depicts an example illustrating that distinct clusters of cells exhibit different regional localization in the brain. A). Gene expression of 14,908 cells presented as a Z-score normalized heatmap. B). Regional compositions of 13 cell clusters are visualized as stacked bar plots with the area corresponding the number of cells in each region. Hippocampal regions are: CA3, CA1, Dentate Gyms (DG). Cortical regions: parietal and temporal. Box plot of the Z scores of 21 representative genes are plotted for each cell class. The major tick marks correspond to Z score 0 while every minor tick is a z score interval of 1. Cell type assignments are shown on the dendrogram. Abbreviations: Hippocampus pyramidal (Hipp), cortex (Cort), Dentate Gyms (DG), Interneurons (Int), Astrocyes(Astro), Microglia (µGlia). C). Subclusters of cluster 6 cells and their regional localization and gene expression profile displayed under the dendrogram. Subcluster 6.1 is enriched in the CA3, while 6.7 is enriched in the DG. D). Subclusters of cluster 7 cells are shown. Almost all cells are localized in the GCL but have different combinatorial expression profiles. Note Calb1 expression, which marks out granule cell maturation, differs amongst subclusters. E). Any random subset of 25 genes can recapitulate approximately 50% of the information in the correlation amongst cells (red), but a larger number of genes are required to accurately assign cells to cluster using a random forest algorithm (blue) (n=10 bootstrap replicates; shading is 95% CI), indicating that fine structures in the data require quantitative measurements of combinatorial expression of many genes. F). Similar to E, while the first ten PCs explain the coarse structure, a larger number of principal components (PCs) are required to describe the full data. Expected variation (green) and accuracy in predicting cell identity using a random forest model (blue).
Figure 40A:
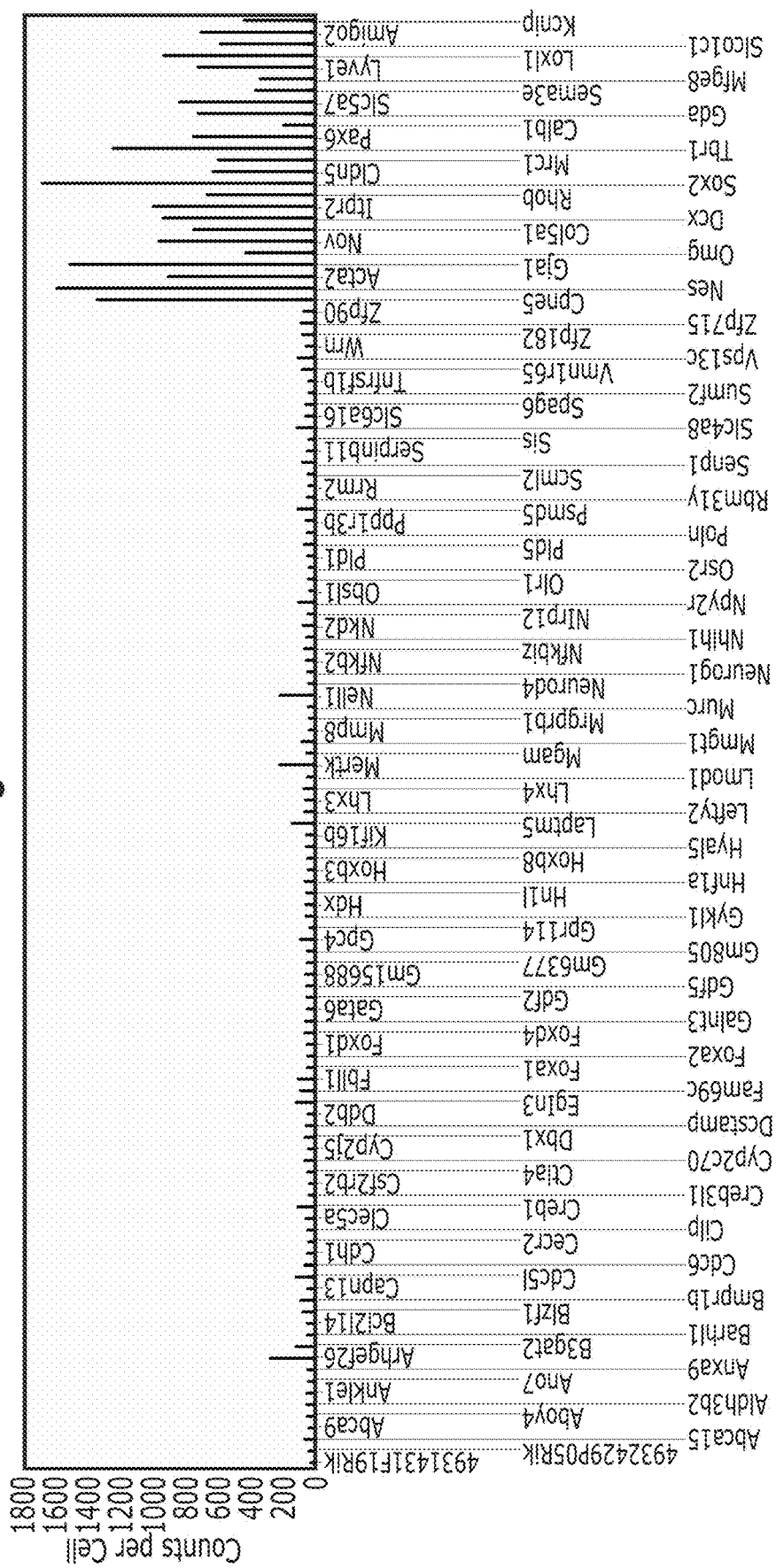
Figure 40B:
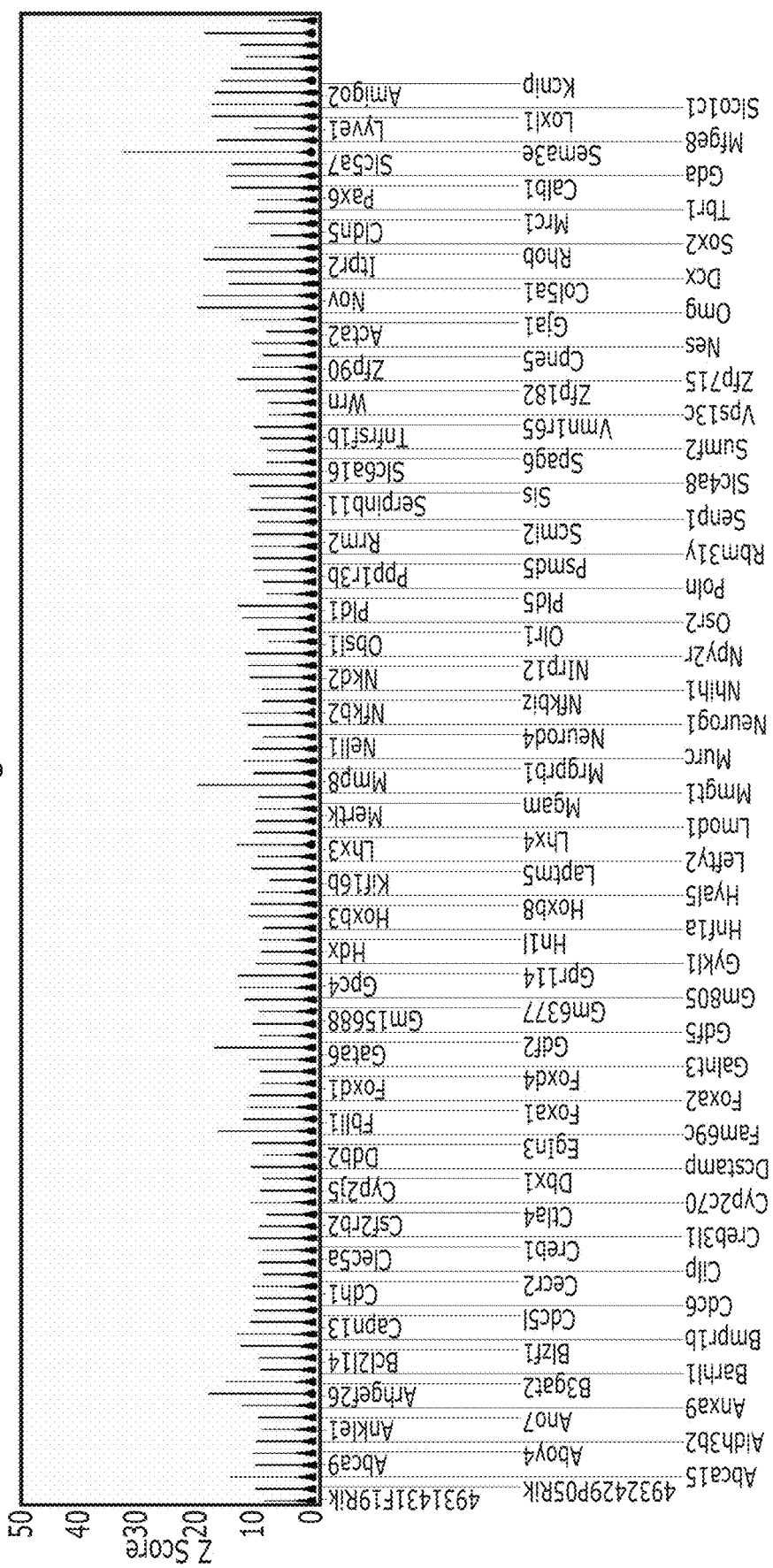
Figure 41M:
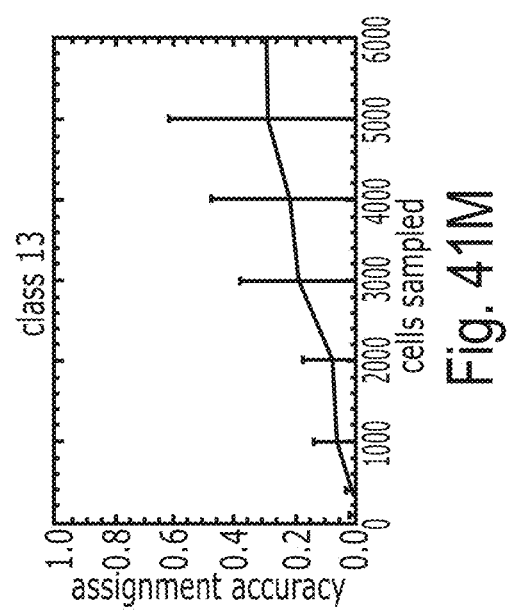

Cluster 12 also expresses Mfge8 while cluster 13 did not, indicating two distinct population of astrocytes (FIG. 31B). There are further subclusters within each of the astrocyte populations with different spatial localization patterns (FIG. 40C). Cluster 11 cells expressed Laptm5, a known microglia marker (Zeisel et al., 2015, Tasic et al 2016). Cluster 3 expressed interneuron genes while cluster 1-2 and 4-5 expressed genes associated with pyramidal neurons (Zeisel et al., 2015, Tasic et al 2016). Some clusters contained many distinct subclusters, such as Amigo2 enriched Mural cells (cluster 9.4) or Omg expressing oligodendrocytes (cluster 10.4 and 10.5). The major clusters were robust to downsampling the number of cells used in clustering (FIG. 41), with some of the hippocampal pyramidal and glia clusters robustly defined even with 400 cells. Similarly, principal component analysis (PCA) visualization of the data (FIG. 40F) recapitulated the major clusters that corresponded to astrocyte, microglia, cortical pyramidal, hippocampal pyramidal, dentate gyrus (DG) granule, and interneuron cells.

Cell Clusters Show Distinct Regional Localization

Many neuronal clusters mapped to distinct regions in the brain (FIG. 31B). Several classes of pyramidal cells (cluster 1-2) showed exclusive localization to the hippocampus, while other classes (4-5) showed predominantly cortical localization. There were also a class of cells (cluster 7) that were almost exclusively present in the DG. Interestingly, these clusters segregated based solely on gene expression profiles without adding any spatial information into the clustering algorithm. These differences in transcriptional states of neurons could be due to intrinsic differences in the cells or due to different local environment and activity patterns.

In contrast, astrocyte, microglia and other non-neuronal cell clusters were generally uniformly present in all areas of the brain (FIG. 31B). However, subclusters of astrocytes did localize to different regions of the brain preferentially (FIG. 40C), with subcluster 12.3 localized preferentially to the cortex, while 12.1 subcluster was uniformly distributed. Similarly, cluster 9 cells contain subclusters (9.3, 9.5 and 9.6) that localize exclusively to the DG, while other subcluster (9.1) localize almost exclusively to the cortex. The regional localization of neurons are especially pronounced with cluster 1 and 2 localized almost exclusively to the hippocampus, with some of the subclusters localized predominantly to the CA3. Furthermore, while pyramidal cell clusters 4 and 5 are preferentially cortically localized, the few hippocampal cells in these clusters form their own subclusters (4.4 and 5.4) (FIG. 40C). In cluster 6 cells, many subclusters with distinct expression profiles are localized almost exclusively in the CA1, CA3 or the DG (FIGS. 31C, 40C). In contrast, cluster 7 cells show a relatively homogenous regionalization pattern, but further subdivide based on combinatorial expression patterns (FIG. 31D). Subclusters of cluster 9 also show significant regionalization where subclusters 9.1, 9.3, 9.5, and 9.6 show localization to the SGZ (FIG. 40C). Overall, cell clusters with similar expression profiles exhibited similar spatial localizations across the brain with a correlation coefficient of 0.67 (FIG. 40E), indicating the existence of archetypal regional expression patterns and potential spatial markers in the brain. These results show that the tissue-optimized HCR seqFISH approach can directly identify a variety of transcriptional states and quantify broad spatial patterns of expression.

Combinatorial Expression Patterns Define Fine Clusters.

While certain cell clusters contain strong expression of marker genes, not all clusters are defined based on a few genes. How much power do individual genes or groups of genes have in explaining the observed cell clusters? To understand this, we examined whether subsets of genes can recapitulate the observed clusters (FIG. 31E). We found that any set of 25 genes recovers about half of the correlation structure in the cell-to-cell correlation map (FIGS. 31E, 42B-C, and 41, N=10 bootstrap replicates). The fact that the selection of any 25 genes can explain the gross patterns in the data is likely due to the high correlations amongst the expression patterns of genes, as shown in the gene-to-gene correlation map (FIG. 42A). Thus, a small subset of the measured genes can provides sufficient information to infer the gross transcriptional states of the cells. Interestingly, this may be the same reason why low-coverage single cell sequencing methods such as drop-seq and inDrop (Klein et al., 2015; Macosko et al., 2015) can capture the large distinction of cell types, because many highly expressed genes are correlated to other genes that collectively define cell types.

Figure 40D:
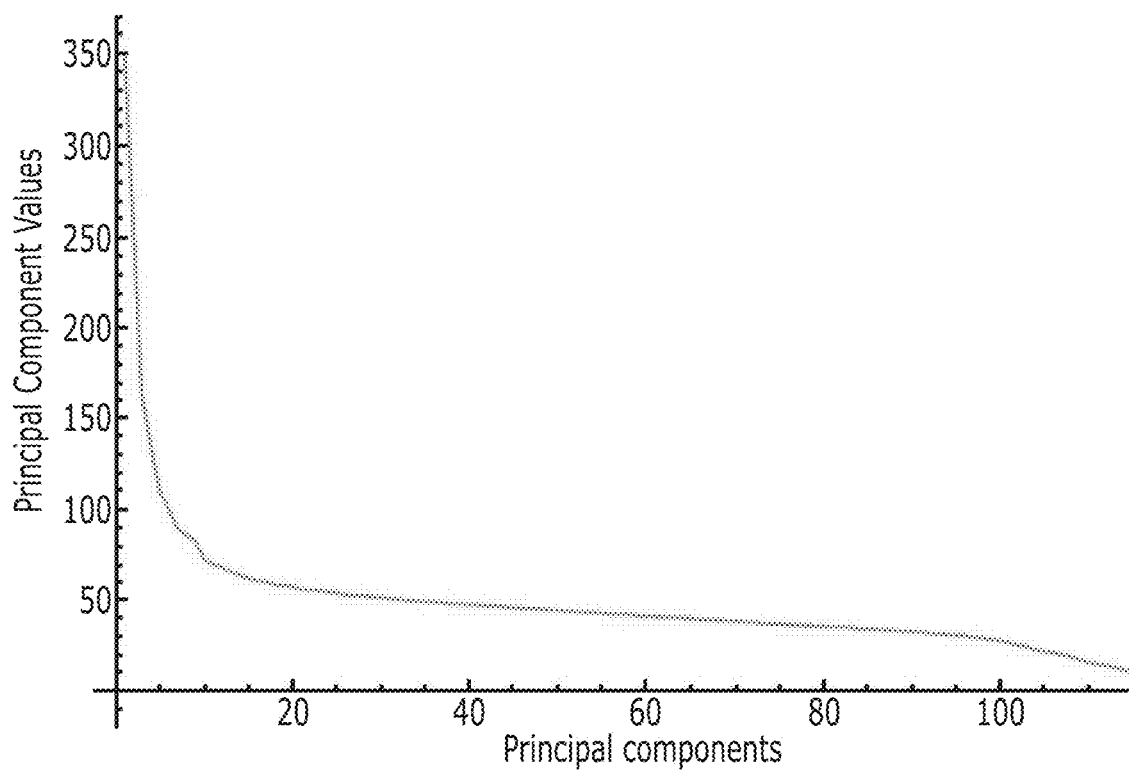
Figure 40E:
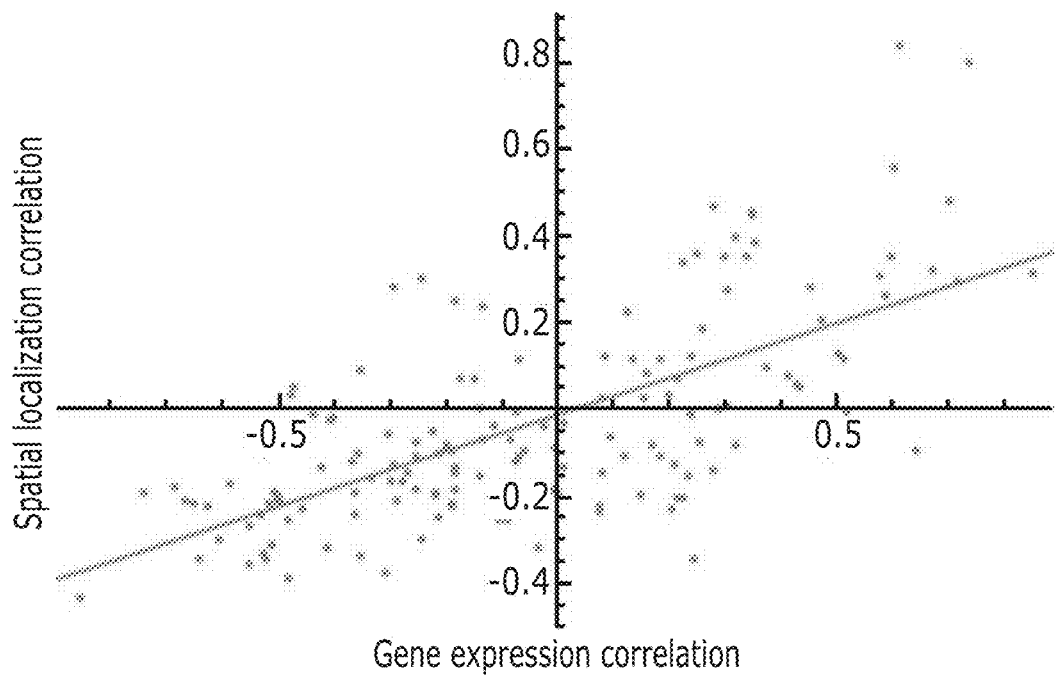
Figure 40F:
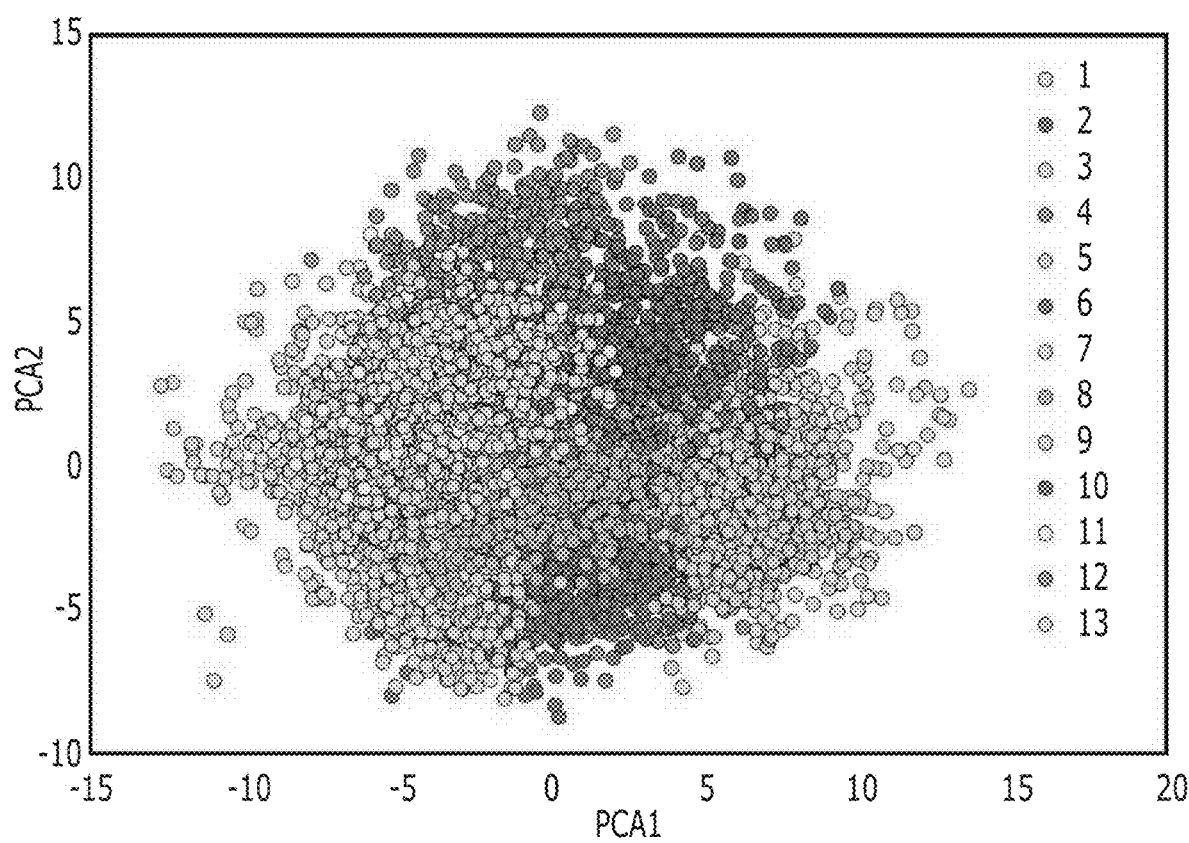

At the same time, the finer correlation structure in the data, required to define the cell clusters accurately, can only be captured with more genes (FIGS. 31F, 42B-C). Consistent with this, using a "random-forest" machine learning algorithm (Breiman, 2001) to classify cell clusters, we found that 75 genes are needed to classify cells with 50% accuracy, indicating that correct cluster assignment requires more detailed information from many genes (FIG. 31E). Supporting this view, the first 10 principal components (PC) explained 59.5% of the variation in the data, while the rest of the variation required the remaining 115 PCs (FIGS. 31F, 40D). The "random forest" algorithm required 10 PCs to predict the cell cluster assignments with 50% accuracy (FIG. 31F), but accuracy steadily increased with more PCs. These observation indicated two levels of information in the data: a coarse level, where large distinctions in cell clusters are observable by a few genes, and a fine level, where subtle distinctions require many more genes.

These results suggest two points experimentally. First, multiplexing at the level of 20 genes by seqFISH can give broad cell cluster identification that is not available with 2-3 gene smFISH experiments. Although single marker genes are useful for inference, we find that they frequently are not sufficient for cell classification. For example, all DG specific granule cells (clusters 7) have Gpc4 and Vps13c as their enriched marker genes (FIG. 31B); yet, Gpc4 and Vps13c are also strongly expressed in other hippocampal cells outside of the DG, as seen in both our experiments and the ABA. Thus, smFISH against Gpc4 and Vps13c alone would not be sufficient to uniquely identify the DG granule cells. Furthermore, even the strongly bimodal markers that are known to define cell types (i.e. Mgfe8, Gja1, etc.) are correlated enough to overall expression profiles that cells fall into the appropriate cluster even when these genes are excluded. This point suggests that while marker genes can be essential in assigning a cell to a known cell type, they are not necessary to identify unique clusters in the dataset provided enough measurements are made. Second, accurate measurement of combinatorial expression of many genes enabled by seqFISH can allow for more specific cell cluster identification. As a comparison, in single cell RNAseq data, CA1 pyramidal cells are clustered into a single cluster (Zeisel et. al, 2015; Habib et. al 2016) potentially because of the relatively lower detection efficiency of the method. In our seqFISH experiments, measuring hundreds of genes quantitatively, we can resolve several clusters and subclusters with robust regionalization within the CA1 (FIGS. 31B, 40C).

Cells are Patterned in the Dentate Gyrus.

Figure 32:
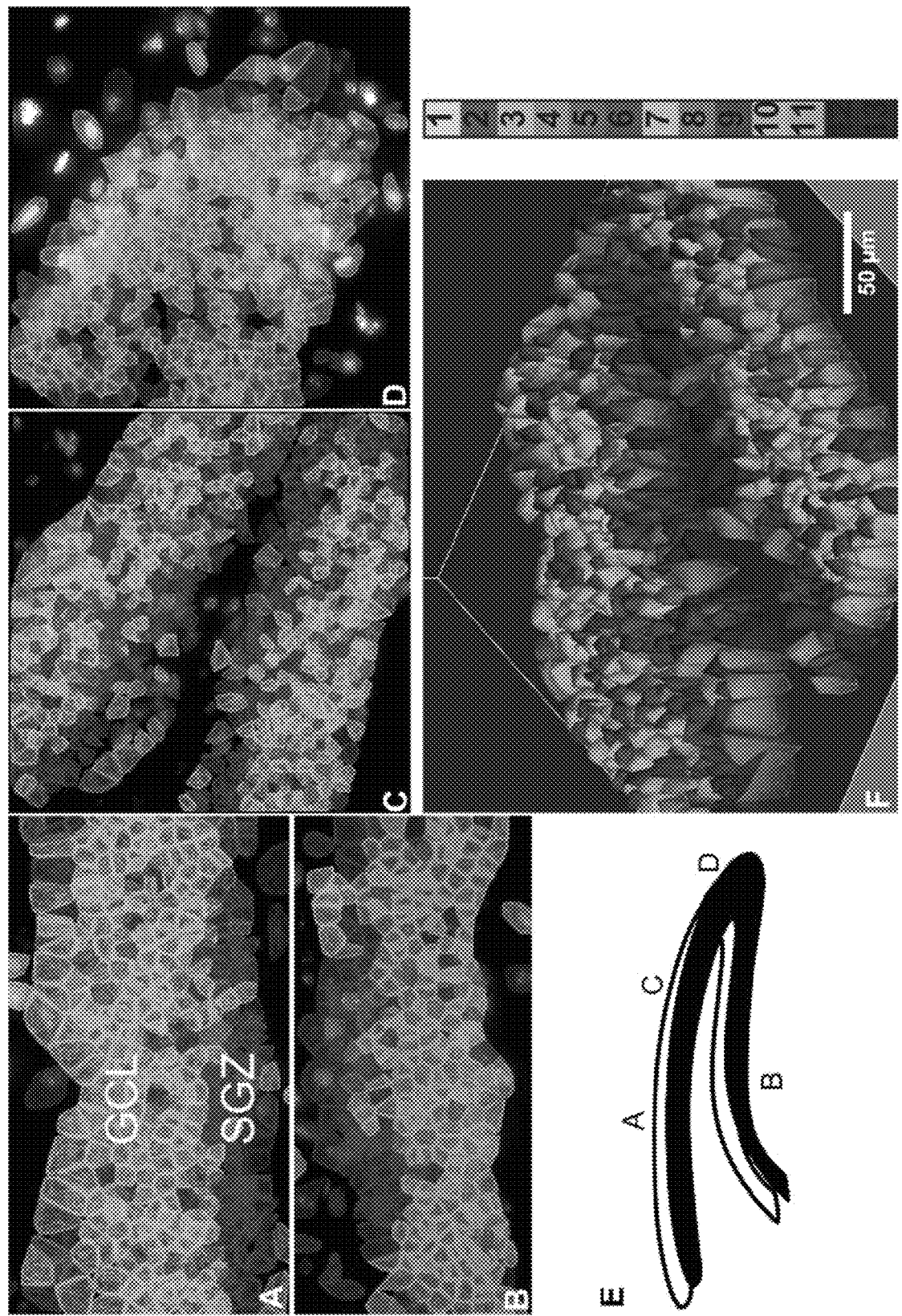
FIG. 32 depicts an example embodiment, illustrating spatial layering of cell classes in the Dentate Gyms (DG). A-B). Suprapyramidal and infrapyramidal blades of DG. Cells of the subgranular zone (SGZ) and granule cell layer (GCL) are arranged in lamina layers in mirror symmetric patterns on the upper and lower blades. C). The SGZ stays on the inner layer of the DG fork. D). Cells are patterned in the crest. Numbered color key corresponds to cluster numbers in FIG. 31b. E). Letters in the cartoon of DG correspond to images. F). 3D image of the fork region shown in C).

To further visualize the spatial organization of cells, we mapped cluster definitions of cells back into the images. In the DG, we observed a striking lamina layering of cell classes. The two blades of the DG (FIGS. 32A-B) showed mirror arrangements of cells, with cluster 9 cells, forming the subgranular zone (SGZ), leading into a granule cell layer (GCL) dominated by a single cluster of granule cells (cluster 7) (FIG. 31B). In the 125 gene data set, the cells of the GCL were found to be dominated by expression of Gpc4 and Vps13c matching ISH data from the ABA (FIG. 45B). Cluster 7 was found to be further subdivided into 6 sub-clusters (FIG. 40C). These subclusters were found to have varying levels of calbindin D-28K (Calb1) expression which is known to increase with granule cell maturation (FIG. 31D)(Yang et al., 2015). On the other hand, the cells of the SGZ were found to be significantly enriched in astrocyte markers such as Mfge8 and Mertk, which has been also been observed previously (Miller et al, 2013) and in the ABA data (FIG. 50A). However, these cells do not cluster with typical astrocytes (cluster 12 and 13) because their combinatorial expression patterns are different from astrocytes, consistent with their classification as a completely different population of cells.

In the fork region of the DG, the layer of cluster 9 cells appeared on the interior surface of the fork, followed by a layer of granule cells (cluster 7) (FIG. 32C). A different layering pattern is seen at the crest of the DG, where astrocytes, microglia, and some other glial cells line the exterior of the crest ensheathing the GCL (FIG. 32D). In both brains of the 125 gene experiments, the same cell clusters and spatial arrangements are observed. Furthermore, because the mRNAs are imaged in 3D in the 10-15 um brain slices, we can obtain a 3D view of the expression profiles, shown in the fork regions of the DG (FIG. 32F).

Distinct Regions of CA1 and CA3 are Composed of Different Combination of Cell Clusters.

Figure 33:
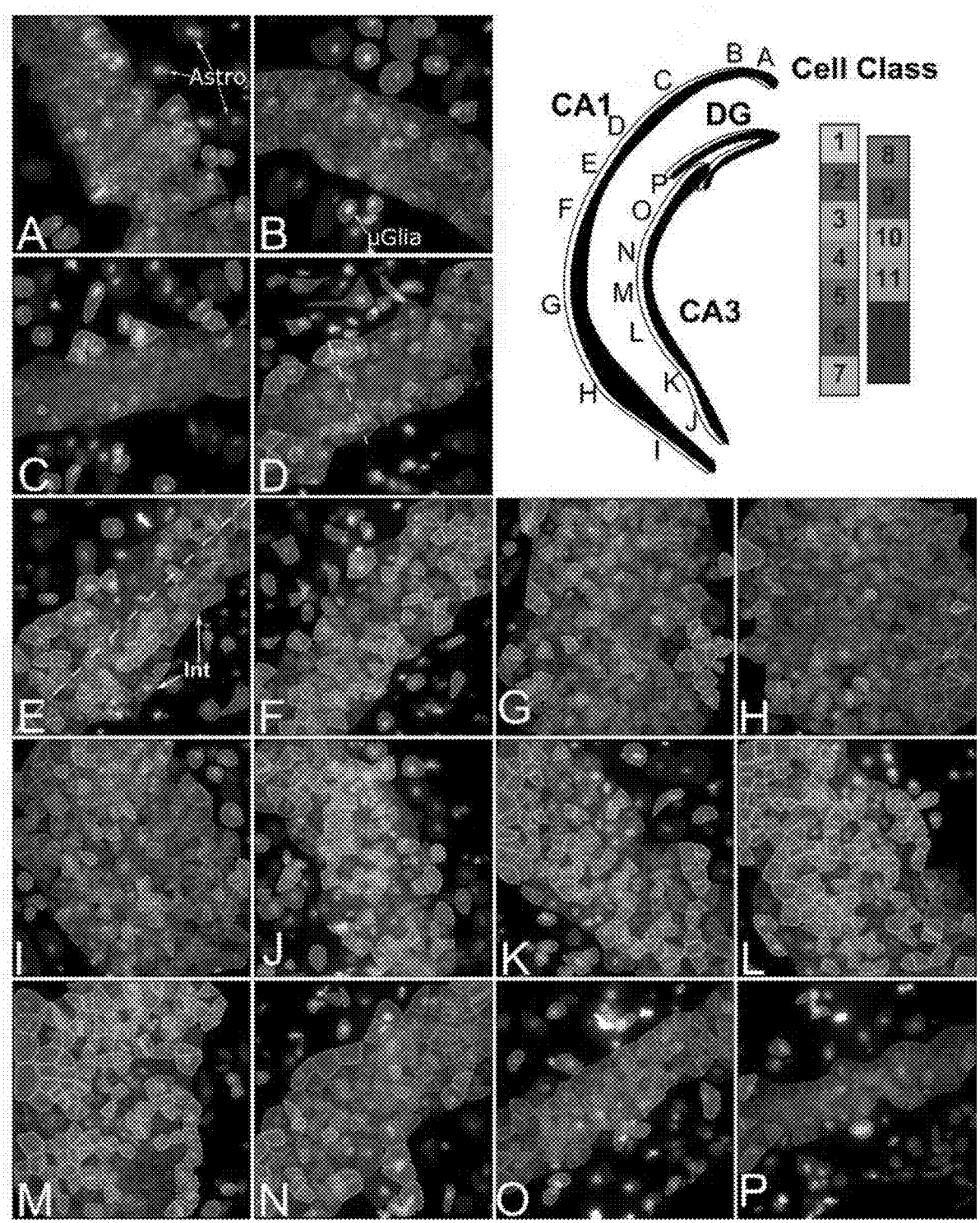
Figures 43A, 43A1, 43A2, 43A3:
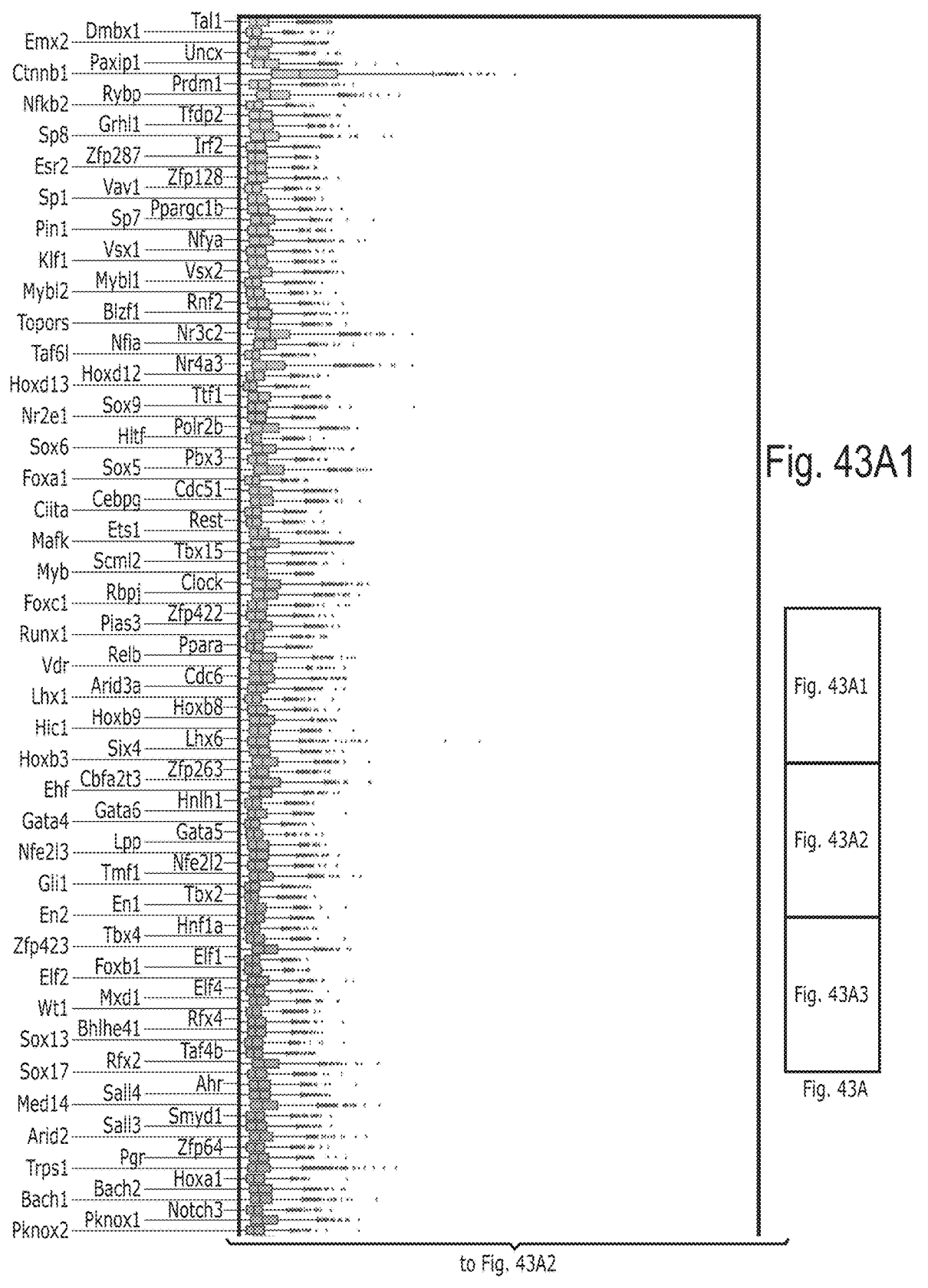

While each region of the DG contains similar compositions of cells, distinct subregions within the CA1 and CA3 contained different combinations of cell classes (FIGS. 33, 43F). In the CA1, there were 3 distinct regions defined by their individual cellular compositions. In the dorsal region of CA1 (CA1d), neuron cluster 6 (enriched in Nell1, a protein kinase C binding protein) was the major cell type in the pyramidal layer, with astrocyte, microglia and other cells (clusters 10-13) intercalating into the stratum pyramidale (SP) (FIGS. 33A-C). Transitioning into the CA1 intermediate region (CA1i) (FIG. 33D), pyramidal cell cluster 4 displaced cell cluster 6 as the dominant cell, with the co-appearance of cluster 1 and 2 pyramidal cells.

As the middle of the CA1i region was reached, a small amount of cluster 4 pyramidal cells remain, while cluster 1 and 2 pyramidal cells dominate (FIGS. 33E-F). Cluster 1 and 2 are enriched in Nell1 (EGF like protein), Npy2r (neuropeptide Y receptor), Slc4a8 (sodium bicarbonate transporter) and B3gat2 (glucuronosyltransferase). The CA1i region displayed a characteristic spatial organization where glial cells line the outermost regions, while pyramidal cell cluster 1 and 2 longitudinally partitioned the pyramidal layer. This separation of the inner versus the outer layers of CA1 matches those observed in previously (Dong et al., 2008). Furthermore, interneurons (cluster 3) were found to preferentially line the inner edge of the pyramidal layer in the CA1i region (FIGS. 33E-F). This patterning of interneurons, particularly subcluster 3.1 cells which were enriched in Slc5a7, a choline transporter, was consistent with the patterning of cholinergic interneurons observed with ChAT-GFP labeling (Yi et al., 2015). Finally, the largest amount of heterogeneity in the CA1 was seen in the ventral CA1 region (CA1v), where cell clusters 3, 5, and 10 began to mix in with clusters 1 and 2 (FIGS. 33G-I).

Similarly, the CA3 was found to have four transcriptionally distinct regions with different pyramidal cell compositions and abrupt transitions. The ventral most region of CA3 contained a high level of heterogeneity of pyramidal cell clusters (FIGS. 33J-K), while the intermediate region of CA3 contain a mixture of cell clusters 1 and 2 (FIGS. 33L-M). As the CA3 progressed towards the hilus of the DG, the cell types transitioned first to primarily cluster 4 neurons (enriched in dcx, doublecortin, and Col5a1, a collagen), and then to almost exclusively cluster 6 neurons in the region most proximal to the DG hilus (FIGS. 33O-P). It is interesting to note that while cluster 6 cells appear in both the CA1 (subcluster 6.8) and CA3 (subclusters 6.1 and 6.4), sub-clusters of 6 show distant regional localization (FIG. 40C), suggesting that the gene expression differences in CA1 and CA3 cells are captured in the seqFISH data.

The regionalized expression patterns we observed in the hippocampus match closely to those observed in previous literature (Thompson et al Neuron 2008 and Dong et al PNAS 2009). For example, CA1d, CA1i, CA1v boundaries correspond to the boundaries shown in FIG. 2B in Dong et al. In CA3, the subregions observed in our experiment match the CA3 subregion 4-7 in Thompson et al. (Thompson et al., 2008).

Figure 43D:
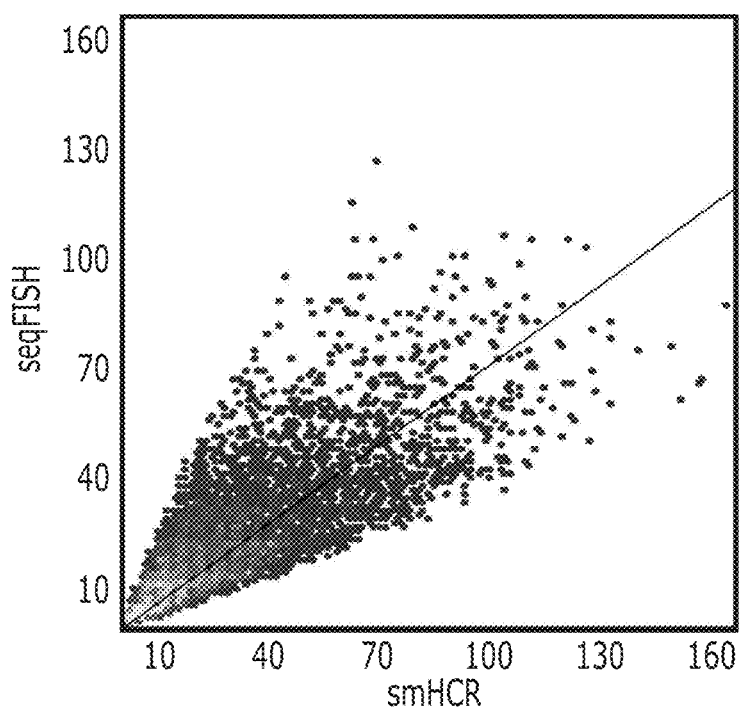
Figure 43E:
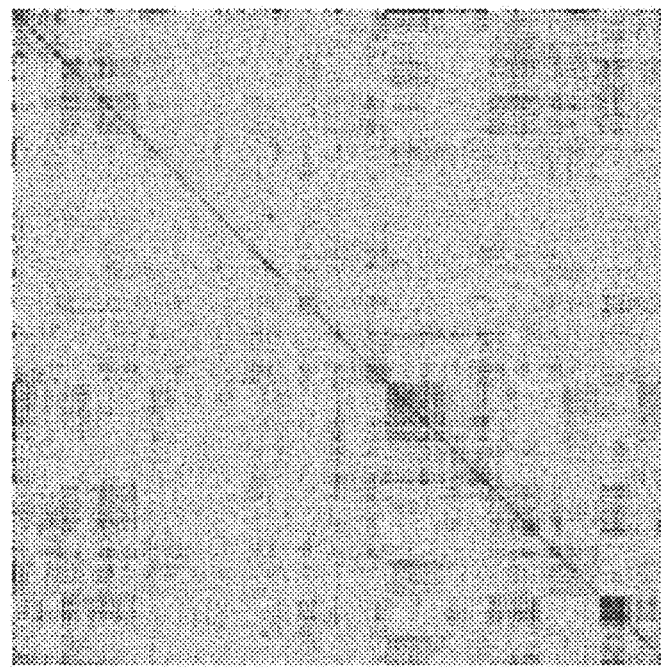
Figure 43G:
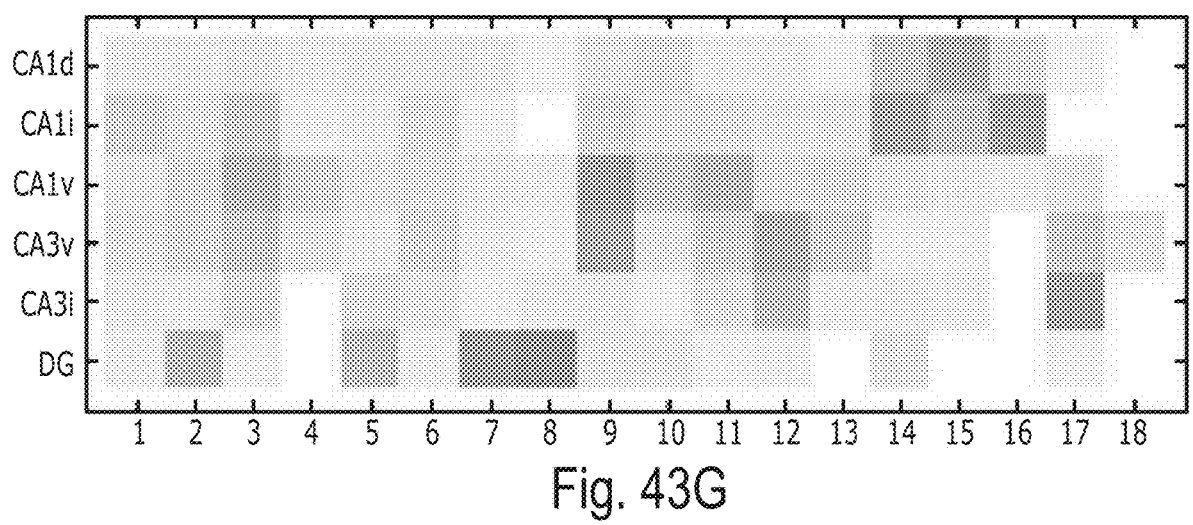

Lastly, we note that the two slices from two different mice in the 125 gene experiment show not only the same subregional structure (FIGS. 32-34), but also the same clusters of cells (FIGS. 33 and 34) in the different subregions of the hippocampus (FIG. 43). In both brains, the CA1d consists of relatively homogenous population of cluster 6 cells, which transition to a mixture of 1 and 2 cells in CA1i, and finally to a mixture of 1-6 and 10 cells in the CA1v (FIG. 43F). These results together show that the sub-regions of the hippocampus are a robust feature in the organization of CA1 and CA3, consisting of cells classes with distinct expression profiles. The stereotypical nature of the spatial arrangement of these structures suggest further experiments with seqFISH and other functional assays to probe the distinct functions of the different cell clusters in the CA1 and CA3.

249 Gene Multiplex Experiments Show the Same Hippocampal Subregions

To further show that the sub-regional structure of the hippocampus is independent of the target genes, we performed a 249 gene seqFISH experiment on a third coronal section. Of these 249 genes, only 22 genes overlapped with the 125 gene experiment set. For this set of genes, 214 were selected from a list of transcription factors and signaling pathway components and the remaining 35 were selected from cell identity markers from another single cell RNAseq dataset (Tasic et al, 2016). The 214 genes were barcoded by 5 rounds of hybridization, while the remaining genes were imaged in 7 rounds of non-barcoding serial hybridization. To quantify the efficiency of this experiment, 4 genes in the barcoding set (Smarca4, Sin3a, Npas3, and Neurod4) were re-probed with smHCR. The barcoding efficiency of the 249 gene probe set was found to be 71% with and R value of 0.80 (FIG. 43D). In single cells, we detect on average 2807±1660 (mean±s.d., N=2050 cells) total barcoded barcodes.

The same arrangement in the DG was observed in the 249 gene experiment, despite different genes used, indicating robust identification of the layering in the DG by seqFISH (FIGS. 35S-T). In particular, the cells in the SGZ are clustered independently from cells in the GCL, similar to the layers observed in the 125 gene experiment. In the SGZ cells, we observed enrichment of Sox11, a key transcription factor in neurogenesis (Miller et al, 2013). Other transcription factors involved in neurogenesis, NFIA and Tbr1 are also enriched in the SGZ cells as seen in our data and the ABA images (FIG. 45A). The observations of this distinct layer in both the 249 and 125 gene experiment and the combined gene enrichment pattern (increased Sox11, Sox9, NFIA, and Tbr1 in the 249 gene experiment and increased Mertk and Mfge8 in the 125 gene experiment) suggests that many cells in this layer are involved in adult neurogenesis in the SGZ. Supplementary FIG. 7B shows distinctive marker gene expression in the GCL of the dentate gyrus.

In addition, the same regionalized cellular patterns are observed in CA1d, CA1i, and CA1v, where different sub-regions utilize different cell classes in characteristic ratios (FIG. 43F). As seen with the 125 gene experiment, while the CA1d uses only a few cell classes and is relatively homogeneous, while the CA1v region is made up of many different cell classes resulting in a high level of cellular heterogeneity. Furthermore, the distinction between CA1 and CA3 cell clusters are more clear in the 249 gene experiment suggesting more resolving power of spatial patterns (FIGS. 35A-K). The 249 gene experiment also suggests that the CA3 may be composed of 3-4 subregions based on cell cluster composition (FIGS. 35L-R). The cellular heterogeneity of the CA3 is again shown to mirror that of the CA1, where the cellular heterogeneity increases along the dorsal to ventral axis. Cells with distinctive marker gene expression in the hippocampus are shown in supplementary FIG. 35A.

Single Cell Data Resolves Cellular Organizations in the Sub-Regions of the CA1 and CA3.

Two conflicting views of the cell types in the hippocampus have been proposed based on the analysis of the Allen Brain Atlas data (Thompson 2008) as well as recent RNA-seq data (Cembrowski et al., 2016, Zeisel et al 2015). Analysis of the ABA in situ data showed that distinct subregions of the hippocampus expressed different molecular markers, indicating that the CA1 and CA3 are "regionalized" into distinct sub-structures (Fanselow and Dong, 2010; Thompson et al., 2008). However, recent bulk RNA-seq experiments on the CA1 found that gene expression patterns changed gradually along the dorsal to ventral axis, contradicting the sharp boundaries observed in the ABA analysis (Cembrowski et al., 2016). Further supporting this "continuous" cell type view of the hippocampus, analysis of the single cell RNA-seq data (Zeisel et al, 2015) identified a single continuous population of cells in the CA1 region.

Figure 34:
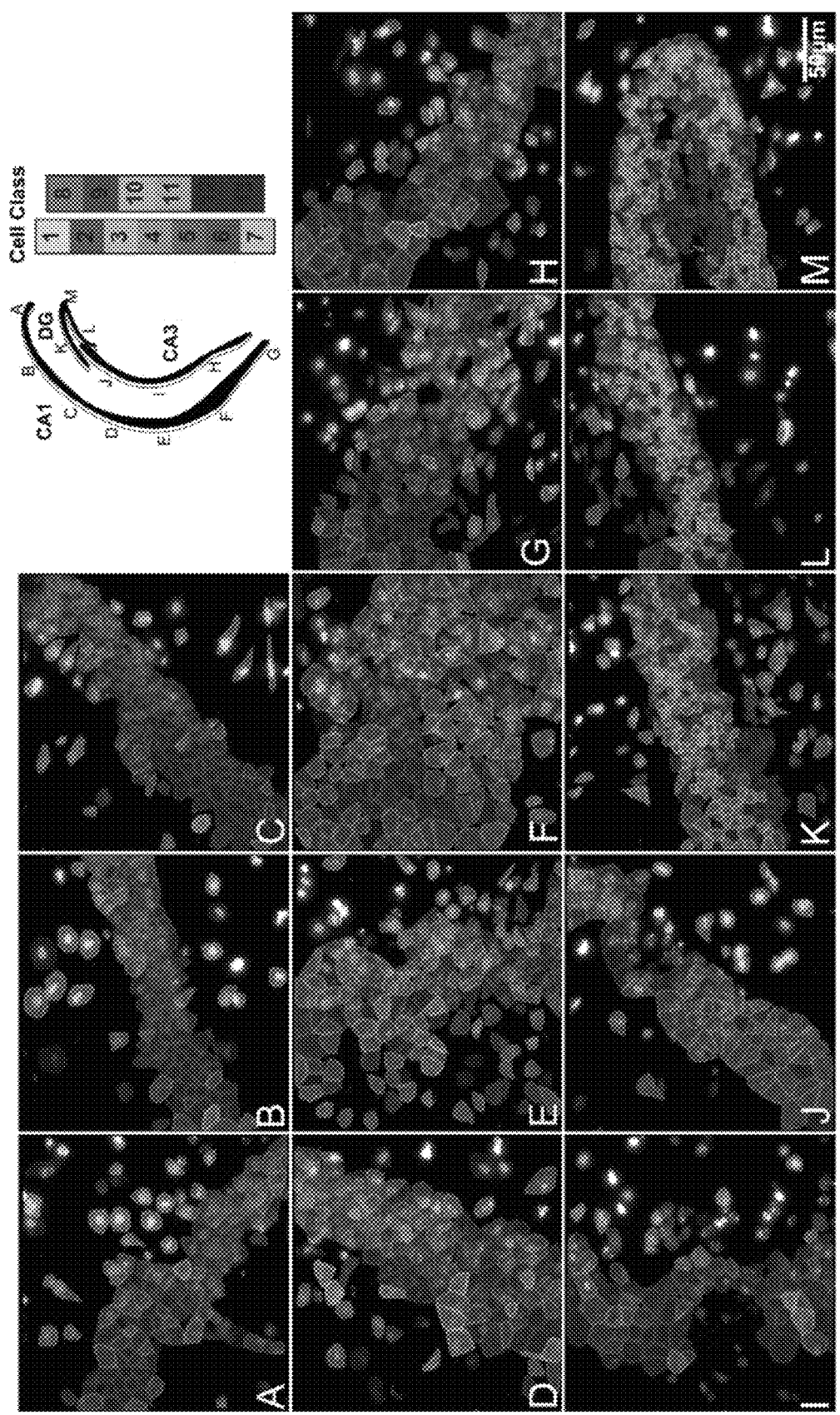
FIG. 34 depicts an example embodiment, showing mapping of cell types to a second brain slice with 125 genes. Upper right panel. Cartoon of hippocampus with imaged regions labeled. Color key corresponds to the classes in FIG. 31b. A-D. Similar to the cell class compositions shown for the hippocampus in FIG. 33, CA1d in this second coronal section from a second mouse is composed of mostly cluster 6 cells. (E) CA1i region and (F-G) the CA1 ventral regions are again composed of similar cell classes to that shown in FIG. 33 with increasing diversity of cell class compositions from the CA1d to the CA1i to finally the CA1v. (H-J) CA3 regions. (K-M) DG regions showing the same cell classes and layer pattern of the GCL and SGZ shown in FIG. 32.
Figure 35:
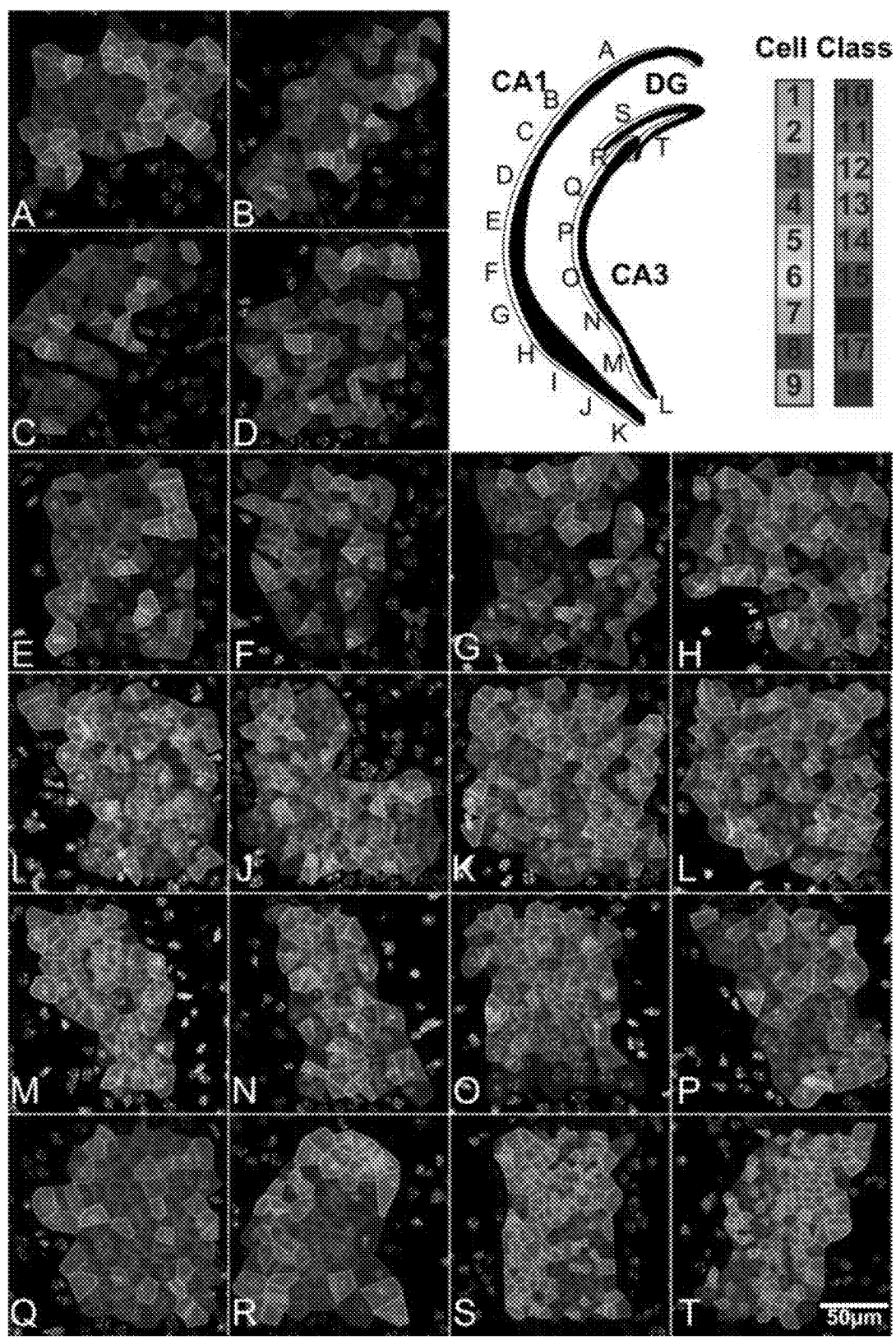
FIG. 35 depicts an example embodiments, showing mapping of cell types to a third brain slice with 249 genes. Upper right panel. Cartoon of hippocampus with imaged regions labeled. Color key corresponds to the classes in FIG. 43C. A-C). Similar to the slice shown in FIGS. 33 and 34, CA1d is relatively homogenous in cell cluster composition. D-G). Images from the CA1i region show that the cell class composition is different from that of the CA1d. H-K). Again, similar to FIGS. 33 and 34, images from the CA1 ventral regions shows a much more complicated cellular composition and a high degree of cellular heterogeneity. L-R). Images from the CA3 region show that the cellular compositions also creates 3-4 subregions within the CA3. The cellular heterogeneity of the CA3 subregions mirrors that of the CA1, where the ventral region of the CA3 is very heterogenous while the dorsal region of the CA3 is relatively homogenous. S-T). The DG regions show the distinct SGZ versus GCL layering pattern seen in the previous two brains.
Figure 36:
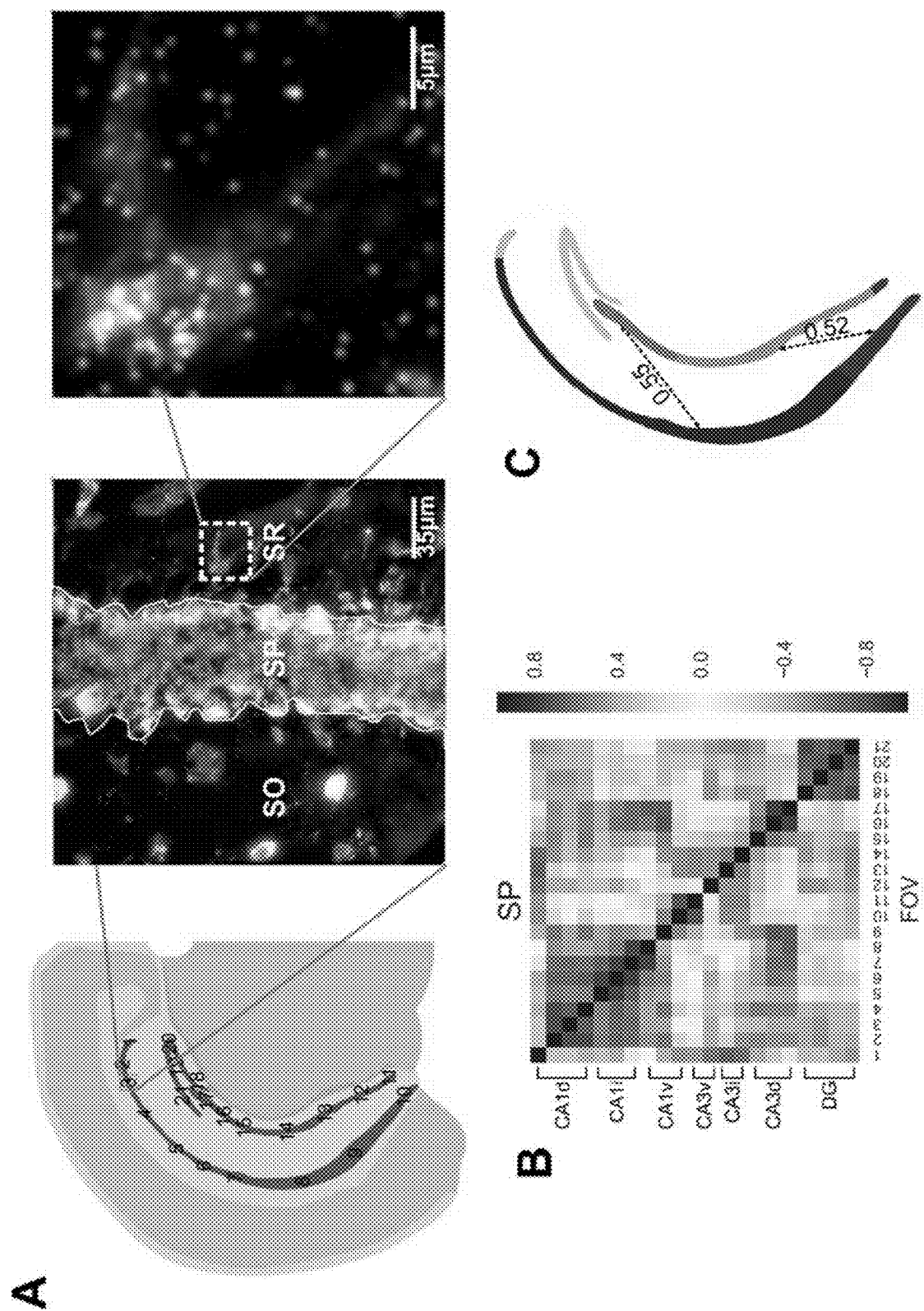
FIG. 36 depicts an example embodiment, showing correlations of the transcription profile across the pyramidal layer A). mRNA counts in the cell bodies in the Stratum Pyramidale (SP) are grouped within each field of view. A single cell in the Stratum Radiatum (SR) is shown to illustrate individual mRNA localization. Stratum Oriens (SO) is labeled for orientation. B). mRNAs in different subregions of pyramidal layer show both long-distance spatial correlations as well as local correlations between neighboring fields. Both CA1 and Dentate Gyms (DG) show high regional correlations. Correlation is calculated based on the 125 gene experiment. C). Illustration of regional and long distance correlation patterns observed in B. Correlated regions are colored and long distance correlations are shown as dotted lines with their median correlation coefficient written over the dotted line.

Our data provides a single cell resolution picture of the spatial organization of cells in the hippocampus and reconciles both the RNA-seq and the ABA data. While our data mostly supports a regionalized view of the hippocampus, we observe that a single cell class does not in general define CA1 and CA3 sub-regions. Instead, we observed that different subregions of CA1 and CA3 are composed of distinct combinations of cell clusters (FIGS. 33-35). For example, CA1d consists primarily of cluster 6 pyramidal cells (FIGS. 33A-C), in addition to the cluster 1, 2, 10, and 12 cells, while CA1v consists of a large set of cell classes including cluster 1-6 and 10 cells, but at different relative abundances (FIGS. 33-34, FIGS. 43F-G). Due to this intermixing of cell classes in each sub-region, a bulk measurement of transcription profiles would find a lack of regionalization, but single cell analysis with spatial resolution would identify these distinct regions based on their unique cell class compositions. Indeed, when we averaged the single cell expression profile within each sub-region of the CA1, we can reproduce the continuous correlation profiles found by bulk RNA-seq between CA1v, CA1i, and CA1d (FIG. 36) (Cembrowski et al., 2016). The bulk RNA-seq observation that CA1i lacked specific marker genes can also be explained. This is in fact consistent with our findings that CA1i contained cell classes present in both CA1d and CA1v (FIGS. 33-35).

This organization of cell classes is observed in both the 125 gene experiments as well as in the 249 gene experiment. It is worth noting that the complexity of cell populations observed in the CA1d versus the CA1v matches the functional differences in CA1. CA1d is responsible for spatial learning and navigation and contains a higher concentration of place cells and send projections to dorsal subiculum and cortical retrosplenial area (Cenquizca and Swanson, 2007; Jung et al., 1994; Risold et al, 1997; O'Keefe and Dostrovsky, 1971). We observed that CA1d is composed of a relatively homogeneous population of cells, predominantly of cluster 6 cells. In contrast, the ventral region is involved in a variety of cognitive tasks, such as stress response, emotional and social behavior (Cenquizca and Swanson, 2007; Jung et al., 1994; Fanselow and Dong, 2010; Kishi et al., 2006; Muller et al., 1996; Petrovich et al., 2001; Pitkanen et al., 2000; Saunders et al., 1988; Witter and Amaral, 1991; Yi et al., 2015). Correspondingly, we observed a large set of cell classes in the CA1v regions. It is intriguing to hypothesize that the different cell classes identified based on molecular profiles may correspond to neurons with distinct connectivity and functional patterns. This hypothesis can be investigated in future experiments combining anterograde tracing as well as electrophysiological recording followed by seqFISH.

A list of the 249 genes being analyzed can be found in the following Table 3.

| Name of Genes being analyzed |
| --- |
| Tal1 |
| Dmbx1 |
| Emx2 |
| Uncx |
| Paxip1 |
| Ctnnb1 |
| Prdm1 |
| Rybp |
| Nfkb2 |
| Tfdp2 |
| Grhl1 |
| Sp8 |
| Irf2 |
| Zfp287 |
| Esr2 |
| Zfp128 |
| Vav1 |
| Sp1 |
| Ppargc1b |
| Sp7 |
| Pin1 |
| Nfya |
| Vsx1 |
| Klf1 |
| Vsx2 |
| Mybl1 |
| Mybl2 |
| Rnf2 |
| Blzf1 |
| Topors |
| Nr3c2 |
| Nfia |
| Taf6l |
| Nr4a3 |
| Hoxd12 |

| Name of Genes being analyzed |
|---|
| Hoxd13 |
| Ttf1 |
| Sox9 |
| Nr2e1 |
| Polr2b |
| Hltf |
| Sox6 |
| Pbx3 |
| Sox5 |
| Foxa1 |
| Cdc5l |
| Cebpg |
| Ciita |
| Rest |
| Ets1 |
| Mafk |
| Tbx15 |
| Scml2 |
| Myb |
| Clock |
| Rbpj |
| Foxc1 |
| Zfp422 |
| Pias3 |
| Runx1 |
| Ppara |
| Relb |
| Vdr |
| Cdc6 |
| Arid3a |
| Lhx1 |
| Hoxb8 |
| Hoxb9 |
| Hic1 |
| Lhx6 |
| Six4 |
| Hoxb3 |
| Zfp263 |
| Cbfa2t3 |
| Ehf |
| Nhlh1 |
| Gata6 |
| Gata4 |
| Gata5 |
| Lpp |
| Nfe2l3 |
| Nfe2l2 |
| Tmf1 |
| Gli1 |
| Tbx2 |
| En1 |
| En2 |
| Hnf1a |
| Tbx4 |
| Zfp423 |
| Elf1 |
| Foxb1 |
| Elf2 |
| Elf4 |
| Mxd1 |
| Wt1 |
| Rfx4 |
| Bhlhe41 |
| Sox13 |
| Taf4b |
| Rfx2 |
| Sox17 |
| Ahr |
| Sall4 |
| Med14 |
| Smyd1 |
| Sall3 |
| Arid2 |
| Zfp64 |
| Pgr |
| Trps1 |
| Hoxa1 |

| Name of Genes being analyzed |
|---|
| Bach2 |
| Bach1 |
| Notch3 |
| Pknox1 |
| Pknox2 |
| Sin3a |
| Etv3 |
| Smad9 |
| Smad5 |
| Alx1 |
| Egf |
| Mn1 |
| Nkx3-1 |
| Rbak |
| Gabpa |
| Nfkbiz |
| Zscan21 |
| Trp73 |
| E2f7 |
| Esrrg |
| Rbpjl |
| Nfatc4 |
| Nr5a1 |
| Neurod4 |
| Esrrb |
| Tbx21 |
| Rorc |
| Mitf |
| Pax7 |
| Pax6 |
| Pax1 |
| Pax3 |
| Pax2 |
| Pax9 |
| Zkscan17 |
| Gfi1 |
| Mzf1 |
| Runx3 |
| Smarca4 |
| Foxd4 |
| Foxd3 |
| Creb1 |
| Srebf1 |
| Sox11 |
| Gmeb2 |
| Irx4 |
| Pou3f2 |
| Ikzf1 |
| Tcf23 |
| Mtf2 |
| Npas3 |
| Nfatc3 |
| Nfil3 |
| Phox2b |
| Plag1 |
| E2f2 |
| Ddx3x |
| Taf2 |
| Pou4f1 |
| Trim33 |
| Tsc2 |
| Lmx1a |
| Nr2f2 |
| Eomes |
| Wwtr1 |
| Foxo1 |
| Ar |
| Zfp354a |
| Elk4 |
| Foxo4 |
| Sall1 |
| Mycn |
| Maml3 |
| Foxp3 |
| Atm |
| Uaca |
| Tbr1 |

| Name of Genes being analyzed |
| --- |
| Pml |
| Lhx3 |
| Atr |
| Zbtb33 |
| Ptch1 |
| Lhx5 |
| Barhl1 |
| Irx5 |
| Tfap2b |
| Tfap2e |
| Rxra |
| Rxrb |
| Gli2 |
| Gli3 |
| Zic4 |
| Zic5 |
| Zic2 |
| Zic3 |
| Satb1 |
| Onecut2 |
| Foxn4 |
| Mnat1 |
| Foxn1 |
| Dlx2 |
| Vezf1 |
| sncg |
| sst |
| th |
| vip |
| xdh |
| slc17a8 |
| slc5a7 |
| slc6a3 |
| slc6a8 |
| smad3 |
| opalin |
| pdgfra |
| palvb |
| reln |
| slc17a7 |
| lyve |
| mfge8 |
| mog |
| myl14 |
| ndnf |
| ctss |
| foxj1 |
| gad1 |
| htr3a |
| igtp |
| acta2 |
| alldh1l1 |
| camk2 |
| chat |
| cldn5 |
| ngef |
| tiam1 |
| slc1a2 |
| gja1 |
| fbll1 | seqFISH Provides a Generalized Method to Multiplex mRNA Imaging in Tissues seqFISH with amplification and error correction provides a highly quantitative method to profile hundreds of mRNA species directly in single cells within their native anatomical context. Our method of stripping the probes from the RNA has many advantages. DNAse digestion of probes allows false positives to be rejected as nonspecifically bound probes do not colocalize between different rounds of hybridization (FIG. 30A). In addition, the same region of the transcript can be hybridized in every round, allowing seqFISH to efficiently target mRNAs shorter than 1 kb, enabling targeting of most genes. Lastly, seqFISH allows exponential scaling of barcode numbers, thus 4-5 rounds of hybridization can code for hundreds of transcripts with a simple error correction scheme. Theoretically, the entire transcriptome can be coded for with error correction by using 8-9 rounds of hybridization with seqFISH. These advantages of HCR seqFISH allows robust multiplexed RNA detection in tissues, shown here in the mouse brain.

Ultimately, the multiplexing capability of seqFISH is limited by the amount of optical space within a cell, and not by the coding capacity of the method (supplementary text). We showed previously that super-resolution microscopy can significantly increase the optical space available in the cell for transcription profile imaging, but super-resolution microscopy experiments proved difficult to image in samples thicker than 1 µm, and were experimentally cumbersome and time consuming to image (Lubeck and Cai, 2012). A recent development in expansion microscopy as well as correlation methods (Coskun et al., 2016) however offers promise for multiplexing to levels of high transcript density (Chen et al., 2015a; Treweek et al., 2015, Chen et al., 2016). In addition, by labeling subcellular components (i.e., dendrites and axons) with antibodies, the local transcriptome in compartments of the cell can be measured.

It was observed that, because expression patterns amongst genes are highly correlated, the distinction between large classes of cells can be determined from 10-20 genes, while a finer classification of cell clusters depends on the quantitative measurement of the combinatorial expression patterns of many genes (FIGS. 31E and F). This correlation amongst genes can be used to "stitch" our seqFISH data with single cell RNAseq data, similar to the approach explored with single cell RNAseq and ISH in Satija et al (Satija et al., 2015). By correlating seqFISH data to single cell RNA-seq expression data, cells types identified based on RNA-seq can be "mapped" back into our seqFISH data.

As shown here, seqFISH with hundreds of genes in tissues can become a general and widely used tool to answer a wide range of fundamental questions in biology and medicine. For neuroscience, by combining the insights into the spatial organization of transcription provided by seqFISH with connectomics and electrophysiological measurements, we can obtain a comprehensive understanding of the molecular basis of the neuroanatomy of the brain.

Example 4

Supplementary Experimental Procedure for Brain Slide Analysis

Probe Design.

Genes were selected from the Allen Brain Atlas database. We identified genes that are heterogeneously expressed in coronal sections containing the hippocampus at Bregma coordinates −2.68 mm anterior. Using the ABA region definitions, we break down the voxels representing the ABA data in those brain sections into 160 distinct regions and average the expression values within each region. We selected 100 genes that had high variances across these distinct regions and that also had low-medium expression levels. These genes included transcription factors and signaling pathways components as well as ion channels and other functional genes. Lastly, we chose 25 genes from single cell RNA-seq data that were enriched in certain cell types. Briefly, the design criteria used were 1) constant regions of all spliced isoforms were identified, 2) Masked regions of UCSC genome were removed from possible probe design, 3) 35mer sequences were tiled 4 nt apart, 4) sets of non-overlapping probes with tightest GC range around 55% were found, 5) probes were blasted for off-target hits. Any probe with an expected total off-target copy number of more than 5000 was dropped. Once all possible probes for every target gene was acquired, the probe set oligo-pool was optimized using the following criteria: 1) Expected # of off-target hits for entire probe pool was calculated, 2) probes were sequentially dropped from genes until any off-target gene was hit by no more than 6 probes from entire pool, 3) HCR adapters were added to designed probes and 10 nt in either direction of the adapter junction was blasted and screened for off-target hits, 4) probe pools were searched for regions of 18mer complementary, 5) the probe sets for a given transcript was refined down to 24 probes by dropping probes in order of the expected number of off-target hits, 6) Cutting sites and hybridization specific primers were added to probes.

Probe Generation.

All oligoarray pools were purchased as 92 k synthesis from Customarray Inc. Probes were amplified from array-synthesized oligo pool), with the following modifications: (i) a 35 nt RNA-targeting sequence for in situ hybridization, (ii) a 35 nt HCR initiator sequence designed to initiate one color of 5 possible HCR polymers, (iii) two hybridization specific flanking primer sequences to allow PCR amplification of the probe set and (iv) EcoRI (5'-GAATTC-3') and KpnI (5'-GGTACC-3') sites for cutting out flanking primers to reduce probe size. Ethanol precipitation was used to purify the final digested probes.

Brain Extraction and Sample Mounting.

C57BL/6 with Ai6 Cre-reporter (uncrossed) (Jackson Labs, SN: 007906) female mice aged 50-80 days were anesthetized with isoflurane according to institute protocols (protocol #1701-14). No randomization of mice was used and blinding was not necessary as the study was exploratory. Mice were perfused for 8 minutes with perfusion buffer (10 U/ml heparin, 0.5% $NaNO_2$ (w/v) in 0.1M PBS at 4 C). Mice were then perfused with fresh 4% PFA\0.1M PBS buffer at 4 C for 8 minutes. The mouse brain was dissected out of the skull and immediately placed in a 4% PFA buffer for 2 hours at room temperature under gentle mixing. The brain was then immersed in 4 C 30% RNAse-free Sucrose (Amresco 0335-2.5KG)\1×PBS until the brain sank. After the brain sank, the brain was frozen in an dry ice\sopropanol bath in OCT media and stored at −80 C. Fifteen micron sections were cut using a cryotome and immediately placed on an aminosilane modified coverslip.

Sample Permeabilization, Hybridization, and Imaging.

Brain sections mounted to coverslips were permeabilized in 4 C 70% EtOH for 12-18 hours. Brains were further permeabilized by the addition of rnase-free 8% SDS (Ambion AM9822) for 10 minutes. Samples were rinsed to remove SDS, desiccated and a hybridization chamber (Grace Bio-Labs 621505) was adhered around the brain section. Samples were hybridized overnight at 37 C with Split Color PGK1 Probes in Hybridization Buffer (2×SSC (Invitrogen 15557-036), 10% Formaldehyde (v/v) (Ambion AM9344), 10% Dextran Sulfate (Sigma D8906), 2 mM Vanadyl Ribonucleoside Complex (VRC; NEB S1402S) in Ultrapure water (Invitrogen 10977-015)). Samples were washed in 30% Wash Buffer (WBT: 2×SSC, 30% Formaldehyde (v/v)] 10% Dextran Sulfate, 0.1% Triton-X 100 (Sigma X-100), 2 mM VRC in Ultrapure water) for 30 minutes. While washing aliquoted HCR hairpins (Molecular Instruments Inc) were heated to 95 C for 1.5 minutes and allowed to cool to RT for 30 minutes. HCR hairpins were diluted to a concentration of 120 nM per hairpin in amplification buffer (2×SSC, 10% Dextran Sulfate) and added to washed tissue for 45 minutes. Following amplification, samples were washed in the same 30% WBT for at least 10 minutes to remove excess hairpins. Samples were stained with DAPI and submerged in pyranose oxidase antibleaching buffer. Sample port covers were closed with a glass coverslip or a transparent polycarbonate sheet to exclude oxygen.

Samples were imaged using a standard epifluorescence microscope (Nikon Ti Eclipse with custom built laser assembly) for the 125-gene experiment. Exposures times were 200 ms for cy7 and alexa 488 channels and 100 ms for alexa 647, alexa 594, and cy3b channels. For the 249-gene experiment, a Yokogawa CSU-W1 spinning disk confocal unit attached to an Olympus IX-81 base was used for imaging. The exposure times were 500 ms for each channel. At this stage, intact and accessible mRNA should always appear in two channels. If the RNA was deemed to be intact, DAPI data was collected in this hybridization. Samples were digested with DNAse I (Roche 04716728001) for 4 hours at room temperature on the scope. Following DNAse I the sample was washed several times with 30% WBT and hybridized overnight with 70% Formamide HB and the experiment probes at 1 nM concentration per probe sequence at room temperature. Samples were again washed and amplified as before. Barcode digits were developed by repeating this cycle with the appropriate probes for each hybridization. Fluorescent Nissl stain (ThermoFisher N-21480) was collected at the end of the experiment along with images of multispectral beads to aid chromatic aberration corrections.

Image Processing.

To remove the effects of chromatic aberration, the multispectral beads were first used to create geometric transforms to align all fluorescence channels. Next, the background illumination profile of every fluorescence channel was mapped using a morphological image opening with a large structuring element. These illumination profile maps were used to flatten the illumination in post-processing resulting in relatively uniform background intensity and preservation of the intensity profile of fluorescent points. The background signal was then subtracted using the imagej rolling ball background subtraction algorithm with a radius of 3 pixels. Finally, the calculated geometric transforms were applied to each channel respectively. The 150 pixel border region around the image was ignored in all analysis to avoid errors from edge effects of illumination.

Image Registration.

The processed images were then registered by first taking a maximum intensity projection along the z direction in each channel. All of the maximum projections of the channels of a single hybridization were then collapsed resulting in 4 composite images containing all the points in a particular round of hybridization. Each of these composite images of hybridization 1-3 were then cross-correlated individually with the composite image of hybridization 4 and the position of the maxima of the cross-correlation was used as the translation factor to align hybridizations 1-3 to hybridization 4.

Cell Segmentation.

For cells in the cortex, the cells were segmented manually using the DAPI images taken in the first round of hybridization and the fluorescent nissl stain taken at the end of the experiment. Furthermore, the density of the point cloud surrounding a cell was taken into account when forming cell boundaries, especially in cells that did not stain with the nissl stain. For the hippocampus, the cells were segmented by first manually selecting the centroid in 3D of each DAPI signal of every cell. Transcripts were first assigned based on nearest centroids. These point clouds were then used to refine the centroid estimate and create a 3D voronoi tessellation with a 10% boundary-shrinking factor to eliminate ambiguous mRNA assignments from neighboring cells.

Barcode Calling.

The potential mRNA signals were then found by LOG filtering the registered images and finding points of local maxima above a specified threshold value. Once all potential points in all channels of all hybridizations were obtained, dots were matched to potential barcode partners in all other channels of all other hybridizations using a 1 pixel search radius to find symmetric nearest neighbors. Point combinations that constructed only a single barcode were immediately matched to the on-target barcode set. For points that matched to construct multiple barcodes, first the point sets were filtered by calculating the residual spatial distance of each potential barcode point set and only the point sets giving the minimum residuals were used to match to a barcode. If multiple barcodes were still possible, the point was matched to its closest on-target barcode with a hamming distance of 1. If multiple on target barcodes were still possible, then the point was dropped from the analysis as an ambiguous barcode. This procedure was repeated using each hybridization as a seed for barcode finding and only barcodes that were called similarly in at least 3 out of 4 rounds were used in the analysis. The number of each barcode was then counted in each of the assigned cell volumes and transcript numbers were assigned based on the number of on-target barcodes present in the cell volume. All image processing and image analysis code can be obtained upon request.

Clustering.

Figure 42:
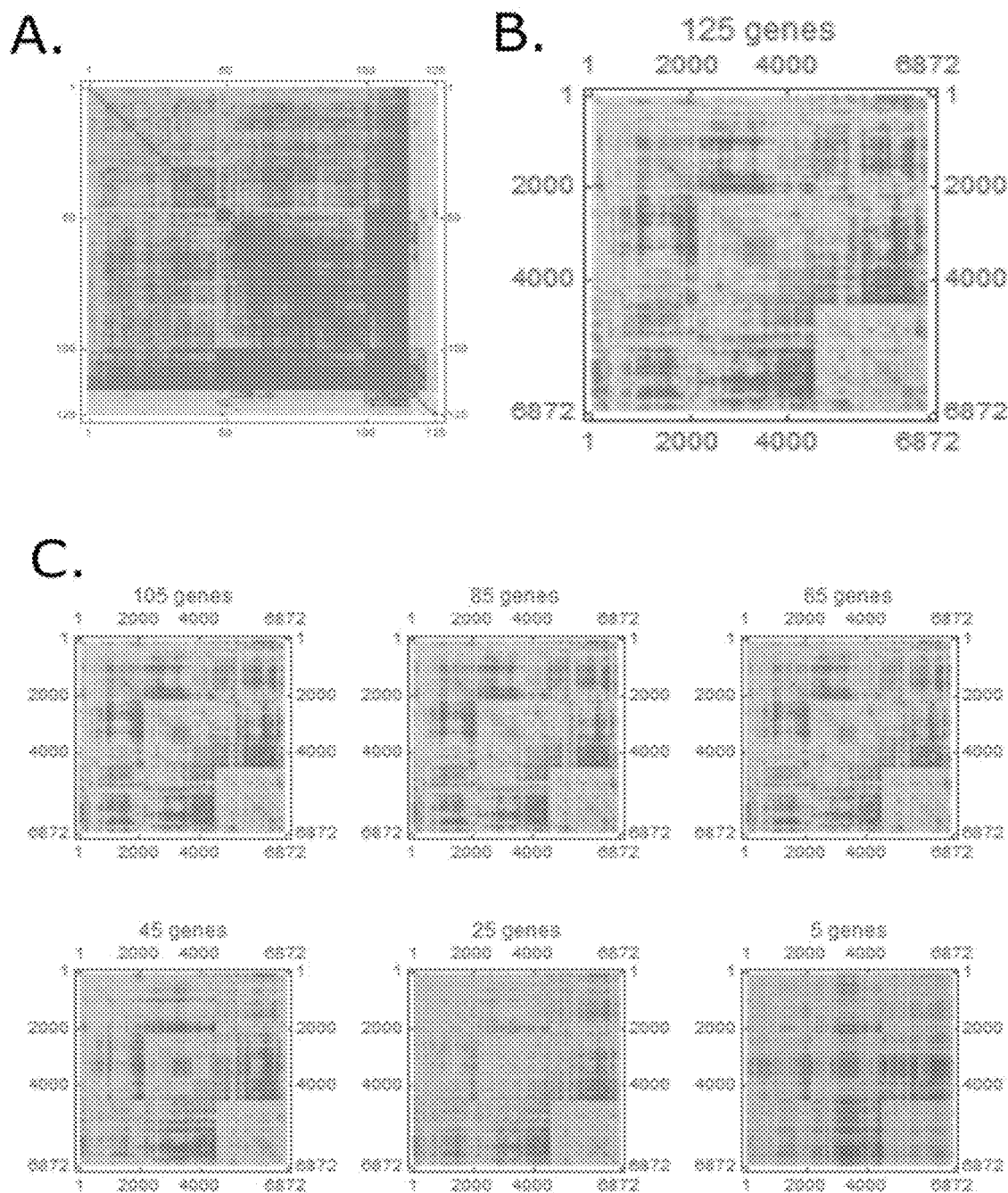
FIG. 42 depicts an example embodiment, showing cell-to-cell correlation analysis as a function of dropping genes (related to FIG. 31). A). Clustered gene to gene correlation map for all 125 genes. There are many blocks of highly correlated genes. A few genes do not fall into any blocks. B). The full cell-to-cell correlation map using all genes in the data set. C). Representative cell-to-cell correlation with the indicated number of genes used to construct the matrix indicated above each plot. Dropping genes from the data results in degradation of the fine structure of the correlation map.

To cluster the dataset with 14,908 cells and 125 genes profiled, we first z-score normalized the data based on gene expression. Once the single cell gene expression data is converted into z-scores, we compute a matrix of cell-to-cell correlations using Pearson correlation coefficients. Then hierarchical clustering with Ward linkage is performed on the cell-to-cell correlation data with cells in the center field of view. The cluster definitions are then propagated to the remaining cells using a random forest machine learning algorithm. To analyze the robustness of individual clusters, a random forest model was trained using varying subsets of the data and used to predict the cluster assignment of the remaining cells. A bootstrap analysis by dropping different sets of cells was performed in increments (FIG. 42). To determine the effect of dropping out genes on the accuracy of the clustering analysis, we used a random forest decision tree to learn the cluster definition based on the 125 gene data. Then we ask the decision tree to re-compute the cluster assignment on cell-to-cell correlation matrices with fewer and fewer genes (FIG. 31F, green line). Bootstrap resampling was also performed with this analysis (FIG. 31F, bluelines). The PCA and tSNE analysis were performed using the same cell-to-cell z-scored Pearson correlation matrix. The cell-to-cell correlation in FIG. 31E was calculated with increasing number of principal components dropped (have their eigenvalues set to zero). The cluster assignment accuracy is again computed through the random forest decision tree.

Optical Space for Barcodes in Cells.

The theoretical upper limit for the number of barcodes that can be identified accurately within a cells primarily depends on the volume of the cell. As mRNA spots are diffraction limited, if a microscope is configured to have sub-diffraction limited pixel size, the ability to identify smFISH signal without any super-resolution would require no two mRNA signals to be immediately adjacent to each other in x, y or z dimension. These minimum required voxels are called "coding voxels." The absolute upper limit of the number of transcripts that can be coded unambiguously without any super-resolution methods is solely a function of the number of coding voxels present in a cell. Assuming a diffraction limit of $\lambda$ um and a resolution of z um in the z direction, there exists $v/(3\lambda)^2 z$ coding voxels per cell, where V is the volume of the cell in microns. In the seqFISH method, we use 5 or more channels to hold mRNA spots which would increase the total number of coding voxels by a multiplicative factor equal to the number of channels used for barcoding. Therefore, $$\#B = \frac{FV}{(3\lambda)^2 z}$$

where #B is the maximum number of unambiguous barcodes a cell can hold, and F is the number of channels used. As mammalian cells range from about 500-4000 microns in volume, these cells can accommodate roughly between 6100-49,000 barcodes assuming 5 fluorescence channels are being used, the diffraction limit is 0.3 um, and the z resolution is 0.5 um. In principle, this calculation would provide the total number of perfectly discernible spots a cell can accommodate. In our actual experimental data, we have some amount of dropped barcodes due to ambiguity in barcode assignment due to spot overlaps. This is one of the main factors that reduces the efficiency of seqFISH as compared to single transcript detection (i.e., smFISH or smHCR). Expansion microscopy could further increase the number of coding voxels in a cell by the expansion factor leading to fewer drops and imaging of denser transcripts.

Additional background information can be found in the following references, each of which is hereby incorporated by reference in its entirety.

Beliveau, B. J., Joyce, E. F., Apostolopoulos, N., Yilmaz, F., Fonseka, C. Y., McCole, R. B., Chang, Y., Li, J. B., Senaratne, T. N., Williams, B. R., et al. (2012). Versatile design and synthesis platform for visualizing genomes with Oligopaint FISH probes. Proc. Natl. Acad. Sci. U.S.A 109, 21301-21306.

Betzig, E., Patterson, G. H., Sougrat, R., Lindwasser, O. W., Olenych, S., Bonifacino, J. S., Davidson, M. W., Lippincott-Schwartz, J., and Hess, H. F. (2006). Imaging Intracellular Fluorescent Proteins at Nanometer Resolution. Science 313, 1642-1645.

Breiman, L. (2001). Random Forests. Mach. Learn. 45, 5-32.

Cajigas, I. J., Tushev, G., Will, T. J., Dieck, S. tom, Fuerst, N., and Schuman, E. M. (2012). The Local Transcriptome in the Synaptic Neuropil Revealed by Deep Sequencing and High-Resolution Imaging. Neuron 74, 453-466.

Cembrowski, M. S., Bachman, J. L., Wang, L., Sugino, K., Shields, B. C., and Spruston, N. (2016). Spatial Gene-Expression Gradients Underlie Prominent Heterogeneity of CA1 Pyramidal Neurons. Neuron 89, 351-368.

Cenquizca, L. A., and Swanson, L. W. (2007). Spatial organization of direct hippocampal field CA1 axonal projections to the rest of the cerebral cortex. Brain Res. Rev. 56, 1-26.

Chen, F., Tillberg, P. W., and Boyden, E. S. (2015a). Expansion microscopy. Science 347, 543-548.

Chen, F., Wassie, A. T., Cote, A. J., Sinha, A., Alon, S., Asano, S., Daugharthy, E. R., Chang, J.-B., Marblestone, A., Church, G. M., Raj, A., Boyden, E. S., 2016. Nanoscale imaging of RNA with expansion microscopy. Nat Meth advance online publication.

Chen, K. H., Boettiger, A. N., Moffitt, J. R., Wang, S., and Zhuang, X. (2015b). Spatially resolved, highly multiplexed RNA profiling in single cells. Science 348, aaa6090.

Choi, H. M. T., Beck, V. A., and Pierce, N. A. (2014). Next-Generation in Situ Hybridization Chain Reaction: Higher Gain, Lower Cost, Greater Durability. ACS Nano 8, 4284-4294.

Darmanis, S., Sloan, S. A., Zhang, Y., Enge, M., Caneda, C., Shuer, L. M., Gephart, M. G. H., Barres, B. A., and Quake, S. R. (2015). A survey of human brain transcriptome diversity at the single cell level. Proc. Natl. Acad. Sci. 112, 7285-7290.

Dong, H.-W., Swanson, L. W., Chen, L., Fanselow, M. S., and Toga, A. W. (2009). Genomic-anatomic evidence for distinct functional domains in hippocampal field CA1. Proc. Natl. Acad. Sci. 106, 11794-11799.

Fan, Y., Braut, S. A., Lin, Q., Singer, R. H., and Skoultchi, A. I. (2001). Determination of transgenic loci by expression FISH. Genomics 71, 66-69.

Fanselow, M. S., and Dong, H.-W. (2010). Are the dorsal and ventral hippocampus functionally distinct structures? Neuron 65, 7-19.

Femino, A. M., Fay, F. S., Fogarty, K., and Singer, R. H. (1998). Visualization of Single RNA Transcripts in Situ. Science 280, 585-590.

Habib, N., Li, Y., Heidenreich, M., Swiech, L., Trombetta, J. J., Zhang, F., Regev, A., 2016. Div-Seq: A single nucleus RNA-Seq method reveals dynamics of rare adult newborn neurons in the CNS. bioRxiv 045989.

Jung, M. W., Wiener, S. I., and McNaughton, B. L. (1994). Comparison of spatial firing characteristics of units in dorsal and ventral hippocampus of the rat. J. Neurosci. 14, 7347-7356.

Ke, R., Mignardi, M., Pacureanu, A., Svedlund, J., Botling, J., Wahlby, C., and Nilsson, M. (2013). In situ sequencing for RNA analysis in preserved tissue and cells. Nat. Methods 10, 857-860.

Kishi, T., Tsumori, T., Yokota, S., and Yasui, Y. (2006). Topographical projection from the hippocampal formation to the amygdala: A combined anterograde and retrograde tracing study in the rat. J. Comp. Neurol. 496, 349-368.

Klein, A. M., Mazutis, L., Akartuna, I., Tallapragada, N., Veres, A., Li, V., Peshkin, L., Weitz, D. A., and Kirschner, M. W. (2015). Droplet Barcoding for Single-Cell Transcriptomics Applied to Embryonic Stem Cells. Cell 161, 1187-1201.

Lee, J. H., Daugharthy, E. R., Scheiman, J., Kalhor, R., Yang, J. L., Ferrante, T. C., Terry, R., Jeanty, S. S. F., Li, C., Amamoto, R., et al. (2014). Highly Multiplexed Subcellular RNA Sequencing in Situ. Science 343, 1360-1363.

Lein, E. S., Hawrylycz, M. J., Ao, N., Ayres, M., Bensinger, A., Bernard, A., Boe, A. F., Boguski, M. S., Brockway, K. S., Byrnes, E. J., et al. (2007). Genome-wide atlas of gene expression in the adult mouse brain. Nature 445, 168-176.

Lubeck, E., and Cai, L. (2012). Single-cell systems biology by super-resolution imaging and combinatorial labeling. Nat. Methods 9, 743-748.

Lubeck, E., Coskun, A. F., Zhiyentayev, T., Ahmad, M., and Cai, L. (2014). Single-cell in situ RNA profiling by sequential hybridization. Nat. Methods 11, 360-361.

Macosko, E. Z., Basu, A., Satija, R., Nemesh, J., Shekhar, K., Goldman, M., Tirosh, I., Bialas, A. R., Kamitaki, N., Martersteck, E. M., et al. (2015). Highly Parallel Genome-wide Expression Profiling of Individual Cells Using Nanoliter Droplets. Cell 161, 1202-1214.

Madisen, L., Zwingman, T. A., Sunkin, S. M., Oh, S. W., Zariwala, H. A., Gu, H., Ng, L. L., Palmiter, R. D., Hawrylycz, M. J., Jones, A. R., et al. (2010). A robust and high-throughput Cre reporting and characterization system for the whole mouse brain. Nat. Neurosci. 13, 133-140.

Madisen, L., Mao, T., Koch, H., Zhuo, J., Berenyi, A., Fujisawa, S., Hsu, Y.-W. A., Iii, A. J. G., Gu, X., Zanella, S., et al. (2012). A toolbox of Cre-dependent optogenetic transgenic mice for light-induced activation and silencing. Nat. Neurosci. 15, 793-802.

Miller, J A. Jason Nathanson, Daniel Franjic, Sungbo Shim, Rachel A. Dalley, Sheila Shapouri, Kimberly A. Smith, Susan M. Sunkin, Amy Bernard, Jeffrey L. Bennett, Chang-Kyu Lee, Michael J. Hawrylycz, Allan R. Jones, David G. Amaral, Nenad Sestan, Fred H. Gage, Ed S. Lein (2013). Conserved molecular signatures of neurogenesis in the hippocampal subgranular zone of rodents and primates. Development. 140(22): 4633-4644.

Muller, R., Stead, M., and Pach, J. (1996). The hippocampus as a cognitive graph. J. Gen. Physiol. 107, 663-694.

O'Keefe, J., and Dostrovsky, J. (1971). The hippocampus as a spatial map. Preliminary evidence from unit activity in the freely-moving rat. Brain Res. 34, 171-175.

Petrovich, G. D., Canteras, N. S., and Swanson, L. W. (2001). Combinatorial amygdalar inputs to hippocampal domains and hypothalamic behavior systems. Brain Res. Brain Res. Rev. 38, 247-289.

Pitkanen, A., Pikkarainen, M., Nurminen, N., and Ylinen, A. (2000). Reciprocal Connections between the Amygdala and the Hippocampal Formation, Perirhinal Cortex, and Postrhinal Cortex in Rat: A Review. Ann. N. Y. Acad. Sci. 911, 369-391.

Raj, A., Peskin, C. S., Tranchina, D., Vargas, D. Y., and Tyagi, S. (2006). Stochastic mRNA Synthesis in Mammalian Cells. PLoS Biol 4, e309.

Risold, P. Y., and Swanson, L. W. (1996). Structural evidence for functional domains in the rat hippocampus. Science 272, 1484-1486.

Rust, M. J., Bates, M., and Zhuang, X. (2006). Sub-diffraction-limit imaging by stochastic optical reconstruction microscopy (STORM). *Nat Meth* 3, 793-796.

Satija, R., Farrell, J. A., Gennert, D., Schier, A. F., Regev, A., 2015. Spatial reconstruction of single-cell gene expression data. Nat Biotech 33, 495-502.

Saunders, R. C., Rosene, D. L., and Van Hoesen, G. W. (1988). Comparison of the efferents of the amygdala and the hippocampal formation in the rhesus monkey: II. Reciprocal and non-reciprocal connections. J. Comp. Neurol. 271, 185-207.

Shah, S., Lubeck, E., Schwarzkopf, M., He, T., Greenbaum, A., Sohn, C. ho, Lignell, A., Choi, H. M. T., Gradinaru, V., Pierce, N. A., Cai, L., 2016. Single-molecule RNA detection at depth via hybridization chain reaction and tissue hydrogel embedding and clearing. Development dev.138560. doi:10.1242/dev.138560

Ståhl, P. L., Salmén, F., Vickovic, S., Lundmark, A., Navarro, J. F., Magnusson, J., Giacomello, S., Asp, M., Westholm, J. O., Huss, M., Mollbrink, A., Linnarsson, S., Codeluppi, S., Borg, Å., Pontén, F., Costea, P. I., Sahlén, P., Mulder, J., Bergmann, O., Lundeberg, J., Frisén, J., 2016. Visualization and analysis of gene expression in tissue sections by spatial transcriptomics. Science 353, 78-82. doi: 10.1126/science.aaf2403

Tasic, B., Menon, V., Nguyen, T. N., Kim, T. K., Jarsky, T., Yao, Z., Levi, B., Gray, L. T., Sorensen, S. A., Dolbeare, T., et al. (2016). Adult mouse cortical cell taxonomy revealed by single cell transcriptomics. Nat. Neurosci. advance online publication.

Thompson, C. L., Pathak, S. D., Jeromin, A., Ng, L. L., MacPherson, C. R., Mortrud, M. T., Cusick, A., Riley, Z. L., Sunkin, S. M., Bernard, A., et al. (2008). Genomic Anatomy of the Hippocampus. Neuron 60, 1010-1021.

Treweek, J. B., Chan, K. Y., Flytzanis, N. C., Yang, B., Deverman, B. E., Greenbaum, A., Lignell, A., Xiao, C., Cai, L., Ladinsky, M. S., et al. (2015). Whole-body tissue stabilization and selective extractions via tissue-hydrogel hybrids for high-resolution intact circuit mapping and phenotyping. Nat. Protoc. 10, 1860-1896.

Van der Maaten, L., and Hinton, G. (2008). Visualizing data using t-SNE. J. Mach. Learn. Res. 9, 85.

Witter, M. P. (1993). Organization of the entorhinal-hippocampal system: A review of current anatomical data. Hippocampus 3, 28-44.

Witter, M. P., and Amaral, D. G. (1991). Entorhinal cortex of the monkey: V. Projections to the dentate gyrus, hippocampus, and subicular complex. J. Comp. Neurol. 307, 437-459.

Yang, B., Treweek, J. B., Kulkarni, R. P., Deverman, B. E., Chen, C.-K., Lubeck, E., Shah, S., Cai, L., and Gradinaru, V. (2014). Single-Cell Phenotyping within Transparent Intact Tissue through Whole-Body Clearing. Cell.

Yang S M, Alvarez D D, Schinder A F. (2015). Reliable Genetic Labeling of Adult-Born Dentate Granule Cells Using Ascl1 CreERT2 and Glast CreERT2 Murine Lines. J Neurosci. 35(46):15379-90.

Yi, F., Catudio-Garrett, E., Gábriel, R., Wilhelm, M., Erdelyi, F., Szabo, G., Deisseroth, K., and Lawrence, J. (2015). Hippocampal "cholinergic interneurons" visualized with the choline acetyltransferase promoter: anatomical distribution, intrinsic membrane properties, neurochemical characteristics, and capacity for cholinergic modulation. Front. Synaptic Neurosci. 7.

Zeisel, A., Manchado, A. B. M., Codeluppi, S., Lönnerberg, P., Manno, G. L., Juréus, A., Marques, S., Munguba, H., He, L., Betsholtz, C., et al. (2015). Cell types in the mouse cortex and hippocampus revealed by single-cell RNA-seq. Science aaa1934.

EQUIVALENTS

Having described some illustrative embodiments of the invention, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives. Acts, elements, and features discussed only in connection with one embodiment are not intended to be excluded from a similar role in other embodiments. Further, for the one or more means-plus-function limitations recited in the following claims, the means are not intended to be limited to the means disclosed herein for performing the recited function, but are intended to cover in scope any means, known now or later developed, for performing the recited function.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

The invention claimed is:

1. A sequential hybridization method, comprising:
identifying a plurality of target genes; and
associating, via sequential hybridization of binding probes to the plurality of target genes, a first plurality of unique codes with the plurality of target genes, wherein each target gene in the plurality of target genes is represented by a unique code in the first plurality of unique codes, wherein the sequential hybridization comprises n rounds of hybridization (where n≥2), and wherein each round of hybridization in n rounds of hybridization comprises:
contacting the plurality of target genes with a plurality of binding probes, wherein each probe in the plurality of binding probes comprises:
a binding sequence that specifically binds a target sequence in a gene in the plurality of target genes, wherein target genes from the plurality of target genes are spatially transfixed from each other, and wherein each probe is capable of emitting a detectable visual signal upon binding of the probe to a target sequence;
detecting visual signals that reflect the binding between the plurality of binding probes and the plurality of target genes; and
removing the visual signals, prior to the next round of hybridization;
wherein probes used in the n rounds of hybridization are capable of emitting at least F types of detectable visual signals (where F≥2 and $F^n$ is greater than the number of target genes in the plurality of target genes),
wherein a unique code in the first plurality of unique codes for a target gene consists of n components,
wherein each component is determined by visual signals that reflect the binding between binding probes and the target gene during one of the n rounds of hybridization,
wherein the n rounds of hybridization include m rounds of error correction n≥m≥1), wherein each m error correction round comprises one round of the n rounds of hybridization, and each m round of hybridization is a repeat of one of the remaining one or more (n−1) rounds of the n rounds of hybridization, wherein a second plurality of unique codes for the plurality of target genes is generated after each m error correction round is removed from the n rounds of hybridization, and wherein each unique code in the second plurality of unique codes consists of (n−m) components and uniquely represents a target gene in the plurality of target genes.

2. The sequential hybridization method of claim 1, wherein the plurality of target genes are located on immobilized nucleic acids selected from the group consisting of mRNAs, chromosomal DNAs and combinations thereof.

3. The sequential hybridization method of claim 1, wherein n is 4 or greater, 5 or greater, or 10 or greater.

4. The sequential hybridization method of claim 1, wherein m≤0.5n.

5. The sequential hybridization method of claim 1, wherein the at least F types of detectable visual signals comprise one selected from the group consisting of a fluorescence signal, a color signal, a red signal, a green signal, a yellow signal, a combined color signal representing two or more colors, and combinations thereof.

6. The sequential hybridization method of claim 1, wherein a probe in the plurality of binding probes further comprises a signal moiety that emits a detectable visual signal upon binding of the probe to a target sequence.

7. The sequential hybridization method of claim 6, wherein the signal moiety is connected to the binding sequence of the probe via a cleavable linker.

8. The sequential hybridization method of claim 1, wherein each component of a n-component unique code in the first plurality of unique codes is assigned a numerical value that corresponds to one of the at least F types of detectable visual signals; and wherein at least one component of the n-component unique code is determined based on the numerical values of all or some of the other n−1 components.

9. The sequential hybridization method of claim 8, wherein the n-component unique code is determined as:

$$\{j_1, j_2 \ldots (a_1{}^*j_1 + a_2{}^*j_2 + \ldots + a_n{}^*j_n + C) \bmod F, \ldots j_n\},$$

wherein $j_1$ is a numerical value that corresponds the detectable visual signals used in the first round of hybridization, $j_2$ is a numerical value that corresponds the detectable visual signals used in the second round of hybridization, and $j_n$ is a numerical value that corresponds the detectable visual signals used in the nth round of hybridization; and wherein $j_1, j_2, \ldots j_n$, $a_1, a_2, \ldots a_n$ and n are integers and C is an integer.

10. A hybridization method, comprising:
identifying a plurality of target genes;
performing sequential hybridization of binding probes to the plurality of target genes, wherein the sequential hybridization comprises n rounds of hybridization (where n≥2), and wherein each round of hybridization in n rounds of hybridization comprises:
  contacting the plurality of target genes with a plurality of binding probes, wherein each probe in the plurality of binding probes comprises:
    a binding sequence that specifically binds a target sequence in a gene in the plurality of target genes, wherein target genes from the plurality of target genes are spatially transfixed from each other, and
  wherein each probe is capable of emitting a detectable visual signal upon binding of the probe to a target sequence;
detecting visual signals that reflect the binding between the plurality of binding probes and the plurality of target genes, wherein each target gene in the plurality of target genes is represented by visual signals that are unique for the target gene, and wherein probes used in the n rounds of hybridization are capable of emitting at least F types of detectable visual signals (where F≥2, and $F^n$ is greater than the number of target genes in the plurality of target genes); and
removing the visual signals, prior to the next round of hybridization; and
performing serial hybridizations against one or more target genes, wherein the expression level of each target gene is above a predetermined threshold value, wherein each serial hybridization comprises:
  contacting the one or more target genes with a plurality of binding probes, wherein each probe in the plurality of binding probes comprises:
    a binding sequence that specifically binds a target sequence in a target gene in the one or more target genes, wherein one or more target genes are spatially transfixed from each other,
  wherein each probe is capable of emitting a detectable visual signal upon binding of the probe to the target sequence, and wherein probes binding to target sequences in the same target gene emit the same detectable visual signals; and
detecting visual signals that reflect the binding between the plurality of binding probes and the one or more target gene.

11. The hybridization method of claim 10, wherein then rounds of hybridization generate a first plurality of unique codes, wherein each target gene in the plurality of target genes is represented by a unique code in the first plurality of unique codes.

12. The hybridization method of claim 11, wherein a unique code in the first plurality of unique codes for a target gene consists of n components, and wherein each component is determined by visual signals that reflect the binding between binding probes and the target gene during one of the n rounds of hybridization.

13. The hybridization method of claim 11, wherein the n rounds of hybridization include m error correction round (m≥1), wherein the m error correction round comprises one round of then rounds of hybridization, and the n rounds of hybridization is a repeat of one of the remaining one or more (n−1) rounds of the n rounds of hybridization, and wherein a second plurality of unique codes for the plurality of target genes is generated after the m error correction round is removed from the n rounds of hybridization, and wherein each unique code in the second plurality of unique codes consists of (n−m) components and uniquely represents a target gene in the plurality of target genes.

14. The hybridization method of claim 10, further comprising:
identifying the one or more target genes based on expression levels of candidate target genes.

15. The hybridization method of claim 10, wherein the plurality of target genes are located on immobilized nucleic acids selected from the group consisting of mRNAs, chromosomal DNAs and combinations thereof.

16. The hybridization method of claim 10, wherein the one or more target genes are located on immobilized nucleic acids selected from the group consisting of mRNAs, chromosomal DNAs and combinations thereof.

17. The hybridization method of claim 11, wherein each unique code in the first plurality of unique codes consists of n component, wherein each component of a n-component unique code in the first plurality of unique codes is assigned a numerical value that corresponds to one of the at least F types of detectable visual signals; and wherein at least one component of the n-component unique code is determined based on the numerical values of all or some of the other n−1 components.

18. The hybridization method of claim 17, wherein the n-component unique code is determined as:

$$\{j_1, j_2 \ldots (a_1*j_1 + a_2*j_2 + \ldots + a_n*j_n + C) \bmod F, \ldots, j_n\},$$

wherein $j_1$ is a numerical value that corresponds the detectable visual signals used in the first round of hybridization, $j_2$ is a numerical value that corresponds the detectable visual signals used in the second round of hybridization, and $j_n$ is a numerical value that corresponds the detectable visual signals used in the nth round of hybridization; and wherein $j_1, j_2, \ldots j_n, a_1, a_2, \ldots a_n$ are non-zero integers and C is an integer.

19. A non-transitory computer-readable medium containing instructions that, when executed by a computer processor, cause the computer processor to:

associate, via sequential hybridization of binding probes to a plurality of target genes, a first plurality of unique codes with the plurality of target genes, wherein each target gene in the plurality of target genes is represented by a unique code in the first plurality of unique codes, wherein the sequential hybridization comprises n rounds of hybridization (where n≥2), and wherein each round of hybridization inn rounds of hybridization comprises:

contacting the plurality of target genes with a plurality of binding probes, wherein each probe in the plurality of binding probes comprises:

a binding sequence that specifically binds a target sequence in a gene in the plurality of target genes, wherein target genes from the plurality of target genes are spatially transfixed from each other, and wherein each probe is capable of emitting a detectable visual signal upon binding of the probe to a target sequence;

detecting visual signals that reflect the binding between the plurality of binding probes and the plurality of target genes; and removing the visual signals, when applicable, prior to the next round of hybridization;

wherein probes used in the n rounds of hybridization are capable of emitting at least F types of detectable visual signals (where F≥2 and $F^n$ is greater than the number of target genes in the plurality of target genes), wherein a unique code in the first plurality of unique codes for a target gene consists of n components, wherein each component is determined by visual signals that reflect the binding between binding probes and the target gene during one of the n rounds of hybridization, wherein the n rounds of hybridization include m error correction round (m≥1), wherein a second plurality of unique codes for the plurality of target genes is generated after the m error correction round is removed from the n rounds of hybridization, and wherein each unique code in the second plurality of unique codes consists of (n−m) components and uniquely represents a target gene in the plurality of target genes.

20. A non-transitory computer-readable medium containing instructions that, when executed by a computer processor, cause the computer processor to:

perform sequential hybridization of binding probes to a plurality of target genes, wherein the sequential hybridization comprises n rounds of hybridization (where n≥2), and wherein each round of hybridization in n rounds of hybridization comprises:

contacting the plurality of target genes with a plurality of binding probes, wherein each probe in the plurality of binding probes comprises:

a binding sequence that specifically binds a target sequence in a gene in the plurality of target genes, wherein target genes from the plurality of target genes are spatially transfixed from each other, and wherein each probe is capable of emitting a detectable visual signal upon binding of the probe to a target sequence;

detecting visual signals that reflect the binding between the plurality of binding probes and the plurality of target genes, wherein each target gene in the plurality of target genes is represented by visual signals that are unique for the target gene, and wherein probes used in the n rounds of hybridization are capable of emitting at least F types of detectable visual signals (where F≥2, and $F^n$ is greater than the number of target genes in the plurality of target genes); and removing the visual signals, when applicable, prior to the next round of hybridization; and perform hybridizations against one or more target genes, wherein the expression level of each target gene is above a predetermined threshold value, wherein each hybridization comprises:

contacting the one or more target genes with a plurality of binding probes, wherein each probe in the plurality of binding probes comprises:

a binding sequence that specifically binds a target sequence in a target gene in the one or more target genes, wherein one or more target genes are spatially transfixed from each other, wherein each probe is capable of emitting a detectable visual signal upon binding of the probe to the target sequence, and wherein probes binding to target sequences in the same target gene emit the same detectable visual signals; and detecting visual signals that reflect the binding between the plurality of binding probes and the one or more target gene.

* * * * *